(12) United States Patent
Ju et al.

(10) Patent No.: US 9,175,342 B2
(45) Date of Patent: Nov. 3, 2015

(54) SYNTHESIS OF CLEAVABLE FLUORESCENT NUCLEOTIDES AS REVERSIBLE TERMINATORS FOR DNA SEQUENCING BY SYNTHESIS

(71) Applicants: Jingyue Ju, Englewood Cliffs, NJ (US); Huanyan Cao, New York, NY (US); Zengmin Li, New York, NY (US); Qinglin Meng, Sunnyvale, CA (US); Jia Guo, Mountain View, CA (US); Shenglong Zhang, New York, NY (US)

(72) Inventors: Jingyue Ju, Englewood Cliffs, NJ (US); Huanyan Cao, New York, NY (US); Zengmin Li, New York, NY (US); Qinglin Meng, Sunnyvale, CA (US); Jia Guo, Mountain View, CA (US); Shenglong Zhang, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 125 days.

(21) Appl. No.: 13/951,269

(22) Filed: Jul. 25, 2013

(65) Prior Publication Data
US 2014/0093869 A1    Apr. 3, 2014

Related U.S. Application Data

(63) Continuation of application No. 12/734,227, filed as application No. PCT/US2008/011891 on Oct. 17, 2008, now abandoned.

(60) Provisional application No. 60/999,576, filed on Oct. 19, 2007.

(51) Int. Cl.
| | | |
|---|---|---|
| *C07H 17/00* | (2006.01) |
| *C07H 21/02* | (2006.01) |
| *C07H 19/04* | (2006.01) |
| *C12Q 1/68* | (2006.01) |
| *C12P 19/34* | (2006.01) |
| *C07H 19/06* | (2006.01) |
| *C07H 19/10* | (2006.01) |
| *C07H 19/14* | (2006.01) |
| *C07H 19/16* | (2006.01) |
| *C07H 19/20* | (2006.01) |

(52) U.S. Cl.
CPC .............. *C12Q 1/6869* (2013.01); *C07H 19/06* (2013.01); *C07H 19/10* (2013.01); *C07H 19/14* (2013.01); *C07H 19/16* (2013.01); *C07H 19/20* (2013.01)

(58) Field of Classification Search
CPC ........... C12Q 1/6869; C12Q 2525/117; C12Q 2563/107; C07H 19/04
USPC .......... 435/6.1, 91.1, 91.2; 536/4.1, 23.1, 26.6
See application file for complete search history.

(56) References Cited

U.S. PATENT DOCUMENTS

| | | |
|---|---|---|
| 4,711,955 A | 12/1987 | Ward et al. |
| 4,772,691 A | 9/1988 | Herman |
| 4,824,775 A | 4/1989 | Dattagupta |
| 4,863,849 A | 9/1989 | Melamede |
| 4,888,274 A | 12/1989 | Radding et al. |
| 5,043,272 A | 8/1991 | Hartley |
| 5,118,605 A | 6/1992 | Urdea |
| 5,174,962 A | 12/1992 | Brennan |
| 5,175,269 A | 12/1992 | Stavrianopoulos et al. |
| 5,302,509 A | 4/1994 | Cheeseman |
| 5,308,990 A | 5/1994 | Takahashi |
| 5,328,824 A | 7/1994 | Ward et al. |
| 5,332,666 A | 7/1994 | Prober et al. |
| 5,436,143 A | 7/1995 | Hyman |
| 5,437,975 A | 8/1995 | McClelland et al. |
| 5,449,767 A | 9/1995 | Ward et al. |
| 5,476,928 A | 12/1995 | Ward et al. |
| 5,516,664 A | 5/1996 | Hyman |
| 5,534,424 A | 7/1996 | Uhlen |
| 5,547,839 A | 8/1996 | Dower |
| 5,547,859 A | 8/1996 | Goodman |
| 5,556,748 A | 9/1996 | Douglas |
| 5,599,675 A | 2/1997 | Brenner |
| 5,602,000 A | 2/1997 | Hyman |
| 5,637,469 A | 6/1997 | Wilding et al. |
| 5,654,419 A | 8/1997 | Mathies |
| 5,658,736 A | 8/1997 | Wong |
| 5,709,999 A | 1/1998 | Shattuck et al. |
| 5,728,528 A | 3/1998 | Mathies |
| 5,763,594 A | 6/1998 | Hiatt et al. |
| 5,770,365 A | 6/1998 | Lane et al. |
| 5,770,367 A | 6/1998 | Southern et al. |
| 5,789,167 A | 8/1998 | Konrad |
| 5,798,210 A | 8/1998 | Canard et al. |
| 5,804,386 A | 9/1998 | Ju |
| 5,808,045 A | 9/1998 | Hiatt et al. |
| 5,814,454 A | 9/1998 | Ju |

(Continued)

FOREIGN PATENT DOCUMENTS

| | | |
|---|---|---|
| CA | 2425112 | 9/2011 |
| DE | 4141178 | 6/1993 |

(Continued)

OTHER PUBLICATIONS

Exhibit 2105, filed Dec. 15, 2013 in connection with IPR2012-00006, IPR2012-00007, and IPR2013-00011: Columbia's Demonstratives Under 42.70(b) for Dec. 17, 2013 Oral Hearing.

(Continued)

*Primary Examiner* — Jezia Riley

(74) *Attorney, Agent, or Firm* — John P. White; Cooper & Dunham LLP

(57) ABSTRACT

This invention provides novel azido linkers for deoxynucleotide analogues having a detectable marker attached thereto.

12 Claims, 46 Drawing Sheets

(56) References Cited

U.S. PATENT DOCUMENTS

| | | |
|---|---|---|
| 5,821,356 A | 10/1998 | Khan et al. |
| 5,834,203 A | 11/1998 | Katzir |
| 5,849,542 A | 12/1998 | Reeve et al. |
| 5,853,992 A | 12/1998 | Glazer |
| 5,856,104 A | 1/1999 | Chee et al. |
| 5,869,255 A | 2/1999 | Mathies |
| 5,872,244 A | 2/1999 | Hiatt et al. |
| 5,876,936 A | 3/1999 | Ju |
| 5,885,775 A | 3/1999 | Haff et al. |
| 5,908,755 A | 6/1999 | Kumar et al. |
| 5,945,283 A | 8/1999 | Kwok |
| 5,952,180 A | 9/1999 | Ju |
| 5,959,089 A | 9/1999 | Hannessian |
| 5,962,228 A | 10/1999 | Brenner |
| 6,001,566 A | 12/1999 | Canard et al. |
| 6,001,611 A | 12/1999 | Gordon |
| 6,008,379 A | 12/1999 | Benson et al. |
| 6,013,445 A | 1/2000 | Albrecht et al. |
| 6,028,190 A | 2/2000 | Mathies |
| 6,046,005 A | 4/2000 | Ju |
| 6,074,823 A | 6/2000 | Hubert |
| 6,087,095 A | 7/2000 | Rosenthal et al. |
| 6,136,543 A | 10/2000 | Anazawa |
| 6,175,107 B1 | 1/2001 | Juvinall |
| 6,197,557 B1 | 3/2001 | Markarov |
| 6,207,831 B1 | 3/2001 | Auer et al. |
| 6,210,891 B1 | 4/2001 | Nyren |
| 6,214,987 B1 | 4/2001 | Hiatt |
| 6,218,118 B1 | 4/2001 | Sampson |
| 6,218,530 B1 | 4/2001 | Rothschild |
| 6,221,592 B1 | 4/2001 | Schwartz |
| 6,232,465 B1 | 5/2001 | Hiatt et al. |
| 6,242,193 B1 | 6/2001 | Anazawa et al. |
| 6,245,507 B1 | 6/2001 | Bogdanov |
| 6,255,475 B1 | 7/2001 | Kwiatkowski |
| 6,274,320 B1 | 8/2001 | Rothberg et al. |
| 6,277,607 B1 | 8/2001 | Tyagi et al. |
| 6,287,821 B1 | 9/2001 | Shi et al. |
| 6,294,324 B1 | 9/2001 | Bensimon et al. |
| 6,309,829 B1 | 10/2001 | Livak et al. |
| 6,309,836 B1 | 10/2001 | Kwiatkowski |
| 6,312,893 B1 | 11/2001 | Van Ness et al. |
| 6,316,230 B1 | 11/2001 | Egholm |
| 6,361,940 B1 | 3/2002 | Van Ness et al. |
| 6,380,378 B1 | 4/2002 | Kitamura et al. |
| 6,524,829 B1 | 2/2003 | Seeger |
| 6,555,349 B1 | 4/2003 | O'Donnell |
| 6,613,508 B1 | 9/2003 | Ness et al. |
| 6,613,513 B1 | 9/2003 | Parce et al. |
| 6,627,748 B1 | 9/2003 | Ju |
| 6,632,655 B1 | 10/2003 | Mehta et al. |
| 6,639,088 B2 | 10/2003 | Kwiatkowski |
| 6,664,079 B2 | 12/2003 | Ju et al. |
| 6,664,399 B1 | 12/2003 | Sabesan |
| 6,713,255 B1 | 3/2004 | Makino et al. |
| 6,780,591 B2 | 8/2004 | Williams et al. |
| 6,787,308 B2 | 9/2004 | Balasubramanian et al. |
| 6,818,395 B1 | 11/2004 | Quake et al. |
| 6,833,246 B2 | 12/2004 | Balasubramanian et al. |
| 6,864,052 B1 | 3/2005 | Drmanac et al. |
| 6,911,345 B2 | 6/2005 | Quake et al. |
| 6,934,636 B1 | 8/2005 | Skierczynski et al. |
| 6,982,146 B1 | 1/2006 | Schneider et al. |
| 7,037,687 B2 | 5/2006 | Williams et al. |
| 7,056,661 B2 | 6/2006 | Korlach et al. |
| 7,056,666 B2 | 6/2006 | Dower et al. |
| 7,057,026 B2 | 6/2006 | Barnes et al. |
| 7,057,031 B2 | 6/2006 | Olejnik |
| 7,074,597 B2 | 7/2006 | Ju |
| 7,078,499 B2 | 7/2006 | Odedra et al. |
| 7,105,300 B2 | 9/2006 | Parce et al. |
| 7,279,563 B2 | 10/2007 | Kwiatkowski |
| 7,329,496 B2 | 2/2008 | Dower et al. |
| 7,345,159 B2 | 3/2008 | Ju et al. |
| 7,393,533 B1 | 7/2008 | Crotty et al. |
| 7,414,116 B2 | 8/2008 | Milton et al. |
| 7,427,673 B2 | 9/2008 | Balasubramanian et al. |
| 7,459,275 B2 | 12/2008 | Dower et al. |
| 7,566,537 B2 | 7/2009 | Balasubramanian et al. |
| 7,622,279 B2 | 11/2009 | Ju |
| 7,635,578 B2 | 12/2009 | Ju et al. |
| 7,713,698 B2 | 5/2010 | Ju et al. |
| 7,785,790 B1 | 8/2010 | Church et al. |
| 7,790,869 B2 | 9/2010 | Ju et al. |
| 7,883,869 B2 | 2/2011 | Ju et al. |
| 7,982,029 B2 | 7/2011 | Ju et al. |
| 8,088,575 B2 | 1/2012 | Ju et al. |
| 8,298,792 B2 | 10/2012 | Ju et al. |
| 8,796,432 B2 | 8/2014 | Ju et al. |
| 8,889,348 B2 | 11/2014 | Ju |
| 2002/0012966 A1 | 1/2002 | Shi et al. |
| 2002/0102586 A1 | 8/2002 | Ju et al. |
| 2002/0168642 A1 | 11/2002 | Drukier |
| 2003/0008285 A1 | 1/2003 | Fischer |
| 2003/0022225 A1 | 1/2003 | Monforte |
| 2003/0027140 A1 | 2/2003 | Ju et al. |
| 2003/0044871 A1 | 3/2003 | Cutsforth et al. |
| 2003/0054360 A1 | 3/2003 | Gold et al. |
| 2003/0099972 A1 | 5/2003 | Olejnik et al. |
| 2003/0166282 A1 | 9/2003 | Brown et al. |
| 2003/0180769 A1 | 9/2003 | Metzker |
| 2003/0186256 A1 | 10/2003 | Fischer |
| 2003/0190680 A1 | 10/2003 | Rothschild et al. |
| 2003/0198982 A1 | 10/2003 | Seela et al. |
| 2004/0014096 A1 | 1/2004 | Anderson et al. |
| 2004/0096825 A1 | 5/2004 | Chenna et al. |
| 2004/0185466 A1 | 9/2004 | Ju et al. |
| 2005/0032081 A1 | 2/2005 | Ju et al. |
| 2005/0170367 A1 | 8/2005 | Quake et al. |
| 2005/0239134 A1 | 10/2005 | Gorenstein et al. |
| 2006/0003352 A1 | 1/2006 | Lipkin et al. |
| 2006/0057565 A1 | 3/2006 | Ju et al. |
| 2006/0105461 A1 | 5/2006 | Tom-Moy et al. |
| 2006/0160081 A1 | 7/2006 | Milton et al. |
| 2006/0240439 A1 | 10/2006 | Smith et al. |
| 2006/0252038 A1 | 11/2006 | Ju |
| 2007/0166705 A1 | 7/2007 | Milton et al. |
| 2007/0275387 A1 | 11/2007 | Ju |
| 2008/0131895 A1 | 6/2008 | Ju et al. |
| 2008/0199868 A1 | 8/2008 | Ju et al. |
| 2008/0319179 A1 | 12/2008 | Ju et al. |
| 2009/0088332 A1 | 4/2009 | Ju et al. |
| 2009/0240030 A1 | 9/2009 | Ju et al. |
| 2009/0263791 A1 | 10/2009 | Ju et al. |
| 2009/0298072 A1 | 12/2009 | Ju et al. |
| 2009/0325154 A1 | 12/2009 | Ju et al. |
| 2010/0159531 A1 | 6/2010 | Gordon et al. |
| 2010/0323350 A1 | 12/2010 | Gordon et al. |
| 2011/0014611 A1 | 1/2011 | Ju et al. |
| 2011/0039259 A1 | 2/2011 | Ju et al. |
| 2011/0124054 A1 | 5/2011 | Olejnik et al. |
| 2012/0052489 A1 | 3/2012 | Gordon et al. |
| 2012/0142006 A1 | 6/2012 | Ju et al. |
| 2012/0156680 A1 | 6/2012 | Ju et al. |
| 2013/0264207 A1 | 10/2013 | Ju et al. |
| 2013/0280700 A1 | 10/2013 | Ju et al. |
| 2014/0206553 A1 | 7/2014 | Ju et al. |
| 2014/0315191 A1 | 10/2014 | Ju et al. |
| 2014/0377743 A1 | 12/2014 | Ju et al. |

FOREIGN PATENT DOCUMENTS

| | | |
|---|---|---|
| DE | 20122767.3 | 8/2007 |
| EP | 0995804 | 4/2000 |
| EP | 1182267 | 2/2002 |
| EP | 1291354 | 3/2003 |
| EP | 0808320 | 4/2003 |
| EP | 1337541 | 3/2007 |
| EP | 1218391 | 4/2007 |
| EP | 1790736 | 5/2007 |
| EP | 0992511 | 3/2009 |
| EP | 2209911 B1 | 10/2013 |
| GB | 2446083 | 3/2011 |
| GB | 2446084 | 3/2011 |

(56) References Cited

FOREIGN PATENT DOCUMENTS

| | | |
|---|---|---|
| GB | 2457402 | 9/2011 |
| WO | WO 89/09282 | 10/1989 |
| WO | WO 90/13666 | 11/1990 |
| WO | WO 91/06678 | 5/1991 |
| WO | WO 92/10587 | 6/1992 |
| WO | WO 93/12340 | 10/1993 |
| WO | WO 93/21340 | 10/1993 |
| WO | WO 94/14972 | 7/1994 |
| WO | WO 93/05183 | 3/1995 |
| WO | WO 96/07669 | 3/1996 |
| WO | WO 96/23807 | 8/1996 |
| WO | WO 96/27025 | 9/1996 |
| WO | WO 97/08183 | 3/1997 |
| WO | WO 97/27317 | 7/1997 |
| WO | WO 97/35033 | 9/1997 |
| WO | WO 98/30720 | 7/1998 |
| WO | WO 98/44151 | 10/1998 |
| WO | WO 99/05315 | 2/1999 |
| WO | WO 99/57321 | 11/1999 |
| WO | WO 00/02895 | 1/2000 |
| WO | WO 00/06770 | 2/2000 |
| WO | WO 00/09753 | 2/2000 |
| WO | WO 00/15844 | 3/2000 |
| WO | WO 00/18956 | 4/2000 |
| WO | WO 00/21974 | 4/2000 |
| WO | WO 00/50172 | 8/2000 |
| WO | WO 00/50642 | 8/2000 |
| WO | WO 00/53805 | 9/2000 |
| WO | WO 00/53812 | 9/2000 |
| WO | WO 00/70073 | 11/2000 |
| WO | 01/16375 | 3/2001 |
| WO | WO 01/23610 | 4/2001 |
| WO | WO 01/25247 | 4/2001 |
| WO | WO 01/27625 | 4/2001 |
| WO | WO 01/32930 | 5/2001 |
| WO | WO 01/57248 | 8/2001 |
| WO | WO 01/57249 | 8/2001 |
| WO | WO 01/92284 | 12/2001 |
| WO | WO 02/02813 | 1/2002 |
| WO | WO 02/21098 | 3/2002 |
| WO | WO 02/22883 A1 | 3/2002 |
| WO | WO 02/29003 | 4/2002 |
| WO | WO 02/072892 | 9/2002 |
| WO | WO 02/079519 A1 | 10/2002 |
| WO | WO 02/088381 | 11/2002 |
| WO | WO 02/088382 | 11/2002 |
| WO | WO 03/002767 | 1/2003 |
| WO | WO 03/020968 | 3/2003 |
| WO | WO 03/048178 | 6/2003 |
| WO | WO 03/048387 | 6/2003 |
| WO | WO 03/085135 | 10/2003 |
| WO | WO 2004/007773 | 1/2004 |
| WO | WO 2004/055160 | 1/2004 |
| WO | WO 2004/055160 | 1/2004 |
| WO | WO 2004/018493 | 3/2004 |
| WO | WO 2004/018497 | 3/2004 |
| WO | WO 2004/055160 | 7/2004 |
| WO | WO 2005/084367 | 9/2005 |
| WO | WO 2006/073436 | 7/2006 |
| WO | WO 2006/097320 A2 | 9/2006 |
| WO | WO 2007/02204 | 1/2007 |
| WO | WO 2007/053702 | 5/2007 |
| WO | WO 2007/053719 | 5/2007 |
| WO | WO 2007/062105 | 5/2007 |
| WO | WO 2008/069973 A2 | 6/2008 |
| WO | WO 2009/051807 A1 | 4/2009 |
| WO | WO 2013/154999 | 10/2013 |
| WO | WO 2013/191793 | 12/2013 |
| WO | WO 2014/144883 | 9/2014 |
| WO | WO 2014/144898 | 9/2014 |

OTHER PUBLICATIONS

Exhibit 1057, filed Dec. 16, 2013 in connection with IPR2012-00006, IPR2012-00007, and IPR2013-00011: Illumina's Invalidity Demonstratives for Final Hearing Dec. 17, 2013.

Exhibit 1021, filed Dec. 23, 2013 in connection with IPR2013-00128: Excerpts from *Protective Groups in Organic Synthesis* (Theodora W. Greene & Peter G. M. Wuts eds., John Wiley & Sons, Inc. 3rd ed. 1999) (1991).

Exhibit 1022, filed Dec. 23, 2013 in connection with IPR2013-00128: Signed Deposition Transcript of Dr. Bruce Branchaud on Oct. 3, 2013, plus errata.

Dec. 30, 2013 Illumina Motion to Amend Under 37 C.F.R. §42.121 in connection with IPR2013-00266.

Exhibits 2004, 2005, and 2028, filed Dec. 30, 2013 in connection with IPR2013-00266: Floyd Romesburg Declaration, CV, and List of Documents Considered by Romesburg.

Exhibit 2006, filed Dec. 30, 2013 in connection with IPR2013-00266: U.S. Appl. No. 12/804,025 application as filed on Jul. 13, 2010 by Balasubramanian et al. [WO 03/048387].

Exhibit 2007, filed Dec. 30, 2013 in connection with IPR2013-00266: U.S. Appl. No. 10/227,131—Barnes et al., filed Aug. 23, 2002.

Exhibit 2008, filed Dec. 30, 2013 in connection with IPR2013-00266: Maxam & Gilbert, PNAS 74:560-564 (Feb. 1977).

Exhibit 2009, filed Dec. 30, 2013 in connection with IPR2013-00266: Sanger et al., DNA Sequencing, PNAS 74:5463-5467 (1977).

Exhibit 2010, filed Dec. 30, 2013 in connection with IPR2013-00266: U.S. Pat. No. 5,302,509, issued Apr. 12, 1994 to Cheeseman.

Exhibit 2011, filed Dec. 30, 2013 in connection with IPR2013-00266: Metzker et al., Nucleic Acids Research, 22:4259-4267 (1994).

Exhibit 2012, filed Dec. 30, 2013 in connection with IPR2013-00266: Welch and Burgess, Nucleosides & Nucleotides, 18:197-201 (1999).

Exhibit 2013, filed Dec. 30, 2013 in connection with IPR2013-00266: Bruce P. Branchaud, Ph.D., Jun. 4, 2013 Declaration in IPR2013-00324.

Exhibit 2014, filed Dec. 30, 2013 in connection with IPR2013-00266: U.S. Pat. No. 5,047,519, issued Sep. 10, 1991 to Hobbs.

Exhibit 2015, filed Dec. 30, 2013 in connection with IPR2013-00266: U.S. Pat. No. 5,242,796, issued Sep. 7, 1993 to Prober.

Exhibit 2016, filed Dec. 30, 2013 in connection with IPR2013-00266: Ruby et al., Methods in Enzymology, 181:97-121 (1990).

Exhibit 2017, filed Dec. 30, 2013 in connection with IPR2013-00266: PCT International Publication No. WO 96/27025, published Sep. 6, 1996 to Rabini.

Exhibit 2018, filed Dec. 30, 2013 in connection with IPR2013-00266: PCT International Publication No. WO 89/10977, published Nov. 16, 1989 to Southern.

Exhibit 2019, filed Dec. 30, 2013 in connection with IPR2013-00266: U.S. Pat. No. 4,772,691, issued Sep. 20, 1998 to Herman.

Exhibit 2020, filed Dec. 30, 2013 in connection with IPR2013-00266: PCT International Publication No. WO 99/49082, published Sep. 30, 1999 to Short.

Exhibit 2021, filed Dec. 30, 2013 in connection with IPR2013-00266: Bystrom, Branchaud et al., Bioorganic & Medicinal Chemistry Letters, 7:2613-2616 (1997).

Exhibit 2022, filed Dec. 30, 2013 in connection with IPR2013-00266: Pages from Handbook of Reagents for Organic Synthesis: Reagents for Silicon-Mediated Organic Synthesis (Philip L. Fuchs, ed.) (2011).

Exhibit 2023, filed Dec. 30, 2013 in connection with IPR2013-00266: Eric Vermaas Declaration—Redacted version.

Exhibit 2024, filed Dec. 30, 2013 in connection with IPR2013-00266: Excerpts from Oct. 3, 2013 Bruce Branchaud Deposition Transcript in IPR2013-00128.

Exhibit 2025, filed Dec. 30, 2013 in connection with IPR2013-00266: U.S. Pat. No. 6,001,566, issued Dec. 14, 1999 to Canard.

Exhibit 2026, filed Dec. 30, 2013 in connection with IPR2013-00266: Prober et al., Science 238:336-341 (1987).

Exhibit 2027, filed Dec. 30, 2013 in connection with IPR2013-00266: CEQ 2000 DNA Analysis System User's Guide, Beckman Coulter (Jun. 2000).

Supplementary European Search Report and European Search Opinion issued Dec. 17, 2013 in connection with European Patent Application No. 08839081.0.

(56) References Cited

OTHER PUBLICATIONS

Extended European Search Report and Search Opinion issued Dec. 17, 2013 in connection with European Patent Application No. 08839081.0.
Oct. 28, 2014 Final Written Decision in connection with IPR2013-00266.
Patentee Opposition to Petitioner Motion to Exclude Evidence, filed Sep. 15, 2014 in connection with IPR2013-00517.
Patentee's Reply to Petitioner's Opposition to Patentee Motion to Exclude Evidence, filed Sep. 22, 2014 in connection with IPR2013-00517.
Petitioner's Reply to Patentee's Opposition to Motion to Amend, filed Sep. 22, 2014 in connection with IPR2013-00517.
Patentee Demonstratives for Oral Hearing, filed Oct. 3, 2014 in connection with IPR2013-00517.
Petitioner Demonstratives for Oral Hearing, filed Oct. 3, 2014 in connection with IPR2013-00517.
Transcript of Oct. 10, 2014 Oral Hearing, entered Feb. 2, 2015 in connection with IPR2013-00517.
Feb. 11, 2015 Final Written Decision in connection with IPR2013-00517.
Oct. 27, 2014 Pre-Appeal Brief Request for Review in connection with U.S. Appl. No. 12/734,229.
Office Action issued Dec. 10, 2014 in connection with U.S. Appl. No. 12/734,229.
Mar. 10, 2015 Response to Office Action issued Dec. 10, 2014 in connection with U.S. Appl. No. 12/734,229.
Oct. 28, 2014 Response to Apr. 1, 2014 Communication transmitting Extended European Search Report and European Search Opinion in connection with European Patent Application No. 13188731.7.
Communication under Rule 71(3) EPC issued Nov. 17, 2014 in connection with European Patent Application No. 08839081.0.
Apr. 6, 2015 Notice of Allowance in connection with U.S. Appl. No. 12/734,229.
U.S. Appl. No. 13/959,660, filed Aug. 5, 2013, Ju et al.
U.S. Appl. No. 14/119,846, filed Nov. 22, 2013, Ju et al.
U.S. Appl. No. 14/242,487, filed Apr. 1, 2014, Ju et al.
Pending claims in U.S. Appl. No. 11/922,385, filed Jul. 29, 2009 by Ju et al. (published as 2009/0325154 A1, Dec. 31, 2009).
Pending claims in U.S. Appl. No. 12/084,457, filed Apr. 30, 2008 by Ju et al. (published as 2009/0263791 A1, Oct. 22, 2009).
Pending claims in U.S. Appl. No. 12/734,229, filed Nov. 3, 2010, Ju et al. (published as 2011/0039259 A1, Feb. 17, 2011).
Pending claims in U.S. Appl. No. 13/186,353, filed Jul. 19, 2011 by Ju et al (published as 2012/0156680 A1, Jun. 21, 2012).
Pending claims in U.S. Appl. No. 13/959,660.
Office Action issued May 27, 2014 in connection with U.S. Appl. No. 12/734,229.
Notice of Abandonment issued Sep. 30, 2013 in connection with U.S. Appl. No. 12/734,227.
Apr. 1, 2014 Communication transmitting Extended European Search Report and European Search Opinion in connection with European Patent Application No. 13188731.7.
Highlander, S.K. et al., Complete nucleotide sequence of a P2 family lysogenic bacteriophage, Mha1-PHL101, from Mannheimia haemolytica serotype A1, Virology, 350:79-89 (2006).
Feb. 13, 2014 Decision of Institution of Inter Partes Review IPR2013-00517.
May 5, 2014 Patent Owner Response in connection with IPR2013-00517.
Exhibit 2005, filed May 5, 2014 in connection with IPR2013-00517: IBS's Answer, Affirmative Defenses & Counterclaims to Illumina, Inc. and Illumina Cambridge Ltd.'s Second Amended Counterclaims to Amended Complaint, *Columbia* v. *Illumina*, No. 12-CV-00376 (D. Del).
Exhibit 2006, filed May 5, 2014 in connection with IPR2013-00517: Excerpts from file history of U.S. Appl. No. 13/305,415, filed Nov. 28, 2011, Gordon et al.
Exhibit 2010, filed May 5, 2014 in connection with IPR2013-00517: Excerpts from prosecution history of U.S. Pat. No. 7,566,537, issued Jul. 28, 2009, Barnes et al.
Exhibit 2011, filed May 5, 2014 in connection with IPR2013-00517: May 5, 2014 Declaration of Floyd Romesberg, Ph. D.
Exhibit 2013, filed May 5, 2014 in connection with IPR2013-00517: Ranganathan et al., "Facile Conversion of Adenosine into New 2'-Substituted-2'-Deoxy-Arabinofuranosyladenine Derivatives: Stereospecific Syntheses of 2'-Deoxy-β-D-Arabinofuranosyladenines" Tetrahedron Letters 45:4341-44 (1978).
Exhibit 2014, filed May 5, 2014 in connection with IPR2013-00517: Mungall et al., "Use of the Azido Group in the Synthesis of 5' Terminal Aminodeoxythymidine Oligonucleotides" J. Org. Chem., 40:1659-1662 (1975).
Exhibit 2016, filed May 5, 2014 in connection with IPR2013-00517: Pilard et al., "A Stereospecific Synthesis of (±), αConhydrine and (+) β-Conhydrine)" Tet. Lett., 25:1555-1556.
Exhibit 2017, filed May 5, 2014 in connection with IPR2013-00517: "Synthesis of a Novel Stable $GM_3$ -Lactone Analogue as Hapten for a Possible Immunization against Cancer" Tietze et al., Angew. Chem. Int. Ed., 36:1615, 1616 (1997).
Exhibit 2018, filed May 5, 2014 in connection with IPR2013-00517: Kit, "Deoxyribonucleic Acids" Annual Rev. Biochem, 32:43 (1963).
Exhibit 2019, filed May 5, 2014 in connection with IPR2013-00517: Canard et al., "Catalytic editing properties of DNA polymerases" PNAS USA 92:10859 (1995).
Exhibit 2020, filed May 5, 2014 in connection with IPR2013-00517: The Merck Index, p. 9815 (entry for Triphenylphosphine) ($13^{th}$ Edition, 2001).
Exhibit 2021, filed May 5, 2014 in connection with IPR2013-00517: Lee et al., "Unwinding of double-stranded DNA helix by dehydration" PNAS 78:2838-42 (1981).
Exhibit 2022, filed May 5, 2014 in connection with IPR2013-00517: Christensen et al., "Specific Chemical Synthesis of Ribonucleoside O-Benzyl Ethers" J. Am. Chem. Soc., 37:3398 (1972).
Exhibit 2023, filed May 5, 2014 in connection with IPR2013-00517: Watkins et al., "Synthesis of Oligodeoxyribonucleotides Using N-Benzyloxycarbonyl-Blocked Nucleosides", J. Am. Chem. Soc. 104:5702-08 (1982).
Exhibit 2025, filed May 5, 2014 in connection with IPR2013-00517: Yoshimoto et al., "Tris(2,4,6-trimethoxyphenyl)phosphine (TTMPP): A Novel Catalyst for Selective Deacetylation" Chemistry Letters 30:934-35 (2001).
Exhibit 2026, filed May 5, 2014 in connection with IPR2013-00517: Chapter 3 of Protective Groups in Organic Synthesis (Theodora W. Greene & Peter G. M. Wuts eds., John Wiley & Sons, Inc. 3rd ed. 1999) (1991).
Exhibit 2027, filed May 5, 2014 in connection with IPR2013-00517: Bentley et al., `"Accurate whole human genome sequencing using reversible terminator chemistry" Nature 456:53-59 (2008).
Exhibit 2029, filed May 5, 2014 in connection with IPR2013-00517: Shendure et al., "Advanced Sequencing Technologies: Methods and Goals" Nature Reviews Genetics, 5:335-44 (2004).
Exhibit 2039, filed May 5, 2014 in connection with IPR2013-00517: Transcript of Apr. 8, 2014 Deposition of Bruce Branchaud, Ph. D.
Exhibit 2044, filed May 5, 2014 in connection with IPR2013-00517: Excerpts of Transcript of Mar. 20, 2013 Deposition of Dr. Xiaohai Liu in *Columbia* v. *Illumina*, 12-cv-376 (D. Del).
Exhibit 2047, filed May 5, 2014 in connection with IPR2013-00517: Ruparel et al., `"Design and synthesis of a 3-*O* -allyl photocleavable fluorescent nucleotide as a reversible terminator for DNA sequencing by synthesis" PNAS 102:5932-5937 (2005).
Exhibit 2050, filed May 5, 2014 in connection with IPR2013-00517: Mardis, "A decade's perspective on DNA sequencing technology" Nature 470:198-203 (2011).
Exhibit 2051, filed May 5, 2014 in connection with IPR2013-00517: Meng et al., "Design and Synthesis of a Photocleavable Fluorescent Nucleotide 3'-*O* -Allyl-dGTP-PC-Bodipy-FL-510 as a Reversible Terminator for DNA Sequencing by Synthesis" J. Org. Chem 71:3248-52 (2006).
Exhibit 2052, filed May 5, 2014 in connection with IPR2013-00517: Bi et al., "Design and Synthesis of a Chemically Cleavable Fluores-

(56) References Cited

OTHER PUBLICATIONS cent Nucleotide, 3'-O-Allyl-dGTP-allyl-Bodipy-FL-510, as a Reversible Terminator for DNA Sequencing by Synthesis" J Am Chem Soc, 128:2542-43 (2006).

Exhibit 2053, filed May 5, 2014 in connection with IPR2013-00517: Meng, "Tandem Aldol-Allylation Reactions Promoted by Strained Silacycles and Design and Synthesis of Modified Fluorescent Nucleotides for DNA Sequencing by Synthesis", Student Thesis (2006).

Exhibit 2054, filed May 5, 2014 in connection with IPR2013-00517: Wu et al., "3'-O-modified nucleotides as reversible terminators for pyrosequencing" PNAS, 104:16462-67 (2007).

Exhibit 2055, filed May 5, 2014 in connection with IPR2013-00517: Kim, "Four-Color DNA Sequencing by Synthesis on a Chip Using Cleavable Fluorescent Nucleotide Reversible Terminators", Student Thesis (2008).

Exhibit 2056, filed May 5, 2014 in connection with IPR2013-00517: Wu, "Molecular Engineering of Novel Nucleotide Analogues for DNA Sequencing by Synthesis", Student Thesis (2008).

Exhibit 2057, filed May 5, 2014 in connection with IPR2013-00517: Zhang, "Development of New DNA Sequencing Approaches and Investigation of Vision-related Proteins Using Synthetic Chemistry", Student Thesis (2008).

Exhibit 2058, filed May 5, 2014 in connection with IPR2013-00517: Guo et al., "Four-color DNA sequencing with 3'-O-modified nucleotide reversible terminators and chemically cleavable fluorescent dideoxynucleotides", PNAS 105:9145.

Exhibit 2059, filed May 5, 2014 in connection with IPR2013-00517: Guo, "Molecular Engineering of Novel Nucleotide Analogues for DNA Sequencing and Analysis", Student Thesis (2009).

Exhibit 2060, filed May 5, 2014 in connection with IPR2013-00517: Yu, "Novel Strategies to Increase Read Length and Accuracy for DNA Sequencing by Synthesis", Student Thesis (2010).

Exhibit 2062, filed May 5, 2014 in connection with IPR2013-00517: Qui, "Novel Molecular Engineering Approaches for Genotyping and DNA Sequencing", Student Thesis (2010).

Exhibit 2073, filed May 5, 2014 in connection with IPR2013-00517: Kraevskii et al., "Substrate Inhibitors of DNA Biosynthesis", Molecular Biology 21:25-29 (1987).

Exhibit 2074, filed May 5, 2014 in connection with IPR2013-00517: Dantas et al., "Stannous chloride mediates single strand breaks in plasmid DNA through reactive oxygen species formation", Toxicology Ltrs. 110:129-36 (1999).

Exhibit 2077, filed May 5, 2014 in connection with IPR2013-00517: Burgess et al., "An Approach to Photolabile, Fluorescent Protecting Groups", J. Org. Chem 62:5165-68 (1997).

Exhibit 2079, filed May 5, 2014 in connection with IPR2013-00517: Welch et al., "Syntheses of Nucleosides Designed for Combinatorial DNA Sequencing", Chem. Eur. J. 5:951-60 (1999).

Feb. 13, 2014 Decision of Institution of Inter Partes Review IPR2013-00518.

May 5, 2014 Patentee Request for Adverse Judgment in IPR2013-00518.

May 6, 2014 Decision of Adverse Judgment in IPR2013-00518.

Feb. 10, 2014 Record of Dec. 17, 2013 Oral Hearing in connection with IPR2012-00006, IPR2012-00007, and IPR2013-00011.

Mar. 6, 2014 Final Written Decision in connection with IPR2012-00006.

Mar. 6, 2014 Final Written Decision in connection with IPR2012-00007.

Mar. 6, 2014 Final Written Decision in connection with IPR2013-00011.

Jan. 24, 2014 Intelligent Bio-Systems Opposition to Illumina's Motion to Amend in connection with IPR2013-00128.

Exhibit 1030, filed Jan. 24, 2014 in connection with IPR2013-00128: Dawson et al., "Affinity Isolation of Transcriptionally Active Murine Erythroleukemia Cell DNA Using a Cleavable Biotinylated Nucleotide Analog" J. of Biol. Chem., 264, 12830-37 (1989).

Exhibit 1032, filed Jan. 24, 2014 in connection with IPR2013-00128: Mitra et al., "Fluorescent in situ sequencing on polymerase colonies" Analytical Biochem. 320, 55-65 (2003).

Exhibit 1033, filed Jan. 24, 2014 in connection with IPR2013-00128: Deposition of Floyd Romesberg, Ph.D., from Jan. 14, 2014.

Exhibit 1034, filed Jan. 24, 2014 in connection with IPR2013-00128: 1999/2000 Pierce Chemical Company catalog (1999).

Exhibit 1035, filed Jan. 24, 2014 in connection with IPR2013-00128: Second Declaration of Dr. Bruce Branchaud, dated Jan. 23, 2014.

Exhibit 1039, filed Jan. 24, 2014 in connection with IPR2013-00128: Excerpts from the file history of European Patent Application No: 02781434.2.

Exhibit 1041, filed Jan. 24, 2014 in connection with IPR2013-00128: Lukesh et al., "A Potent, Versatile Disulfide-Reducing Agent from Aspartic Acid" J. Am. Chem. Soc., 134:4057-59 (2012).

Exhibit 1042, filed Jan. 24, 2014 in connection with IPR2013-00128: Klausner, "DuPont's DNA Sequencer Uses New Chemistry" Nat. Biotech., 5:1111-12 (1987).

Exhibit 1043, filed Jan. 24, 2014 in connection with IPR2013-00128: Murakami et al., "Structure of a *Plasmodium yoelii* gene-encoded protein homologous to the $Ca^{2+}$-ATPase of rabbit skeletal muscle sarcoplasmic reticulum" J. Cell Sci., 97, 487-95 (1990).

Exhibit 1044, filed Jan. 24, 2014 in connection with IPR2013-00128: Letsinger et al., "2,4-Dinitrobenzenesulfenyl as a Blocking Group for Hydroxyl Functions in Nucleosides" J. Org. Chem., 29: 2615-2618 (1964).

Exhibit 1045, filed Jan. 24, 2014 in connection with IPR2013-00128: Handlon & Oppenheimer, "Thiol Reduction of 3'-Azidothymidine to 3'-Aminothymidine: Kinetics and Biomedical Implications" Pharm. Res., 5:297-99 (1988).

Exhibit 1047, filed Jan. 24, 2014 in connection with IPR2013-00128: Burns et al., "Selective Reduction of Disulfides by Tris(2-carboxyethyl)phosphine" J. Org. Chem., 56:2648-50 (1991).

Feb. 19, 2014 Substitute Motion to Amend Under 37 C.F.R. §42.121 in connection with IPR2013-00128.

Exhibit 2009, filed Feb. 19, 2014 in connection with IPR2013-00128: Substitute Declaration of Floyd Romesberg, Ph.D., in Support of Patent Owner's Motion to Amend.

Exhibit 2028, filed Feb. 19, 2014 in connection with IPR2013-00128: Substitute Declaration of Eric Vermaas Accompanying Patent Owner's Motion To Amend.

Feb. 24, 2014 Patent Owner Illumina's Reply to Petitioner's Opposition to Illumina's Motion to Amend.

Exhibit 2029, filed Feb. 24, 2014 in connection with IPR2013-00128: Supplementary information for Ex. 1032 (Mitra et al., Analytical Biochem. 320, 55-65, 2003).

Exhibit 2031, filed Feb. 24, 2014 in connection with IPR2013-00128: Ju et al., "Four-color DNA Sequencing by Synthesis Using Cleavable Fluorescent Nucleotide Reversible Terminators," PNAS USA, 103:19635-19640 (2006).

Exhibit 2032, filed Feb. 24, 2014 in connection with IPR2013-00128: ScanArray Express Line of Microarray Scanners—Brochure.

Exhibit 2034, filed Feb. 24, 2014 in connection with IPR2013-00128: Feb. 11, 2014 Second Deposition Transcript of Bruce Branchaud, Ph.D.

Exhibit 2037, filed Feb. 24, 2014 in connection with IPR2013-00128: Mullis et al., "Specific Synthesis of DNA in Vitro via a Polymerase-Catalyzed Chain Reaction," pp. 335-350, in Methods in Enzymology, vol. 155, Recombinant DNA, Part F, ed. Wu, Academic Press, Inc., San Diego (1987).

Exhibit 2038, filed Feb. 24, 2014 in connection with IPR2013-00128: Brown et al., `"Modern machine-aided methods of oligodeoxyribonucleotide synthesis," pp. 1-11; and Ruth, "Oligodeoxynucleotides with reporter groups attached to the base," p. 255, in Oligonucleotides and Analogues, A Practical Approach, ed. Eckstein, Oxford Univ. Press. New York (1991).

Exhibit 2039, filed Feb. 24, 2014 in connection with IPR2013-00128: Dawson and Herman et al., "Affinity isolation of active murine erythroleukemia cell chromatin: Uniform distribution of ubiquitinated histone H2A between active and inactive fractions", Journal of Cellular Biochemistry 46:166-173 (1991).

(56) References Cited

OTHER PUBLICATIONS

Exhibit 2040, filed Feb. 24, 2014 in connection with IPR2013-00128: Rigas et al., "Rapid plasmid library screening using RecA-coated biotinylated probes," PNAS USA 83:9591-9595 (1986).
Exhibit 2042, filed Feb. 24, 2014 in connection with IPR2013-00128: Westheimer et al., "Why nature chose phosphates" Science 235:1173-1178 (1987).
Mar. 18, 2014 Petitioner's Motion to Exclude in connection with IPR2013-00128.
Exhibit 1048, filed Mar. 18, 2014 in connection with IPR2013-00128: Petitioner's Objections to Patentee's Exhibits submitted with its Reply to Petitioner's Opposition to Patentee's Motion to Amend.
Mar. 18, 2014 Patentee's Motion to Exclude Petitioner's Evidence in connection with IPR2013-00128.
Demonstrative Exhibits of Intelligent Bio-Systems, Inc., for Apr. 23, 2014 hearing, filed Apr. 18, 2014 in connection with IPR2013-00128.
Demonstrative Exhibits of Illumina for Apr. 23, 2014 hearing, filed Apr. 21, 2014 in connection with IPR2013-00128.
May 22, 2014 Record of Apr. 23, 2014 Oral Hearing in connection with IPR2013-00128.
Petitioner's Feb. 28, 2014 Opposition to Patentee Motion to Amend in connection with IPR2013-00266.
Exhibit 1020, filed Feb. 28, 2014 in connection with IPR2013-00266: Mitra et al, "Fluorescent in situ sequencing on polymerase colonies" Analytical Biochem. 320:55-65 (2003).
Exhibit 1021, filed Feb. 28, 2014 in connection with IPR2013-00266: Second Declaration of Dr. Bruce Branchaud in support of Intelligent Bio-Systems, Inc.'s Opposition to Illumina's Motion to Amend, from Feb. 28, 2014.
Exhibit 1022, filed Feb. 28, 2014 in connection with IPR2013-00266: Deposition of Floyd Romesberg, Ph.D., from Jan. 14, 2014.
Exhibit 1027, filed Feb. 28, 2014 in connection with IPR2013-00266: Dawson et al., "Affinity Isolation of Transcriptionally Active Murine Erythroleukemia Cell DNA Using a Cleavable Biotinylated Nucleotide Analog" J. of Biol. Chem., 264:12830-37 (1989).
Exhibit 1028, filed Feb. 28, 2014 in connection with IPR2013-00266: Canard et al., "DNA polymerase fluorescent substrates with reversible 3'-tags" Gene, 148:1-6 (1994).
Exhibit 1029, filed Feb. 28, 2014 in connection with IPR2013-00266: Deposition of Eric Vermaas from Jan. 13, 2014.
Exhibit 1031, filed Feb. 28, 2014 in connection with IPR2013-00266: Lukesh et al., "A Potent, Versatile Disulfide-Reducing Agent from Aspartic Acid" J. Am. Chem. Soc., 134:4057-59 (2012).
Exhibit 1032, filed Feb. 28, 2014 in connection with IPR2013-00266: Prober et al., "A System for Rapid DNA Sequencing with Fluorescent Chain Terminating Dideoxynucleotides" Science, 238:336-341 (1987).
Exhibit 1033, filed Feb. 28, 2014 in connection with IPR2013-00266: Klausner, Nat. Biotech., "DuPont's New DNA Sequencer Uses New Chemistry" 5:1111-12 (1987).
Exhibit 1034, filed Feb. 28, 2014 in connection with IPR2013-00266: Murakami, et al., "Structure of a *Plasmodium yoelii* gene-encoded protein homologous to the $Ca^{2+}$-ATPase of rabbit skeletal muscle sarcoplasmic reticulum" J. Cell Sci., 97, 487-95 (1990).
Exhibit 1035, filed Feb. 28, 2014 in connection with IPR2013-00266: Excerpts from Protective Groups in Organic Synthesis (Theodora W. Greene & Peter G. M. Wuts eds., John Wiley & Sons, Inc. 3rd ed. 1999) (1991).
Exhibit 1036, filed Feb. 28, 2014 in connection with IPR2013-00266: Letsinger, et al., "2,4-Dinitrobenzenesulfenyl as a Blocking Group for Hydroxyl Functions in Nucleosides" J. Org. Chem., 29, 2615-2618 (1964).
Exhibit 1037, filed Feb. 28, 2014 in connection with IPR2013-00266: Handlon & Oppenheimer, "Thiol Reduction of 3'-Azidothymidine to 3'-Aminothymidine: Kinetics and Biomedical Implications" Pharm. Res., 5:297-99 (1988).
Exhibit 1038, filed Feb. 28, 2014 in connection with IPR2013-00266: Zavgorodny et al., "1-Alkylthioalkylation of Nucleoside Hydroxyl Functions and Its Synthetic Applications: A New Versatile Method in Nucleoside Chemistry" 32 Tetrahedron Letters 7593 (1991).

Exhibit 1039, filed Feb. 28, 2014 in connection with IPR2013-00266: Burns, et al., "Selective Reduction of Disulfides by Tris(2-carboxyethyl)phosphine" J. Org. Chem., 56, 2648-50 (1991).
Mar. 21, 2014 Patent Owner's Reply to Petitioner's Opposition to Patent Owner's Motion to Amend in connection with IPR2013-00266.
Exhibit 2030, filed Mar. 21, 2014 in connection with IPR2013-00266: Mar. 11, 2014 Bruce Branchaud Deposition Transcript.
Exhibit 2032, filed Mar. 21, 2014 in connection with IPR2013-00266: Excerpts from Feb. 11, 2014 Bruce Branchaud Deposition Transcript in related IPR2013-00128.
Exhibit 2034, filed Mar. 21, 2014 in connection with IPR2013-00266: ScanArray Express Line of Microarray Scanners—Brochure.
Exhibit 2036, filed Mar. 21, 2014 in connection with IPR2013-00266: Supplementary information for Ex. 1020 (Mitra et al., Analytical Biochem. 320, 55-65, 2003).
Exhibit 2038, filed Mar. 21, 2014 in connection with IPR2013-00266: Dawson and Herman et al., '"Affinity Isolation of Active Murine Erythroleukemia Cell Chromatin: Uniform Distribution of Ubiquitinated Histone H2A Between Active and Inactive Fractions" Journal of Cellular Biochemistry 46:166-173 (1991).
Exhibit 2039, filed Mar. 21, 2014 in connection with IPR2013-00266: Rigas et al., "Rapid plasmid library screening using RecA-coated biotinylated probes" PNAS USA 83:9591-9595 (1986).
Exhibit 2041, filed Mar. 21, 2014 in connection with IPR2013-00266: Westheimer et al., "Why Nature Chose Phosphates" Science 235:1173-1178 (1987).
Exhibit 2043, filed Mar. 21, 2014 in connection with IPR2013-00266: English translation of Loubinoux et al., "Protection of Phenols by the Azidomethylene Group Application to the Synthesis of Unstable Phenols" Tetrahedron, 44:6055-6064 (1988).
Exhibit 2044, filed Mar. 21, 2014 in connection with IPR2013-00266: Excerpts from Oct. 3, 2013 Bruce Branchaud Deposition Transcript in related Inter Partes Review IPR2013-00128.
Exhibit 2045, filed Mar. 21, 2014 in connection with IPR2013-00266: Welch et al., "Syntheses of Nucleosides Designed for Combinatorial DNA Sequencing" Chem. Eur. J., 5:951-960 (1999).
Exhibit 2046, filed Mar. 21, 2014 in connection with IPR2013-00266: Welch et al., Corrigenda to "Syntheses of Nucleosides Designed for Combinatorial DNA Sequencing" Chem. Eur. J., 11:7145 (2005).
Exhibit 2047, filed Mar. 21, 2014 in connection with IPR2013-00266: Wu et al., "Termination of DNA synthesis by $N^6$-alkylated, not 3'-0-alkylated, photocleavable 2'-deoxyadenosine triphosphates", Nucleic Acids Research 35:6339-6349 (2007).
Exhibit 2048, filed Mar. 21, 2014 in connection with IPR2013-00266: Taylor et al., "Rise per base pair in helices of double-stranded rotavirus RNA determined by electron microscopy" Virus Research, 2:175-182 (1985).
Exhibit 2049, filed Mar. 21, 2014 in connection with IPR2013-00266: Watson et al., Molecular Biology of the Gene, Fifth Edition, Chapter 6 (2004).
Exhibit 2050, filed Mar. 21, 2014 in connection with IPR2013-00266: Shen et al., "RNA structure at high resolution" Faseb J., 9:1023-1033 (1995).
Exhibit 2051, filed Mar. 21, 2014 in connection with IPR2013-00266: Holtzman et al., "Electron microscopy of complexes of isolated acetylcholine receptor, biotinyl-toxin, and avidin" Proc. Natl. Acad. Sci. USA, 79:310-314 (1982).
Exhibit 2052, filed Mar. 21, 2014 in connection with IPR2013-00266: Pugliese et al., "Three-dimensional Structure of the Tetragonal Crystal Form of Egg-white Avidin in its Functional Complex with Biotin at 2.7 Angstrom Resolution" Journal of Molecular Biology, 231:698-710 (1993).
Exhibit 2053, filed Mar. 21, 2014 in connection with IPR2013-00266: Fersht, "Fidelity of replication of phage X174 DNA by DNA polymerase III holoenzyme: Spontaneous mutation by misincorporation" Proc. Natl. Acad. Sci. USA, 76:4946-4950 (1979).
Exhibit 2054, filed Mar. 21, 2014 in connection with IPR2013-00266: Fersht et al., "DNA polymerase accuracy and spontaneous mutation rates: Frequencies of purine-purine, purine-pyrimidine, and pyrimidine-pyrimidine mismatches during DNA replication" Proc. Natl. Acad. Sci. USA, 78:4251-4255 (1981).

(56) References Cited

OTHER PUBLICATIONS

Exhibit 2055, filed Mar. 21, 2014 in connection with IPR2013-00266: Bebenek et al., "Frameshift errors initiated by nucleotide misincorporation" Proc. Natl. Acad. Sci. USA, 87:4946-4950 (1990).
Exhibit 2056, filed Mar. 21, 2014 in connection with IPR2013-00266: Bebenek et al., "The Effects of dNTP Pool Imbalances on Frameshift Fidelity during DNA Replication" J. Biol. Chem., 267:3589-3596 (1992).
Exhibit 2057, filed Mar. 21, 2014 in connection with IPR2013-00266: Greene and Wuts, Protective Groups in Organic Synthesis, 3rd ed., Chapter 1 (1999).
Apr. 18, 2014 Petitioner Motion for Observations on the Cross—Examination Testimony of Dr. Romesberg, in connection with IPR2013-00266.
Apr. 18, 2014 Petitioner Motion to Exclude Evidence in connection with IPR2013-00266.
Exhibit 1042, filed Apr. 18, 2014 in connection with IPR2013-00266: Apr. 10, 2014 transcript of Deposition of Floyd Romesberg.
Apr. 18, 2014 Patentee Motion to Exclude Evidence in connection with IPR2013-00266.
May 2, 2014 Patentee Response to Petitioner Motion for Observations on Romesberg Testimony, in connection with IPR2013-00266.
Exhibit 1045, filed May 22, 2014 in connection with IPR2013-00266: Petitioner Demonstratives for May 28, 2014 Oral Hearing.
Exhibit 2060, filed May 22, 2014 in connection with IPR2013-00266: Patentee Demonstratives for May 28, 2014 Oral Hearing.
Aug. 19, 2013 Petition 2 of 2 for Inter Partes Review of U.S. Pat. No. 7,566,537, issued Aug. 19, 2013.
Exhibit 1001, filed Aug. 19, 2013 in connection with IPR2013-00518: U.S. Pat. No. 7,566,537, issued Jul. 28, 2009 to Shankar Balasubramanian et al.
Exhibit 1002, filed Aug. 19, 2013 in connection with IPR2013-00518: U.S. Pat. No. 6,664,079, issued Dec. 16, 2003 to Jingyue Ju et al.
Exhibit 1003, filed Aug. 19, 2013 in connection with IPR2013-00518: U.S. Appl. No. 09/684,670, filed Oct. 6, 2000 by Jingyue Ju et al.
Exhibit 1004, filed Aug. 19, 2013 in connection with IPR2013-00518: Kamal et al., A Mild and Rapid Regeneration of Alcohols from their Allylic Ethers by Chlorotrimethylsilane/ Sodium Iodide, 40 Tetrahedron Letters 371 (1999).
Exhibit 1005, filed Aug. 19, 2013 in connection with IPR2013-00518: Jung et al., Conversion of Alkyl Carbamates into Amines via Treatment with Trimethylsilyl Iodide, 7 J.C.S. Chem. Comm. 315 (1978).
Exhibit 1006, filed Aug. 19, 2013 in connection with IPR2013-00518: WO 91/06678, issued May 16, 1991 to Roger Tsien et al.
Exhibit 1007, filed Aug. 19, 2013 in connection with IPR2013-00518: Prober et al., A System for Rapid DNA Sequencing with Fluorescent Chain-Terminating Dideoxynucleotides, 238 Science 336 (1987).
Exhibit 1008, filed Aug. 19, 2013 in connection with IPR2013-00518: WO 00/53805, issued Sep. 14, 2000 to Derek Stemple et al.
Exhibits 1009-1010, filed Aug. 19, 2013 in connection with IPR2013-00518: English translation of Takeshi Anazawa et al., WO 98/33939 (Aug. 6, 1998) and Translation Affidavit (Submitted by Illumina, Inc. as Exhibits 1011-1012 in IPR2012-00007).
Exhibit 1011, filed Aug. 19, 2013 in connection with IPR2013-00518: U.S. Pat. No. 7,078,499, issued Jul. 18, 2006 to Raj Odedra et al.
Exhibit 1012, filed Aug. 19, 2013 in connection with IPR2013-00518: WO 01/92284, published Dec. 6, 2001 to Raj Odedra et al.
Exhibit 1013, filed Aug. 19, 2013 in connection with IPR2013-00518: U.S. Pat. No. 5,547,839, issued Aug. 20, 1996 to William Dower et al.
Exhibit 1014, filed Aug. 19, 2013 in connection with IPR2013-00518: EP 0251786 B1, issued Nov. 30, 1994 to George Leonard Trainor.
Exhibit 1015, filed Aug. 19, 2013 in connection with IPR2013-00518: Aug. 16, 2013 Declaration of Dr. Bruce Branchaud.
Exhibit 1016, filed Aug. 19, 2013 in connection with IPR2013-00518: Excerpts from the '537 Patent File History.
Exhibit 1017, filed Aug. 19, 2013 in connection with IPR2013-00518: Excerpts from the file history of European Patent Application No: 02781434.2.
Exhibit 1018, filed Aug. 19, 2013 in connection with IPR2013-00518: Sep. 16, 2012 Petition for Inter Partes Review of U.S. Pat. No. 7,713,698.
Exhibit 1019, filed Aug. 19, 2013 in connection with IPR2013-00518: Sep. 16, 2012 Petition for Inter Partes Review of U.S. Pat. No. 7,790,869.
Exhibit 1020, filed Aug. 19, 2013 in connection with IPR2013-00518: Sep. 16, 2012 Petition for Inter Partes Review of U.S. Pat. No. 8,088,575.
Amendment filed Jul. 15, 2014 in response to Jan. 9, 2014 Communication Pursuant to Rules 70(2) and 70a(2) in connection with European Patent Application No. 08839081.0.
Allowed claims in U.S. Appl. No. 12/084,457, filed Apr. 30, 2008 by Ju et al. (published as 2009/0263791 A1, Oct. 22, 2009).
Transcript of May 28, 2014 Oral Hearing in IPR2013-00266, entered Jul. 8, 2014.
Arbo et al. (1993) "Solid Phase Synthesis of Protected Peptides Using New Cobalt (III) Amine Linkers," Int. J. Peptide Protein Res. 42:138-154.
Axeirod, V.D. et al. (1978) "Specific termination of RNA polymerase synthesis as a method of RNA and DNA sequencing," Nucleic Acids Res. 5(10):3549-3563.
Badman, E. R. et al. (2000) "A Parallel Miniature Cylindrical Ion Trap Array," Anal. Chem (2000) 72:3291-3297.
Badman, E. R. et al. (2000) "Cylindrical Ion Trap Arra with Mass Selection by Variation in Trap Dimensions," Anal. Chem. 72:5079-5086.
Bai et al. (2003) "Photocleavage of a 2-nitrobenzyl Linker Bridging a Fluorophore to the 5' end of DNA," PNAS, vol. 100, No. 2, pp. 409-413.
Benson, S.C., Mathies, R.A., and Glazer, A.N. (1993) "Heterodimeric DNA-binding dyes designed for energy transfer: stability and applications of the DNA complexes," Nucleic Acids Res. 21:5720-5726.
Benson, S.C., Singh, P., and Glazer, A.N. (1993) "Heterodimeric DNA-binding dyes designed for energy transfer: synthesis and spectroscopic properties," Nucleic Acids Res, 21:5727-5735.
Bergmann et al. (1995) "Allyl As Internucleotide Protecting Group in DNA Synthesis to be Cleaved Off by Ammonia," Tetrahedron,. 51:6970-6976.
Bergseid M., Baytan A.R., Wiley J.P., Ankener W. M., Stolowitz, Hughs K.A., and Chestnut J.D. (2000) "Small-molecule base chemical affinity system for the purification of proteins," BioTechniques 29:1126-1133.
Brunckova, J. et al. (1994) "Intramolecular Hydrogen Atom Abstrction in Carbohydrates and Nucleosides: Inversion of an $\alpha$- to $\beta$-Mannopyranoside and Generation of Thymidine C-4' Radicals." Tetrahedron Letters, vol. 35, pp. 6619-6622.
Buck, G.A. et al, (1999) "Design Strategies and Performance of Custom DNA Sequencing Primers," BioTechniques 27(3):528-536.
Burgess, K. et al. (1997) "Photolytic Mass Laddering for Fast Characterization of Oligomers on Single Resin Beads," J. Org. Chem. 62:5662-5663.
Buschmann et al, (1999) "The Complex Formation of alpha,omega—Dicarboxylic Acids and alpha,omega—Diols with Cucurbituril and alpha-Cyclodextrin," Acta Chim. Slov. 46(3):405-411.
Buschmann et al. (2003) "Spectroscopic Study and Evaluation of Red-Absorbing Fluorescent Dyes," Bioconjugate Chem., 14:195-204.
Canard, B. et al. (1994) "DNA polymerase fluorescent substrates with reversible 3'-tags," Gene, 148:1-5.
Canard, B. et al. (1995) "Catalytic editing properties of DNA polymerases," Proc. Natl. Acad. Sci. USA 92:10859-10863.
Caetano-Anolies (1994) "DNA Amplification Fingerprinting Using Arbitrary Mini-hairpin Oligonucleotide Primers." Nature Biotechnology, 12:619-623.
Caruthers, M.H. (1985) "Gene synthesis machines: DNA chemistry and its uses," Science 230:281-285.

(56) References Cited

OTHER PUBLICATIONS

Chee, M. et al. (1996) "Accessing genetic information with high density DNA arrays," Science 274:610-614.
Chen, X. and Kwok, P.-Y. (1997) "Template-directed dye—terminator incorporation (TDI) assay: a homogeneous DNA diagnostic method based on fluorescence resonance energy transfer," Nucleic Acids Res. 25:347-353.
Chiu, N. H., Tang, K., Yip, P., Braun, A., Koster, H., and Cantor, C.R. (2000) "Mass spectrometry of single-stranded restriction fragments captured by an undigested complementary sequence," Nucleic Acids Res. 28:E31.
Crespo-Hernandez et al., (2000) "Part 1. Photochemical an Photophysical Studies of Guanine Derivatives: Intermediates Contributing to its Photodestruction Mechanism in Aqueous Solution and the Participation of the Electron Adduct," Photochemistry and Photobiology, 71(5):534-543.
Elango, N. et al. (1983) "Amino Acid Sequence of Huma Respiratory Syncytial Virus Nucleocapsid Protein," Nucleic cids Research 11(17):5941-5951.
Fallahpour, R.A. (2000) "Photochemical and Thermal reactions raf Azido-Oligopyridines: Diazepinones, a New Class of Metal-Complex Ligands," Helvetica Chimica Acta. 83:384-393.
Fei, Z. et al. (1998) "MALDI-TOF mass spectrometric typing of single nucleotide polymorphisms with mass-tagged ddNTPs," Nucleic Acids Research 26(11):2827-2828.
Finzi, L. et al. (1995) "Measurement of Lactose Repressor—Mediated Loop Formation and Breakdown in Single DNA Molecules." Science, 267:378-380.
Gibson, K.J. et al. (1987) "Synthesis and Application of Derivatizable Oligonucleotides," Nucleic Acids Research, 15(16): 6455-6467.
Godovikova, T.S. et al. (1999) "5-[3-(E)-(4-Azido-2,3,5,6,-tetrafluorobenzamido)propenyl-1]-2'deoxyuridine-5'-triphosphate Substitutes for Thymidine-5'triphosphate in the Polymerase Chain Reaction," Bioconjugate Chem., 10: 529-537.
Green, T.W. et al. and Wuts, P.G.M. "Protective Groups in Organic Synthesis" 3rd ed. New York: John Wiley & Sons, Inc., 1999. 96-99, 190-191, 260-261, 542-543, and 750-751.
Griffin, T.J. et al. (1999) "Direct Genetic Analysis by Matrix-Assisted Laser Desorption/Ionization Mass Spectrometry," Proc. Nat. Acad. Sci. USA 96:6301-6306.
Guibé(1997) "Allylic Protecting Groups and Their use in a Complex Environment Part I: Allylic Protection of Alcohols," Tetrahedron, 53:13509-13556.
Guibé(1998) "Allylic Protecting Groups and Their Use in a Complex Environment Part II: Allylic Protecting Groups and their Removal through Catalytic Palladium π-Allyl methodology," Tetrahedron, 54:2967-3042.
Hacia J.G., Edgemon K., Sun B., Stern D., Fodor S.A., and Collins F.S, (1998) "Two Color Hybridization Analysis Using High Density Oligonucleotide Arrays and Energy Transfer Dyes," Nucleic Acids Res. 26:3865-6.
Haff L.A., et al. (1997) "Multiplex Genotyping of PCR Products with Mass Tag-Labeled Primers," Nucleic Acids Res. 25(18):3749-3750.
Hafliger, D. et al. (1997) "Seminested RT-PCR Systems for Small Round Structured Viruses and Detection of Enteric Viruses in Seafood," International Journal of Food Microbiology 37:27-36.
Hanshaw et al. (2004) "An Indicator Displacement System for Fluorescent Detection of Phosphate Oxyanions Under Physiological Conditions," Tetrahedron Letters, vol. 45, pp. 8721-8724.
Hayakawa et al. (1993) "O-Allyl Protection of Guanine and Thymine Residues in Oligodeoxyribonucleotides," J. Org. Chem., 58:5551-5555.
Henner, W.D. et al. (1983) "Enzyme Action at 3' Termini of Ionizing Radiation-Induced DNA Strand Breaks," J. Biol. Chem. 258(24):15198-15205.
Hovinen et al. (1994) "Synthesis of 3'-O-(ω-Aminoalkoxymethyl) thymidine 5'-Triphosphates, Terminators of DNA Snythesis that Enable 3'-Labelling," J. Chem. Soc. Perkin Trans., 1:211-217.
Hu et al. (1999) "Optical Mapping of DNA Polymerase I Action and Products," BBRC, 254:466-473.

Huang, B.G. et al. "Synthesis and in vitro Antitumor Activity of Some Amino-deoxy 3-hexofuranosylpyrrolo[2,3-d]pyrimidines." Carbohydrate Research, 1998, 308(3-4):319-328.
Huber et al. (1999) "Monitoring Solid Phase Synthesis by Infrared Spectroscopic Techniques." Analytica Chimica Acta, 393:213.
Hultman et al. (1989) "Direct Solid Phase Sequencing of Genomic and Plasmid DNA Using Magnetic Beads as Solid Support," Nucleic Acids Research 17(3):4937-4946.
Ikeda, K. et al. (1995) "A Non-Radioactive DNA Sequencing Method Using Biotinylated Dideoxynucleoside Triphosphates and Delta TTH DNA Polymerase," DNA Research 2(31):225-227.
Ireland, R.E. and Varney, M.D. (1986) "Approach to the total synthesis of chlorothricolide: synthesis of (±)-19.20-dihydro-24-0-methylchlorothricolide, methyl ester, ethyl carbonate," J. Org. Chem. 51:635-648.
Jiang-Baucom, P. et al. (1997) "DNA Typing of Human Leukocyte Antigen Sequence Polymorphisms by Peptide Nucleic Acid Probes and MALDI-TOF Mass Spectrometry," Anal. Chem. 69:4894-4896.
Jurinke, C., van de Boom, D., Collazo, V., Luchow, A., Jacob, A., and Koster H. (1997) "Recovery of nucleic acids from immobilized biotin-streptavidin complexes using ammonium hydroxide and application in MALDI-TOF mass spectrometry," Anal. Chem. 69:904-910.
Kamal, A., Laxman, E., and Rao, N. V. (1999) "A mild and rapid regeneration of alcohols from their allylic ethers by chlorotrimethylsilane/sodium iodide," Tetrahedron Lett 40:371-372.
Kim Sobin et al. (2002) "Solid Phase Capturable Dideoxynucleotides for Multiplex Genotyping Using Mass Spectrometry," Nucleic Acids Research 30(16):e85.1-e85.6.
Kim, S. et al. (2003) "Multiplex Genotyping of the Human Beta2-adrenergic Receptor Gene Using Solid-phase Capturable Dideoxynucleotides and Mass Spectrometry," Analytical Biochemistry 316:251-258.
Kimzey A.L. et al. (1998) "Specific Regions of Contact Between Human T-cell Leukemia Virus Type I Tax Protein and DNA Identified by Photocross-linking," Journal of Biological Chemistry, 273(22): 13768-13775.
Kitamura et al. (2002) "(P(C6H5)3)CpRu+Catalyzed Deprotection of Allyl Carboxylic Esters," J. Org. Chem.,.
Kloosterman et al. (1985) "The relative stability of allyl ether, allyloxycarbonyl ester and prop-2 enylidene acetal, protective groups toward Iridium, Rhodium and Palladium catalysts," Tetrahedron Letters, 26:5045-5048.
Kokoris, M. et al. (2000) "High-throughput SNP Genotyping With the Masscode System," Molecular Diagnosis 5(4):329-3.
Kolb et al. (2001) "Click Chemistry: Diverse Chemical Function From a Few Good Reactions," Angew. Chem. Int. Ed. 40:2004-2021.
Kraevskii, A.A. e. al. (1987) "Substrate Inhibitors of DNA Biosynthesis," Molecular Biology 21:25-29.
Krečmerová(1990) "Synthesis of 5.-O-Phosphonomethyl Derivatives of Pyrimidine 2'-Deoxynucleosides." Coll. Czech. Chem. Commun., 55:2521-2536.
Kurata et al. (2001) "Fluorescent quenching-based quantitative detection of specific DNA/RNA using BODIPY® FL-labeled probe of primer," Nucleic Acids Research, vol. 29, No. 6, p. e34.
Kvam et al., (1994) "Characterization of singlet oxygen-induced guanine residue damage after photochemical treatment of free nucleosides and DNA," Biochemica et Biophysica Acta., 1217:9-15.
Lee, L.G., et al, (1992) "DNA sequencing with dye labeled terminators and T7 DNA polymerase effect of dyes and dNTPs on incorporation of dye terminators and probability analysis of termination fragments," Nucleic Acids Res. 20:2471-2483.
Lee, L.G. et al, (1997) "New energy transfer dyes for DNA sequencing," Nucleic Acids Res. 25:2816-2822.
Leroy, E.M. et al. (2000) "Diagnosis of Ebola Haemorrhagic Fever by RT-PCR in an Epidemic Setting," Journal of Medical Virology 60:463-467.
Lewis et al. (2002) "Click Chemistry in Situ: Acetylcholinesterase as a Reaction Vessel for the Selective Assembly of a Femtomolar Inhibitor from an Array of Building Blocks," Angew. Chem. Int. Ed. 41(6):1053-1057.

(56) References Cited

OTHER PUBLICATIONS

Li, J. (1999) "Single Oligonucleotide Polymorphism Determination Using Primer Extension and Time-of-Flight Mass Spectrometry," Electrophoresis 20:1258-1265.

Liu, H. et al. (2000) "Development of Multichannel Devices with an Array of Electrospray Tips for High-Throughput Mass Spectrometry," Anal. Chem. 72:3303-3310.

Loubinoux, B. et al. "Protection Des Phenols Par Le Groupement Azidomethylene Application A La Synthese De Phenols Instables," Tetrahedron, 1998, 44(19): 6055 (English Abstract Only).

Lyamichev, V. et al. (1999) "Polymorphism Identification and Quantitative Detection of Genomic DNA by Invasive Cleavage of Oligonucleotide Probes," Nat. Biotech 17:292-296.

Maier et al. (1995) "Synthesis and Properties of New Fluorescein-Labeled Oligonucleotides," Nucleosides and Nucleotides, 14:961-965.

Markiewicz et al. (1997) "A new method of synthesis of fluorescently labeled oligonucleotides and their application in DNA sequencing," Nucleic Acids Research, 25:3672-3690.

Marquez et al. (2003) "Selective Fluorescence Quenching of 2,3-Diazabicyclo[2.2.2]oct-2-ene by Nucleotides," Organic Letters, 5:3911-3914.

Mathew C.K. et al. (1985) "Chemical Synthesis of Oligonucleotides," Biochemistry, 2nd Edition, pp. 127-128.

Monforte, J.A. and Becker, C.H. (1997) "High-throughput DNA analysis by time-of-flight mass spectrometry," Nat. Med. 3(3):360-362.

Nazarenko et al. (2002) "Effect of primary and secondary structure of oligodeoxyribonucleotides on the fluorescent properties of conjugated dyes," Nucleic Acids Research, 30:2089-2095.

Nickel et al. (1992) "Interactions of Azidothymidine triphosphate with the Cellular DNA polymerases alpha, delta, and episilon and with DNA Primase," J. Biol. Chem. 267(2):848-854.

Nielsen et al. (2004) "Multiplexed Sandwich Assays in Microarray Format," Journal of Immunological Methods, vol. 290, pp. 107-120.

Nishino et al. (1991) "Efficient Deanilidation of Phosphoranilidanes by the Use of Nitrites and Acetic Anhydride." Heteroatom Chemistry, vol. 2, pp. 187-196.

Olejnik, J. et al. (1995) "Photocleavable biotin derivatives: a versatile approach for the isolation of biomolecules," Proc. Natl. Acad. Sci. USA. 92:7590-7594.

Olejnik, J. et al. (1999) "Photocleavable peptide DNA conjugates: synthesis and applications to DNA analysis using MALDI MS," Nucleic Acids Res. 27:4626-4631.

Pastinen et al. (1997) "Minisequencing: A Specific Tool for DNA Analysis and Diagnostics on Oligonucleotide Arrays," Genomic Res., 7:606-614.

Quaedflieg et al. (1992) "An Alternative Approach Toward the Synthesis of (3'->5') Methylene Acetal Linked Dinucleosides." Tetrahedron Letters, vol. 33, pp. 3081-3084.

Rao et al. (2001) "Four Color FRET Dye Nucleotide Terminators for DNA Sequencing," Nucleosides, Nucleotides and Nucleic Acids, 20:673-676.

Rasolonjatovo at al. (1998) "6-N-(N-Methylanthranylamido)-4-Oxo-Hexanoic Acid: A New Fluorescent Protecting Group Applicable to a New DNA Sequencing Method," Nucleosides and Nucleotides, 17:2021-2025.

Ronaghi, (1998) "PCR-Introduced Loop Structure As Primer in DNA Sequencing." BioTechniques, 25:876.

Ross, P.L. et al. (1997) "Discrimination of Single-Nucleotide Polymorphisms in Human DNA Using Peptide Nucleic Acid Probes Detected by MALDI-TOF Mass Spectrometry," Anal. Chem. 69:4197-4202.

Ross, P. et al. (1998) High Level Multiplex Genotyping by MALDI-TOF Mass Spectrometry. Nat. Biotech 16:1347-1351.

Sarfati et al., (1995) "Synthesis of fluorescent derivatives of 3'-O-(6-aminohexanoyl)-pyrimidine nucleosides 5'-triphosphates that act as DNA polymerase substrates reversibly tagged at C-3'," JCS Perkin Trans, 1163-1171.

Saxon, E. and Bertozzi, C.R. (2000) "Cell surface engineering by a modified Staudinger reaction," Science 287:2007-2010.

Schena, M., Shalon, D. and Davis, R. Brown P.O. (1995) "Quantitative monitoring of gene expression patterns with a cDNA microarray," Science 270: 467-470.

Seeger (1998) "Single Molecule Fluorescence: High-Performance Molecular Diagnosis and Screening," Bioforum, Git Verlag, Darmstadt, DE vol. 21.

Seo et al. (2003) "Click Chemistry to Construct Fluorescent Oligonucleotides for DNA Sequencing," J. Org. Chem. 68:609.

Speicher, M.R., Ballard, S.G., and Ward, D.C. (1996) "Karyotyping human chromosomes by combinatorial multi-fluor FISH," Nature Genetics 12: 368-375.

Stoerker, J. et al. (2000) "Rapid Genotyping by MALDI-monitored nuclease selection from probe Libraries," Nat. Biotech 18:1213-1216.

Tang, K., Fu, D.J., Julien, D., Braun, A., Cantor, C.R., and Koster, H. (1999) "Chip-based genotyping by mass spectrometry," Proc. Natl. Acad, Sci, USA. 96:10016-10020.

Tong, X. and Smith, L.M. (1992) "Solid-Phase Method for the Purification of DNA Sequencing Reactions," Anal. Chem. 64:2672-2677.

Torimura et al. (2001) "Fluorescence-Quenching Phenomenon by Photoinduced Electron Transfer between a Fluorescent Dye and Nucleotide Base," Analytical Sciences, 17:155-160.

Tuncel et al. (1999) "Catalytically Self-Threading Polyrotaxanes," Chem. Comm. 1509-1510.

Veeneman at al. (1991) "An Efficient Approach to the Synthesis of Thymidine Driatives Containing Phosphate-Isoteric Methylene Acetyl Linkages," Tetrahedron, 47:1547-1562.

Wads et al. (2001) "2-(Azidomethyl)benzoyl as a new protecting group in nucleosides," Tetrahedron Letters, 42:1069-10.

Weiss (1999) "Fluorescent Spectroscopy of Single Biomolecules." Science, 283:1676.

Welch et al. (1999) "Synthesis of Nucleosides Designed for Combinatorial DNA Sequencing," Chemistry, European Journal, 5:951-960.

Wendy, Jen. et al. (2000) "New Strategies for Organic Catalysis: The First Enantioselective Orgacnocatalytic 1,3-Dipolar Cycloaddition," J. Am. Chem, Soc. 122:9874-9875.

Woolley, A. T. et al. (1997) "High-Speed DNA Genotyping Using Microfabricated Capillary Array Electrophoresis Chips," Anal. Chem. 69:2181-2186.

Yamashita et al, (1987) "Studies on Antitumor Agents VII. Antitumor Activities of O-Alkoxyalkyl Derivatives of 2'-Deoxy-5-trifluoromethyluridine." Chem Pharm. Bull., vol. 35, pp. 2373-2381.

Zavgorodny, S. et al, (1991) "1-Alkylthioalkylation of Nucleoside Hydroxyl Functions and Its Synthetic Applications: A New Versatile Method in Nucleoside Chemistry," Tetrahedron Letters, 32(51): 7593-7596.

Zavgorodny et al. (2000) Nucleosides, Nucleotides and Nucleic Acids, 19(10-12):1977-1991.

Zhang et al. (2002) "Synthesis of Releasable Electrophore Tags for Applications in Mass Spectrometry," Bioconjugate Chem., vol. 13, pp. 1002-1101.

Partial European Search Report issued Apr. 26, 2007 in connection with European Patent Application No. 07004522.4.

Extended European Search Report issued Jul. 18, 2007 in connection with European Patent Application No. 07004522.4.

Official Action issued Mar. 3, 2007 in connection with European Patent Application No. 07004522.4.

Communication Pursuant to Article 94(3) EPC issued Apr. 30, 2009 in connection with counterpart European Patent Application No. 07004522.4.

International Search Report issued Jan. 23, 2002 in connection with PCT/US01/28967.

International Search Report issued May 13, 2002 in connection with PCT/US01/31243.

International Search Report issued Sep. 18, 2002 connection with PCT/US02/09752.

International Preliminary Examination Report issued on Feb. 25, 2003 in connection with PCT/US01/28967.

International Preliminary Examination Report issued on Mar. 17, 2003 in connection with PCT/US02/09752.

(56) References Cited

OTHER PUBLICATIONS

International Preliminary Examination Report issued on Jun. 13, 2003 in connection with PCT/US01/31243.
International Search Report issued Sep. 26, 200 in connection with PCT/US03/21818.
International Preliminary Examination Report issued on Mar. 18, 2005 in connection with PCT/US03/21818.
International Preliminary Report on Patentability issued on Sep. 5, 2006 in connection with PCT/US05/06960.
International Search Report issued Oct. 29, 2007 in connection with PCT International Application No. PCT/US07/13559.
International Search Report issued Jun. 8, 2004 in connection with PCT/US03/39354.
International Search Report issued Nov. 4, 2005 in connection with PCT/U505/06960.
International Search Report issued Dec. 15, 2006 in connection with PCT/US05/13883.
Supplementary European Search Report issued Feb. 16, 2004 in connection with European Patent Application No. 01977533.
Supplementary European Search Report issued May 25, 2005 in. connection with European Patent Application No. 02728606.1.
Supplementary European Search Report issued Jun. 7, 2005 in connection with European Patent Application No. 01968905.
Supplementary European Search Report issued Feb. 9, 2007 in connection with European Patent Application No. 03764568.6.
Supplementary European Search Report issued Sep. 9, 2008 in connection with PCT International Application No. PCT/US05/06960.
Written Opinion of the international Searching Authority issued Oct. 27, 2005 in connection with PCT/US05/06960.
Written Opinion of the International Searching Authority issued. Dec. 15, 2006 in connection with PCT/US05/13883.
Office Action issued. Oct. 25, 2002 in connection with U.S. Appl. No. 09/972,364.
Office Action issued Mar. 14, 2003 in connection with U.S. Appl. No. 09/972,364.
Office Action issued Aug. 10, 2007 in connection with U.S. Appl. No. 11/119,231.
Office Action issued Sep. 21, 2007 in connection with U.S. Appl. No. 10/380,256.
Restriction Requirement issued Oct. 1, 2007 in connection with U.S. Appl. No. 10/521,206.
Office Action issued Nov. 14, 2007 in connection with U.S. Appl. No. 10/735,081.
Office Action issued Jun. 24, 2008 in connection with Appl. No. 11/894,690.
Office Action issued Jun. 5, 2009 in connection with U.S. Appl. No. 11/894,690.
Office Action issued Sep. 3, 2008 in connection with U.S. Appl. No. 11/894,808.
Office Action issued Jul. 8, 2008 in connection with U.S. Appl. No. 10/591,520.
Official Action issued Mar. 31, 2006 in connection with European Patent Application No. 01968905.8.
Official Action issued May 21, 2007 in connection with European Patent Application No. 01968905.8.
Notice of Allowance issued Sep. 6, 2007 in connection with U.S. Appl. No. 10/702,203.
Notification of Transmittal of International Search Report and Written Opinion, issued Nov. 23, 2007 in connection with International Application No, PCT/US06/42698.
Notification of Transmittal of International Search Report and Written Opinion, issued Feb. 6, 2008 in connection with International Application No. PCT/US06/42739.
Notification Concerning Transmittal of International Preliminary Report on Patentability (Including Written Opinion of the International Searching Authority) issued May 15, 2008 in connection with PCT/US2006/042698.
Notification of Transmittal of International Search Report and Written Opinion, issued May 22, 2008 in connection with, International Application No. PCT/US06/45180.
Notification of Transmittal of International Search Report and Written Opinion, issued Aug. 12, 2008 in connection with International Application No. PCT/US07/24646.
Notification of Transmittal of International Search Report and the Written Opinion of the International Searching Authority, or the Declaration issued Sep. 9, 2008 in connection with International Application No. PCT/US06/24157.
International Search Report issued by the International Searching Authority (ISA/US) on Aug. 12, 2008 in connection with International Application No. PCT/US2007/024646.
Notice of Allowance issued Feb. 24, 2009 in connection with U.S. Appl. No. 11/894,690.
Notice of Allowance issued Mar. 23, 2009 in connection with U.S. Appl. No. 11/894,808.
Notification Concerning Transmittal of International Preliminary Report on Patentability issued Jun. 11, 2009 in connection with International Application No. PCT/US07/024646.
Collins, F. S.; Morgan, M.; Patrinos, A. (2003) "The Human Genome Project: Lessons from Large-Scale Biology." Science, 300, pp. 286-290.
Prober JM, Trainor GL, Dam RJ, Hobbs FW, Robertson CW, Zagursky RJ, Cocuzza AJ, Jensen MA, Baumeister K. (1987) "A system for rapid DNA sequencing with fluorescent chain-terminating dideoxynucleotides". Science 238: 336-341.
Ju J., Ruan C., Fuller, C.W., Glazer, A.N., and Mathies, R.A. (1995) Fluorescence energy transfer dye-labeled primers for DNA sequencing and analysis. Proc. Natl. Acad. Sci, USA 92: 4347-4351.
Kan, C.W.; Doherty, E. A. S.; Barron, A. E. (2003) "A novel thermogelling matrix for microchannei DNA sequencing based on poly-N-alkoxyaikylacrylamide copolymers." Electrophoresis, 24, pp. 4161-4169.
Drmanac, S.; Kita, D.; Labat, I.; et al. (1998) "Accurate sequencing by hybridization for DNA diagnostics and individual genomics." Nat. Biotech., 16, pp. 54-58.
Fu, D.J., Tang, K., Braun, A., Reuter, D., Darnhofer-Demar, B., Little, D.P., O'Donnell, M.J., Cantor, C.R., and Koster, H. (1998) "Sequencing exons 5 to 8 of the p53 gene by MALDI-TOF mass spectrometry." Nat. Biotechnol. 16:381-384.
Roskey, M.T, Juhasz, P., Smirnov, I.P., Takach, E.J., Martin, S.A., and Haff, L.A. (1996) "DNA sequencing by delayed extraction-matrix-assisted laser desorption/ionization time of flight mass spectrometry." Proc. Natl. Acad. Sci. USA. 93:4724-4729.
Edwards, J. et al. (2001) DNA sequencing using biotinylated dideoxynucleotides and mass spectrometry. Nucleic Acids Res., 29(21), pp. 1041-1046.
Kasianowicz, J.J., Brandin, B., Branton, D. and Deamer, D,W. Characterization of individual polynucleotide molecules using a membrane channel. Proc. Nati. Acad. Sci. USA 1996, 93, 13770-13773.
Shendure, J.; Porreca, C. J.; Reppas, N. B.; et al. (2005) "Accurate Multiplex Polony Sequencing of an Evolved Bacterial Genome." Science, 309, pp. 1728-1732.
Ronaghi M, Uhlen M, Nyren P. (1998) "A sequencing Method based on real-time pyrophosphate". Science 281: 364-365.
Braslaysky, I.; Hebert, B.; Kartalov, E.; et al. (2003) "Sequence information can be obtained from single DNA molecules." Proc. Natl. Acad. Sci., 100(7), pp. 3960-3964.
Mitra, R. D.; Shendure J.; Olejnik, J.; et al. (2003) "Fluoreseent in situ sequencing on polymerase colonies." Anal. Biochem., 320, pp. 55-65.
Hyman ED, (1988) "A new method of sequencing DNA". Analytical Biochemistry 174: 423-436.
Margulies, M.; Egholm, M.; Altman, W. E.; et al. (2005) "Genome sequencing in microfabricated high-density picolitre reactors." Nature, 437, pp. 376-380.
Metzker ML, Raghavachari R, Richards S, Jacutin SE, Civitello A, Burgess K, Gibbs RA. (1994) "Termination of DNA synthesis by novel 3' modified deoxyribonucleoside 5' triphosphates". Nucleic Acids Res. 22: 4259-4267.
Welch MB, Burgess K, (1999) "Synthesis of fluorescent, photolabile 3'-O-protected nucleoside triphosphates for the base addition sequencing scheme". Nucleosides and Nucleotides 18:197-201.

(56) References Cited

OTHER PUBLICATIONS

Lu, G. and Burgess, K. (2006) "A diversity oriented synthesis of 3'-O-modified nucleoside triphosphates for DNA 'sequencing by synthesis'" Bioorg. Med. Chem. Lett., 16, pp. 3902-3905.
Metzker M. L. (2005) "Emerging technologies in DNA sequencing." Genome Res., 15, pp. 1767-1776.
Pelletier H, Sawaya MR, Kumar A, Wilson SH, Kraut J. (1994) "Structures of ternary complexes of rat DNA polymerase β, a DNA template-primer, and ddCTP". Science 264: 1891-1903.
Rosenblum, B,B. et al. (1997) "New dye-labeled terminators for improved DNA sequencing patterns". Nucleic Acids Res. 25: 4500-4504.
Seo et al., (2005) "Four-Color DNA Sequencing by Synthesis on a Chip Using Photocleavable Fluorescent Nucleotides" PNAS 102(17):5926-5931.
Bi, L.; Kim D. H.; and Ju, J. (2006) "Design and Synthesis of a Chemically Cleavable Fluorescent Nucleotide, 3'-O-Allyl-dGTP-allyl-Bodipy-FL-510, as a Reversible Terminator for DNA Sequencing by Synthesis" J. Am. Chem. Soc., 128, pp. 2542-2543.
Ruparel et al., (2005) "Design and Synthesis of a 3'-O-Allyl Photocleavable Fluorescent Nucleotide as a Reversible Terminator for DNA Sequencing by Synthesis" PNAS, 102(17):5932-5937.
Meng et al., (2006) "Design and Synthesis of a Photocleavable Fluorescent Nucleotide 3'-O-Allyl-dGTP-PC-Biodipy-FL-510 as a Reversible Terminator for Dna Sequencing by Synthesis" J. Org. Chem 71:3248-3252.
Ju J., et al. (1996) Cassette labeling for facile construction of energy transfer fluorescent primers. Nucleic Acids Res. 24(6):1144-1148.
Ju J., Glazer, A.N., and Mathies, R.A. (1996) Energy transfer primers: A new fluorescence labeling paradigm for DNA sequencing and analysis. Nature Medicine 2: 246-249.
Ju J., et al. Four-color DNA sequencing by synthesis using cleavable fluorescent nucleotide reversible terminators. Proc Nati Acad Sci U S A. Dec. 26, 2006;103(52):19635-40. Epub 2006 Dec. 14.
Bai, X., Kim, S., Li, Z., Turro, N. J. and Ju, J. Design and synthesis of a photocleavable biotinylated nucleotide for DNA analysis by mass spectrometry. Nucleic Acids Research 2004, 32(2); pp. 534-541.
Li, Z., Bai, X., Ruparel, H., Kim, S., Turro, N. J. and Ju, J. A photocleavable fluorescent nucleotide for DNA sequencing and analysis. Proc. Natl. Acad. Sci. USA 2003, 100, 414-419.
Seo, T. S., Bai, X., Ruparel, H., Li, Z., Turro, N. J. and Ju, J. Photocleavable fluorescent nucleotides for DNA sequencing on a chip constructed by site-specific coupling chemistry. Proc. Natl. Acad. Sci. USA 2004, 101, 5488-5493.
Smith, L. M.; Sanders, J. Z.; Kaiser, R. J.; et al. Fluorescence detection in automated DNA sequence analysis. nature 1986, 321, pp. 674-679.
Zhu, Z.; Chao, J.; Yu, H; et al. Directly labeled DNA robes using fluorescent nucleotides with different length linkers. Nucleic Acids Res. 1994, 22, pp. 3418-3422.
Notice of Allowance issued Apr. 2, 2010 in connection with U.S. Appl. No. 11/810,509.
Extended European Search Report and Search Opinion issued Jul. 24, 2012 in connection with European Patent Application No. 08841439.6.
Guo et al., "Four-Color DNA Sequencing With 3'-O-modified Nucleotide Reversible Terminators and Chemically Cleavable Fluorescent Dideoxynucleotides", PNAS, 2008, 105:9145-9150.
Guo et al., "An Integrated System for DNA Sequencing by Synthesis Using Novel Nucleotide Analogues", Accounts of Chem. Res., 2010, 43:551-563.
Office Action issued Oct. 3, 2012 in connection with U.S. Appl. No. 12/734,229.
International Search Report issued by the International Searching Authority (ISA/US) on Feb. 10, 2009 in connection with International Application No. PCT/US2008/011891.
Written Opinion of the International Searching Authority issued by the International Searching Authority (ISA/US) on Feb. 10, 2009 in connection with International Application No, PCT/US2008/011891.
Ju et al. (Dec. 26, 2006). Four-color DNA sequencing by synthesis using cleavable fluorescent nucleotide reversible terminators. PNAS, 103(52), 19635-19640.
Office Action issued Sep. 18, 2012 in connection with U.S. Appl. No. 12/734,227.
Amendment filed Mar. 18, 2013 in response to Office Action issued Sep. 18, 2012 in connection with U.S. Appl. No. 12/734,227.
Notice of Allowance issued Apr. 26, 2013 in connection with U.S. Appl. No. 12/734,227.
Jul. 25, 2014 Final Written Decision in connection with IPR2013-00128.
Petitioner Reply to Patent Owner Response, filed Jul. 28, 2014 in connection with IPR2013-00517.
Exhibit 1019, filed Jul. 28, 2014 in connection with IPR2013-00517: Ireland et al., Approach to the Total Synthesis of Chlorothricolide: Synthesis of (+)-19,20-Dihydro-24-O-methylchlorothricolide, Methyl Ester, Ethyl Carbonate, 51 J. Org. Chem. 635 (1986).
Exhibit 1020, filed Jul. 28, 2014 in connection with IPR2013-00517: Gordon et al., Abstract, The Relationship of Structure to Effectiveness of Denaturing Agents for DNA, Biophysical Society 6th Annual Meeting (Washington, 1962).
Exhibit 1022, filed Jul. 28, 2014 in connection with IPR2013-00517: p. 295 from Mar. 20, 2003 deposition of Dr. Xiaohai Liu, *The Trustees of Columbia University and Intelligent Bio-Systems, Inc.* v. *Illumina*, 12-376 (GMS) (D. Del.).
Exhibit 1025, filed Jul. 28, 2014 in connection with IPR2013-00517: Transcript, Jul. 8, 2014 Deposition of Floyd Romesberg, Ph.D.
Exhibit 1026, filed Jul. 28, 2014 in connection with IPR2013-00517: Transcript, Jul. 15, 2014 Deposition of Kevin Burgess, Ph. D.
Exhibit 1030, filed Jul. 28, 2014 in connection with IPR2013-00517: Patent prosecution excerpt from file history of United States U.S. Pat. No. 7,566,537 (U.S. Appl. No. 11/301,578).
Exhibit 1031, filed Jul. 28, 2014 in connection with IPR2013-00517: Second Declaration of Dr. Bruce Branchaud in Support of Intelligent Bio-Systems, Inc.'s Reply to Illumina's Patent Owner Response.
Exhibit 1032, filed Jul. 28, 2014 in connection with IPR2013-00517: Gololobov and Kasukhin, Recent advances in the Staudinger reaction, Tetrahedron 48:1353-1406 (1992).
Exhibit 1034, filed Jul. 28, 2014 in connection with IPR2013-00517: Saxon and Bertozzi, Cell Surface Engineering by a Modified Staudinger Reaction, Science 287:2007-2010 (2000).
Exhibit 1036, filed Jul. 28, 2014 in connection with IPR2013-00517: Faucher and Grand-Maitre, tris(2-Carboxyethyl)phosphine (TCEP) for the Reduction of Sulfoxides, Sulfonylchlorides, N-Oxides, and Azides, Synthetic Communications 33:3503-3511 (2003).
Exhibits 1037 and 1038, filed Jul. 28, 2014 in connection with IPR2013-00517: Knouzi et al., Reductions of Azides by Triphenylphosphine in the presence of water: a General and chemoselective method of access to primary amines, Bull. Soc. Chim. Fr., 1-12 (1985), and translation.
Exhibit 1041, filed Jul. 28, 2014 in connection with IPR2013-00517: Mag and Engels, Synthesis and selective cleavage of oligodeoxyribonucleotides containing non-chiral internucleotide phosphoramidate linkages, Nucleic Acids Research 15:5973-5988 (1989).
Exhibit 1043, filed Jul. 28, 2014 in connection with IPR2013-00517: Chang and Bollum, Molecular biology of terminal transferase, CRC Critical Reviews in Biochemistry 21:27-52 (1986).
Exhibit 1044, filed Jul. 28, 2014 in connection with IPR2013-00517: Chen, DNA polymerases drive DNA sequencing-by-synthesis technologies: both past and present, Frontiers in Microbiology, vol. 5, Article 305, 1-11 (2014).
Exhibit 1046, filed Jul. 28, 2014 in connection with IPR2013-00517: Jul. 27, 2014 Declaration of Dr. Michael Metzker in Support of Intelligent Bio-Systems, Inc's Reply to Illumina's Patent Owner Response.
Exhibit 1047, filed Jul. 28, 2014 in connection with IPR2013-00517: Lebreton et al., Structure-Immunosuppressive Activity Relationships of New Analogues of 15-Deoxyspergualin. 2. Structural Modifications of the Spermidine Moiety, Journal of Medicinal Chemistry 42:4749-4763 (1999).

(56) References Cited

OTHER PUBLICATIONS

Exhibit 1048, filed Jul. 28, 2014 in connection with IPR2013-00517: Levine et al., The Relationship of Structure to the Effectiveness of Denaturing Agents for Deoxyribonucleic Acid, Biochemistry 2:168-175 (1963).
Exhibit 1049, filed Jul. 28, 2014 in connection with IPR2013-00517: Efimov et al., An azidomethyl protective group in the synthesis of oligoribonucleotides by the phosphotriester method, 35:250-253 (2009).
Exhibit 1050, filed Jul. 28, 2014 in connection with IPR2013-00517: Kirby, A new method for the isolation of deoxyribonucleic acids: Evidence of the nature of bonds between deoxyribonucleic acids and proteins, Biochemical Journal 66:495-504 (1957).
Exhibit 1051, filed Jul. 28, 2014 in connection with IPR2013-00517: Bentley et al., Accurate whole human genome sequencing using reversible terminator chemistry. Nature 456:53 (2008)—Supplementary Information.
Petitioner Motion to Exclude Evidence, filed Sep. 2, 2014 in connection with IPR2013-00517.
Patent Owner Motion to Exclude Evidence, filed Sep. 2, 2014 in connection with IPR2013-00517.
Patent Owner Motion for Observations on the Cross-Examination Testimony of Bruce Branchaud, Ph.D. and Michael Metzker, Ph.D., filed Sep. 2, 2014 in connection with IPR2013-00517.
Exhibit 2139, filed Sep. 2, 2014 in connection with IPR2013-00517: Metzker, "Sequencing Technologies—The Next Generation" Nature Reviews Genetics, 11:31-46 (2010).
Exhibit 2140, filed Sep. 2, 2014 in connection with IPR2013-00517: Tsai et al., "Versatile and Efficient Synthesis of a New Class of Aza-Based Phosphinic Amide Ligands via Unusual P-C Cleavage" Helvetica Chimica Acta, 89:3007-3017 (2006).
Exhibit 2141, filed Sep. 2, 2014 in connection with IPR2013-00517: Treinin, General and Theoretical Aspects, Chapter 1 (pp. 1-55) in the Chemistry of the Azido Group (Saul Patai, Ed.).
Exhibit 2142, filed Sep. 2, 2014 in connection with IPR2013-00517: Hanlon, "The Importance of London Dispersion Forces in the Maintenance of the Deoxyribonucleic Acid Helix" Biochemical and Biophysical Research Communications, 23:861-867 (1966).
Exhibit 2144, filed Sep. 2, 2014 in connection with IPR2013-00517: "Phenol," in The Merck Index, pp. 1299-1300 (13th Ed., 2001).
Exhibit 2146, filed Sep. 2, 2014 in connection with IPR2013-00517: Metzker, "Emerging technologies in DNA sequencing" Genome Research, 15:1767-1776, (2005).
Exhibit 2147, filed Sep. 2, 2014 in connection with IPR2013-00517: Gardner et al., "Rapid incorporation kinetics and improved fidelity of a novel class of 3'-OH unblocked reversible terminators" Nucleic Acids Research, 40:7404-7415 (2012).
Exhibit 2148, filed Sep. 2, 2014 in connection with IPR2013-00517: Lander et al., "Initial sequencing and analysis of the human genome" Nature, 409:860-921 (2001).
Exhibit 2149, filed Sep. 2, 2014 in connection with IPR2013-00517: Wu et al., "Termination of DNA synthesis by $N^6$-alkylated, not 3'-O-alkylated, photocleavable 2'-deoxyadenosine triphosphates" Nucleic Acids Research, 35:6339-6349 (2007).
Exhibit 2150, filed Sep. 2, 2014 in connection with IPR2013-00517: Aldrich, Fine Chemicals catalogue, p. 1337 (1986).
Exhibit 2151, filed Sep. 2, 2014 in connection with IPR2013-00517: Sebastian et al., "Dendrimers with N,N-Disubstituted Hydrazines as End Groups, Useful Precursors for the Synthesis of Water-Soluble Dendrimers Capped with Carbohydrate, Carboxylic or Boronic Acid Derivatives" Tetrahedron, 56:6269-6277 (2000).
Exhibit 2152, filed Sep. 2, 2014 in connection with IPR2013-00517: Reardon et al., "Reduction of 3'-Azido-3'-deoxythymidine (AZT) and AZT Nucleotides by Thiols" The Journal of Biological Chemistry, 269:15999-16008 (1994).
Exhibit 2154, filed Sep. 2, 2014 in connection with IPR2013-00517: Transcript, Aug. 12, 2014 Deposition of Michael L. Metzker, Ph.D.
Exhibit 2155, filed Sep. 2, 2014 in connection with IPR2013-00517: Transcript, Aug. 26, 2014 Deposition of Bruce P. Branchaud, Ph. D.

Petitioner Opposition to Patentee Motion to Exclude Evidence, filed Sep. 15, 2014 in connection with IPR2013-00517.
International Search Report issued by the International Searching Authority (ISA/US) on Jan. 30, 2009 in connection with International Application No. PCT/US2008/011913.
Written Opinion of the International Searching Authority issued by the International Searching Authority (ISA/US) on Jan. 30, 2009 in connection with International Application No. PCT/US2008/011913.
Sep. 16, 2012 Petition for Inter Partes Review of U.S. Pat. No. 7,713,698, issued May 11, 2010.
Sep. 16, 2012 Motion to Waive Page Limit and Proposed Petition in connection with Petition for Inter Partes Review of U.S. Pat. No. 7,713,698, issued May 11, 2010.
Dec. 20, 2012 Preliminary Response under 37 C.F.R. 42.107 in connection with IPR2012-00006.
Mar. 12, 2013 Decision on Petition for Inter Partes Review in connection with IPR2012-00006.
Mar. 26, 2013 Request for Reconsideration in connection with IPR2012-00006.
Apr. 26, 2013 Opposition to Request for Reconsideration (Rehearing) Under 37 C.F.R. 42.71.(C) in connection with IPR2012-00006.
May 10, 2013 Decision on Request for Rehearing in connection with IPR2012-00006.
Aug. 30, 2013 Substitute Patent Owner Response Under 37 C.F.R. 42.120 in connection with IPR2012-00006.
Aug. 30, 2013 Substitute Patent Owner Motion to Amend Under 37 C.F.R. 42.121 in connection with IPR2012-00006.
Sep. 27, 2013 Petitioner Opposition to Motion to Amend in connection with IPR2012-00006.
Sep. 27, 2013 Petitioner Reply to Response to Petition in connection with IPR2012-00006.
Nov. 18, 2013 Patent Owner Substitute Reply on Motion to Amend in connection with IPR2012-00006.
Exhibit 1001, filed Sep. 16, 2012 in connection with IPR2012-00006: U.S. Pat. No. 7,713,698, issued May 11, 2010.
Exhibit 1002, filed Sep. 16, 2012 in connection with IPR2012-00006: PCT International Application No. PCT/US90/06678 filed Oct. 26, 1990, published on May 16, 1991 as Publication No. WO 91/06678 to SRI INTERNATIONAL.
Exhibit 1003, filed Sep. 16, 2012 in connection with IPR2012-00006: Prober et al. (1987), "A System for Rapid DNA Sequencing with Fluorescent Chain-Terminating Dideoxynucleotides", *Science* vol. 238, Oct. 16, 1987, pp. 336-341.
Exhibit 1004, filed Sep. 16, 2012 in connection with IPR2012-00006: U.S. Pat. No. 5,242,796 issued Sep. 7, 1993 to Prober et al.
Exhibit 1005, filed Sep. 16, 2012 in connection with IPR2012-00006: U.S. Pat. No. 5,547,839 issued Aug. 20, 1996 to Dower et al.
Exhibit 1006, filed Sep. 16, 2012 in connection with IPR2012-00006: PCT International Application No. PCT/US96/02342 filed Feb. 21, 1996, published on Sep. 6, 1996 as Publication No. WO 96/27025 to Ely Rabani.
Exhibit 1007, filed Sep. 16, 2012 in connection with IPR2012-00006: PCT International Application No. PCT/GB00/00873 filed Mar. 10, 2000, published on Sep. 14, 2000 as Publication No. WO 00/53805 to ASM Scientific, Inc.
Exhibit 1008, filed Sep. 16, 2012 in connection with IPR2012-00006: U.S. Pat. No. 7,270,951 issued Sep. 18, 2007 to Stemple et al.
Exhibit 1009, filed Sep. 16, 2012 in connection with IPR2012-00006: U.S. Application for a Method for Direct Nucleic Acid Sequencing; U.S. Appl. No. 09/266,187, filed Mar. 10, 1999.
Exhibits 1010-1012, filed Sep. 16, 2012 in connection with IPR2012-00006: PCT International Application No. PCT/JP97/00239, filed Jan. 31, 1997, published on Aug. 6, 1998 as Publication No. WO 98/33939 to Hitachi, Ltd. with certified English translation, and Translation Affidavit.
Exhibit 1013, filed Sep. 16, 2012 in connection with IPR2012-00006: U.S. Pat. No. 5,047,519 issued Sep. 10, 1991 to Hobbs, Jr. et al.
Exhibit 1014, filed Sep. 16, 2012 in connection with IPR2012-00006: U.S. Pat. No. 4,804,748 issued Feb. 14, 1989 to Seela.
Exhibit 1015, filed Sep. 16, 2012 in connection with IPR2012-00006: U.S. Pat. No. 5,844,106 issued Dec. 1, 1998 to Seela et al.

(56) References Cited

OTHER PUBLICATIONS

Exhibit 1016, filed Sep. 16, 2012 in connection with IPR2012-00006: PCT International Application No. PCT/US89/02170, filed May 18, 1989, published on Nov. 30, 1989 as Publication No. WO 89/11548 to Cetus Corporation.
Exhibit 1017, filed Sep. 16, 2012 in connection with IPR2012-00006: U.S. Pat. No. 7,037,687 issued May 2, 2006 to Williams et al.
Exhibit 1018, filed Sep. 16, 2012 in connection with IPR2012-00006: U.S. Pat. No. 6,255,083 issued Jul. 3, 2001 to Williams.
Exhibit 1019, filed Sep. 16, 2012 in connection with IPR2012-00006: U.S. Pat. No. 6,001,566 issued Dec. 14, 1999 to Canard et al.
Exhibit 1020, filed Sep. 16, 2012 in connection with IPR2012-00006: PCT International Application No. PCT/GB93/00848, filed Apr. 22, 1993, published on Oct. 28, 1993 as Publication No. WO 93/21340 to Medical Research Council.
Exhibit 1021, filed Sep. 16, 2012 in connection with IPR2012-00006: Sep. 15, 2012 Declaration of George Weinstock Under Rule 37 C.F.R. §1.132.
Exhibit 1022, filed Sep. 16, 2012 in connection with IPR2012-00006: Excerpts of File History of U.S. Pat. No. 7,713,698.
Exhibit 1025, filed Apr. 30, 2013 in connection with IPR2012-00006: Columbia's Amended Complaint from *the Trustees of Columbia University in the City of New York* v. *Illumina, Inc., D. Del* C.A. No. 12-376 (GMS), filed Apr. 11, 2012.
Exhibit 1026, filed Apr. 30, 2013 in connection with IPR2012-00006: Illumina's Answer to Amended Complaint from *The Trustees of Columbia University in the City of New York* v. *Illumina, Inc., D. Del* C.A. No. 12-376 (GMS), filed Dec. 21, 2012.
Exhibit 1029, filed Jun. 18, 2013 in connection with IPR2012-00006: U.S. Pat. No. 4,772,691, issued Sep. 20, 1988 to Herman.
Exhibit 1030, filed Jun. 18, 2013 in connection with IPR2012-00006: Rosenblum et al., "New Dye-Labeled Terminators for Improved DNA Sequencing Patterns," Nucleic Acid Research, 1997, vol. 25, No. 22, pp. 4500-4504.
Exhibit 1031, filed Jun. 18, 2013 in connection with IPR2012-00006: PCT International Publication No. WO 99/49082, published Sep. 30, 1999 to Invitrogen Corporation.
Exhibit 1032, filed Jun. 18, 2013 in connection with IPR2012-00006: U.S. Pat. No. 5,449,767, issued Sep. 12, 1995.
Exhibit 1033, filed Jun. 18, 2013 in connection with IPR2012-00006: U.S. Pat. No. 5,948,648, issued Sep. 7, 1999 to Khan et al.
Exhibit 1034, filed Jun. 18, 2013 in connection with IPR2012-00006: Jun. 8, 2013 Videotaped Deposition Transcript of George M. Weinstock, Ph. D.
Exhibit 1036, filed Sep. 27, 2013 in connection with IPR2012-00006: "Next Generation Genomics: World Map of High-throughput Sequencers," Sep. 1, 2013.
Exhibit 1037, filed Sep. 27, 2013 in connection with IPR2012-00006: GB Application No. 2001 0029012, filed Dec. 4, 2001 by Balasubramanian et al.
Exhibit 1039, filed Sep. 27, 2013 in connection with IPR2012-00006: Videotaped Deposition Transcript of Dr. Xiaohai Liu, Mar. 20, 2013.
Exhibit 1040, filed Sep. 27, 2013 in connection with IPR2012-00006: Excerpt from videotaped Deposition Transcript of George M. Weinstock, Ph.D., Jun. 8, 2013.
Exhibit 1041, filed Sep. 27, 2013 in connection with IPR2012-00006: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.
Exhibit 1042, filed Sep. 27, 2013 in connection with IPR2012-00006: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2012-00006: Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2012-00006: Seela et al., "Duplex Stability of Oligonucleotides Containing 7-Substituted 7-Deaza- and 8-Aza-7-Deazapurine Nucleosides," Nucleosides & Nucleotides, 16(7-9), pp. 963-966, 1997.
Exhibit 1045, filed Sep. 27, 2013 in connection with IPR2012-00006: Burgess et al., "Syntheses of Nucleosides Designed for Combinatorial DNA Sequencing," Chemistry—A European Journal, vol. 5, No. 3, pp. 951-960, 1999.
Exhibit 1046, filed Sep. 27, 2013 in connection with IPR2012-00006: U.S. Pat. No. 5,151,507, issued Sep. 29, 1992 to Hobbs, Jr. et al.
Exhibit 1047, filed Sep. 27, 2013 in connection with IPR2012-00006: U.S. Pat. No. 7,078,499, issued Jul. 18, 2006 to Odedra et al.
Exhibit 1048, filed Sep. 27, 2013 in connection with IPR2012-00006: GB Application No. 2000 0013276, filed Jun. 1, 2000 by Odedra et al.
Exhibit 1049, filed Sep. 27, 2013 in connection with IPR2012-00006: Jan. 28, 2013 Declaration of Dr. Bruce P. Branchaud in Support of Petition for Inter Partes Review of U.S. Pat. No. 7,057,026.
Exhibit 1050, filed Sep. 27, 2013 in connection with IPR2012-00006: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Sep. 27, 2013 in connection with IPR2012-00006: http://www.answers.com/topic/incubate, Accessed Sep. 27, 2013.
Exhibit 1052, filed Sep. 27, 2013 in connection with IPR2012-00006: http://en.wikipedia.org/wiki/Fluorenylmethyloxycarbonyl_chloride, Accessed Sep. 27, 2013.
Exhibit 1053, filed Sep. 27, 2013 in connection with IPR2012-00006: Sep. 27, 2013 Declaration of Kevin Burgess.
Exhibit 1054, filed Sep. 27, 2013 in connection with IPR2012-00006: Fuji, et al., "An Improved Method for Methoxymethylation of Alcohols under Mild Acidic Conditions," Synthesis—The Journal of Synthetic Organic Chemistry, pp. 276-277, Apr. 1975.
Exhibit 2001, filed Dec. 20, 2012 in connection with IPR2012-00006: U.S. Pat. No. 5,383,858, issued Jan. 24, 1995 to Reilly et al.
Exhibit 2006, filed Apr. 26, 2013 in connection with IPR2012-00006: Dower patent with highlights.
Exhibit 2010, filed Jun. 24, 2013 in connection with IPR2012-00006: U.S. Pat. No. 8,088,575 (filed Jul. 19, 2010, issued Jan. 3, 2012) (Exhibit 1001 in IPR2013-00011).
Exhibit 2011, filed Jun. 24, 2013 in connection with IPR2012-00006: U.S. Pat. No. 7,713,698 (filed Aug. 20, 2007, issued May 11, 2010) (Exhibit 1001 in IPR2012-00006).
Exhibit 2012, filed Jun. 24, 2013 in connection with IPR2012-00006: U.S. Pat. No. 7,790,869 (filed Jun. 5, 2007, issued Sep. 7, 2010) (Exhibit 1001 in IPR2012-00007).
Exhibit 2013, filed Jun. 24, 2013 in connection with IPR2012-00006: Oct. 2, 2012 Declaration of George Weinstock Under 37 CFR 1.132 (Exhibit 1021 in IPR2013-00011).
Exhibit 2014, filed Jun. 24, 2013 in connection with IPR2012-00006: Petition for Inter Partes Review of U.S. Pat. No. 8,088,575 (Paper 4 in IPR2013-00011).
Exhibit 2015, filed Jun. 24, 2013 in connection with IPR2012-00006: Metzker et al. (1994) Termination of DNA synthesis by novel 3'-modified-deoxyribonucleoside 5'-triphosphates. Nucleic Acids Res. 22:4259-4267.
Exhibit 2016, filed Jun. 24, 2013 in connection with IPR2012-00006: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2017, filed Jun. 24, 2013 in connection with IPR2012-00006: Sep. 15, 2012 Declaration of George Weinstock Under 37 CFR 1.132 (Exhibit 1021 in IPR2012-00007).
Exhibit 2018, filed Jun. 24, 2013 in connection with IPR2012-00006: Sep. 15, 2012 Declaration of George Weinstock Under 37 CFR 1.132 (Exhibit 1021 in IPR2012-00006).
Exhibit 2019, filed Jun. 24, 2013 in connection with IPR2012-00006: Definition of "DNA microarray." http://en/wikipedia.org/wiki/DNA_microarray.
Exhibit 2020, filed Jun. 24, 2013 in connection with IPR2012-00006: Brettin et al. (2005) Expression capable library for studies of Neisseria gonorrhoeae, version 1.0 BMC Microbiology. 5:50.
Exhibit 2021, filed Jun. 24, 2013 in connection with IPR2012-00006: George M. Weinstock, Handbook of Molecular Microbial Ecology,

(56) References Cited

OTHER PUBLICATIONS vol. 1-Chapter 18: The Impact of Next-Generation Sequencing Technologies on Metagenomics 141-147 Frans J. de Bruijn ed., John Wiley & Sons, Inc. (2011).
Exhibit 2022, filed Jun. 24, 2013 in connection with IPR2012-00006: Sep. 16, 2012 Petition for Inter Partes Review of U.S. Pat. No. 7,713,698 (Paper 3 in IPR2012-00006).
Exhibit 2023, filed Jun. 24, 2013 in connection with IPR2012-00006: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2012-00006: Maxam and Gilbert (1977) A new method for sequencing DNA, Proc. Natl. Acad. Sci. USA. 74:560-564.
Exhibit 2025, filed Jun. 24, 2013 in connection with IPR2012-00006: Sanger et al. (1977) DNA sequencing with chain-terminating inhibitors, Proc. Natl. Acad. Sci. USA. 74:5463-5467.
Exhibit 2026, filed Jun. 24, 2013 in connection with IPR2012-00006: Pennisi (2000) DOE Team Sequences Three Chromosomes, Science. 288:417-419.
Exhibit 2027, filed Jun. 24, 2013 in connection with IPR2012-00006: Welch and Burgess (1999) Synthesis of Fluorescent, Photolabile 3'-O-Protected nucleoside Triphosphates for the Base Addition Sequencing Scheme, nucleosides & Nucleotides. 18:197-201.
Exhibit 2028, filed Jun. 24, 2013 in connection with IPR2012-00006: Hyman (1998) A New Method of Sequencing DNA, Analytical Biochemistry 174:423-436.
Exhibit 2029, filed Jun. 24, 2013 in connection with IPR2012-00006: U.S. Pat. No. 5,302,509 (filed Feb. 27, 1991, issued Apr. 12, 1994).
Exhibit 2030, filed Jun. 24, 2013 in connection with IPR2012-00006: Canard and Sarfati (1994) DNA polymerase fluorescent substrates with reversible 3'-tags, Gene. 1481-6.
Exhibit 2031, filed Jun. 24, 2013 in connection with IPR2012-00006: U.S. Pat. No. 8,399,188 (filed Sep. 4, 2007, issued Mar. 19, 2013).
Exhibit 2032, filed Jun. 24, 2013 in connection with IPR2012-00006: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2012-00006: Jun. 25, 2013 Substitute Declaration of Dr. George L. Trainor [redacted].
Exhibit 2034, filed Jun. 25, 2013 in connection with IPR2012-00006: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2013 in connection with IPR2012-00006: Batista et al. (2008) PRG-1 and 21U-RNAs Interact to Form the piRNA Complex Required for Fertility in C. elegans. Molecular Cell 31:1-12.
Exhibit 2036, filed Jun. 25, 2013 in connection with IPR2012-00006: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2037, filed Jun. 25, 2013 in connection with IPR2012-00006: Oct. 1, 2006 Request for opinion on manuscript by J. Ju et. al., Proceedings of National Academy of Sciences, U.S.A.
Exhibit 2038, filed Jun. 25, 2013 in connection with IPR2012-00006: Correspondence between George Rupp, Chancellor, Columbia University and Richard T. Schlossberg, President, The David and Lucile Packard Foundation (2001).
Exhibit 2039, filed Jun. 25, 2013 in connection with IPR2012-00006: The David and Lucile Packard Foundation, Packard Fellowships for Science and Engineering, http://www.packard.org/what-wefund/conservation-and- science/packard-fellowships-for-science-andengineering/ (last visited Jun. 25, 2013).
Exhibit 2040, filed Jun. 25, 2013 in connection with IPR2012-00006: "Chemistry for Next-Generation Sequencing." http://www.illumina.com/technology/sequencing_technology.ilmn.
Exhibit 2041, filed Jun. 25, 2013 in connection with IPR2012-00006: Chiang et al. (2010) Mammalian microRNAs: experimental evaluation of novel and previously annotated genes, Genes & Dev. 24:992, 993.
Exhibit 2042, filed Jun. 25, 2013 in connection with IPR2012-00006: Seo et al. (2004) Photocleavable fluorescent nucleotides for DNA sequencing on a chip constructed by site-specific coupling chemistry, Proc. Natl Acad. Sci. 101(15):5488-5493.
Exhibit 2043, filed Jun. 25, 2013 in connection with IPR2012-00006: Curriculum vitae of Mr. Raymond S. Sims.
Exhibit 2044, filed Jun. 25, 2013 in connection with IPR2012-00006: Prior Testimony of Mr. Raymond S. Sims.
Exhibit 2045, filed Jun. 25, 2013 in connection with IPR2012-00006: Documents reviewed by Mr. Raymond S. Sims in this Proceedings.
Exhibit 2052, filed Jun. 25, 2013 in connection with IPR2012-00006: Gary Schroth Proof of Chiang Paper.
Exhibit 2074, filed Jun. 25, 2013 in connection with IPR2012-00006: Information about Dr. Ju's intellectual property sent.
Exhibit 2090, filed Jun. 26, 2013 in connection with IPR2012-00006: IPR Default Protective Order.
Exhibit 2091, filed Jun. 26, 2013 in connection with IPR2012-00006: Declaration of Raymond S. Sims.
Exhibit 2092, filed Oct. 10, 2013 in connection with IPR2012-00006: Rough Transcript of the Sep. 4, 2013 deposition of Dr. George L. Trainor.
Exhibit 2093, filed Oct. 1, 2013 in connection with IPR2012-00006: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2012-00006: Final transcript of the Sep. 4-6, 2013 deposition of Dr. George L. Trainor.
Exhibit 2095, filed Oct. 1, 2013 in connection with IPR2012-00006: Final transcript of the Sep. 3, 2013 deposition of Raymond S. Sims.
Nov. 12, 2013 Petitioner Motion to Exclude Evidence in connection with IPR2012-00006.
Exhibit 1056, filed Nov. 19, 2013 in connection with IPR2012-00006: Videotaped Deposition Transcript of Kevin Burgess, Ph.D., Oct. 28, 2013, signed with errata.
Nov. 12, 2013 Patent Owner Motion for Observations on the Cross-Examination Testimony of Kevin Burgess, Ph.D. in. connection with IPR2012-00006.
Nov. 12, 2013 Patent Owner Motion to Exclude Evidence in connection with IPR2012-00006.
Exhibit 2099, filed Nov. 12, 2013 in connection with IPR2012-00006: Welch, M., et al (2005) Corrigenda to Syntheses of Nucleosides Designed for Combinatorial DNA Sequencing Chem. Eur.J., 1999, 951-960. Published in Chem. Eur. J, 2005, 11, 7136-7145.
Exhibit 2100, filed Nov. 12, 2013 in connection with IPR2012-00006: Welch, M (1999) "Base Additions Sequencing Scheme (Bass) and Studies Toward New Sequencing Methodologies." PhD. Dissertation, Texas A&M University.
Exhibit 2101, filed Nov. 12, 2013 in connection with IPR2012-00006: Lu and Burgess (2006) "A Diversity Oriented Synthesis of 3'-O-modified nucleoside triphosphates for DNA 'Sequencing by Synthesis'." Bioorganic & Medicinal Chemistry Letters, 16, 3902-3905.
Exhibit 2102, filed Nov. 12, 2013 in connection with IPR2012-00006: Advanced Sequencing Technology Awards 2004. http://www.genome.gov/12513162 (accessed Oct. 14, 2013).
Exhibit 2103, filed Nov. 12, 2013 in connection with IPR2012-00006: Welch and Burgess (2006) Erratum to Synthesis of Fluorescent, Photolabile 3'-O-Protected Nucleoside Triphosphates for the Base Addition Sequencing Scheme, Nucleosides & Nucleotides,18:197-201. Published in Nucleosides, Nucleotides and Nucleic Acids, 25:1, 119.
Nov. 26, 2013 Petitioner Response to Motion for Observations in connection with IPR2012-00006.
Nov. 26, 2013 Patent Owner Opposition to Petitioner's Motion to Exclude in connection with IPR2012-00006.
Nov. 26, 2013 Petitioner Opposition to Motion to Exclude in connection with IPR2012-00006.

(56) References Cited

OTHER PUBLICATIONS

Dec. 3, 2013 Petitioner Reply to Patent Owner's Opposition to Motion to Exclude in connection with IPR2012-00006.
Dec. 3, 2013 Patent Owner Reply on Motion to Exclude in connection with IPR2012-00006.
Sep. 16, 2012 Petition for Inter Partes Review of U.S. Pat. No. 7,790,869.
Sep. 17, 2012 Motion to Waive Page Limit and Proposed Petition in connection with Petition for Inter Partes Review of U.S. Pat. No. 7,790,869.
Dec. 21, 2012 Preliminary Response under 37 C.F.R. 42.107 in connection with IPR2012-00007.
Mar. 12, 2013 Decision on Petition for Inter Partes Review in connection with IPR2012-00007.
Mar. 26, 2013 Request for Reconsideration in connection with IPR2012-00007.
Mar. 26, 2013 Request for Rehearing under 37 C.F.R. 42.71 of Decision to Institute Inter Partes Review in connection with IPR2012-00007.
Apr. 26, 2013 Opposition to Request for Reconsideration (Rehearing) Under 37 C.F.R. 42.71.(C) in connection with IPR2012-00007.
May 10, 2013 Decision on Request for Rehearing in connection with IPR2012-00007.
Aug. 30, 2013 Substitute Patent Owner Response Under 37 C.F.R. 42.120 in connection with IPR2012-00007.
Aug. 30, 2013 Substitute Patent Owner Motion to Amend Under 37 C.F.R. 42.121 in connection with IPR2012-00007.
Sep. 27, 2013 Petitioner Opposition to Motion to Amend in connection with IPR2012-00007.
Sep. 27, 2013 Petitioner Reply to Response to Petition in connection with IPR2012-00007.
Nov. 18, 2013 Substitute Patent Owner Reply on Motion to Amend in connection with IPR2012-00007.
Exhibit 1001, filed Sep. 16, 2012 in connection with IPR2012-00007: U.S. Pat. No. 7,790,869 issued Sep. 7, 2010 to Ju et al.
Exhibit 1002, filed Sep. 16, 2012 in connection with IPR2012-00007: PCT International Application No. PCT/US90/06678 filed Oct. 26, 1990, published on May 16, 1991 as Publication No. WO 91/06678 to SRI INTERNATIONAL.
Exhibit 1003, filed Sep. 16, 2012 in connection with IPR2012-00007: Prober et al. (1987), "A System for Rapid DNA Sequencing with Fluorescent Chain-Terminating Dideoxynucleotides", *Science* vol. 238, Oct. 16, 1987, pp. 336-341.
Exhibit 1004, filed Sep. 16, 2012 in connection with IPR2012-00007: U.S. Pat. No. 5,242,796 issued Sep. 7, 1993 to Prober et al.
Exhibit 1005, filed Sep. 16, 2012 in connection with IPR2012-00007: U.S. Pat. No. 5,547,839 issued Aug. 20, 1996 to Dower et al.
Exhibit 1006, filed Sep. 16, 2012 in connection with IPR2012-00007: PCT International Application No. PCT/US96/02342 filed Feb. 21, 1996, published on Sep. 6, 1996 as Publication No. WO 96/27025 to Ely Rabani.
Exhibit 1007, filed Sep. 16, 2012 in connection with IPR2012-00007: PCT International Application No. PCT/GB00/00873 filed Mar. 10, 2000, published on Sep. 14, 2000 as Publication No. WO 00/53805 to ASM Scientific, Inc.
Exhibit 1008, filed Sep. 16, 2012 in connection with IPR2012-00007: U.S. Pat. No. 7,270,951 issued Sep. 18, 2007 to Stemple et al.
Exhibit 1009, filed Sep. 16, 2012 in connection with IPR2012-00007: U.S. Application for a Method for Direct Nucleic Acid Sequencing; U.S. Appl. No. 09/266,187, filed Mar. 10, 1999.
Exhibits 1010-1012, filed Sep. 16, 2012 in connection with IPR2012-00007: PCT International Application No. PCT/JP97/00239, filed Jan. 31, 1997, published on Aug. 6, 1998 as Publication No. WO 98/33939 to Hitachi, Ltd. with certified English translation, and Translation Affidavit.
Exhibit 1013, filed Sep. 16, 2012 in connection with IPR2012-00007: U.S. Pat. No. 5,047,519 issued Sep. 10, 1991 to Hobbs, Jr. et al.
Exhibit 1014, filed Sep. 16, 2012 in connection with IPR2012-00007: U.S. Pat. No. 4,804,748 issued Feb. 14, 1989 to Seela.
Exhibit 1015, filed Sep. 16, 2012 in connection with IPR2012-00007: U.S. Pat. No. 5,844,106 issued Dec. 1, 1998 to Seela et al.
Exhibit 1016, filed Sep. 16, 2012 in connection with IPR2012-00007: PCT International Application No. PCT/US89/02170, filed May 18, 1989, published on Nov. 30, 1989 as Publication No. WO 89/11548 to Cetus Corporation.
Exhibit 1017, filed Sep. 16, 2012 in connection with IPR2012-00007: U.S. Pat. No. 7,037,687 issued May 2, 2006 to Williams et al.
Exhibit 1018, filed Sep. 16, 2012 in connection with IPR2012-00007: U.S. Pat. No. 6,255,083 issued Jul. 3, 2001 to Williams.
Exhibit 1019, filed Sep. 16, 2012 in connection with IPR2012-00007: U.S. Pat. No. 6,001,566 issued Dec. 14, 1999 to Canard et al.
Exhibit 1020, filed Sep. 16, 2012 in connection with IPR2012-00007: PCT International Application No. PCT/GB93/00848, filed Apr. 22, 1993, published on Oct. 28, 1993 as Publication No. WO 93/21340 to Medical Research Council.
Exhibit 1021, filed Sep. 16, 2012 in connection with IPR2012-00007: Sep. 15, 2012 Declaration of George Weinstock Under Rule 37 C.F.R. §1.132.
Exhibit 1022, filed Sep. 16, 2012 in connection with IPR2012-00007: Excerpts of File History of U.S. Pat. No. 7,790,869.
Exhibit 1025, filed Apr. 30, 2013 in connection with IPR2012-00007: Columbia's Amended Complaint from *the Trustees of Columbia University in the City of New York* v. *Illumina, Inc.,* D. Del C.A. No. 12-376 (GMS), filed Apr. 11, 2012.
Exhibit 1026, filed Apr. 30, 2013 in connection with IPR2012-00007: Illumina's Answer to Amended Complaint from *the Trustees of Columbia University in the City of New York* v. *Illumina, Inc.,* D. Del C.A. No. 12-376 (GMS), filed Dec. 21, 2012.
Exhibit 1029, filed Jun. 18, 2013 in connection with IPR2012-00007: U.S. Pat. No. 4,772,691, issued Sep. 20, 1988 to Herman.
Exhibit 1030, filed Jun. 18, 2013 in connection with IPR2012-00007: Rosenblum et al., "New Dye-Labeled Terminators for Improved DNA Sequencing Patterns," Nucleic Acid Research, 1997, vol. 25, No. 22, pp. 4500-4504.
Exhibit 1031, filed Jun. 18, 2013 in connection with IPR2012-00007: PCT International Publication No. WO 99/49082, published Sep. 30, 1999 to Invitrogen Corporation.
Exhibit 1032, filed Jun. 18, 2013 in connection with IPR2012-00007: U.S. Pat. No. 5,449,767, issued Sep. 12, 1995 to Ward et al.
Exhibit 1033, filed Jun. 18, 2013 in connection with IPR2012-00007: U.S. Pat. No. 5,948,648, issued Sep. 7, 1999 to Khan et al.
Exhibit 1034, filed Jun. 18, 2013 in connection with IPR2012-00007: Jun. 8, 2013 Videotaped Deposition Transcript of George M. Weinstock, Ph. D.
Exhibit 1036, filed Sep. 27, 2013 in connection with IPR2012-00007: "Next Generation Genomics: World Map of High-throughput Sequencers," Sep. 1, 2013.
Exhibit 1037, filed Sep. 27, 2013 in connection with IPR2012-00007: GB Application No. 2001 0029012, filed Dec. 4, 2001 by Balasubramanian et al.
Exhibit 1039, filed Sep. 27, 2013 in connection with IPR2012-00007: Videotaped Deposition Transcript of Dr. Xiaohai Liu, Mar. 20, 2013.
Exhibit 1040, filed Sep. 27, 2013 in connection with IPR2012-00007: Excerpt from videotaped Deposition Transcript of George M. Weinstock, Ph.D., Jun. 8, 2013.
Exhibit 1041, filed Sep. 27, 2013 in connection with IPR2012-00007: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.
Exhibit 1042, filed Sep. 27, 2013 in connection with IPR2012-00007: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2012-00007: Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2012-00007: Seela et al., "Duplex Stability of Oligonucleotides Containing 7-Substituted 7-Deaza- and 8-Aza-7-Deazapurine Nucleosides," Nucleosides & Nucleotides, 16(7-9), pp. 963-966, 1997.

(56) References Cited

OTHER PUBLICATIONS

Exhibit 1045, filed Sep. 27, 2013 in connection with IPR2012-00007: Burgess et al., "Syntheses of Nucleosides Designed for Combinatorial DNA Sequencing," Chemistry—A European Journal, vol. 5, No. 3, pp. 951-960, 1999.
Exhibit 1046, filed Sep. 27, 2013 in connection with IPR2012-00007: U.S. Pat. No. 5,151,507, issued Sep. 29, 1992 to Hobbs, Jr. et al.
Exhibit 1047, filed Sep. 27, 2013 in connection with IPR2012-00007: U.S. Pat. No. 7,078,499, issued Jul. 18, 2006 to Odedra et al.
Exhibit 1048, filed Sep. 27, 2013 in connection with IPR2012-00007: GB Application No. 2000 0013276, filed Jun. 1, 2000 by Odedra et al.
Exhibit 1049, filed Sep. 27, 2013 in connection with IPR2012-00007: Jan. 28, 2013 Declaration of Dr. Bruce P. Branchaud in Support of Petition for Inter Partes Review of U.S. Pat. No. 7,057,026.
Exhibit 1050, filed Sep. 27, 2013 in connection with IPR2012-00007: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Sep. 27, 2013 in connection with IPR2012-00007: http://www.answers.com/topic/incubate, Accessed Sep. 27, 2013.
Exhibit 1052, filed Sep. 27, 2013 in connection with IPR2012-00007: http://en.wikipedia.org/wiki/Fluorenylmethyloxycarbonyl_chloride, Accessed Sep. 27, 2013.
Exhibit 1053, filed Sep. 27, 2013 in connection with IPR2012-00007: Sep. 27, 2013 Declaration of Kevin Burgess.
Exhibit 1054, filed Sep. 27, 2013 in connection with IPR2012-00007: Fuji, et al., "An Improved Method for Methoxymethylation of Alcohols under Mild Acidic Conditions," Synthesis—The Journal of Synthetic Organic Chemistry, pp. 276-277, Apr. 1975.
Exhibit 2001, filed Dec. 21, 2012 in connection with IPR2012-00007: Composition of a Nucleotide.
Exhibit 2006, filed Jun. 25, 2013 in connection with IPR2012-00007: Dower patent with highlights.
Exhibit 2010, filed Jun. 24, 2013 in connection with IPR2012-00007: U.S. Pat. No. 8,088,575 (filed Jul. 19, 2010, issued Jan. 3, 2012) (Exhibit 1001 in IPR2013-00011).
Exhibit 2011, filed Jun. 24, 2013 in connection with IPR2012-00007: U.S. Pat. No. 7,713,698 (filed Aug. 20, 2007, issued May 11, 2010) (Exhibit 1001 in IPR2012-00006).
Exhibit 2012, filed Jun. 24, 2013 in connection with IPR2012-00007: U.S. Pat. No. 7,790,869 (filed Jun. 5, 2007, issued Sep. 7, 2010) (Exhibit 1001 in IPR2012-00007).
Exhibit 2013, filed Jun. 24, 2013 in connection with IPR2012-00007: Oct. 2, 2012 Declaration of George Weinstock Under 37 CFR 1.132 (Exhibit 1021 in IPR2013-00011).
Exhibit 2014, filed Jun. 24, 2013 in connection with IPR2012-00007: Petition for Inter Partes Review of U.S. Pat. No. 8,088,575 (Paper 4 in IPR2013-00011).
Exhibit 2015, filed Jun. 24, 2013 in connection with IPR2012-00007: Metzker et al. (1994) Termination of DNA synthesis by novel 3'-modified-deoxyribonucleoside 5'-triphosphates. Nucleic Acids Res. 22:4259-4267.
Exhibit 2016, filed Jun. 24, 2013 in connection with IPR2012-00007: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2017, filed Jun. 24, 2013 in connection with IPR2012-00007: Sep. 15, 2012 Declaration of George Weinstock Under 37 CFR 1.132 (Exhibit 1021 in IPR2012-00007).
Exhibit 2018, filed Jun. 24, 2013 in connection with IPR2012-00007: Sep. 15, 2012 Declaration of George Weinstock Under 37 CFR 1.132 (Exhibit 1021 in IPR2012-00006).
Exhibit 2019, filed Jun. 24, 2013 in connection with IPR2012-00007: Definition of "DNA microarray." http://en/wikipedia.org/wiki/DNA_microarray.
Exhibit 2020, filed Jun. 24, 2013 in connection with IPR2012-00007: Brettin et al. (2005) Expression capable library for studies of Neisseria gonorrhoeae, version 1.0 BMC Microbiology. 5:50.
Exhibit 2021, filed Jun. 24, 2013 in connection with IPR2012-00007: George M. Weinstock, Handbook of Molecular Microbial Ecology, vol. 1-Chapter 18: The Impact of Next-Generation Sequencing Technologies on Metagenomics 141-147 Frans J. de Bruijn ed., John Wiley & Sons, Inc. (2011).
Exhibit 2022, filed Jun. 24, 2013 in connection with IPR2012-00007: Sep. 16, 2012 Petition for Inter Partes Review of U.S. Pat. No. 7,713,698 (Paper 3 in IPR2012-00006).
Exhibit 2023, filed Jun. 24, 2013 in connection with IPR2012-00007: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2012-00007: Maxam and Gilbert (1977) A new method for sequencing DNA, Proc. Natl. Acad. Sci. USA. 74:560-564.
Exhibit 2025, filed Jun. 24, 2013 in connection with IPR2012-00007: Sanger et al. (1977) DNA sequencing with chain-terminating inhibitors, Proc. Natl. Acad. Sci. USA. 74:5463-5467.
Exhibit 2026, filed Jun. 24, 2013 in connection with IPR2012-00007: Pennisi (2000) DOE Team Sequences Three Chromosomes, Science. 288:417-419.
Exhibit 2027, filed Jun. 24, 2013 in connection with IPR2012-00007: Welch and Burgess (1999) Synthesis of Fluorescent, Photolabile 3'-O-Protected nucleoside Triphosphates for the Base Addition Sequencing Scheme, nucleosides & Nucleotides. 18:197-201.
Exhibit 2028, filed Jun. 24, 2013 in connection with IPR2012-00007: Hyman (1998) A New Method of Sequencing DNA, Analytical Biochemistry 174:423-436.
Exhibit 2029, filed Jun. 24, 2013 in connection with IPR2012-00007: U.S. Pat. No. 5,302,509 (filed Feb. 27, 1991, issued Apr. 12, 1994).
Exhibit 2030, filed Jun. 24, 2013 in connection with IPR2012-00007: Canard and Sarfati (1994) DNA polymerase fluorescent substrates with reversible 3'-tags, Gene. 1481-6.
Exhibit 2031, filed Jun. 24, 2013 in connection with IPR2012-00007: U.S. Pat. No. 8,399,188 (filed Sep. 4, 2007, issued Mar. 19, 2013).
Exhibit 2032, filed Jun. 24, 2013 in connection with IPR2012-00007: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2012-00007: Jun. 25, 2013 Substitute Declaration of Dr. George L. Trainor [redacted].
Exhibit 2034, filed Jun. 25, 2013 in connection with IPR2012-00007: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2013 in connection with IPR2012-00007: Batista et al. (2008) PRG-1 and 21U-RNAs Interact to Form the piRNA Complex Required for Fertility in C. elegans. Molecular Cell 31:1-12.
Exhibit 2036, filed Jun. 25, 2013 in connection with IPR2012-00007: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2037, filed Jun. 25, 2013 in connection with IPR2012-00007: Oct. 1, 2006 Request for opinion on manuscript by J. Ju et. al., Proceedings of National Academy of Sciences, U. S. A.
Exhibit 2038, filed Jun. 25, 2013 in connection with IPR2012-00007: Correspondence between George Rupp, Chancellor, Columbia University and Richard T. Schlossberg, President, the David and Lucile Packard Foundation (2001).
Exhibit 2039, filed Jun. 25, 2013 in connection with IPR2012-00007: The David and Lucile Packard Foundation, Packard Fellowships for Science and Engineering, http://www.packard.org/what-wefund/conservation-and-science/packard-fellowships-for-science-andengineering/ (last visited Jun. 25, 2013).
Exhibit 2040, filed Jun. 26, 2013 in connection with IPR2012-00007: "Chemistry for Next-Generation Sequencing." http://www.illumina.com/technology/sequencing_technology.ilmn.
Exhibit 2041, filed Jun. 26, 2013 in connection with IPR2012-00007: Chiang et al. (2010) Mammalian microRNAs: experimental evaluation of novel and previously annotated genes, Genes & Dev. 24:992, 993.

(56) References Cited

OTHER PUBLICATIONS

Exhibit 2042, filed Jun. 26, 2013 in connection with IPR2012-00007: Seo et al. (2004) Photocleavable fluorescent nucleotides for DNA sequencing on a chip constructed by site-specific coupling chemistry, Proc. Natl Acad. Sci. 101(15):5488-5493.
Exhibit 2043, filed Jun. 26, 2013 in connection with IPR2012-00007: Curriculum vitae of Mr. Raymond S. Sims.
Exhibit 2044, filed Jun. 26, 2013 in connection with IPR2012-00007: Prior Testimony of Mr. Raymond S. Sims.
Exhibit 2045, filed Jun. 26, 2013 in connection with IPR2012-00007: Documents reviewed by Mr. Raymond S. Sims in this Proceeding.
Exhibit 2052, filed Jun. 26, 2013 in connection with IPR2012-00007: Gary Schroth Proof of Chiang Paper.
Exhibit 2074, filed Jun. 26, 2013 in connection with IPR2012-00007: Information about Dr. Ju's intellectual property sent to Illumina.
Exhibit 2090, filed Jun. 26, 2013 in connection with IPR2012-00007: IPR Default Protective Order.
Exhibit 2091, filed Jun. 26, 2013 in connection with IPR2012-00007: Declaration of Raymond S. Sims.
Exhibit 2092, filed Oct. 1, 2013 in connection with IPR2012-00007: Rough transcript of the Sep. 4, 2013 deposition of Dr. George L. Trainor.
Exhibit 2093, filed Oct. 1, 2013 in connection with IPR2012-00007: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2012-00007: Final transcript of the Sep. 4-6, 2013 deposition of Dr. George L. Trainor.
Exhibit 2095, filed Oct. 1, 2013 in connection with IPR2012-00007: Final transcript of the Sep. 3, 2013 deposition of Raymond S. Sims.
Nov. 12, 2013 Petitioner Motion to Exclude Evidence in connection with IPR2012-00007.
Exhibit 1056, filed Nov. 19, 2013 in connection with IPR2012-00007: Videotaped Deposition Transcript of Kevin Burgess, Ph.D., Oct. 28, 2013, signed with errata.
Nov. 12, 2013 Patent Owner Motion for Observations on the Cross-Examination Testimony of Kevin Burgess, Ph.D. in connection with IPR2012-00007.
Nov. 12, 2013 Patent Owner Motion to Exclude Evidence in connection with IPR2012-00007.
Exhibit 2099, filed Nov. 12, 2013 in connection with IPR2012-00007: Welch, M., et al (2005) Corrigenda to Syntheses of Nucleosides Designed for Combinatorial DNA Sequencing Chem. Eur. J., 1999, 951-960. Published in Chem. Eur. J, 2005, 11, 7136-7145.
Exhibit 2100, filed Nov. 12, 2013 in connection with IPR2012-00007: Welch, M (1999) "Base Additions Sequencing Scheme (BASS) and Studies Toward New Sequencing Methodologies." PhD. Dissertation, Texas A&M University.
Exhibit 2101, filed Nov. 12, 2013 in connection with IPR2012-00007: Lu and Burgess (2006) "A Diversity Oriented Synthesis of 3'-O-modified nucleoside triphophates for DNA 'Sequencing by Synthesis'. " Bioorganic & Medicinal Chemistry Letters, 16 3902-3905.
Exhibit 2102, filed Nov. 12, 2013 in connection with IPR2012-00007: Advanced Sequencing Technology Awards 2004. http://www.genome.gov/12513162 (accessed Oct. 14, 2013).
Exhibit 2103, filed Nov. 12, 2013 in connection with IPR2012-00007: Welch and Burgess (2006) Erratum to Synthesis of Fluorescent, Photolabile 3'-O-Protected Nucleoside Triphosphates for the Base Addition Sequencing Scheme, Nucleosides & Nucleotides,18:197-201. Published in Nucleosides, Nucleotides and Nucleic Acids, 25:1, 119.
Nov. 26, 2013 Petitioner's Response to Motion for Observations in connection with IPR2012-00007.
Nov. 26, 2013 Patent Owner's Opposition to Petitioner's Motion to Exclude in connection with IPR2012-00007.
Nov. 26, 2013 Petitioner's Opposition to Motion to Exclude in connection with IPR2012-00007.
Dec. 3, 2013 Petitioner Reply to Patent Owner's Opposition to Motion to Exclude in connection with IPR2012-00007.
Dec. 3, 2013 Patent Owner Reply on Motion to Exclude in connection with IPR2012-00007.
Oct. 3, 2012 Petition for Inter Partes Review of U.S. Pat. No. 8,088,575.
Oct. 3, 2012 Motion to Waive Page Limit and Proposed Petition in connection with Petition for Inter Partes Review of U.S. Pat. No. 8,088,575.
Jan. 7, 2013 Preliminary Response under 37 C.F.R. 42.107 in connection with IPR2013-00011.
Mar. 12, 2013 Decision on Petition for Inter Partes Review in connection with IPR2013-00011.
Mar. 26, 2013 Request for Reconsideration in connection with IPR2013-00011.
Mar. 26, 2013 Request for Rehearing under 37 C.F.R. 42.71 of Decision to Institute Inter Partes Review in connection with IPR2013-00011.
Apr. 26, 2013 Opposition to Request for Reconsideration (Rehearing) Under 37 C.F.R. 42.71.(C) in connection with IPR2013-00011
May 10, 2013 Decision on Request for Rehearing in connection with IPR2013-00011.
Jun. 25, 2013 Motion to Amend Under 37 C.F.R. 42.121 in connection with IPR2013-00011.
Aug. 30, 2013 Substitute Patent Owner Response Under 37 C.F.R. 42.120 in connection with IPR2013-00011.
Sep. 27, 2013 Petitioner Opposition to Motion to Amend in connection with IPR2013-00011.
Sep. 27, 2013 Petitioner Reply to Response to Petition in connection with IPR2013-00011.
Nov. 18, 2013 Substitute Patent Owner Reply on Motion to Amend in connection with IPR2013-00011.
Exhibit 1001, filed Oct. 3, 2012 in connection with IPR2013-00011: U.S. Pat. No. 8,088,575 issued Jan. 3, 2012 to Ju et al.
Exhibit 1002, filed Oct. 3, 2012 in connection with IPR2013-00011: PCT International Application No. PCT/US90/06678 filed Oct. 26, 1990, published on May 16, 1991 as Publication No. WO 91/06678 to SRI International.
Exhibit 1003, filed Oct. 3, 2012 in connection with IPR2013-00011: Prober et al. (1987), "A System for Rapid DNA Sequencing with Fluorescent Chain-Terminating Dideoxynucleotides", *Science* vol. 238, Oct. 16, 1987,.
Exhibit 1004, filed Oct. 3, 2012 in connection with IPR2013-00011: U.S. Pat. No. 5,242,796 issued Sep. 7, 1993 to Prober et al.
Exhibit 1005, filed Oct. 3, 2012 in connection with IPR2013-00011: U.S. Pat. No. 5,547,839 issued Aug. 20, 1996 to Dower et al.
Exhibit 1006, filed Oct. 3, 2012 in connection with IPR2013-00011: PCT International Application No. PCT/US96/02342 filed Feb. 21, 1996, published on Sep. 6, 1996 as Publication No. WO 96/27025 to Ely Rabani.
Exhibit 1007, filed Oct. 3, 2012 in connection with IPR2013-00011: PCT International Application No. PCT/GB00/00873 filed Mar. 10, 2000, published on Sep. 14, 2000 as Publication No. WO 00/53805 to ASM Scientific, Inc.
Exhibit 1008, filed Oct. 3, 2012 in connection with IPR2013-00011: U.S. Pat. No. 7,270,951 issued Sep. 18, 2007 to Stemple et al.
Exhibit 1009, filed Oct. 3, 2012 in connection with IPR2013-00011: U.S. Application for a Method for Direct Nucleic Acid Sequencing; U.S. Appl. No. 09/266,187, filed Mar. 10, 1999.
Exhibits 1010-1012, filed Oct. 3, 2012 in connection with IPR2013-00011: PCT International Application No. PCT/JP97/00239, filed Jan. 31, 1997, published on Aug. 6, 1998 as Publication No. WO 98/33939 to Hitachi, Ltd. with certified English translation, and Translation Affidavit.
Exhibit 1013, filed Oct. 3, 2012 in connection with IPR2013-00011: U.S. Pat. No. 5,047,519 issued Sep. 10, 1991 to Hobbs, Jr. et al.
Exhibit 1014, filed Oct. 3, 2012 in connection with IPR2013-00011: U.S. Pat. No. 4,804,748 issued Feb. 14, 1989 to Seela.
Exhibit 1015, filed Oct. 3, 2012 in connection with IPR2013-00011: U.S. Pat. No. 5,844,106 issued Dec. 1, 1998 to Seela et al.

(56) References Cited

OTHER PUBLICATIONS

Exhibit 1016, filed Oct. 3, 2012 in connection with IPR2013-00011: PCT International Application No. PCT/US89/02170, filed May 18, 1989, published on Nov. 30, 1989 as Publication No. WO 89/11548 to Cetus Corporation.
Exhibit 1017, filed Oct. 3, 2012 in connection with IPR2013-00011: U.S. Pat. No. 7,037,687 issued May 2, 2006 to Williams et al.
Exhibit 1018, filed Oct. 3, 2012 in connection with IPR2013-00011: U.S. Pat. No. 6,255,083 issued Jul. 3, 2001 to Williams.
Exhibit 1019, filed Oct. 3, 2012 in connection with IPR2013-00011: U.S. Pat. No. 6,001,566 issued Dec. 14, 1999 to Canard et al.
Exhibit 1020, filed Oct. 3, 2012 in connection with IPR2013-00011: PCT International Application No. PCT/GB93/00848, filed Apr. 22, 1993, published on Oct. 28, 1993 as Publication No. WO 93/21340 to Medical Research Council.
Exhibit 1021, filed Oct. 3, 2012 in connection with IPR2013-00011: Oct. 3, 2012 Declaration of George Weinstock Under Rule 37 C.F.R. §1.132.
Exhibit 1022, filed Oct. 3, 2012 in connection with IPR2013-00011: Excerpts of File History of U.S. Patent No. 8088575.
Exhibit 1025, filed Apr. 30, 2013 in connection with IPR2013-00011: Columbia's Amended Complaint from *The Trustees of Columbia University in the City of New York* v. *Illumina, Inc.*, D. Del C.A. No. 12-376 (GMS), filed Apr. 11, 2012.
Exhibit 1026, filed Apr. 30, 2013 in connection with IPR2013-00011: Illumina's Answer to Amended Complaint from *The Trustees of Columbia University in the City of New York* v. *Illumina, Inc.*, D. Del C.A. No. 12-376 (GMS), filed Dec. 21, 2012.
Exhibit 1029, filed Jun. 18, 2013 in connection with IPR2013-00011: U.S. Pat. No. 4,772,691, issued Sep. 20, 1988.
Exhibit 1030, filed Jun. 18, 2013 in connection with IPR2013-00011: Rosenblum et al., "New Dye-Labeled Terminators for Improved DNA Sequencing Patterns," Nucleic Acid Research, 1997, vol. 25, No. 22, pp. 4500-4504.
Exhibit 1031, filed Jun. 18, 2013 in connection with IPR2013-00011: PCT International Publication No. WO 99/49082, published Sep. 30, 1999 to Invitrogen Corporation.
Exhibit 1032, filed Jun. 18, 2013 in connection with IPR2013-00011: U.S. Pat. No. 5,449,767, issued Sep. 12, 1995 to Ward et al.
Exhibit 1033, filed Jun. 18, 2013 in connection with IPR2013-00011: U.S. Pat. No. 5,948,648, issued Sep. 7, 1999 to Khan et al.
Exhibit 1034, filed Jun. 18, 2013 in connection with IPR2013-00011: Jun. 8, 2013 Videotaped Deposition Transcript of George M. Weinstock, Ph.D.
Exhibit 1036, filed Sep. 27, 2013 in connection with IPR2013-00011: "Next Generation Genomics: World Map of High-throughput Sequencers," Sep. 1, 2013.
Exhibit 1037, filed Sep. 27, 2013 in connection with IPR2013-00011: GB Application No. 2001 0029012, filed Dec. 4, 2001 by Balasubramanian et al.
Exhibit 1039, filed Sep. 27, 2013 in connection with IPR2013-00011: Videotaped Deposition Transcript of Dr. Xiaohai Liu, Mar. 20, 2013.
Exhibit 1040, filed Sep. 27, 2013 in connection with IPR2013-00011: Excerpt from videotaped Deposition Transcript of George M. Weinstock, Ph.D., Jun. 8, 2013.
Exhibit 1041, filed Sep. 27, 2013 in connection with IPR2013-00011: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.
Exhibit 1042, filed Sep. 27, 2013 in connection with IPR2013-00011: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2013-00011: Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2013-00011: Seela et al., "Duplex Stability of Oligonucleotides Containing 7-Substituted 7-Deaza- and 8-Aza-7-Deazapurine Nucleosides," Nucleosides & Nucleotides, 16(7- 9), pp. 963-966, 1997.
Exhibit 1045, filed Sep. 27, 2013 in connection with IPR2013-00011: Burgess et al., "Syntheses of Nucleosides Designed for Combinatorial DNA Sequencing," Chemistry—A European Journal, vol. 5, No. 3, pp. 951-960, 1999.
Exhibit 1046, filed Sep. 27, 2013 in connection with IPR2013-00011: U.S. Pat. No. 5,151,507, issued Sep. 29, 1992 to Hobbs, Jr. et al.
Exhibit 1047, filed Sep. 27, 2013 in connection with IPR2013-00011: U.S. Pat. No. 7,078,499, issued Jul. 18, 2006 to Odedra et al.
Exhibit 1048, filed Sep. 27, 2013 in connection with IPR2013-00011: GB Application No. 2000 0013276, filed Jun. 1, 2000 by Odedra et al.
Exhibit 1049, filed Sep. 27, 2013 in connection with IPR2013-00011: Jan. 28, 2013 Declaration of Dr. Bruce P. Branchaud in Support of Petition for Inter Partes Review of U.S. Pat. No. 7,057,026.
Exhibit 1050, filed Sep. 27, 2013 in connection with IPR2013-00011: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Sep. 27, 2013 in connection with IPR2013-00011: http://www.answers.com/topic/incubate, Accessed Sep. 27, 2013.
Exhibit 1052, filed Sep. 27, 2013 in connection with IPR2013-00011: http://en.wikipedia.org/wiki/Fluorenylmethyloxycarbonyl_chloride, Accessed Sep. 27, 2013.
Exhibit 1053, filed Sep. 27, 2013 in connection with IPR2013-00011: Sep. 27, 2013 in connection with IPR2013-00011: Sep.27, 2013 Declaration of Kevin Burgess.
Exhibit 1054, filed Sep. 27, 2013 in connection with IPR2013-00011: Fuji, et al., "An Improved Method for Methoxymethylation of Alcohols under Mild Acidic Conditions," Synthesis—The Journal of Synthetic Organic Chemistry, pp. 276-277, Apr. 1975.
Exhibit 2001, filed Jan. 7, 2013 in connection with IPR2013-00011: Composition of a Nucleotide.
Exhibit 2006, filed Apr. 26, 2013 in connection with IPR2013-00011: Dower patent with highlights.
Exhibit 2010, filed Jun. 24, 2013 in connection with IPR2013-00011: U.S. Pat. No. 8,088,575 (filed Jul. 19, 2010, issued Jan. 3, 2012) (Exhibit 1001 in IPR2013-00011).
Exhibit 2011, filed Jun. 24, 2013 in connection with IPR2013-00011: U.S. Pat. No. 7,713,698 (filed Aug. 20, 2007, issued May 11, 2010) (Exhibit 1001 in IPR2012-00006).
Exhibit 2012, filed Jun. 24, 2013 in connection with IPR2013-00011: U.S. Pat. No. 7,790,869 (filed Jun. 5, 2007, issued Sep. 7, 2010) (Exhibit 1001 in IPR2012-00007).
Exhibit 2013, filed Jun. 24, 2013 in connection with IPR2013-00011: Oct. 2, 2012 Declaration of George Weinstock Under 37 CFR 1.132 (Exhibit 1021 in IPR2013-00011).
Exhibit 2014, filed Jun. 24, 2013 in connection with IPR2013-00011: Petition for Inter Partes Review of U.S. Pat. No. 8,088,575 (Paper 4 in IPR2013-00011).
Exhibit 2015, filed Jun. 24, 2013 in connection with IPR2013-00011: Metzker et al. (1994) Termination of DNA synthesis by novel 3'-modified-deoxyribonucleoside 5'-triphosphates. Nucleic Acids Res. 22:4259-4267.
Exhibit 2016, filed Jun. 24, 2013 in connection with IPR2013-00011: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2017, filed Jun. 24, 2013 in connection with IPR2013-00011: Sep. 15, 2012 Declaration of George Weinstock Under 37 CFR 1.132 (Exhibit 1021 in IPR2012-00007).
Exhibit 2018, filed Jun. 24, 2013 in connection with IPR2013-00011: Sep. 15, 2012 Declaration of George Weinstock Under 37 CFR 1.132 (Exhibit 1021 in IPR2012-00006).
Exhibit 2019, filed Jun. 24, 2013 in connection with IPR2013-00011: Definition of "DNA microarray." http://en/wikipedia.org/wiki/DNA microarray.
Exhibit 2020, filed Jun. 24, 2013 in connection with IPR2013-00011: Brettin et al. (2005) Expression capable library for studies of Neisseria gonorrhoeae, version 1.0 BMC Microbiology. 5:50.
Exhibit 2021, filed Jun. 24, 2013 in connection with IPR2013-00011: George M. Weinstock, Handbook of Molecular Microbial Ecology,

(56) References Cited

OTHER PUBLICATIONS vol. 1-Chapter 18: The Impact of Next-Generation Sequencing Technologies on Metagenomics 141-147 Frans J. de Bruijn ed., John Wiley & Sons, Inc. (2011).
Exhibit 2022, filed Jun. 24, 2013 in connection with IPR2013-00011: Sep. 16, 2012 Petition for Inter Partes Review of U.S. Pat. No. 7,713,698 (Paper 3 in IPR2012-00006).
Exhibit 2023, filed Jun. 24, 2013 in connection with IPR2013-00011: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2013-00011: Maxam and Gilbert (1977) A new method for sequencing DNA, Proc. Natl. Acad. Sci. USA. 74:560-564.
Exhibit 2025, filed Jun. 24, 2013 in connection with IPR2013-00011: Sanger et al. (1977) DNA sequencing with chain-terminating inhibitors, Proc. Natl. Acad. Sci. USA. 74:5463-5467.
Exhibit 2026, filed Jun. 24, 2013 in connection with IPR2013-00011: Pennisi (2000) DOE Team Sequences Three Chromosomes, Science. 288:417-419.
Exhibit 2027, filed Jun. 24, 2013 in connection with IPR2013-00011: Welch and Burgess (1999) Synthesis of Fluorescent, Photolabile 3'-O-Protected nucleoside Triphosphates for the Base Addition Sequencing Scheme, nucleosides & Nucleotides. 18:197-201.
Exhibit 2028, filed Jun. 24, 2013 in connection with IPR2013-00011: Hyman (1998) A New Method of Sequencing DNA, Analytical Biochemistry 174:423-436.
Exhibit 2029, filed Jun. 24, 2013 in connection with IPR2013-00011: U.S. Pat. No. 5,302,509 (filed Feb. 27, 1991, issued Apr. 12, 1994).
Exhibit 2030, filed Jun. 24, 2013 in connection with IPR2013-00011: Canard and Sarfati (1994) DNA polymerase fluorescent substrates with reversible 3'-tags, Gene. 1481-6.
Exhibit 2031, filed Jun. 24, 2013 in connection with IPR2013-00011: U.S. Pat. No. 8,399,188 (filed Sep. 4, 2007, issued Mar. 19, 2013).
Exhibit 2032, filed Jun. 24, 2013 in connection with IPR2013-00011: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2013-00011: Jun. 25, 2013 Substitute Declaration of Dr. George L. Trainor [redacted].
Exhibit 2034, filed Jun. 25, 2013 in connection with IPR2013-00011: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2013 in connection with IPR2013-00011: Batista et al. (2008) PRG-1 and 21U-RNAs Interact to Form the piRNA Complex Required for Fertility in C. elegans. Molecular Cell 31:1-12.
Exhibit 2036, filed Jun. 25, 2013 in connection with IPR2013-00011: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2037, filed Jun. 25, 2013 in connection with IPR2013-00011: Oct. 1, 2006 Request for opinion on manuscript by J. Ju et. al., Proceedings of National Academy of Sciences, U.S.A.
Exhibit 2038, filed Jun. 25, 2013 in connection with IPR2013-00011: Correspondence between George Rupp, Chancellor, Columbia University and Richard T. Schlossberg, President, The David and Lucile Packard Foundation (2001).
Exhibit 2039, filed Jun. 25, 2013 in connection with IPR2013-00011: The David and Lucile Packard Foundation, Packard Fellowships for Science and Engineering, http://www.packard.org/what-wefund/conservation-and-science/packard-fellowships-for-science-andengineering/ (last visited Jun. 25, 2013).
Exhibit 2040, filed Jun. 26, 2013 in connection with IPR2013-00011: "Chemistry for Next-Generation Sequencing." http://www.illumina.com/technology/sequencing technology.ilmn.
Exhibit 2041, filed Jun. 26, 2013 in connection with IPR2013-00011: Chiang et al. (2010) Mammalian microRNAs: experimental evaluation of novel and previously annotated genes, Genes & Dev. 24:992, 993.
Exhibit 2042, filed Jun. 26, 2013 in connection with IPR2013-00011: Seo et al. (2004) Photocleavable fluorescent nucleotides for DNA sequencing on a chip constructed by site-specific coupling chemistry, Proc. Natl Acad. Sci. 101(15):5488-5493.
Exhibit 2043, filed Jun. 26, 2013 in connection with IPR2013-00011: Curriculum vitae of Mr. Raymond S. Sims.
Exhibit 2044, filed Jun. 26, 2013 in connection with IPR2013-00011: Prior Testimony of Mr. Raymond S. Sims.
Exhibit 2045, filed Jun. 26, 2013 in connection with IPR2013-00011: Documents reviewed by Mr. Raymond S. Sims in this Proceeding.
Exhibit 2052, filed Jun. 26, 2013 in connection with IPR2013-00011: Gary Schroth Proof of Chiang Paper.
Exhibit 2074, filed Jun. 26, 2013 in connection with IPR2013-00011: Information about Dr. Ju's intellectual property sent to Illumina.
Exhibit 2090, filed Jun. 26, 2013 in connection with IPR2013-00011: IPR Default Protective Order.
Exhibit 2091, filed Jun. 26, 2013 in connection with IPR2013-00011: Declaration of Raymond S. Sims.
Exhibit 2092, filed Oct. 1, 2013 in connection with IPR2013-00011: Rough transcript of the Sep. 4, 2013 deposition of Dr. George L. Trainor.
Exhibit 2093, filed Oct. 1, 2013 in connection with IPR2013-00011: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2013-00011: Final transcript of the Sep. 4-6, 2013 deposition of Dr. George L. Trainor.
Exhibit 2095, filed Oct. 1, 2013 in connection with IPR2013-00011: Final transcript of the Sep. 3, 2013 deposition of Raymond S. Sims.
Exhibit 2099, filed Nov. 12, 2013 in connection with IPR2013-00011: Welch, M., et al (2005) Corrigenda to Syntheses of Nucleosides Designed for Combinatorial DNA Sequencing Chem. Eur.J., 1999, 951-960. Published in Chem. Eur. J, 2005, 11, 7136-7145.
Exhibit 2100, filed Nov. 12, 2013 in connection with IPR2013-00011: Welch, M (1999) "Base Additions Sequencing Scheme (BASS) and Studies Toward New Sequencing Methodologies." PhD. Dissertation, Texas A&M University.
Exhibit 2101, filed Nov. 12, 2013 in connection with IPR2013-00011: Lu and Burgess (2006) "A Diversity Oriented Synthesis of 3'-O-modified nucleoside triphosphates for DNA 'Sequencing by Synthesis'." Bioorganic & Medicinal Chemistry Letters, 16, 3902-3905.
Exhibit 2102, filed Nov. 12, 2013 in connection with IPR2013-00011: Advanced Sequencing Technology Awards 2004. http://www.genome.gov/12513162 (accessed Oct. 14, 2013).
Exhibit 2103, filed Nov. 12, 2013 in connection with IPR2013-00011: Welch and Burgess (2006) Erratum to Synthesis of Fluorescent, Photolabile 3'-O-Protected Nucleoside Triphosphates for the Base Addition Sequencing Scheme, Nucleosides & Nucleotides,18:197-201. Published in Nucleosides, Nucleotides and Nucleic Acids, 25:1, 119.
Nov. 26, 2013 Petitioner's Response to Motion for Observations in connection with IPR2013-00011.
Nov. 26, 2013 Patent Owner's Opposition to Petitioner's Motion to Exclude in connection with IPR2013-00011.
Nov. 26, 2013 Petitioner's Opposition to Motion to Exclude in connection with IPR2013-00011.
Dec. 3, 2013 Petitioner Reply to Patent Owner's Opposition to Motion to Exclude in connection with IPR2013-00011.
Dec. 3, 2013 Patent Owner Reply on Motion to Exclude in connection with IPR2013-00011.
May 4, 2013 Petition for Inter Partes Review of U.S. Pat. No. 8,158,346, issued Apr. 17, 2012.
Aug. 5, 2013 Patent Owner Preliminary Response to Petition for Inter Partes Review of U.S. Pat. No. 8,158,246, issued Apr. 17, 2012.

(56) References Cited

OTHER PUBLICATIONS

Exhibit 1001, filed May 4, 2013 in connection with IPR2013-00266: U.S. Pat. No. 8,158,346, issued Apr. 17, 2012 to Shankar Balasubramanian et al.
Exhibit 1002, filed May 4, 2013 in connection with IPR2013-00266: U.S. Pat. No. 6,664,079, issued Dec. 16, 2003 to Jingyue Ju et al.
Exhibit 1003, filed May 4, 2013 in connection with IPR2013-00266: WO 02/29003, published Apr. 11, 2002 to Jingyue Ju et al.
Exhibit 1004, filed May 4, 2013 in connection with IPR2013-00266: Kamal et al., A Mild and Rapid Regeneration of Alcohols from their Allylic Ethers by Chlorotrimethylsilane/ Sodium Iodide, 40 Tetrahedron Letters 371 (1999).
Exhibit 1005, filed May 4, 2013 in connection with IPR2013-00266: Jung et al., Conversion of Alkyl Carbamates into Amines vie Treatment with Trimethylsilyl Iodide, 7 J.C.S. Chem. Comm. 315 (1978).
Exhibit 1006, filed May 4, 2013 in connection with IPR2013-00266: WO 91/06678, published May 16, 1991 to Roger Tsien et al.
Exhibit 1007, filed May 4, 2013 in connection with IPR2013-00266: WO 00/53805, published Sep. 14, 2000 to Derek Stemple et al.
Exhibit 1008, filed May 4, 2013 in connection with IPR2013-00266: U.S. Pat. No. 7,078,499, issued Jul. 18, 2006 to Raj Odedra et al.
Exhibit 1009, filed May 4, 2013 in connection with IPR2013-00266: WO 01/92284, published Dec. 6, 2001 to Raj Odedra et al.
Exhibit 1010, filed May 4, 2013 in connection with IPR2013-00266: U.S. Pat. No. 5,547,839, issued Aug. 20, 1996 to William Dower et al.
Exhibit 1011, filed May 4, 2013 in connection with IPR2013-00266: May 3, 2013 Declaration of Dr. Bruce Branchaud.
Exhibit 1012, filed May 4, 2013 in connection with IPR2013-00266: Excerpts from the '346 Patent File History.
Exhibit 1013, filed May 4, 2013 in connection with IPR2013-00266: Excerpts from the file history of European Patent Application No: 02781434.2.
Exhibit 1014, filed May 4, 2013 in connection with IPR2013-00266: Sep. 16, 2013 Petition for Inter Partes Review of U.S. Pat. No. 7,713,698.
Exhibit 1015, filed May 4, 2013 in connection with IPR2013-00266: Sep. 16, 2013 Petition for Inter Partes Review of U.S. Pat. No. 7,790,869.
Exhibit 1016, filed May 4, 2013 in connection with IPR2013-00266: Oct. 3, 2013 Petition for Inter Partes Review of U.S. Pat. No. 8,088,575.
Exhibit 2001, filed Aug. 5, 2013 in connection with IPR2013-00266: Columbia's Apr. 11, 2012 Amended Complaint in connection with case No. C.A. No. 12-376-GMS.
Exhibit 2002, filed Aug. 5, 2013 in connection with IPR2013-00266: Columbia's Jan. 7, 2013 Amended Answer in connection with case No. C.A. No. 12-376-GMS.
Oct. 28, 2013 Decision Instituting Inter Partes Review in connection with IPR2013-00266.
Jan. 29, 2013 Petition for Inter Partes Review of U.S. Pat. No. 7,057,026.
Feb. 7, 2013 Revised Petition for Inter Partes Review of U.S. Pat. No. 7,057,026.
May 1, 2013 Preliminary Response under 37 C.F.R. 42.107 in connection with IPR2013-00128.
Jul. 29, 2013 Decision on Petition for Inter Partes Review in connection with IPR2013-00128.
Oct. 24, 2013 Patent Owner Motion to Amend the Patent in connection with IPR2013-00128.
Exhibit 1001, filed Jan. 29, 2013 in connection with IPR2013-00128: U.S. Pat. No. 7,057,026 to Colin Barnes et al.
Exhibit 1002, filed Jan. 29, 2013 in connection with IPR2013-00128: PCT Publication WO 00/53805 to Stemple et al.
Exhibits 1003-1005, filed Jan. 29, 2013 in connection with IPR2013-00128: PCT International Application No. PCT/JP97/00239, filed Jan. 31, 1997, published on Aug. 6, 1998 as Publication No. WO 98/33939 to Hitachi, LTD. with certified English translation, and Translation Affidavit.

Exhibit 1006, filed Jan. 29, 2013 in connection with IPR2013-00128: Beckman Coulter CEQTM 2000 DNA Analysis System User's Guide, Jun. 2000.
Exhibit 1007, filed Jan. 29, 2013 in connection with IPR2013-00128: U.S. Pat. No. 5,798,210 to Canard et al.
Exhibit 1008, filed Jan. 29, 2013 in connection with IPR2013-00128: U.S. Pat. No. 6,664,079 to Ju et al.
Exhibit 1009, filed Jan. 29, 2013 in connection with IPR2013-00128: PCT Publication WO 02/29003, published Apr. 11, 2002 to Ju et al.
Exhibit 1010, filed Jan. 29, 2013 in connection with IPR2013-00128: Kamal, Tetrahedron Letters 40(2):371-372, 1999.
Exhibit 1011, filed Jan. 29, 2013 in connection with IPR2013-00128: Jung, J.C.S. Chem. Comm. (7):315-316, 1978.
Exhibit 1012, filed Jan. 29, 2013 in connection with IPR2013-00128: PCT Publication WO 91/06678, published May 16, 1991 to Tsien et al.
Exhibit 1013, filed Jan. 29, 2013 in connection with IPR2013-00128: Prober et al., *Science 238*, 336-341 (1987).
Exhibit 1014, filed Jan. 29, 2013 in connection with IPR2013-00128: U.S. Pat. No. 5,547,839, issued Aug. 20, 1996 to Dower et al.
Exhibit 1015, filed Jan. 29, 2013 in connection with IPR2013-00128: Jan. 28, 2013 Declaration of Dr. Bruce Branchaud.
Exhibit 1016, filed Jan. 29, 2013 in connection with IPR2013-00128: Excerpts from the '026 Patent File History.
Exhibit 1017, filed Jan. 29, 2013 in connection with IPR2013-00128: Sep. 16, 2012 Petition for Inter Partes Review of U.S. Pat. No. 7,713,698.
Exhibit 1018, filed Jan. 29, 2013 in connection with IPR2013-00128: Sep. 16, 2012 Petition for Inter Partes Review of U.S. Pat. No. 7,790,869.
Exhibit 1019, filed Jan. 29, 2013 in connection with IPR2013-00128: Oct. 3, 2012 Petition for Inter Partes Review of U.S. Pat. No. 8,088,575.
Exhibit 1020, filed Jan. 29, 2013 in connection with IPR2013-00128: Transcript of Initial Conference Call Held on Aug. 29, 2013.
Exhibit 2001, filed May 1, 2013 in connection with IPR2013-00128: *The Trustees of Columbia University in the City of New York v. Illumina, Inc.*, 1:12-cv-00376-GMS—Columbia's Amended Complaint.
Exhibit 2002, filed May 1, 2013 in connection with IPR2013-00128: *The Trustees of Columbia University in the City of New York v. Illumina, Inc.*, 1:12-cv-00376-GMS—Columbia's Amended Answer.
Exhibit 2003, filed May 1, 2013 in connection with IPR2013-00128: *The Trustees of Columbia University in the City of New York v. Illumina, Inc.*, 1:12-cv-00376-GMS—INS's Responses to Illumina's Requests for Admission.
Exhibit 2004, filed May 1, 2013 in connection with IPR2013-00128: *The Trustees of Columbia University in the City of New York v. Illumina, Inc.*, 1:12-cv-00376-GMS—Columbia's Responses to Illumina's Requests for Admission.
Exhibit 2006, filed Oct. 24, 2013 in connection with IPR2013-00128: Green & Wuts, Protective Groups in Organic Synthesis, excerpts from "Protection From the Hydroxyl Group," (1999).
Exhibit 2007, filed Oct. 24, 2013 in connection with IPR2013-00128: Katagiri et al., "Selective Protection of the Primary Hydroxyl Groups of Oxetanocin A," Chem. Pharm. Bull. 43:884-886 (1995).
Exhibit 2008, filed Oct. 24, 2013 in connection with IPR2013-00128: U.S. Appl. No. 10/227,131, filed Aug. 23, 2002.
Exhibits 2009, 2010, and 2011, filed Oct. 24, 2013 in connection with IPR2013-00128: Declaration of Floyd Romesberg, Ph.D., Romesburg CV, and Romesburg list of documents reviewed.
Exhibit 2012, filed Oct. 24, 2013 in connection with IPR2013-00128: Oct. 3, 2013 Deposition Transcript of Bruce Branchaud, Ph.D.
Exhibit 2013, filed Oct. 24, 2013 in connection with IPR2013-00128: U.S. Pat. No. 7,078,499—Odedra, filed Mar. 24, 2003.
Exhibit 2014, filed Oct. 24, 2013 in connection with IPR2013-00128: PCT International Publication No. WO 01/92284—Odedra, published Dec. 6, 2001.
Exhibit 2015, filed Oct. 24, 2013 in connection with IPR2013-00128: PCT International Publication No. WO 96/27025—Rabini, published Sep. 6, 1996.

(56) References Cited

OTHER PUBLICATIONS

Exhibit 2016, filed Oct. 24, 2013 in connection with IPR2013-00128: Ruby, Methods in Enzymology (1990).
Exhibit 2017, filed Oct. 24, 2013 in connection with IPR2013-00128: U.S. Pat. No. 4,772,691—Herman, filed Jun. 5, 1985.
Exhibit 2018, filed Oct. 24, 2013 in connection with IPR2013-00128: PCT International Publication No. WO 99/49082—Short, published Sep. 30, 1999.
Exhibit 2019, filed Oct. 24, 2013 in connection with IPR2013-00128: Sanger, "DNA Sequencing with Chain-Inhibiting Terminators" PNAS 74(12):6463-5467 (1977).
Exhibit 2020, filed Oct. 24, 2013 in connection with IPR2013-00128: U.S. Pat. No. 5,302,509—Cheeseman, filed Feb. 27, 1991.
Exhibit 2021, filed Oct. 24, 2013 in connection with IPR2013-00128: Metzker, "Termination of DNA synthesis by novel 3'-modified deoxyribonucleoside 5'-triphosphates", Nucleic Acids Research 22(20): 4259-4267 (1994).
Exhibit 2022, filed Oct. 24, 2013 in connection with IPR2013-00128: Welch & Burgess, Nucleosides and Nucleotides, 18:197-201 (1999).
Exhibit 2023, filed Oct. 24, 2013 in connection with IPR2013-00128: Jun. 4, 2013 Declaration of Bruce Branchaud, Ph.D. in IPR2013-00324.
Exhibit 2024, filed Oct. 24, 2013 in connection with IPR2013-00128: PCT International Publication No. WO 89/10977—Southern, published Nov. 16, 1989.
Exhibit 2025, filed Oct. 24, 2013 in connection with IPR2013-00128: U.S. Pat. No. 7,057,026 file history.
Exhibit 2026, filed Oct. 24, 2013 in connection with IPR2013-00128: Maxam and Gilbert, "A New Method for Sequencing DNA" 74:560-564, PNAS (1977).
Exhibit 2028, filed Oct. 24, 2013 in connection with IPR2013-00128: Eric Vermaas Declaration, Oct. 24, 2013.
Jun. 4, 2013 Petition for Inter Partes Review of U.S. Pat. No. 7,057,026.
Exhibit 1001, filed Jun. 4, 2013 in connection with IPR2013-00324: U.S. Pat. No. 7,057,026, issued Jun. 6, 2006 to Colin Barnes et al.
Exhibit 1002, filed Jun. 4, 2013 in connection with IPR2013-00324: U.S. Pat. No. 7,078,499, issued Jul. 18, 2006 to Raj Odedra et al.
Exhibit 1003, filed Jun. 4, 2013 in connection with IPR2013-00324: WO 01/92284, published Dec. 6, 2001 to Raj Odedra et al.
Exhibit 1004, filed Jun. 4, 2013 in connection with IPR2013-00324: J. Meinwald, An Approach to the Synthesis of Pederin, 49 Pure and Appl. Chem. 1275 (1977).
Exhibit 1005, filed Jun. 4, 2013 in connection with IPR2013-00324: Takeshi Matsumoto et al., A Revised Structure of Pederin, 60 Tetrahedron Letters 6297 (1968).
Exhibit 1006, filed Jun. 4, 2013 in connection with IPR2013-00324: U.S. Pat. No. 5,547,839, issued Aug. 20, 1996 to William Dower et al.
Exhibit 1007, filed Jun. 4, 2013 in connection with IPR2013-00324: U.S. Pat. No. 5,798,210, issued Aug. 25, 1998 to Bruno Canard & Simon Sarfati.
Exhibit 1008, filed Jun. 4, 2013 in connection with IPR2013-00324: Beckman Coulter CEQ™ 2000 DNA Analysis System User's Guide, Jun. 2000.
Exhibit 1009, filed Jun. 4, 2013 in connection with IPR2013-00324: Jun. 4, 2013 Declaration of Dr. Bruce Branchaud.
Exhibit 1010, filed Jun. 4, 2013 in connection with IPR2013-00324: Excerpts from the '026 Patent File History.
Exhibit 1011, filed Jun. 4, 2013 in connection with IPR2013-00324: Excerpts from the file history of European Patent Application No. 02781434.2.
Nov. 21, 2013 Decision Denying Institution of Inter Partes Review of U.S. Pat. No. 7,057,026 in connection with IPR2013-00324.
Aug. 19, 2013 Petition 1 of 2 for Inter Partes Review of U.S. Pat. No. 7,566,537, issued Jul. 28, 2009.
Aug. 30, 2013 Revised Petition 1 of 2 for Inter Partes Review of U.S. Pat. No. 7,566,537, issued Jul. 28, 2009.
Exhibit 1001, filed Aug. 19, 2013 in connection with IPR2013-00517: U.S. Pat. No. 7,566,537, issued Jul. 28, 2009 to Shankar Balasubramanian et al.
Exhibit 1002, filed Aug. 19, 2013 in connection with IPR2013-00517: U.S. Pat. No. 6,664,079, issued Dec. 16, 2003 to Jingyue Ju et al.
Exhibit 1003, filed Aug. 19, 2013 in connection with IPR2013-00517: U.S. Appl. No. 09/684,670, filed Oct. 6, 2000 by Jingyue Ju et al.
Exhibit 1004, filed Aug. 19, 2013 in connection with IPR2013-00517: Zavgorodny et al., 1-Alkylthioalkylation of Nucleoside Hydroxyl Functions and Its Synthetic Applications: A New Versatile Method in Nucleoside Chemistry, 32 Tetrahedron Letters 7593 (1991).
Exhibit 1005, filed Aug. 19, 2013 in connection with IPR2013-00517: Protective Groups in Organic Synthesis (Theodora W. Greene & Peter G. M. Wuts eds., John Wiley & Sons, Inc. 3rd ed. 1999) (1991).
Exhibits 1006-1007, filed Aug. 19, 2013 in connection with IPR2013-00517: English translation of Loubinoux et al., Protection of Phenols by the Azidomethylene Group Application to the Synthesis of Unstable Phenols, 44 Tetrahedron 6055 (1988), and Translation Affidavit.
Exhibit 1008, filed Aug. 19, 2013 in connection with IPR2013-00517: WO 91/06678, published May 16, 1991 to Roger Tsien et al.
Exhibit 1009, filed Aug. 19, 2013 in connection with IPR2013-00517: Prober et al., A System for Rapid DNA Sequencing with Fluorescent Chain-Terminating Dideoxynucleotides, 238 Science 336 (1987).
Exhibit 1010, filed Aug. 19, 2013 in connection with IPR2013-00517: P 0251786 B1, issued Nov. 30, 1994 to George Leonard Trainor.
Exhibit 1011, filed Aug. 19, 2013 in connection with IPR2013-00517: Aug. 16, 2013 Declaration of Dr. Bruce Branchaud.
Exhibit 1012, filed Aug. 19, 2013 in connection with IPR2013-00517: Excerpts from the Mar. 20, 2013 Deposition Transcript of Dr. Xiaohai Liu.
Exhibit 1013, filed Aug. 19, 2013 in connection with IPR2013-00517: Sep. 16, 2012 Petition for Inter Partes Review of U.S. Pat. No. 7,713,698.
Exhibit 1014, filed Aug. 19, 2013 in connection with IPR2013-00517: Sep. 16, 2012 Petition for Inter Partes Review of U.S. Pat. No. 7,790,869.
Exhibit 1015, filed Aug. 19, 2013 in connection with IPR2013-00517: Oct. 3, 2012 Petition for Inter Partes Review of U.S. Pat. No. 8,088,575.
Apr. 3, 2013 Response to Office Action issued Oct. 3, 2012 in connection with U.S. Appl. No. 12/734,229.
Office Action issued Oct. 1, 2013 in connection with U.S. Appl. No. 12/734,229.
Apr. 1, 2014 Response to Office Action issued Oct. 1, 2013 in connection with U.S. Appl. No. 12/734,229.
Feb. 20, 2012 Response to Communication under Rule 70(2) and 70a(2) EPC issued Aug. 10, 2012 in connection with European Patent Application No. 08841439.6.

3'-O-Azido-dATP

3'-O-Azido-dGTP

3'-O-Azido-dCTP

3'-O-Azido-dTTP

SYNTHESIS OF CLEAVABLE FLUORESCENT NUCLEOTIDES AS REVERSIBLE TERMINATORS FOR DNA SEQUENCING BY SYNTHESIS

This application is a continuation of U.S. Ser. No. 12/734,227, filed Apr. 19, 2010, §371 national stage of PCT International Application No. PCT/US2008/011891, filed Oct. 17, 2008, and claims the benefit of U.S. Provisional Application No. 60/999,576, filed Oct. 19, 2007, the contents of each of which are hereby incorporated by reference in their entirety into this application.

This invention was made with government support under grant number P50-HG00358205 awarded by the National Institutes of Health. The government has certain rights in the invention.

This application incorporates-by-reference nucleotide and/or amino acid sequences which are present in the file named "131210_0575_78341-AA-PCT-US_Seq-Listing_JAK.txt", which is 5 kilobytes in size, and which was created Nov. 6, 2013 in the IBM-PCT machine format, having an operating system compatibility with MS-Windows, which is contained in the text file filed Dec. 10, 2013 as part of this application.

Throughout this application, various publications are referenced in parentheses by number. Full citations for these references may be found at the end of the specification immediately preceding the claims. The disclosures of these publications in their entireties are hereby incorporated by reference into this application to more fully describe the state of the art to which this invention pertains.

BACKGROUND OF THE INVENTION

The completion of the Human Genome Project (HGP) in early 2000 (1) was a monumental achievement with incredible amount of combined efforts among genome centers and scientists worldwide. The engine behind this decade long project was the Sanger sequencing method, which still currently maintains as the staple of large-scale genome sequencing methodology in high-throughput genome sequencing centers. The main reason behind this prolonged success was in the basic and efficient, yet elegant method that is Sanger dideoxy chain terminating reaction (2). With incremental improvements in this DNA sequencing technology including the use of laser induced fluorescent excitation of energy transfer dyes (3), engineered DNA polymerases (4) and capillary electrophoresis (5) as well as in the areas of sample preparation, informatics, and sequence analysis software (6-9), the Sanger sequencing platform has been able to maintain its status as champion in the sequencing world. Current state-of-the-art Sanger based DNA sequencers can produce over 700 bases of clearly readable sequence in a single run from templates up to 30 kb in length (10-12). However, as is with most of technological inventions, the continual improvements in this sequencing platform has come to a stagnant plateau, with the current cost estimate for producing a high-quality microbial genome draft sequence at around $10,000 per megabase pair. Current DNA sequencers based on the Sanger method allow up to 384 samples to be analyzed in parallel.

While fluorescent-based SBS methods have almost unlimited ability for parallelization, restricted only by the resolution of the imaging system, to date they have been limited to read lengths of about 35 bases. The successful implementation of sequencing by synthesis (SBS) is effectively dependent on the read length of the target DNA template. One of the major factors that determines the read length when performing SBS is the number of available templates. Our laboratory has recently developed two powerful approaches for SBS: 1) Hybrid SBS with nucleotide reversible terminator (NRTs, 3'-O—$R_1$-dNTPs) in combination with fluorescently labeled dideoxynucleotide (ddNTPs-$R_2$-fluorophore), and 2) SBS with cleavable fluorescent nucleotide reversible terminator (C—F-NRTs, 3'-O—$R_1$-dNTPs-$R_2$-fluorophore). ("Four-color DNA Sequencing with 3'-O-modified Nucleotide Reversible Terminators and Chemically Cleavable Fluorescent Dideoxynucleotides". J. Guo, N. Xu, Z. Li, S. Zhang, J. Wu, D. Kim, M. S. Marma, Q. Meng, H. Cao, X. Li, S. Shi, L. Yu, S. Kalachikov, J. Russo, N. J. Turro, J. Ju. Proceedings of the National Academy of Sciences USA. 2008, 105, 9145-9150) ("Four-Color DNA Sequencing by Synthesis Using Cleavable Fluorescent Nucleotide Reversible Terminators". J. Ju, D. Kim, L. Bi, Q. Meng, X. Bai, Z. Li, X. Li, M. S. Marma, S. Shi, J. Wu, J. R. Edwards, A. Romu, N. J. Turro. Proceedings of the National Academy of Sciences USA. 2006, 103, 19635-19640). Since the incorporation of ddNTPs-$R_2$-fluorophore into a strand of DNA permanently terminates further extensions of that template in the first approach and the incorporation and cleavage of C—F-NRTs leaves a tail of the modified nucleotide that causes possible steric hindrance to lower the incorporation efficiency of the subsequent base in the second approach, the total number of sequenceble templates decreases after each cycle of SBS reaction. Various means can be employed to minimize this rate of template reduction. Among those, a powerful method termed template "walking" can potentially diminish the negative effect of template termination or reduction and extend the read length of SBS at least two to three-fold.

SUMMARY OF THE INVENTION

A composition is provided having a first, second and third portion wherein the second portion has the following structure:

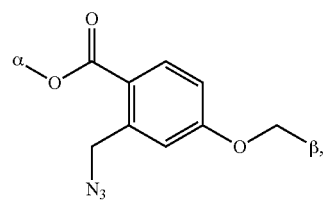

wherein α represents a point of attachment to the first portion and β represents a point of attachment to the third portion.

A method is provided for determining the identity of each of a series of consecutive nucleotide residues in a nucleic acid comprising:

a) contacting the nucleic acid with (i) at least four different deoxynucleotide triphosphate (dNTP) analogues, each having the structure:

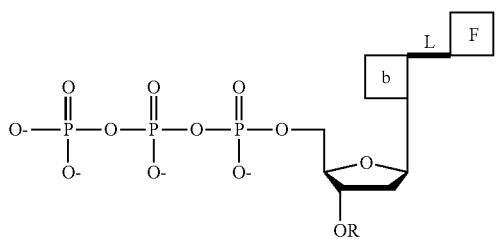

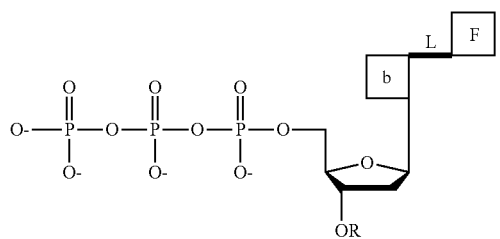

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

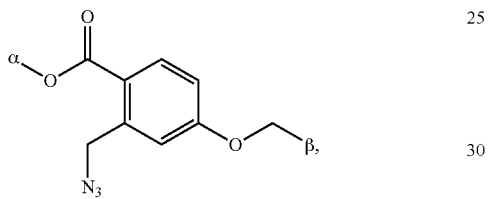

wherein α represents a point of attachment to the base and β represents a point of attachment to the fluorophore, and wherein R is a cleavable chemical group, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method is provided for determining the identity of each of a series of consecutive nucleotide residues in a self-priming nucleic acid comprising:

a) contacting the self-priming nucleic acid with (i) at least four different deoxynucleotide triphosphate (dNTP) analogues, each having the structure:

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

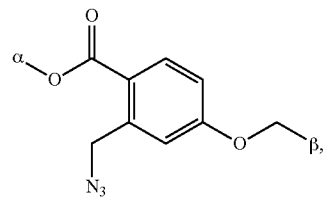

wherein α represents a point of attachment to the base and β represents a point of attachment to the fluorophore, and wherein R is a cleavable chemical group, and (ii) a nucleic acid polymerase, under conditions permitting (a) the self-priming nucleic acid to prime itself and (b) one of the four dNTP analogues that is complementary to the consecutive nucleotide residue to be identified to form a phosphodiester bond with the 3' end of the self-priming nucleic acid primer and thereby extend the self-priming nucleic acid;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the self-priming nucleic acid.

A kit is provided for use in sequencing a nucleic acid comprising:
a) a plurality of four nucleotide analogues having the structure:
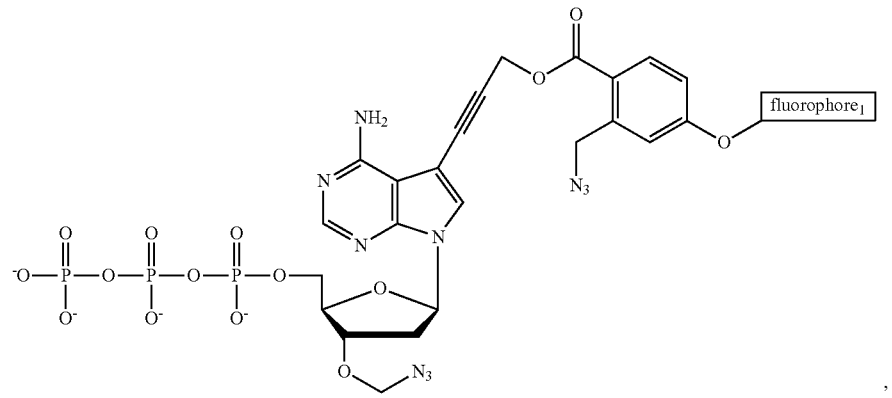
,
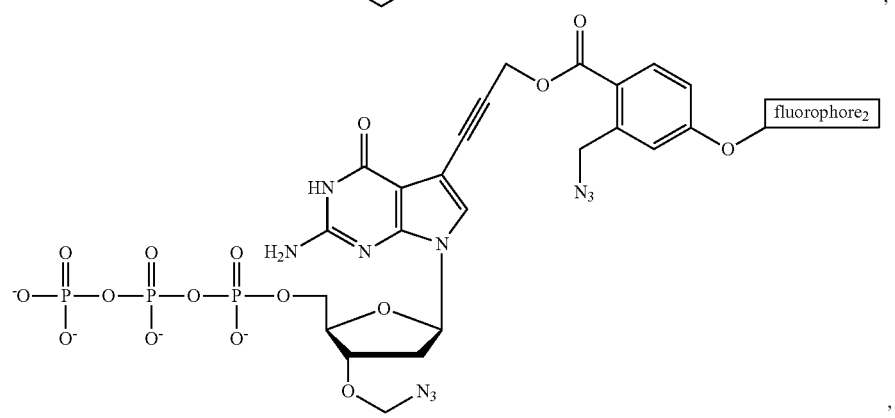
,
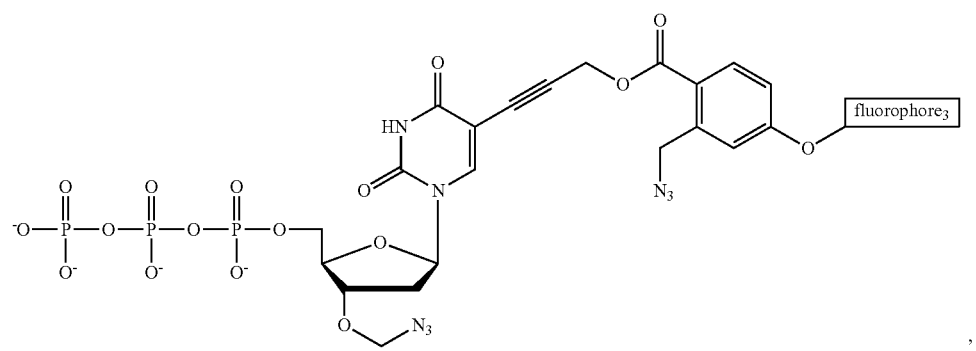
, and
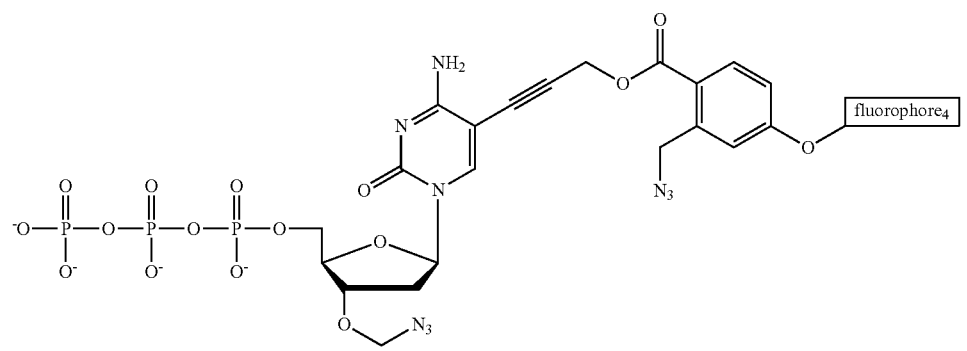
and b) instructions for use.

An array is provided comprising a nucleic acid attached to a solid surface, wherein the nucleic acid comprises an azidomethyl group attached to a 3' O atom thereof and a molecule having the structure:

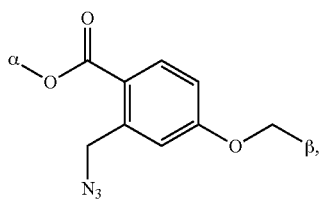

wherein α represents a point of attachment to a 3' base of the nucleic acid and β represents a point of attachment to a detectable marker.

An array is provided comprising a self-priming nucleic acid attached to a solid surface, wherein the nucleic acid comprises an azidomethyl group attached to a 3' O atom thereof and a molecule having the structure:

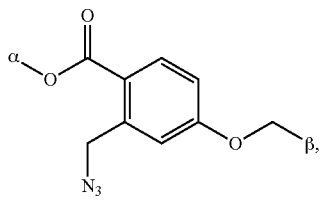

wherein α represents a point of attachment to a 3' base of the nucleic acid and β represents a point of attachment to a detectable marker.

A method is provided for increasing a read length of DNA sequencing by synthesis comprising (a) providing deoxynucleotide triphosphate analogues wherein the deoxynucleotide triphosphate analogues differ from deoxynucleotide triphosphates by having a methylazido group attached to a 3' O atom thereof and by having a detectable marker attached to a 1 nitrogen or a 9 nitrogen of a base thereof through a linker comprising the structure

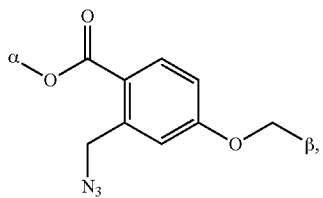

wherein α represents a point of attachment to a the base and β represents a point of attachment to the detectable marker, (b) incorporating a plurality of the deoxynucleotide triphosphate analogues into a nucleic acid being synthesized in the DNA sequencing by synthesis, and (c) cleaving the methylazido and detectable marker from each incorporated dNTP analogue, so as to thereby increase the readlength of the DNA sequence by synthesis.

A method for determining the identity of each of a series of consecutive nucleotide residues in a nucleic acid comprising:

a) contacting the nucleic acid with (i) at least four different deoxynucleotide triphosphate (dNTP) analogues, each having the structure:

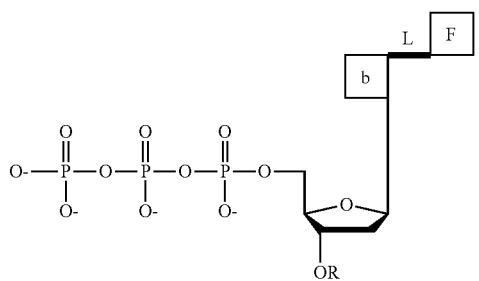

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

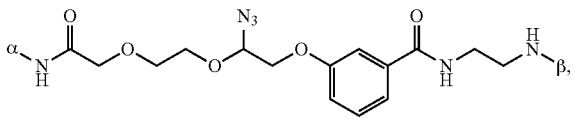

wherein α represents a point of attachment to the base and β represents a point of attachment to the fluorophore, and wherein R is a cleavable chemical group, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method for determining the identity of each of a series of consecutive nucleotide residues in a self-priming nucleic acid comprising:

a) contacting the self-priming nucleic acid with (i) at least four different deoxynucleotide triphosphate (dNTP) analogues, each having the structure:

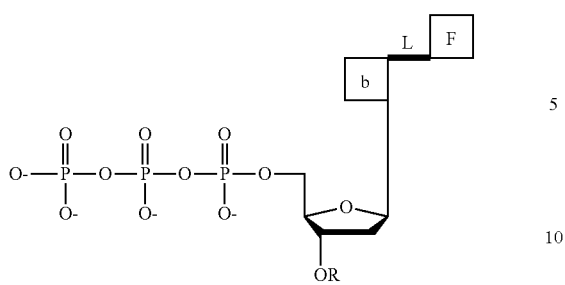

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

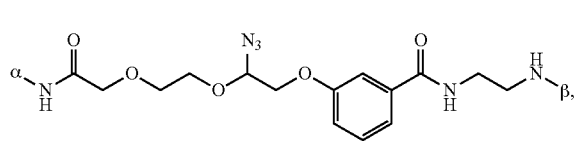

wherein α represents a point of attachment to the base and β represents a point of attachment to the fluorophore, and wherein R is a cleavable chemical group, and (ii) a nucleic acid polymerase, under conditions permitting (a) the self-priming nucleic acid to prime itself and (b) one of the four dNTP analogues that is complementary to the consecutive nucleotide residue to be identified to form a phosphodiester bond with the 3' end of the self-priming nucleic acid primer and thereby extend the self-priming nucleic acid;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the self-priming nucleic acid.

A method for determining the identity of each of a series of consecutive nucleotide residues in a plurality of nucleic acids comprising, the same series of consecutive nucleotides comprising:

a) contacting the nucleic acids with (i) at least four different dideoxynucleotide triphosphate (ddNTP) analogues, each having the structure:

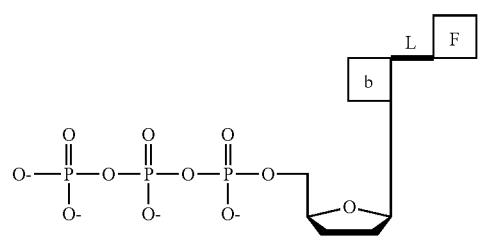

wherein F is a fluorophore, L is a cleavable linker molecule and b is a base which is adenine, guanine, cytosine, uracil or thymine, wherein the fluorophore attached through a linker to each type of base differs in its emission or excitation spectra from a fluorophore attached through a linker to each of the remaining types of bases, and each of the four ddNTP analogues differs from the remaining three ddNTP analogues by having a different base, and wherein L comprises the structure:

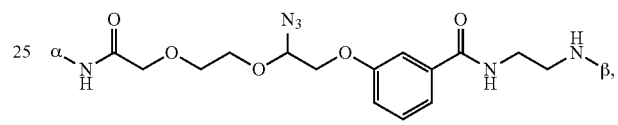

wherein α represents a point of attachment to the base of the dideoxynucleotide and β represents a point of attachment to the fluorophore, and (ii) at least four different deoxynucleotide triphosphate (dNTP) analogue, each having the structure:

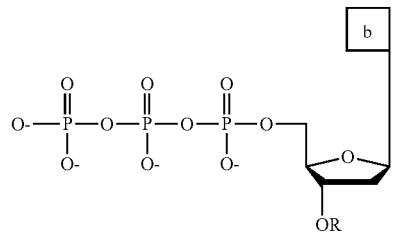

wherein b is a base which is adenine, guanine, cytosine, uracil or thymine, and each of the four dNTP analogues differs from the remaining three dNTP analogues by having a different base, and wherein R is a cleavable chemical group, (iii) a nucleic acid polymerase and (iv) at least two primers each of which hybridizes with a separate nucleic acid of the plurality of nucleic acids, under conditions permitting a ddNTP analogue that is complementary to the consecutive nucleotide residue in the nucleic acid to be identified to form a phosphodiester bond with the 3' end of one of the primers and a dNTP analogue that is complementary to the consecutive nucleotide residue to be identified to form a phosphodiester bond with the 3' end of another of the primers;

b) identifying the fluorophore of the ddNTP analogue which has formed the phosphodiester bond thereby identifying the identify of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method for determining the identity of consecutive nucleotide residues in a self-priming nucleic acid comprising:

a) contacting the nucleic acids with (i) at least four different dideoxynucleotide triphosphate (ddNTP) analogues, each having the structure:

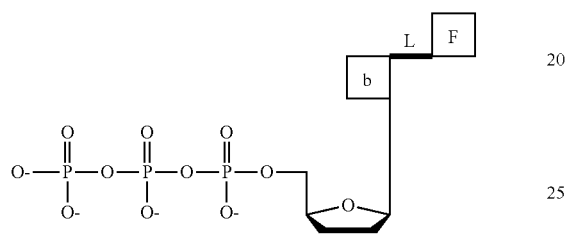

wherein F is a fluorophore, L is a cleavable linker molecule and b is a base which is adenine, guanine, cytosine, uracil or thymine, wherein the fluorophore attached through a linker to each type of base differs in its emission or excitation spectra from a fluorophore attached through a linker to each of the remaining types of bases, and each of the four ddNTP analogues differs from the remaining three ddNTP analogues by having a different base, and wherein L comprises the structure:

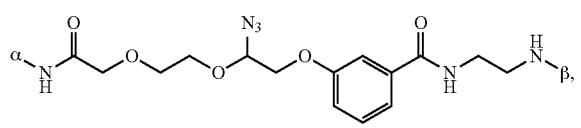

wherein α represents a point of attachment to the base of the dideoxynucleotide and β represents a point of attachment to the fluorophore, and (ii) at least four different deoxynucleotide triphosphate (dNTP) analogue, each having the structure:

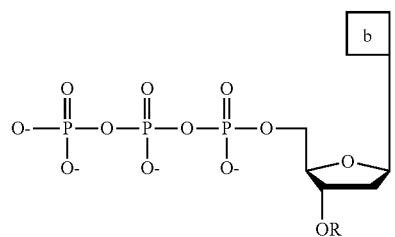

wherein b is a base which is adenine, guanine, cytosine, uracil or thymine, and each of the four dNTP analogues differs from the remaining three dNTP analogues by having a different base, and wherein R is a cleavable chemical group, (iii) a nucleic acid polymerase and (iv) at least two primers each of which hybridizes with a separate nucleic acid of the plurality of nucleic acids, under conditions permitting a ddNTP analogue that is complementary to the consecutive nucleotide residue to be identified to form a phosphodiester bond with the 3' end of one of the self-priming nucleic acids and a dNTP analogue that is complementary to the consecutive nucleotide residue to be identified to form a phosphodiester bond with the 3' end of another of the self-priming nucleic acids;

b) identifying the fluorophore of the ddNTP analogue which has formed the phosphodiester bond thereby identifying the identify of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A kit for use in sequencing a nucleic acid comprising:

a) a plurality of four dideoxynucleotide analogues having the structure:

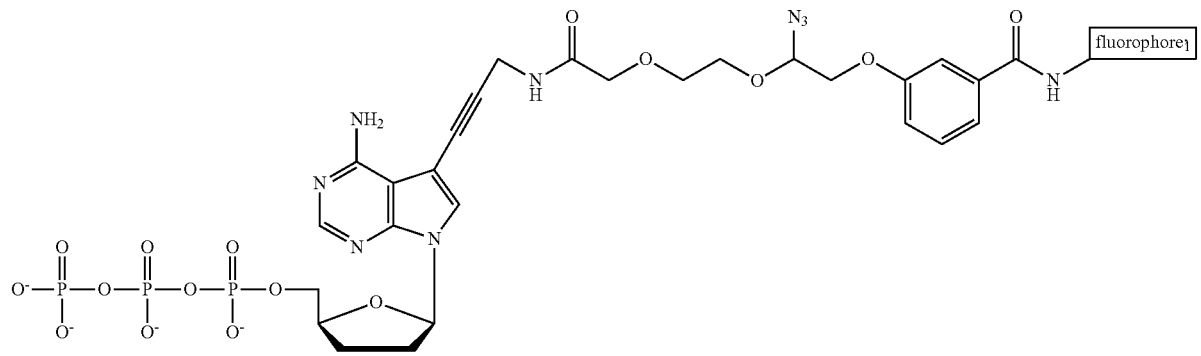

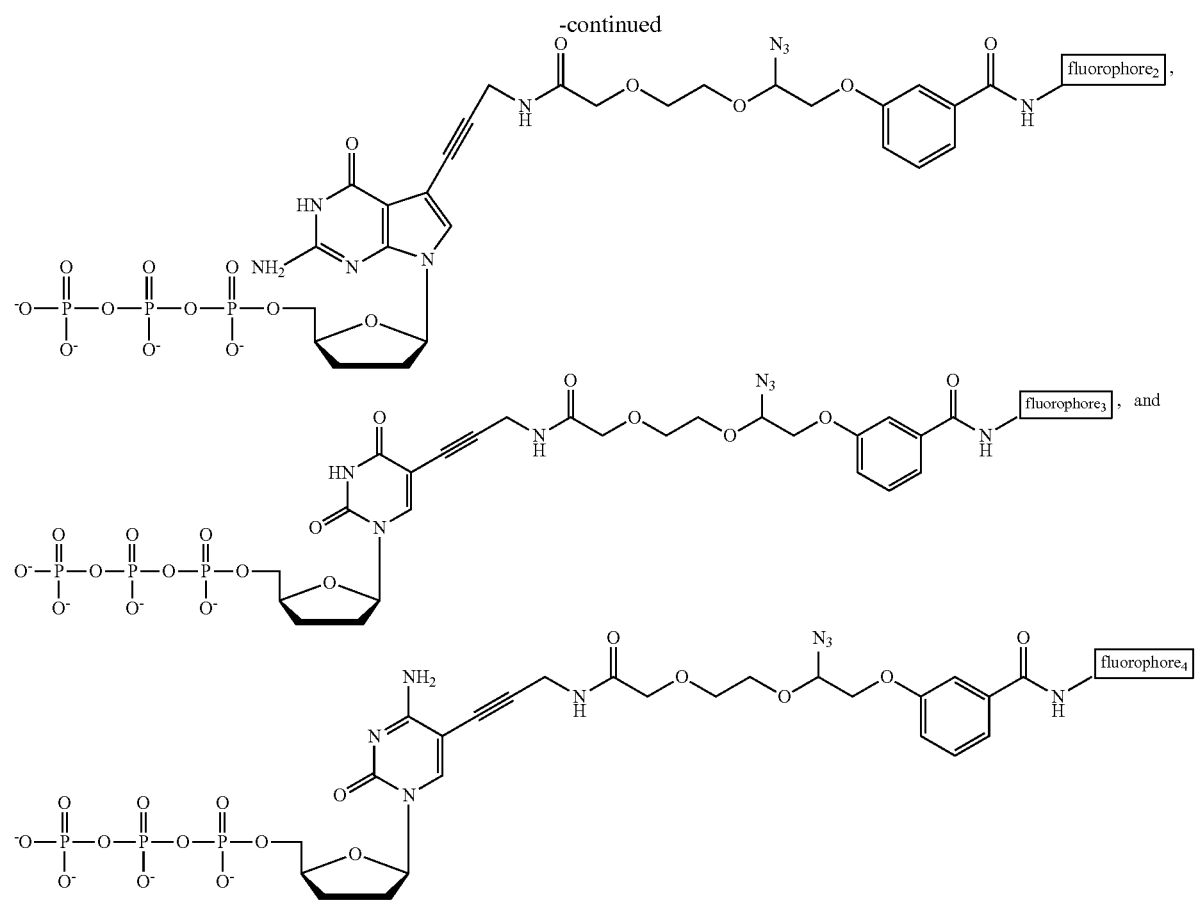
with
(b) a plurality of deoxynucleotide analogues having the structure:
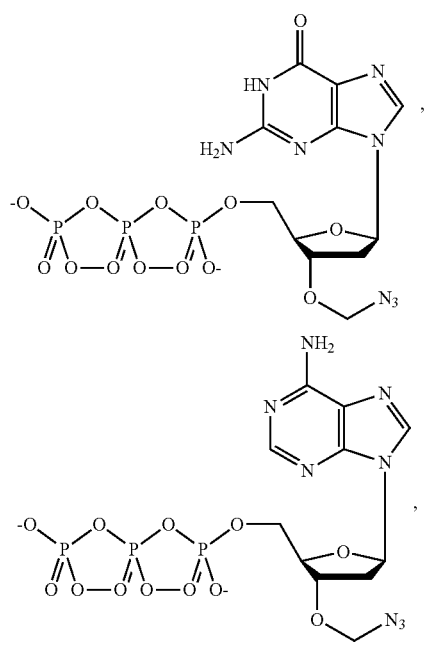
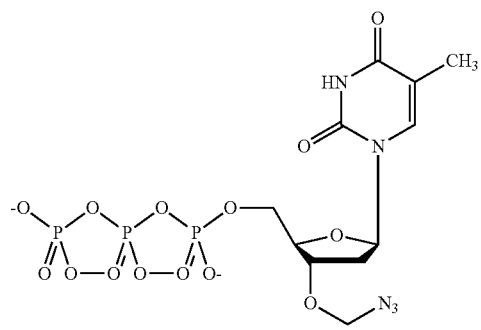
and
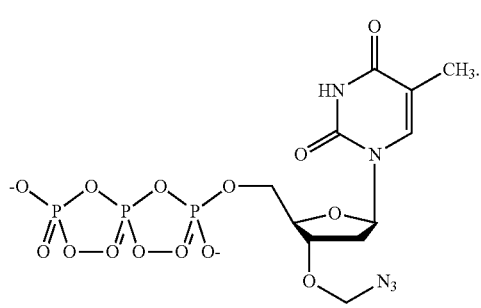
and
(c) instructions for use.

An array comprising a nucleic acid attached to a solid surface, wherein the nucleic acid comprises an azidomethyl group attached to a 3' O atom thereof and a molecule having the structure:

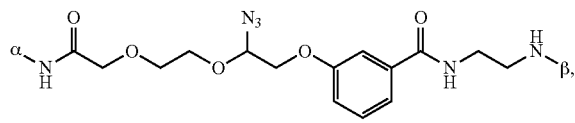

wherein α represents a point of attachment to a 3' base of the nucleic acid and β represents a point of attachment to a detectable marker.

An array comprising a self-priming nucleic acid attached to a solid surface, wherein the nucleic acid comprises an azidomethyl group attached to a 3' O atom thereof and a molecule having the structure:

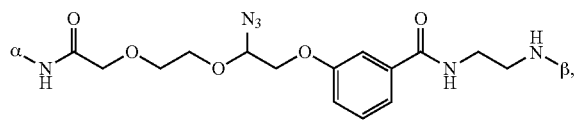

wherein α represents a point of attachment to a 3' base of the nucleic acid and β represents a point of attachment to a detectable marker.

A method is provided for increasing a read length of DNA sequencing by synthesis coupled with Sanger dideoxynucleotide terminating reaction (a) providing deoxynucleotide triphosphate analogues wherein the deoxynucleotide triphosphate analogues differ from deoxynucleotide triphosphates by having a methylazido group attached to a 3' O atom thereof and providing dideoxynucleotide triphosphate analogues wherein the dideoxynucleotide triphosphate analogues differ from dideoxynucleotide triphosphates by having a detectable marker attached to a 1 nitrogen or a 9 nitrogen of a base thereof through a linker comprising the structure

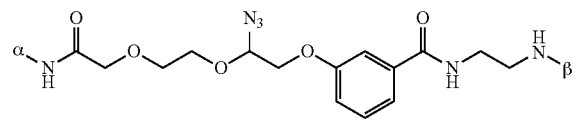

wherein α represents a point of attachment to a the base and β represents a point of attachment to the detectable marker, (b) incorporating a plurality ratio of dideoxynucleotide triphosphate to deoxynucleotide triphosphate analogues into a nucleic acid being synthesized in the DNA sequencing by synthesis and (c) cleaving the methylazido and detectable marker from each incorporated dNTP analogue, so as to thereby increase the readlength of the DNA sequence by synthesis

DETAILED DESCRIPTION OF THE INVENTION

Terms

Figure 1:
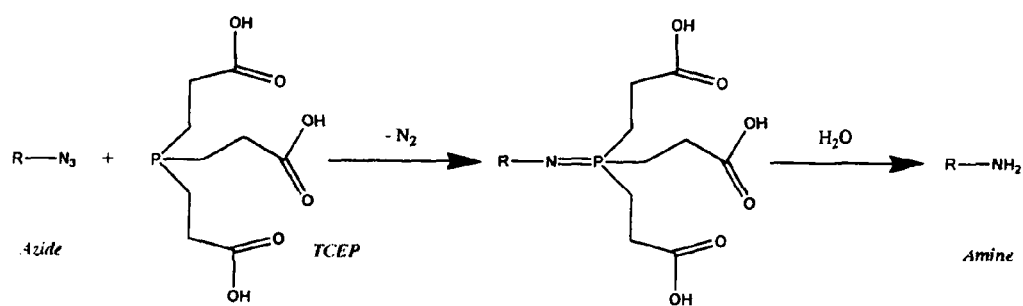
FIG. 1. Staudinger reduction with TCEP.

As used herein, and unless stated otherwise, each of the following terms shall have the definition set forth below.

A—Adenine;

C—Cytosine;

DNA—Deoxyribonucleic acid;

G—Guanine;

RNA—Ribonucleic acid;

T—Thymine; and

U—Uracil.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Type" of nucleotide refers to A, G, C, T or U. "Type" of base refers to adenine, guanine, cytosine, uracil or thymine.

"Mass tag" shall mean a molecular entity of a predetermined size which is capable of being attached by a cleavable bond to another entity.

"Solid substrate" shall mean any suitable medium present in the solid phase to which a nucleic acid or an agent may be affixed. Non-limiting examples include chips, beads and columns.

"Hybridize" shall mean the annealing of one single-stranded nucleic acid to another nucleic acid based on sequence complementarity. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.)

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Embodiments of the Invention

A composition is provided having a first, second and third portion wherein the second portion has the following structure:

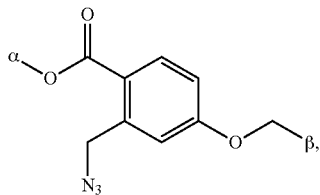

wherein α represents a point of attachment to the first portion and β represents a point of attachment to the third portion.

α may be directly linked to the first portion, e.g. comprising a base, or bonded to the for example base via, e.g. an alkynylene. β may be directly linked to the third portion, e.g. a detectable marker, or bonded to the third portion, for example via another group.

In an embodiment the first portion is a deoxynucleotide or a dideoxynucleotide and the third portion is a detectable marker. In an embodiment the detectable marker is a fluorescent dye. In an embodiment the deoxynucleotide or dideoxynucleotide comprises a methylazido group attached to a 3' O atom thereof.

In an embodiment the composition has the structure:

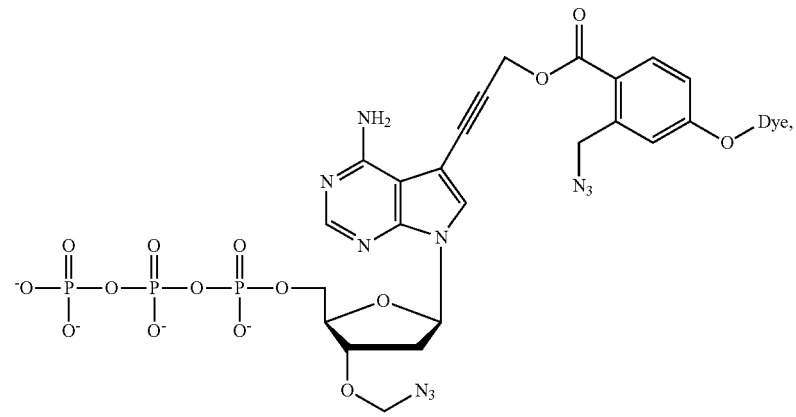

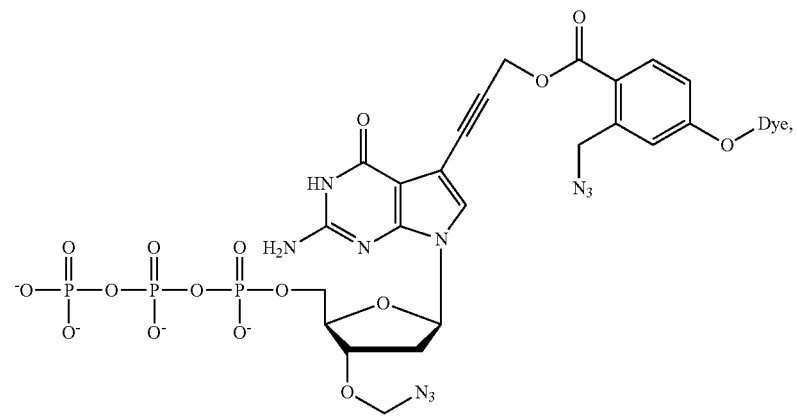

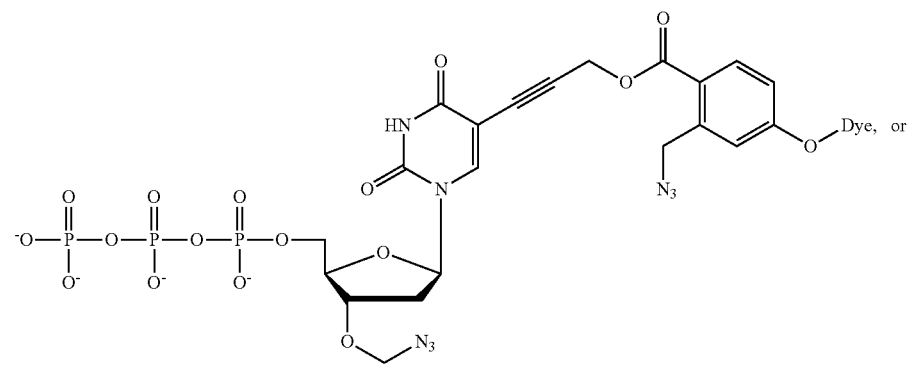

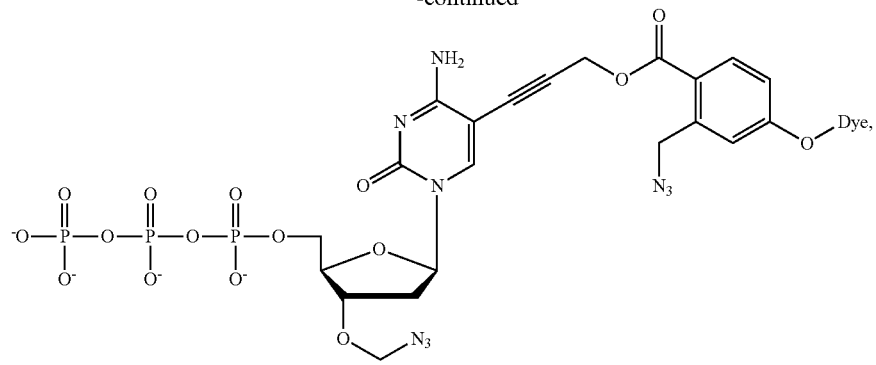
wherein the dye in each structure is a fluorescent dye.
In an embodiment the composition has the structure:
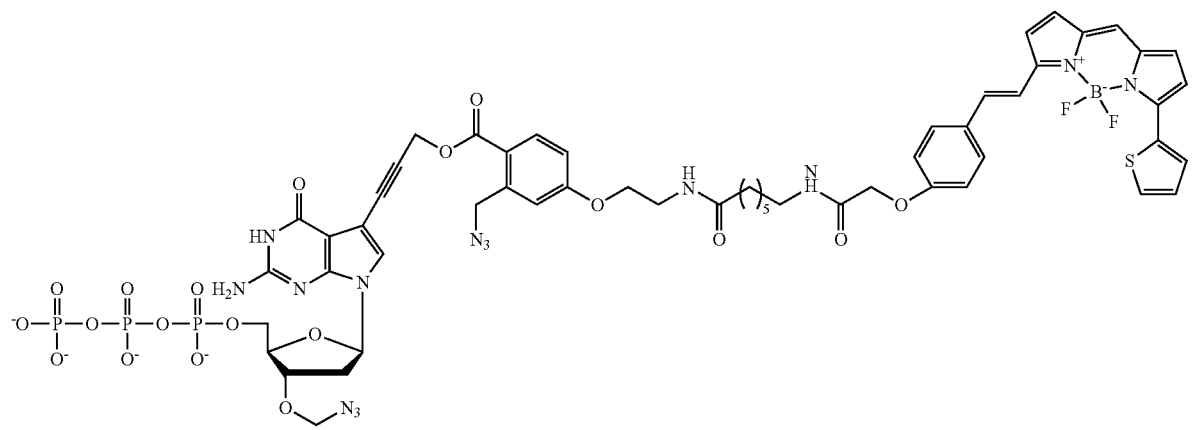
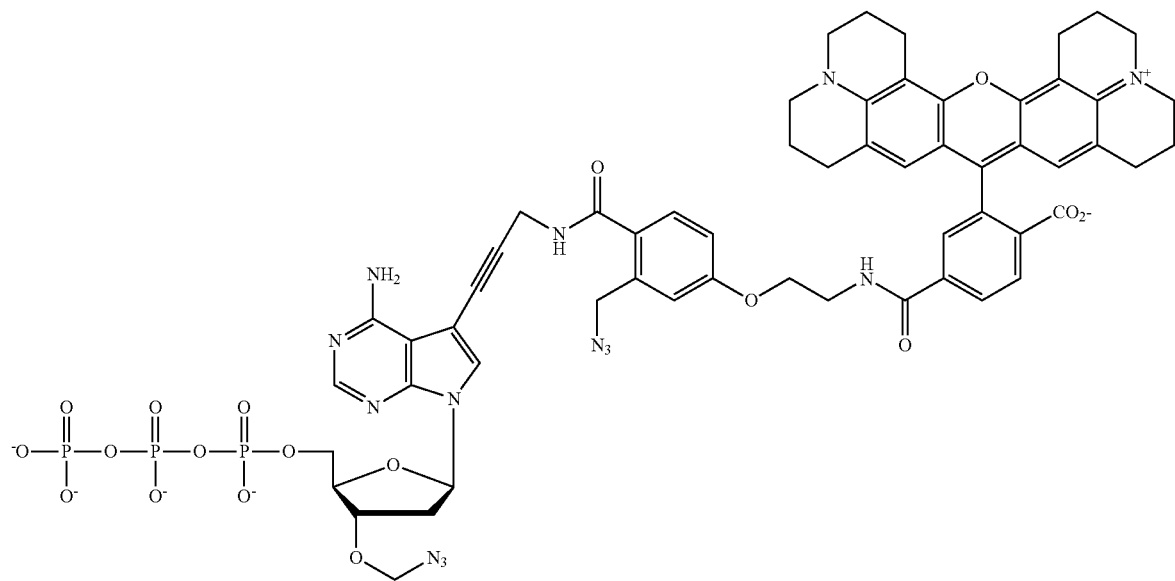

-continued

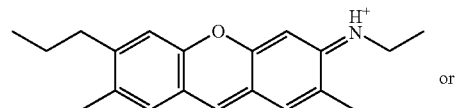
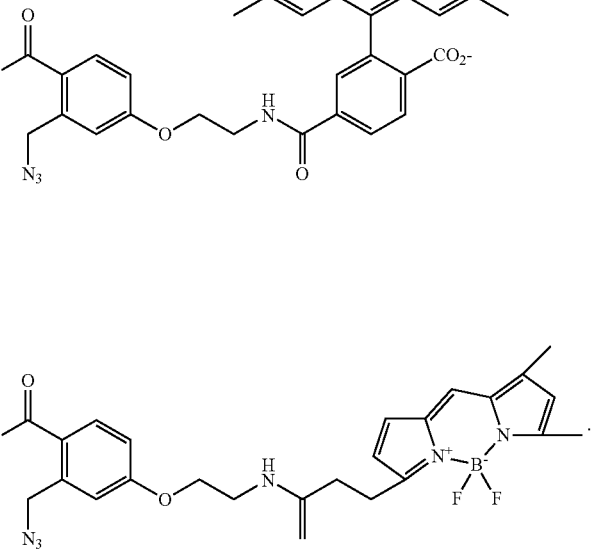

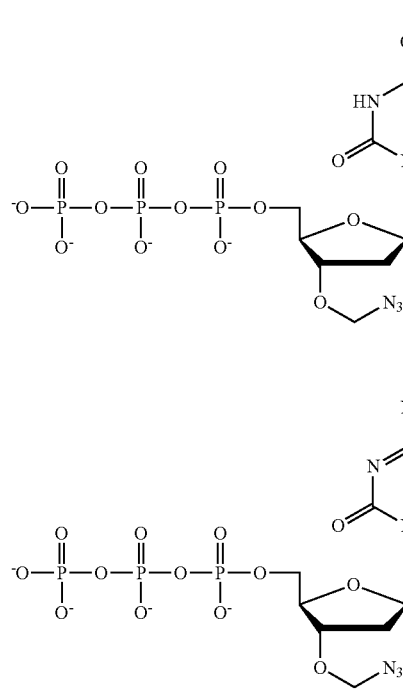

A method is provided for determining the identity of each of a series of consecutive nucleotide residues in a nucleic acid comprising:
a) contacting the nucleic acid with (i) at least four different deoxynucleotide triphosphate (dNTP) analogues, each having the structure:

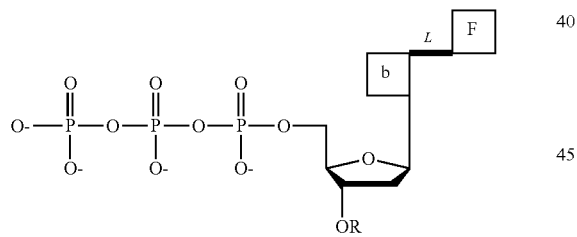

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

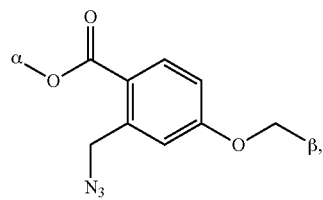

wherein α represents a point of attachment to the base and β represents a point of attachment to the fluorophore, and wherein R is a cleavable chemical group, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method is provided for determining the identity of each of a series of consecutive nucleotide residues in a self-priming nucleic acid comprising:
a) contacting the self-priming nucleic acid with (i) at least four different deoxynucleotide triphosphate (dNTP) analogues, each having the structure:

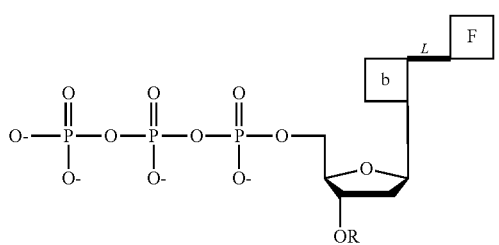

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

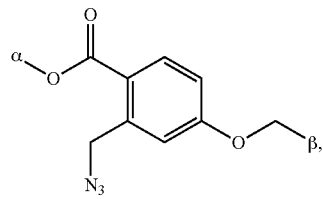

wherein α represents a point of attachment to the base and β represents a point of attachment to the fluorophore, and wherein R is a cleavable chemical group, and (ii) a nucleic acid polymerase, under conditions permitting (a) the self-priming nucleic acid to prime itself and (b) one of the four dNTP analogues that is complementary to the consecutive nucleotide residue to be identified to form a phosphodiester bond with the 3' end of the self-priming nucleic acid primer and thereby extend the self-priming nucleic acid;

b) identifying the fluorophore of the dNTP analogue which has formed the phosphodiester bond, thereby identifying the consecutive nucleotide;

c) contacting the dNTP analogue which has formed the phosphodiester bond with tris(2-carboxyethyl)phosphine so as to thereby (1) cleave the fluorophore and (2) cleave the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the self-priming nucleic acid.

In an embodiment of the instant methods, steps b) and c) can be performed simultaneously, or in the order step b) then step c) or in the order step c) then step b). In an embodiment of the instant methods, the nucleic acid is DNA and the nucleic acid polymerase is a 9°N thermopolymerase.

In an embodiment of the instant methods, the cleavable chemical group is a methylazido group. In an embodiment of the instant methods, the four dNTP analogues have the following structures:

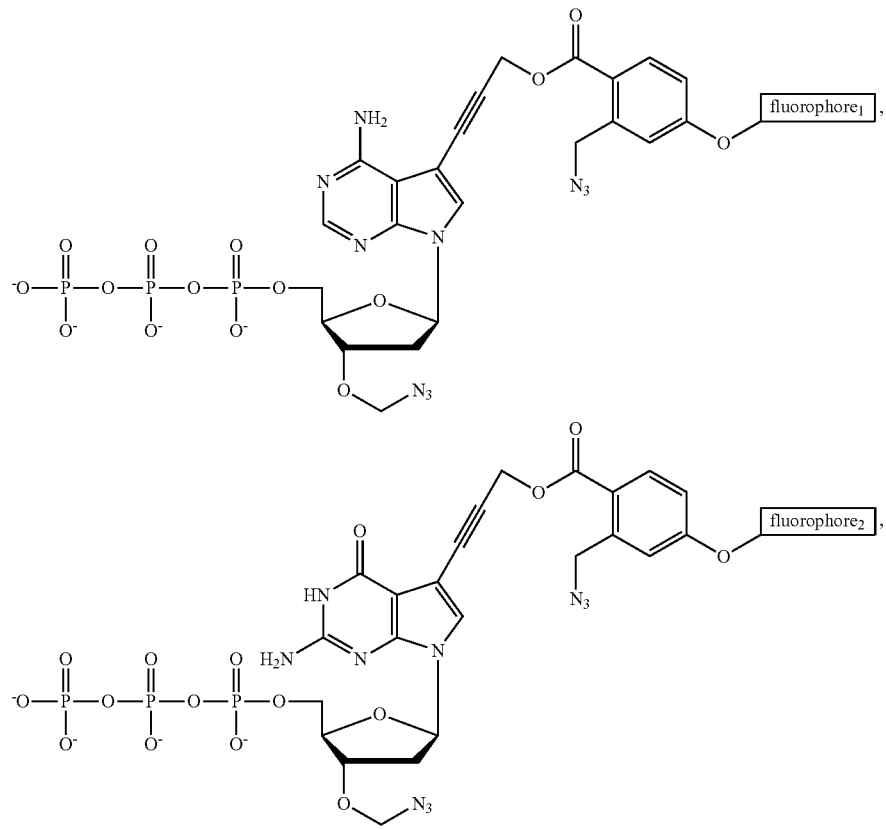

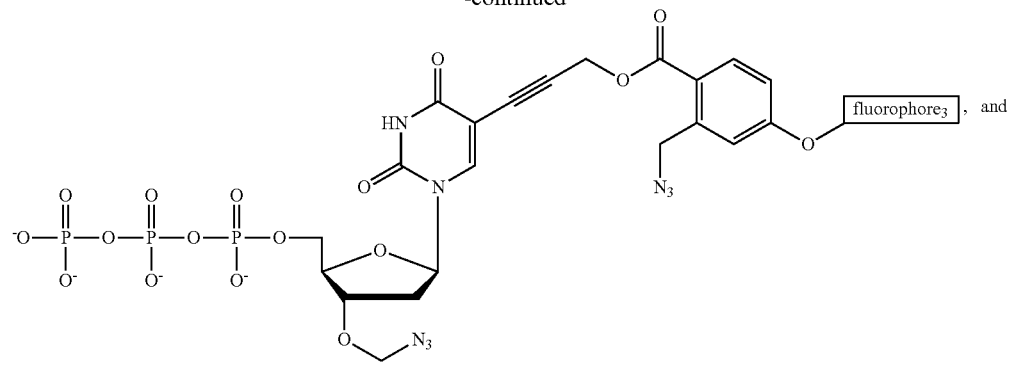
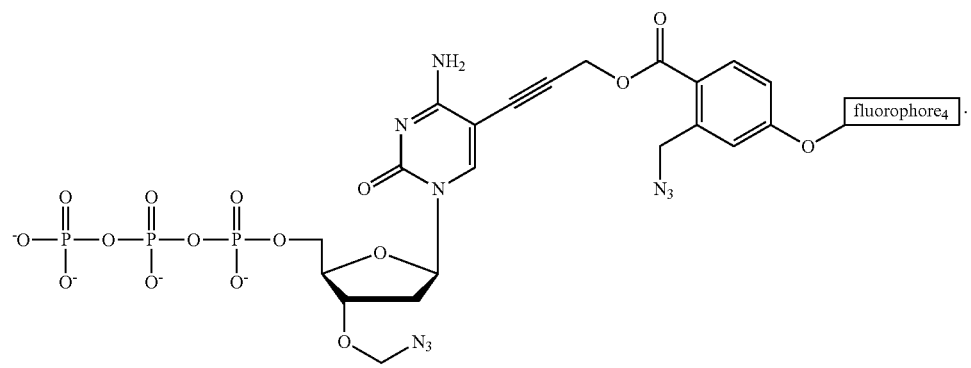
In an embodiment the four dNTP analogues have the following structures:
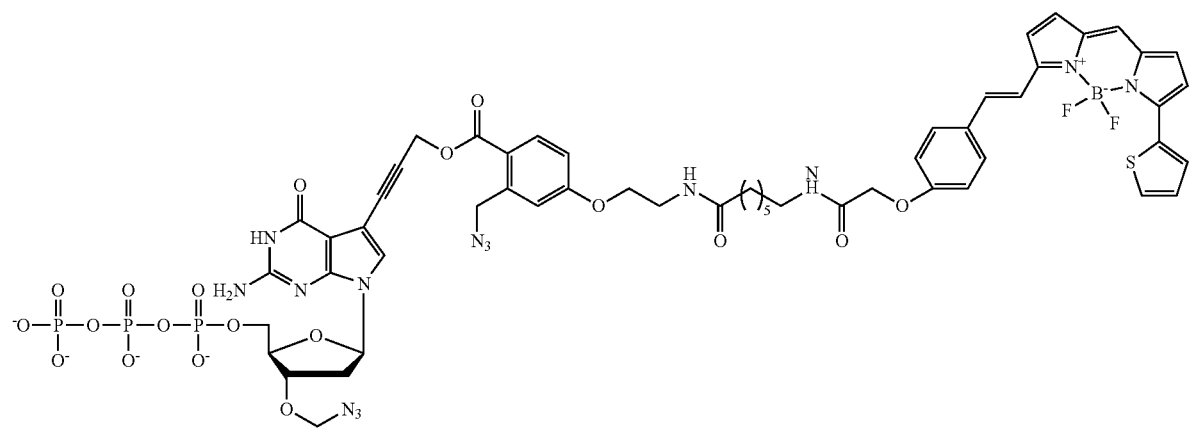

-continued
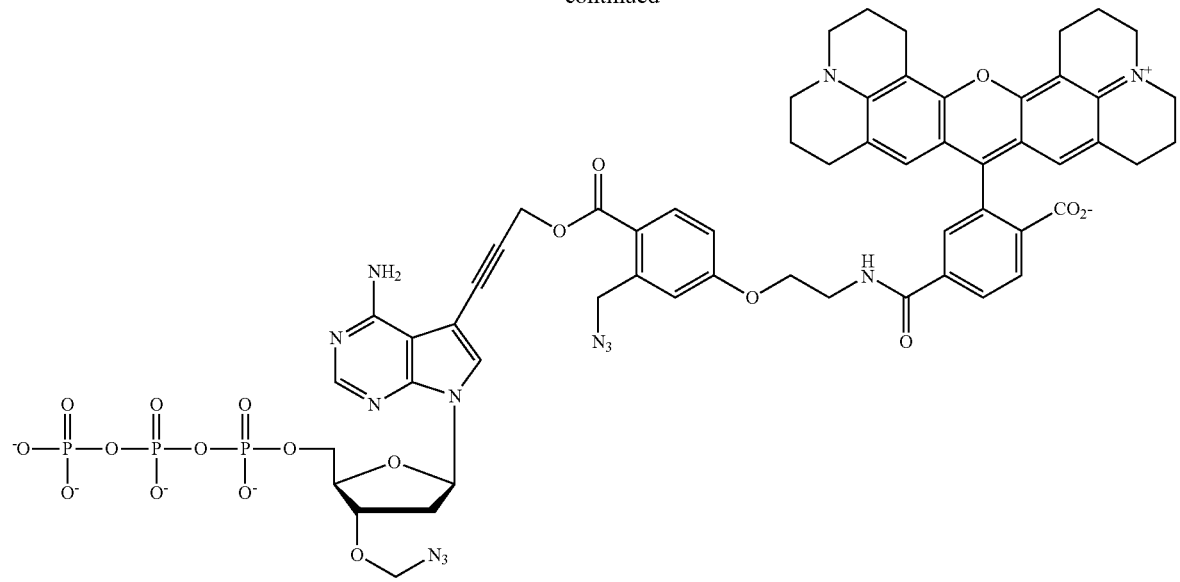
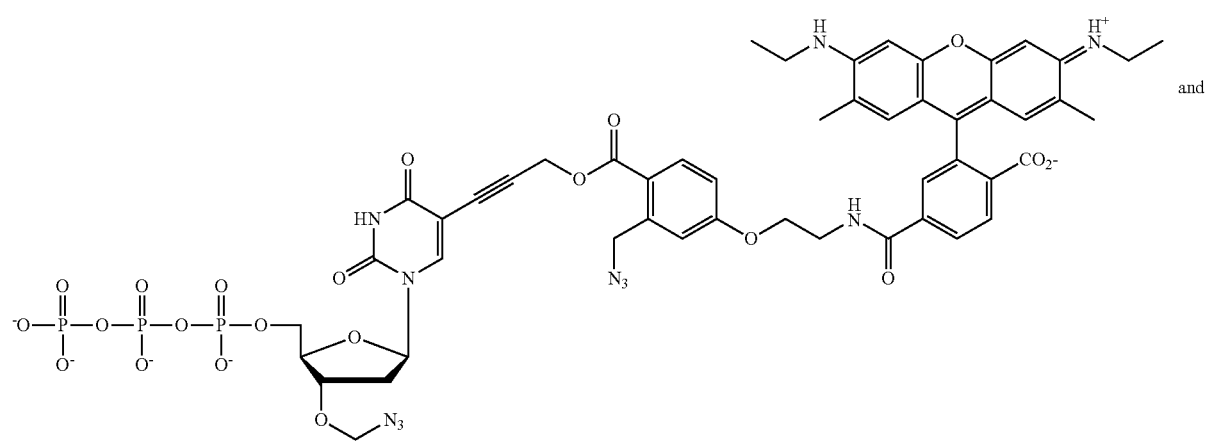
and
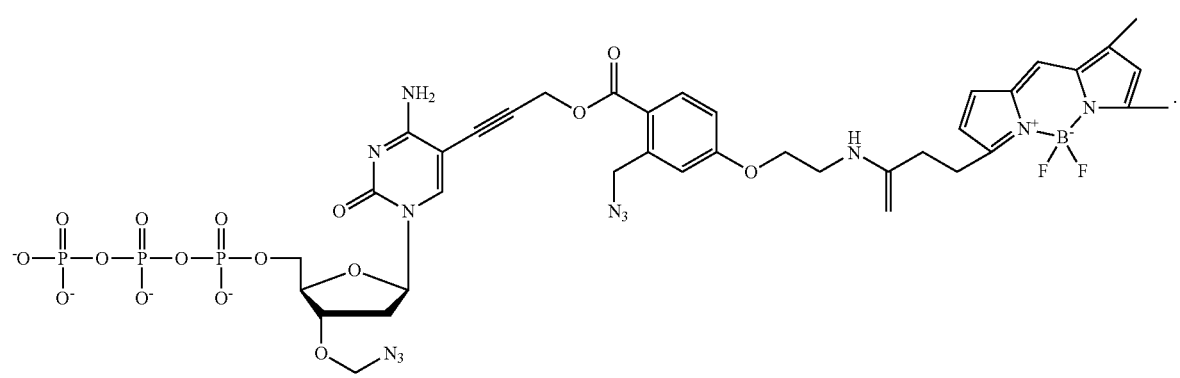
In an embodiment up to 1000 consecutive nucleotides are identified. In an embodiment up to $1 \times 10^4$ consecutive nucleotides are identified. In an embodiment up to $1 \times 10^6$ consecutive nucleotides are identified. In an embodiment the nucleic acid is immobilized on a solid surface. In an embodiment the solid surface is a chip or a bead.

A kit is provided for use in sequencing a nucleic acid comprising:
  a) a plurality of four nucleotide analogues having the structure:
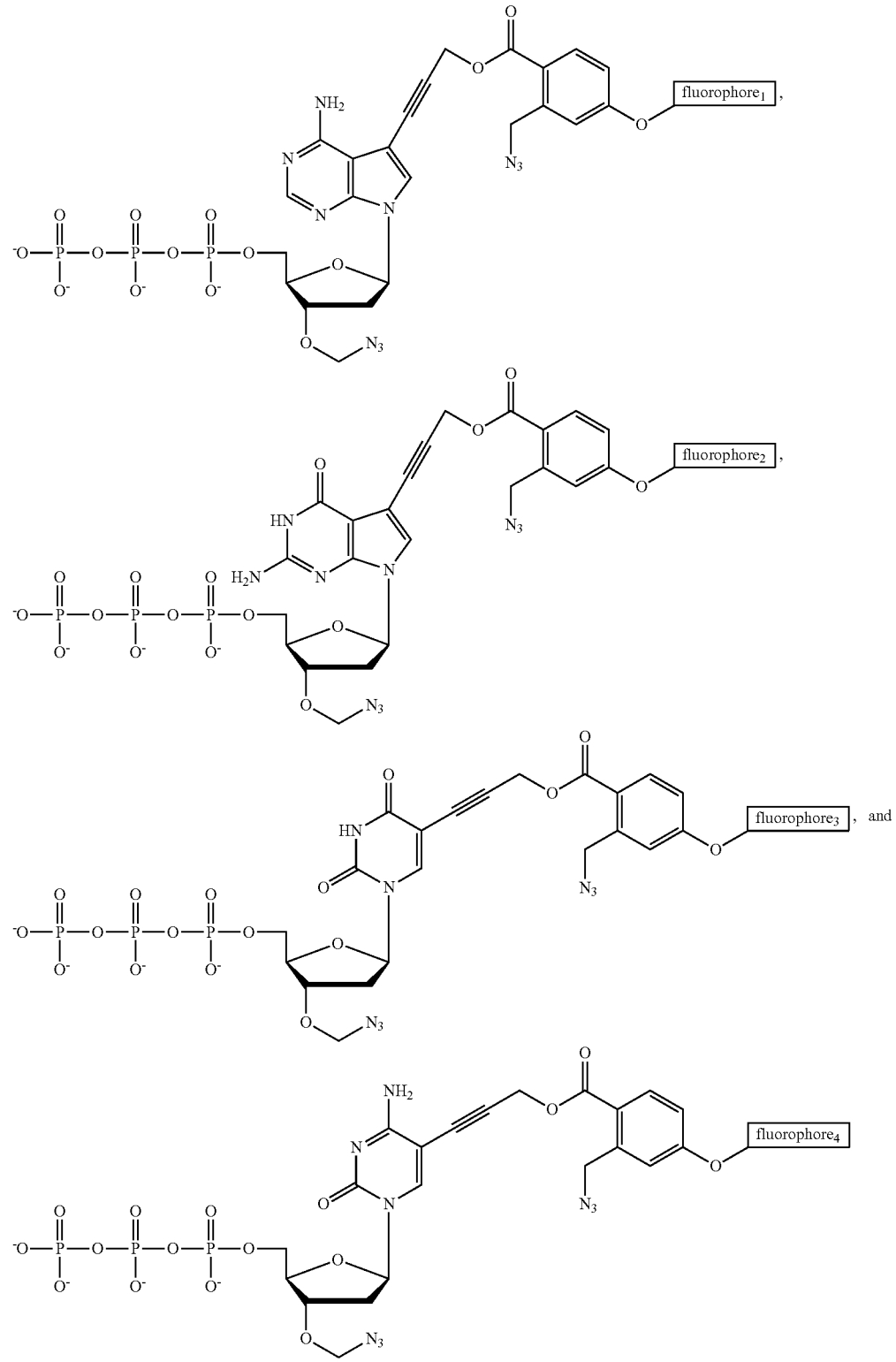
and
  (b) instructions for use.

In an embodiment four nucleotide analogues having the following structures:
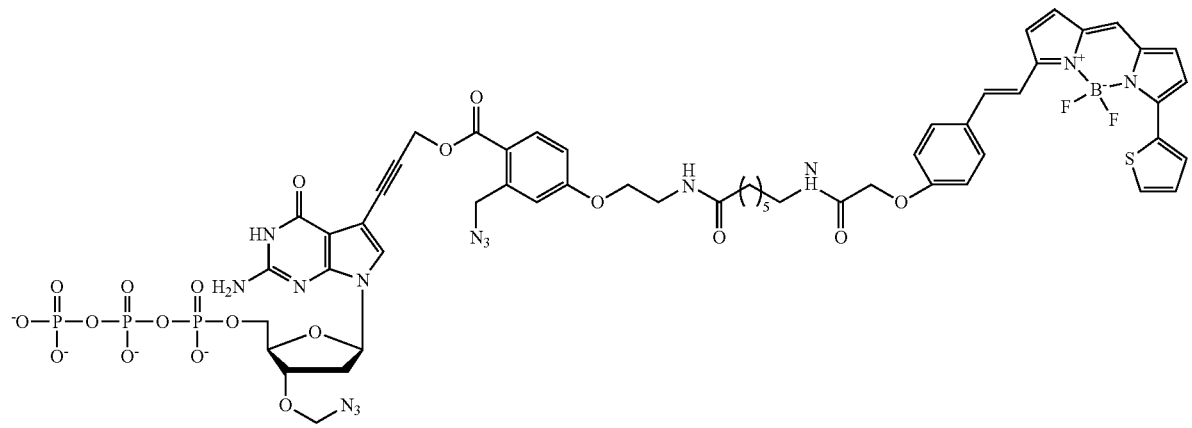
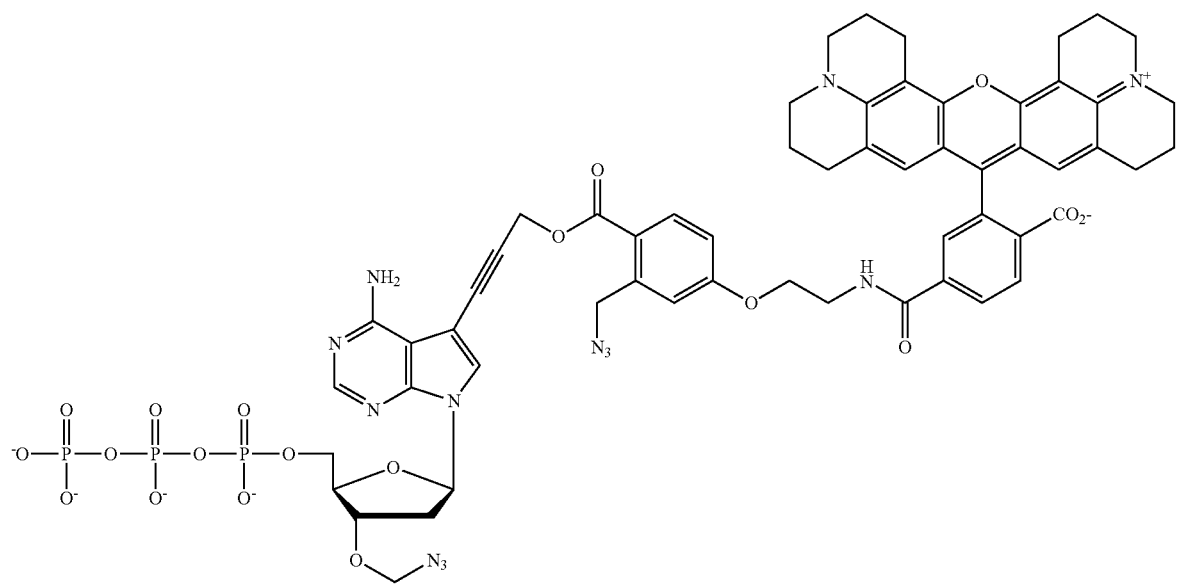
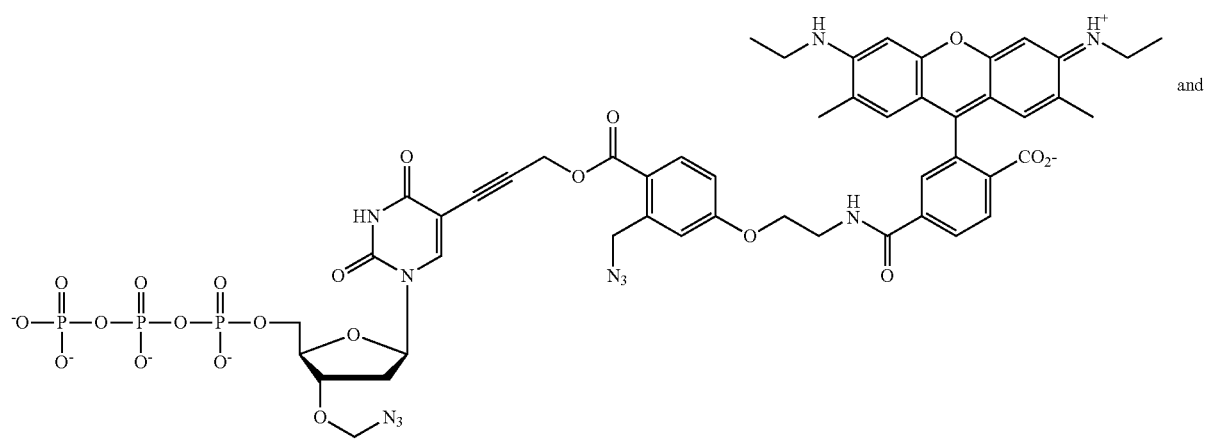

-continued

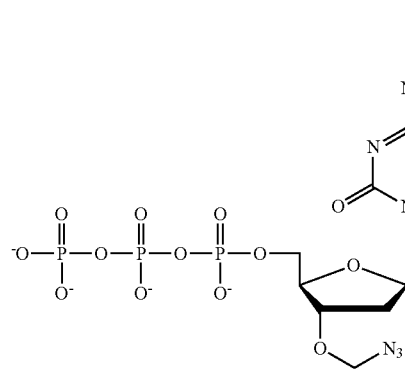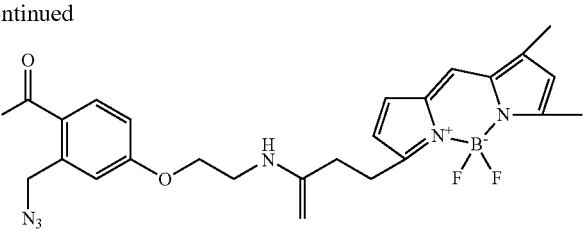

An array is provided comprising a nucleic acid attached to a solid surface, wherein the nucleic acid comprises an azidomethyl group attached to a 3' O atom thereof and a molecule having the structure:

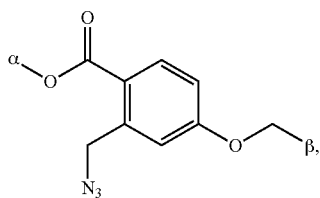

wherein α represents a point of attachment to a 3' base of the nucleic acid and β represents a point of attachment to a detectable marker.

An array is provided comprising a self-priming nucleic acid attached to a solid surface, wherein the nucleic acid comprises an azidomethyl group attached to a 3' O atom thereof and a molecule having the structure:

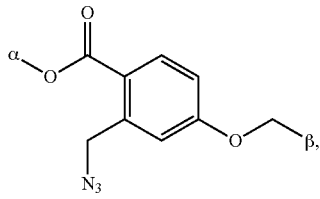

wherein α represents a point of attachment to a 3' base of the nucleic acid and β represents a point of attachment to a detectable marker.

In embodiment the detectable marker is a fluorophore.

A method is provided for increasing a read length of DNA sequencing by synthesis comprising (a) providing deoxynucleotide triphosphate analogues wherein the deoxynucleotide triphosphate analogues differ from deoxynucleotide triphosphates by having a methylazido group attached to a 3' O atom thereof and by having a detectable marker attached to a 1 nitrogen or a 9 nitrogen of a base thereof through a linker comprising the structure

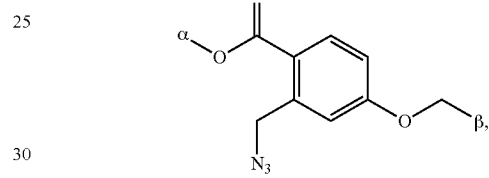

wherein α represents a point of attachment to a the base and β represents a point of attachment to the detectable marker, (b) incorporating a plurality of the deoxynucleotide triphosphate analogues into a nucleic acid being synthesized in the DNA sequencing by synthesis, and (c) cleaving the methylazido and detectable marker from each dNTP analogue, so as to thereby increase the read length of the DNA sequence by synthesis.

A method for determining the identity of each of a series of consecutive nucleotide residues in a nucleic acid comprising:
a) contacting the nucleic acid with (i) at least four different deoxynucleotide triphosphate (dNTP) analogues, each having the structure:

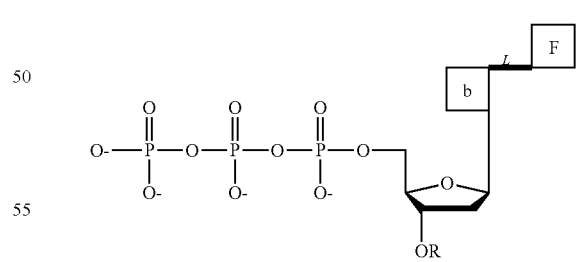

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

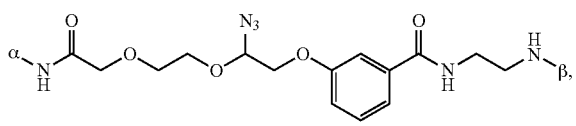

wherein α represents a point of attachment to the base and β represents a point of attachment to the fluorophore, and wherein R is a cleavable chemical group, (ii) a nucleic acid polymerase and (iii) a nucleic acid primer which hybridizes with the nucleic acid,
under conditions permitting one of the four dNTP analogues that is complementary to the consecutive nucleotide residue to be identified to form a phosphodiester bond with the 3' end of the nucleic acid primer and thereby extend the primer;
b) identifying the fluorophore of the dNTP analogue which has formed the phosphodiester bond, thereby identifying the consecutive nucleotide;
c) contacting the dNTP analogue which has formed the phosphodiester bond with tris(2-carboxyethyl)phosphine so as to thereby (1) cleave the fluorophore and (2) cleave the cleavable chemical group from the dNTP;
d) iteratively repeating steps a) through c) for each of the consecutive nucleotide residues to be identified until the final consecutive nucleotide residue is to be identified;
e) repeating steps a) and b) to identify the final consecutive nucleotide residue,
thereby determining the identity of each of the series of consecutive nucleotide residues in the nucleic acid.

A method for determining the identity of each of a series of consecutive nucleotide residues in a self-priming nucleic acid comprising:
a) contacting the self-priming nucleic acid with (i) at least four different deoxynucleotide triphosphate (dNTP) analogues, each having the structure:

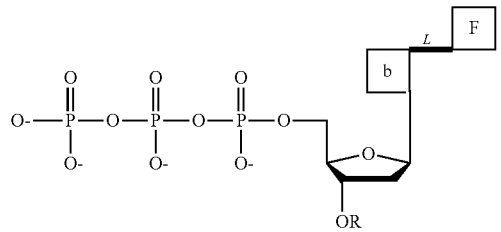

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, and wherein L is a cleavable linker molecule comprising the structure:

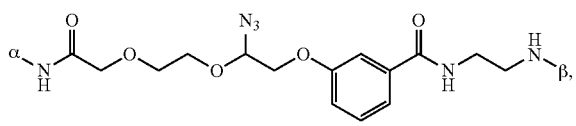

wherein α represents a point of attachment to the base and β represents a point of attachment to the fluorophore, and wherein R is a cleavable chemical group, and (ii) a nucleic acid polymerase,
under conditions permitting (a) the self-priming nucleic acid to prime itself and (b) one of the four dNTP analogues that is complementary to the consecutive nucleotide residue to be identified to form a phosphodiester bond with the 3' end of the self-priming nucleic acid primer and thereby extend the self-priming nucleic acid;
b) identifying the fluorophore of the dNTP analogue which has formed the phosphodiester bond, thereby identifying the consecutive nucleotide;
c) contacting the dNTP analogue which has formed the phosphodiester bond with tris(2-carboxyethyl)phosphine so as to thereby (1) cleave the fluorophore and (2) cleave the cleavable chemical group from the dNTP;
d) iteratively repeating steps a) through c) for each of the consecutive nucleotide residues to be identified until the final consecutive nucleotide residue is to be identified;
e) repeating steps a) and b) to identify the final consecutive nucleotide residue,
thereby determining the identity of each of the series of consecutive nucleotide residues in the self-priming nucleic acid.

In an embodiment of the instant methods, steps b) and c) can be performed simultaneously, or in the order step b) then step c) or in the order step c) then step b). In an embodiment of the instant methods, the nucleic acid is DNA and the nucleic acid polymerase is a 9°N thermopolymerase.

In an embodiment of the instant methods, the cleavable chemical group is a methylazido group. In an embodiment of the instant methods, the four dNTP analogues have the following structures:

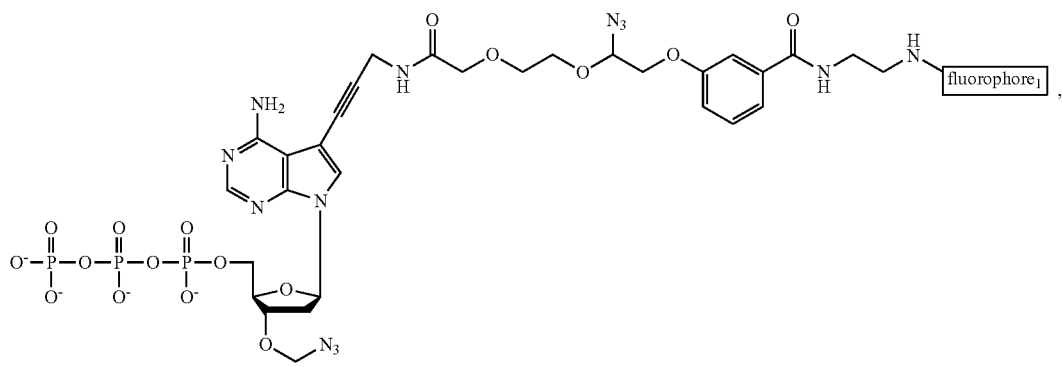

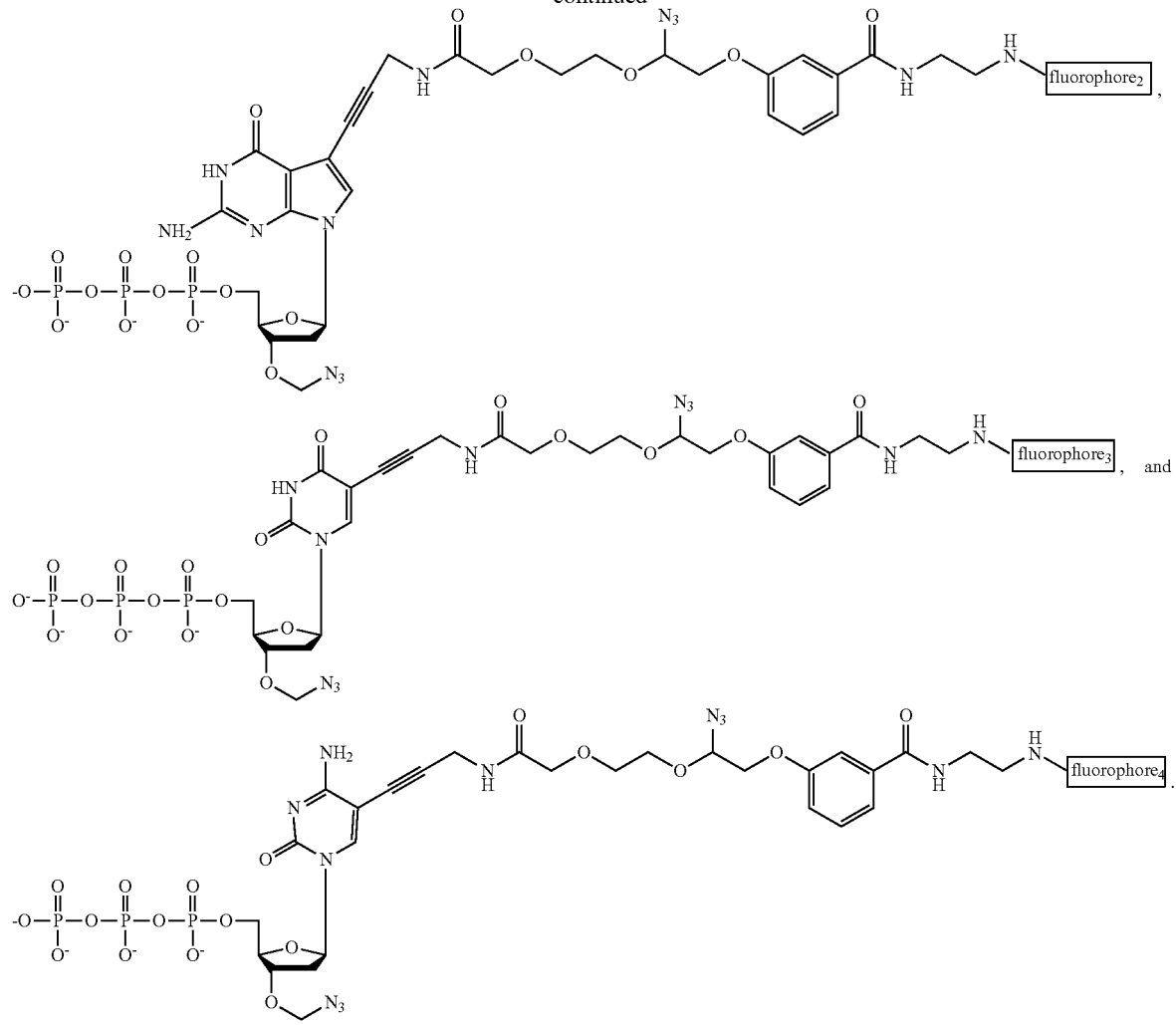
In an embodiment the four dNTP analogues have the following structures:
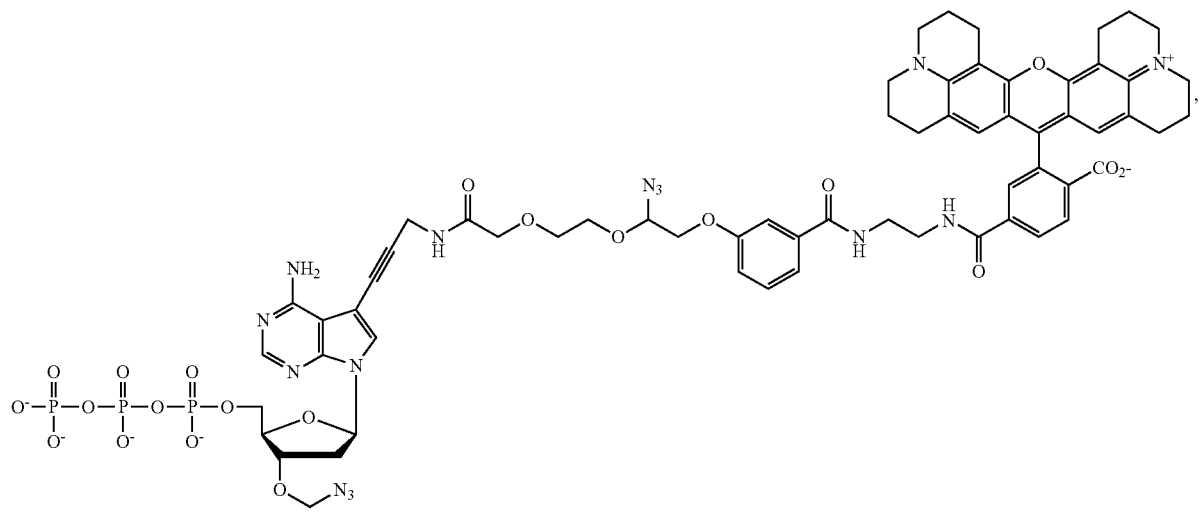

-continued
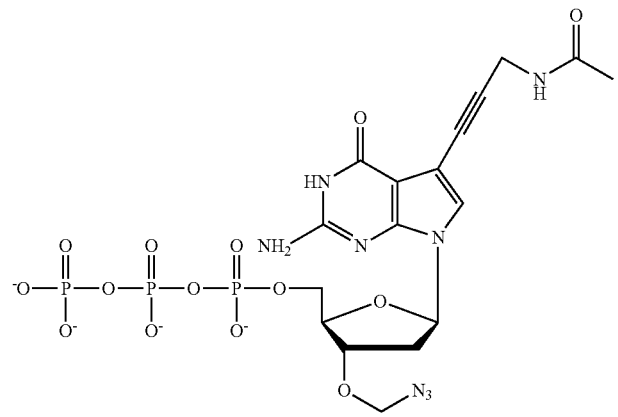
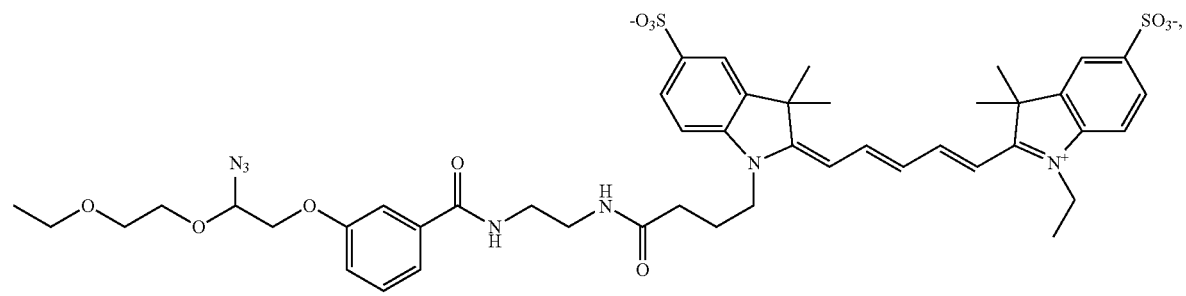
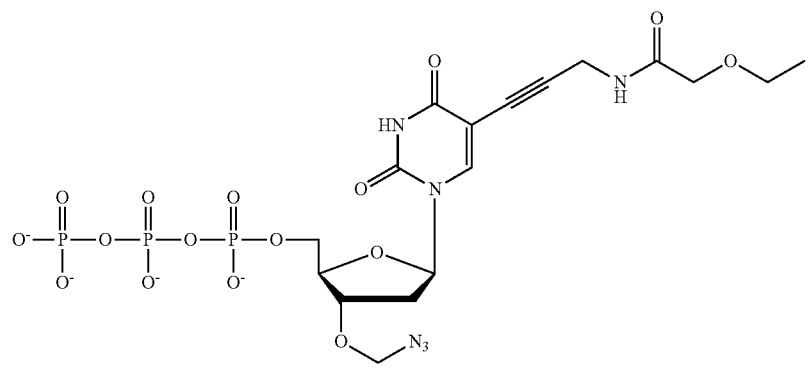
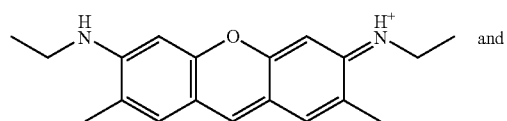
and
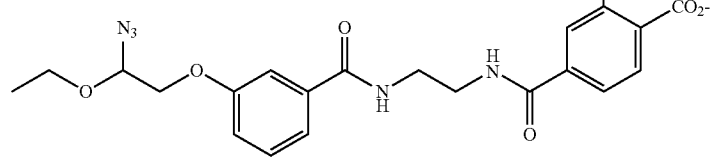

-continued

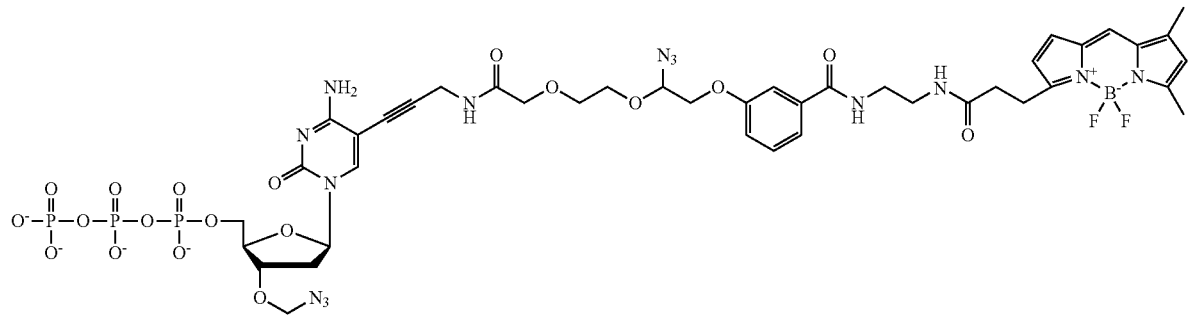

In an embodiment up to 1000 consecutive nucleotides are identified. In an embodiment up to $1\times10^4$ consecutive nucleotides are identified. In an embodiment up to $1\times10^6$ consecutive nucleotides are identified. In an embodiment the nucleic acid is immobilized on a solid surface. In an embodiment the solid surface is a chip or a bead.

A method for determining the identity of each of a series of consecutive nucleotide residues in a plurality of nucleic acids comprising, the same series of consecutive nucleotides comprising:
a) contacting the nucleic acids with (i) at least four different dideoxynucleotide triphosphate (ddNTP) analogues, each having the structure:

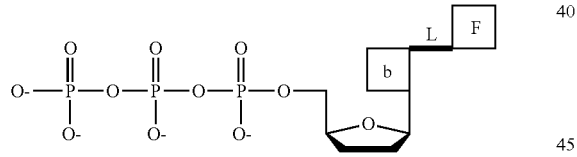

wherein F is a fluorophore, L is a cleavable linker molecule and b is a base which is adenine, guanine, cytosine, uracil or thymine, wherein the fluorophore attached through a linker to each type of base differs in its emission or excitation spectra from a fluorophore attached through a linker to each of the remaining types of bases, and each of the four ddNTP analogues differs from the remaining three ddNTP analogues by having a different base, and wherein L comprises the structure:

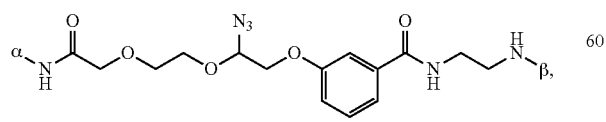

wherein α represents a point of attachment to the base of the dideoxynucleotide and β represents a point of attachment to the fluorophore, and (ii) at least four different deoxynucleotide triphosphate (dNTP) analogue, each having the structure:

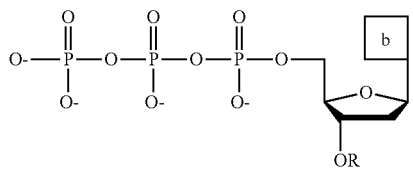

wherein b is a base which is adenine, guanine, cytosine, uracil or thymine, and each of the four dNTP analogues differs from the remaining three dNTP analogues by having a different base, and wherein R is a cleavable chemical group, (iii) a nucleic acid polymerase and (iv) at least two primers each of which hybridizes with a separate nucleic acid of the plurality of nucleic acids, under conditions permitting a ddNTP analogue that is complementary to the consecutive nucleotide residue in the nucleic acid to be identified to form a phosphodiester bond with the 3' end of one of the primers and a dNTP analogue that is complementary to the consecutive nucleotide residue to be identified to form a phosphodiester bond with the 3' end of another of the primers;

b) identifying the fluorophore of the ddNTP analogue which has formed the phosphodiester bond thereby identifying the identity of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

A method for determining the identity of consecutive nucleotide residues in a self-priming nucleic acid comprising:
a) contacting the nucleic acids with (i) at least four different dideoxynucleotide triphosphate (ddNTP) analogues, each having the structure:

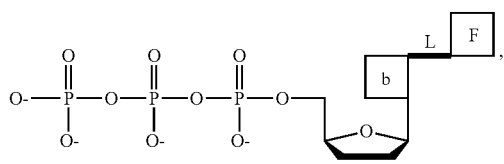

wherein F is a fluorophore, L is a cleavable linker molecule and b is a base which is adenine, guanine, cytosine, uracil or thymine, wherein the fluorophore attached through a linker to each type of base differs in its emission or excitation spectra from a fluorophore attached through a linker to each of the remaining types of bases, and each of the four ddNTP analogues differs from the remaining three ddNTP analogues by having a different base, wherein L comprises the structure:

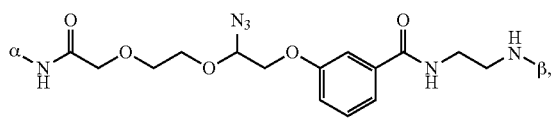

wherein α represents a point of attachment to the base of the dideoxynucleotide and β represents a point of attachment to the fluorophore, and
(ii) at least four different deoxynucleotide triphosphate (dNTP) analogue, each having the structure:

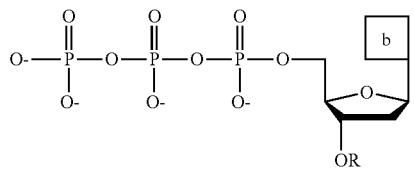

wherein b is a base which is adenine, guanine, cytosine, uracil or thymine, and each of the four dNTP analogues differs from the remaining three dNTP analogues by having a different base, and wherein R is a cleavable chemical group, (iii) a nucleic acid polymerase and (iv) at least two primers each of which hybridizes with a separate nucleic acid of the plurality of nucleic acids, under conditions permitting a ddNTP analogue that is complementary to the consecutive nucleotide residue to be identified to form a phosphodiester bond with the 3' end of one of the self-priming nucleic acids and a dNTP analogue that is complementary to the consecutive nucleotide residue to be identified to form a phosphodiester bond with the 3' end of another of the self-priming nucleic acids;

b) identifying the fluorophore of the ddNTP analogue which has formed the phosphodiester bond thereby identifying the identify of the consecutive nucleotide;

c) cleaving the fluorophore from the ddNTP analogue which has formed the phosphodiester bond and cleaving the cleavable chemical group from the dNTP which has formed the phosphodiester bond;

d) iteratively repeating steps a) through c) for each of the consecutive nucleotide residues to be identified until the final consecutive nucleotide residue is to be identified;

e) repeating steps a) and b) to identify the final consecutive nucleotide residue, thereby determining the identity of each of the series of consecutive nucleotide residues in the nucleic acid.

In an embodiment of the instant methods, steps b) and c) can be performed simultaneously, or in the order step b) then step c) or in the order step c) then step b). In an embodiment of the instant methods, the nucleic acid is DNA and the nucleic acid polymerase is a 9°N thermopolymerase. In an embodiment of the instant methods, the cleavable chemical group is a methylazido group.

In an embodiment of the instant methods, the four ddNTP analogues have the following structures:

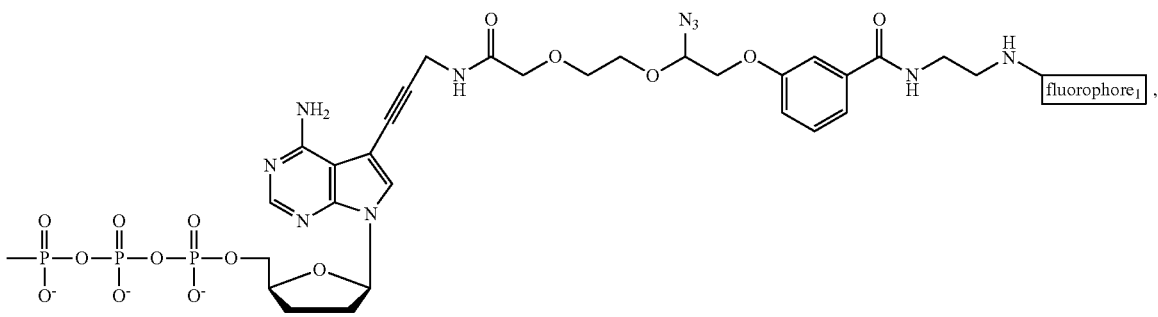

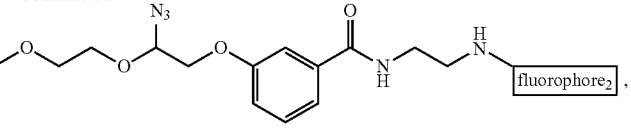
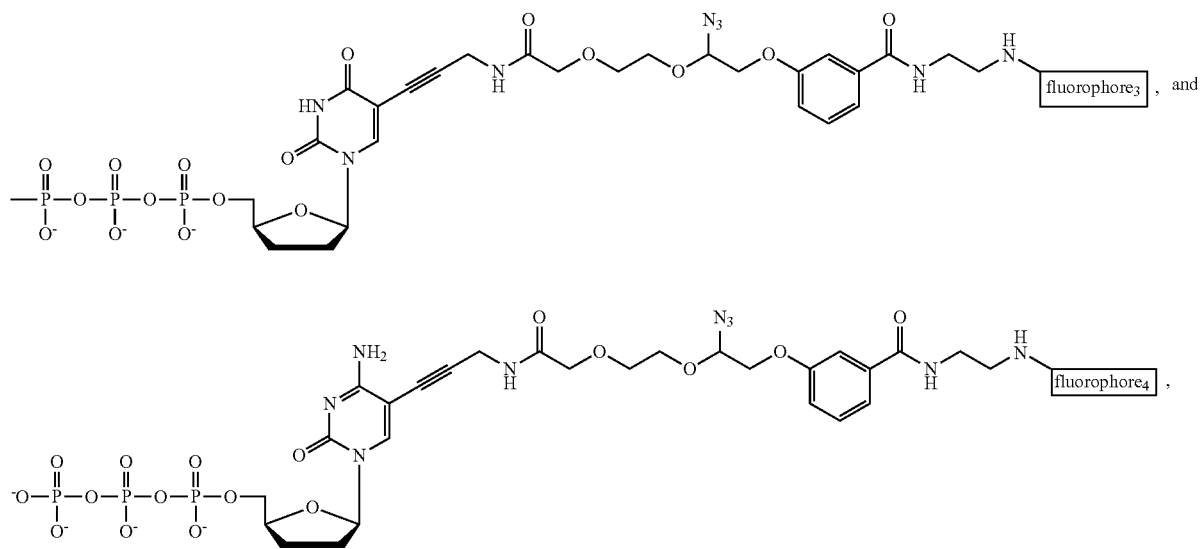
In an embodiment, the four dNTPs have the following structures:
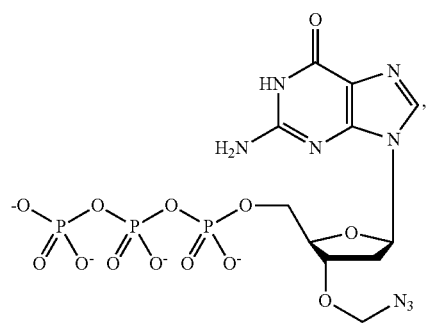
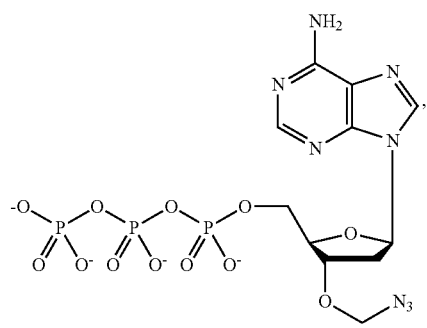
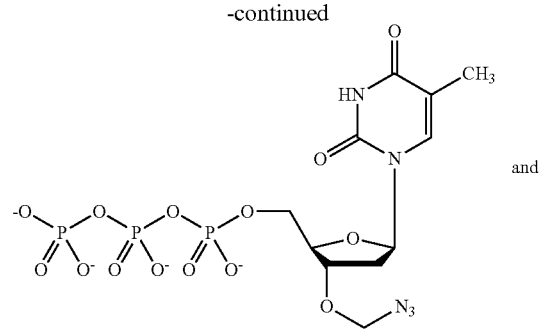
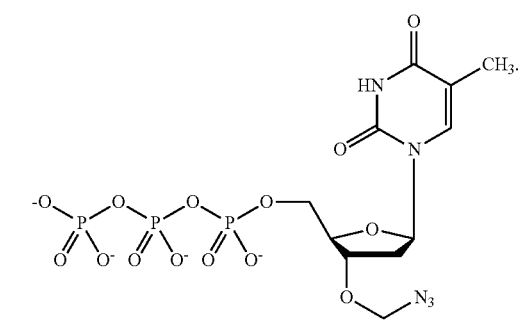

In an embodiment the four ddNTP analogues have the following structures:
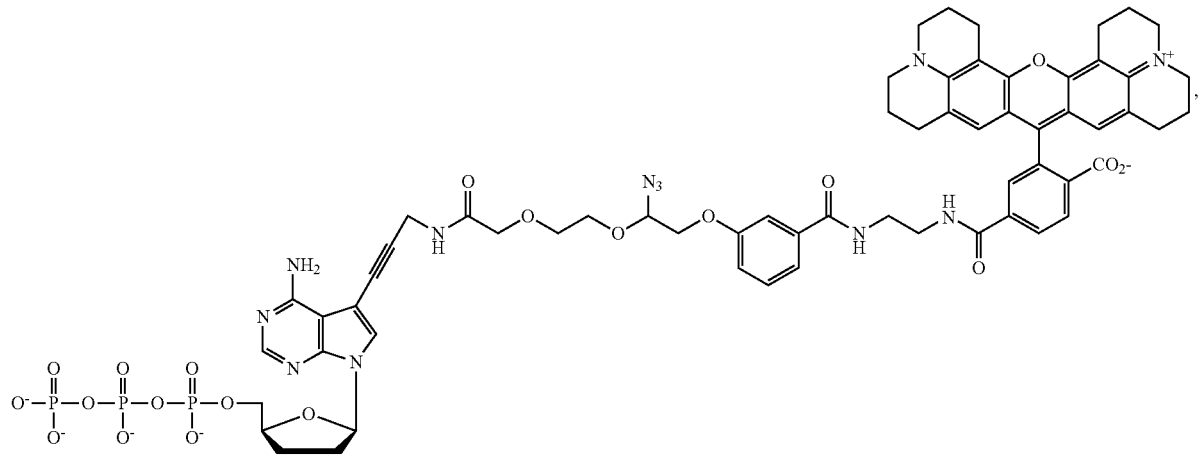
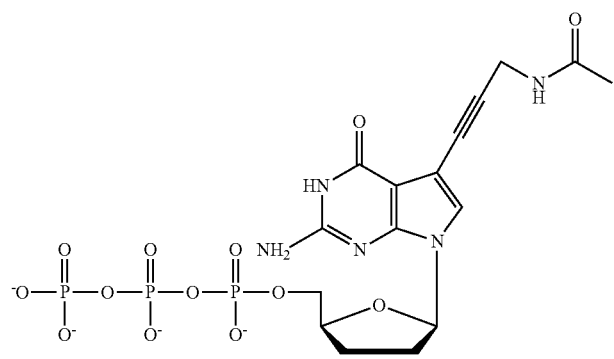
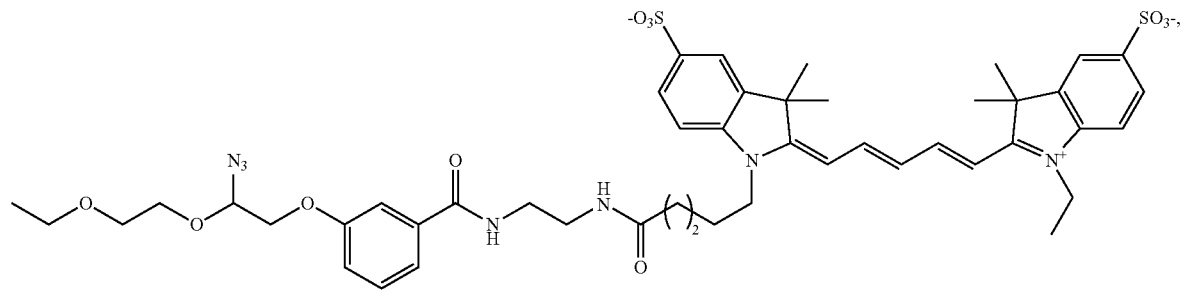
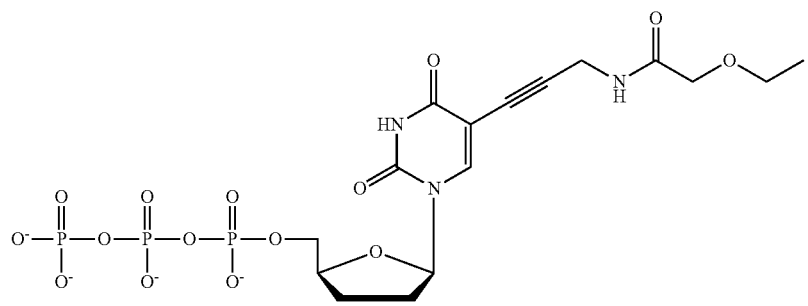

-continued

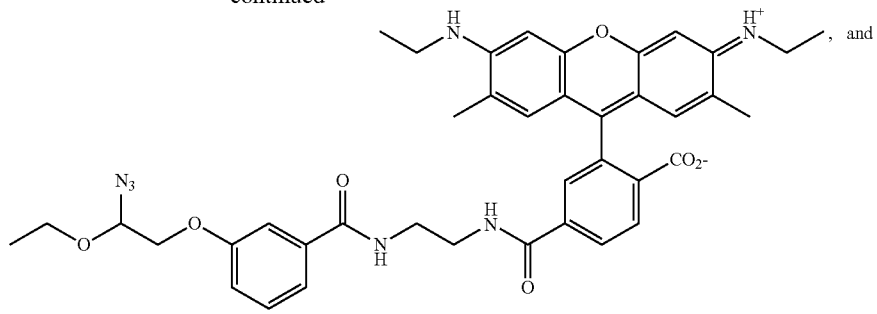, and

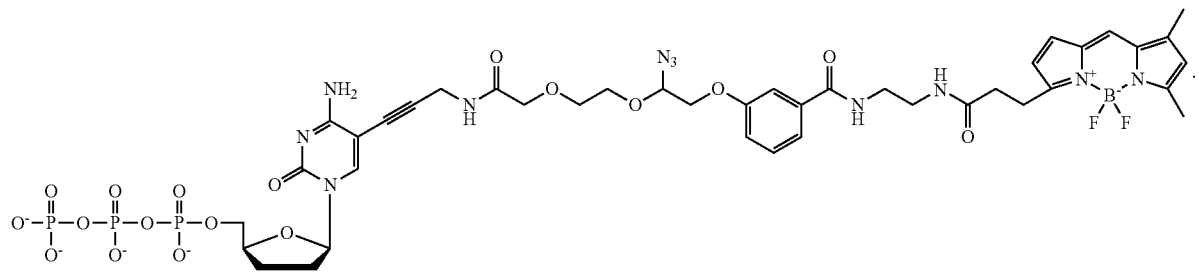

In an embodiment up to 1000 consecutive nucleotides are identified. In an embodiment up to $1\times10^4$ consecutive nucleotides are identified. In an embodiment up to $1\times10^6$ consecutive nucleotides are identified. In an embodiment the nucleic acid is immobilized on a solid surface. In an embodiment the solid surface is a chip or a bead.

A kit is provided for use in sequencing a nucleic acid comprising:

b) a plurality of four nucleotide analogues having the structure:

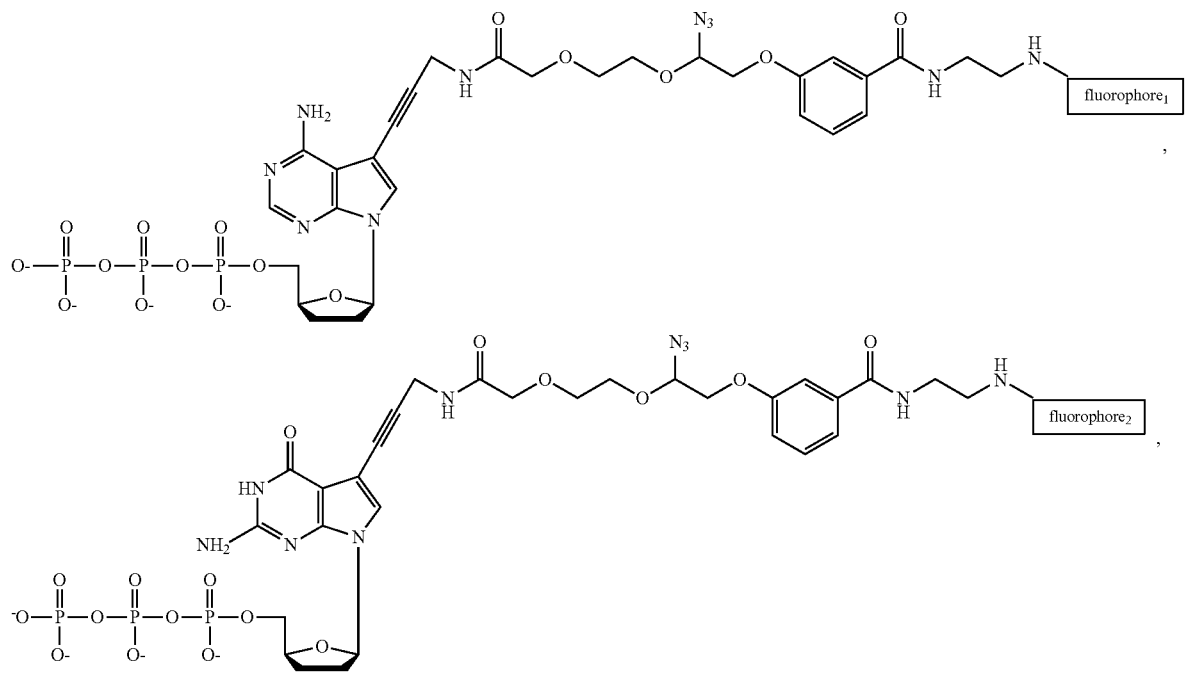

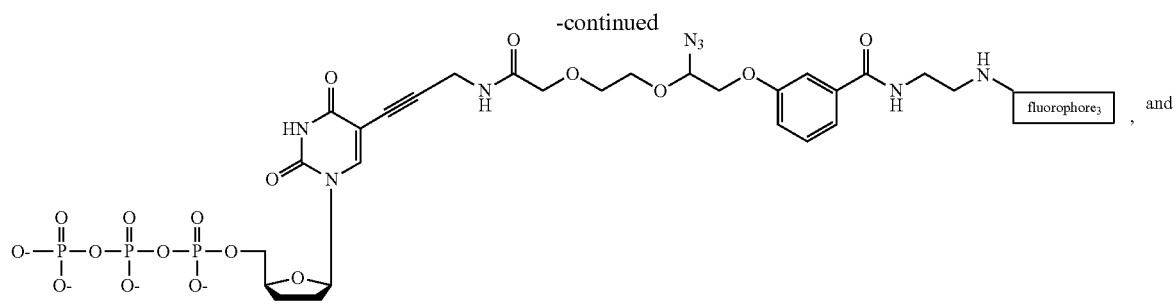
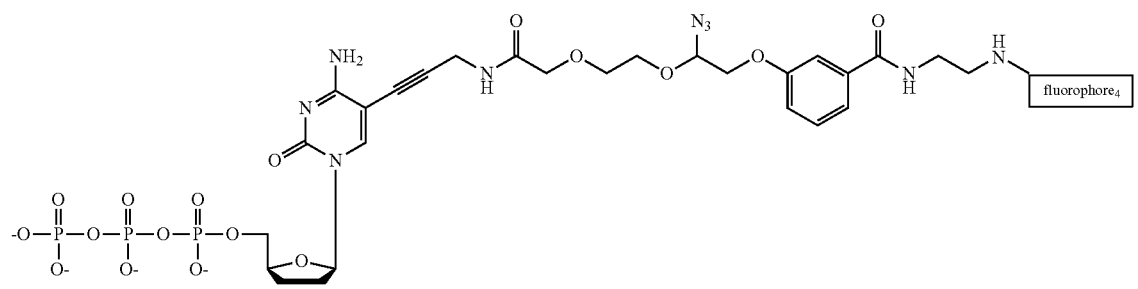
with
(b) a plurality of deoxynucleotide analogues having the structure:
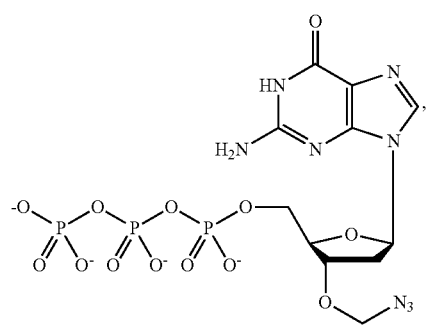
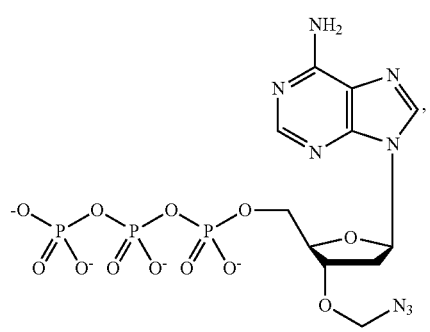
-continued
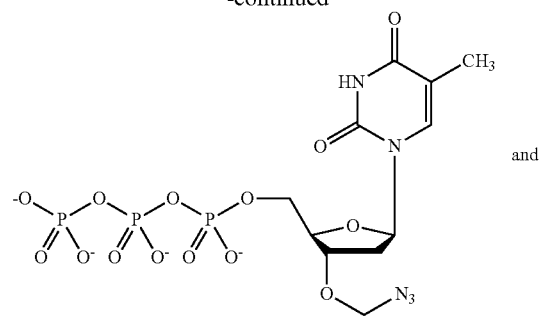
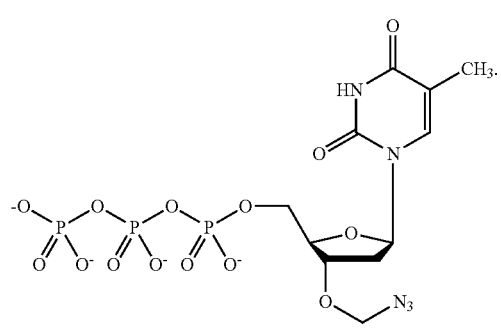
and
(c) instructions for use.

In an embodiment, four dideoxynucleotide analogues having the following structures:
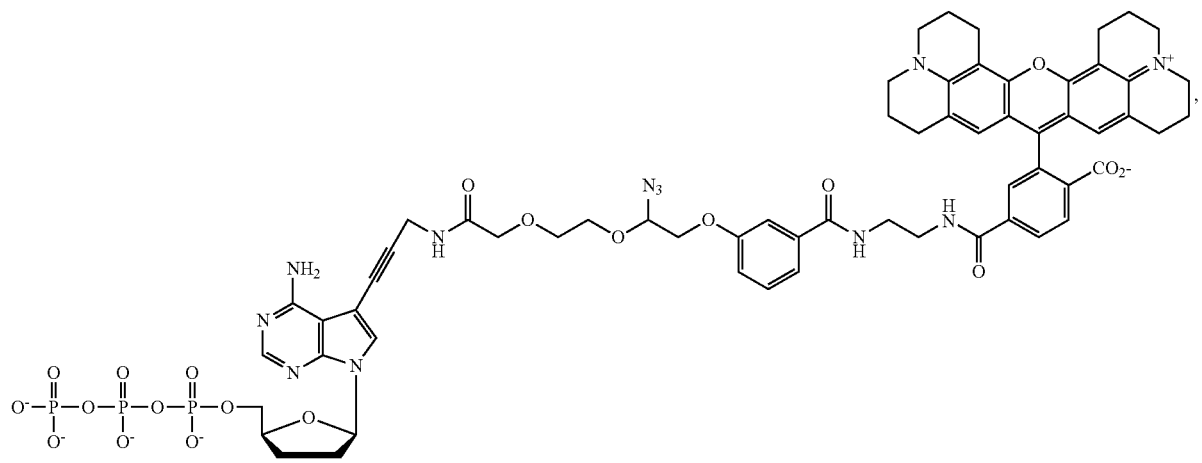
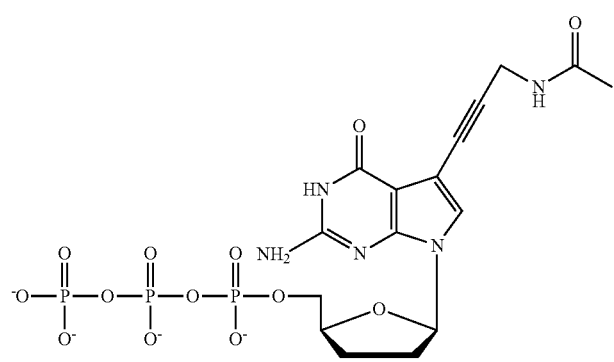
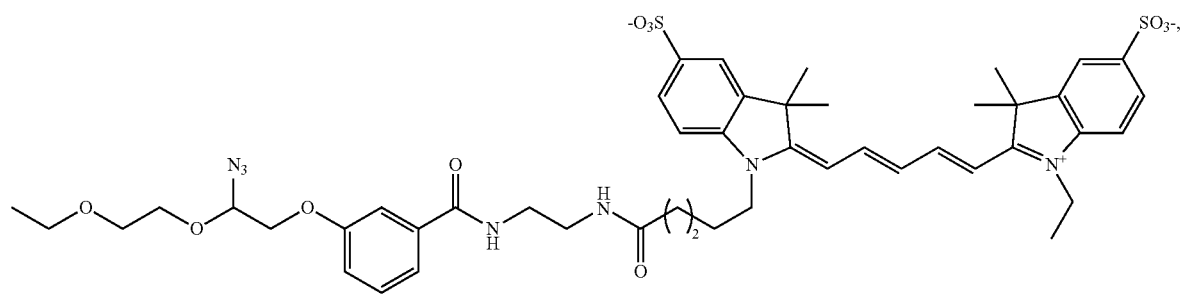
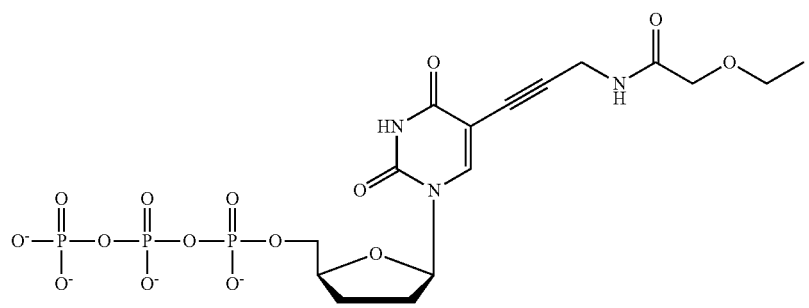

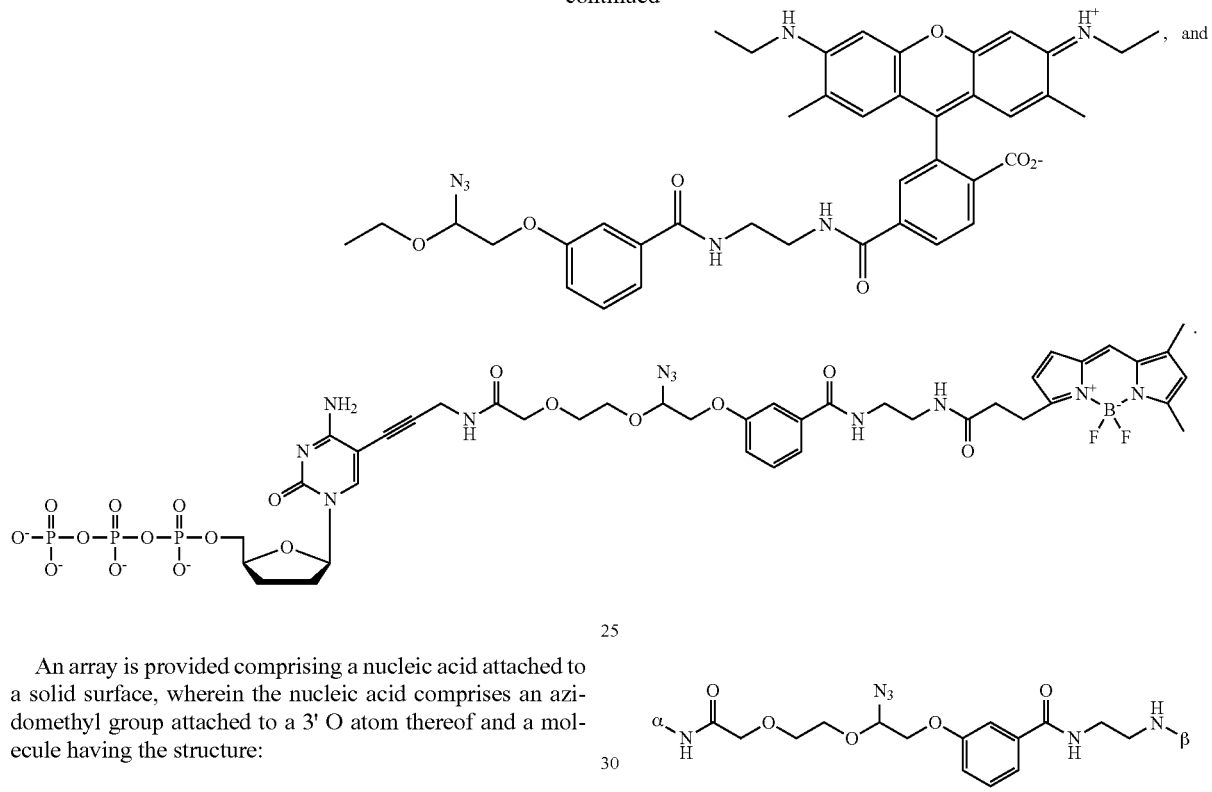

An array is provided comprising a nucleic acid attached to a solid surface, wherein the nucleic acid comprises an azidomethyl group attached to a 3' O atom thereof and a molecule having the structure:

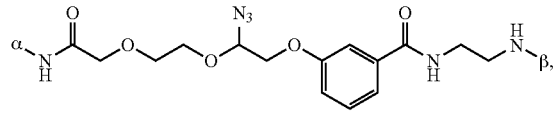

wherein α represents a point of attachment to a 3' base of the nucleic acid and β represents a point of attachment to a detectable marker.

An array is provided comprising a self-priming nucleic acid attached to a solid surface, wherein the nucleic acid comprises an azidomethyl group attached to a 3' O atom thereof and a molecule having the structure:

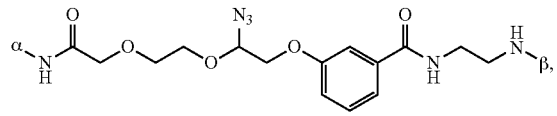

wherein α represents a point of attachment to a 3' base of the nucleic acid and β represents a point of attachment to a detectable marker.

In embodiment the detectable marker is a fluorophore.

A method is provided for increasing a read length of DNA sequencing by synthesis coupled with Sanger dideoxynucleotide terminating reaction (a) providing deoxynucleotide triphosphate analogues wherein the deoxynucleotide triphosphate analogues differ from deoxynucleotide triphosphates by having a methylazido group attached to a 3' O atom thereof and providing dideoxynucleotide triphosphate analogues wherein the dideoxynucleotide triphosphate analogues differ from dideoxynucleotide triphosphates by having a detectable marker attached to a 1 nitrogen or a 9 nitrogen of a base thereof through a linker comprising the structure wherein α represents a point of attachment to a the base and β represents a point of attachment to the detectable marker and (b) incorporating a plurality ratio of dideoxynucleotide triphosphate to deoxynucleotide triphosphate analogues into a nucleic acid being synthesized in the DNA sequencing by synthesis.

This invention provides the instant method, wherein the detectable bound to the base via a cleavable linker is a dye, a fluorophore, a chromophore, a combinatorial fluorescence energy transfer tag, a mass tag, or an electrophore. Combinatorial fluorescence energy tags and methods for production thereof are disclosed in U.S. Pat. No. 6,627,748, which is hereby incorporated by reference.

Detectable tags and methods of affixing nucleic acids to surfaces which can be used in embodiments of the methods described herein are disclosed in U.S. Pat. Nos. 6,664,079 and 7,074,597 which are hereby incorporated by reference.

This invention also provides the instant method, wherein the primer is a self-priming moiety.

This invention also provides the instant method, wherein the DNA is bound to a solid substrate. This invention also provides the instant method, wherein the DNA is bound to the solid substrate via 1,3-dipolar azide-alkyne cycloaddition chemistry. This invention also provides the instant method, wherein the DNA is bound to the solid substrate via a polyethylene glycol molecule. This invention also provides the instant method, wherein the DNA is alkyne-labeled. This invention also provides the instant method, wherein the DNA is bound to the solid substrate via a polyethylene glycol molecule and the solid substrate is azide-functionalized. This invention also provides the instant method, wherein the DNA is immobilized on the solid substrate via an azido linkage, an alkynyl linkage, or biotin-streptavidin interaction.

Immobilization of nucleic acids is described in Immobilization of DNA on Chips II, edited by Christine Wittmann (2005), Springer Verlag, Berlin, which is hereby incorporated by reference. This invention also provides the instant methods, wherein the DNA is bound to the solid substrate via a polyethylene glycol molecule and the solid substrate is azide-functionalized or the DNA is immobilized on the solid substrate via an azido linkage, an alkynyl linkage, or biotin-streptavidin interaction. In an embodiment, the DNA or nucleic acid is attached/bound to the solid surface by covalent site-specific coupling chemistry compatible with DNA.

This invention also provides the instant method, wherein the solid substrate is in the form of a chip, a bead, a well, a capillary tube, a slide, a wafer, a filter, a fiber, a porous media, or a column. This invention also provides the instant method, wherein the solid substrate is gold, quartz, silica, plastic, glass, nylon, diamond, silver, metal, or polypropylene. This invention also provides the instant method, wherein the solid substrate is porous. Chips or beads may be made from materials common for DNA microarrays, for example glass or nylon. Beads/micro-beads may be in turn immobilized to chips.

This invention also provides the instant method, wherein about 1000 or fewer copies of the DNA are bound to the solid substrate. This invention also provides the instant invention wherein $2 \times 10^7$, $1 \times 10^7$, $1 \times 10^6$ or $1 \times 10^4$ or fewer copies of the DNA are bound to the solid substrate.

This invention also provides the instant method, wherein the nucleotide analogues comprise one of the fluorophores Cy5, Bodipy-FL-510, ROX and R6G.

This invention also provides the instant method, wherein the DNA polymerase is a 9°N polymerase or a variant thereof. DNA polymerases which can be used in the instant invention include, for example E. Coli DNA polymerase I, Bacteriophage T4 DNA polymerase, Sequenase™, Taq DNA polymerase and 9°N polymerase (exo-) A485L/Y409V. RNA polymerases which can be used in the instant invention include, for example, Bacteriophage SP6, T7 and T3 RNA polymerases.

Methods for production of cleavably capped and/or cleavably linked nucleotide analogues are disclosed in U.S. Pat. No. 6,664,079, which is hereby incorporated by reference.

A method for determining the identity of each of a series of consecutive nucleotide residues in a nucleic acid comprising:
a) contacting the nucleic acid with (i) at least four different deoxynucleotide triphosphate (dNTP) analogues, each having the structure:

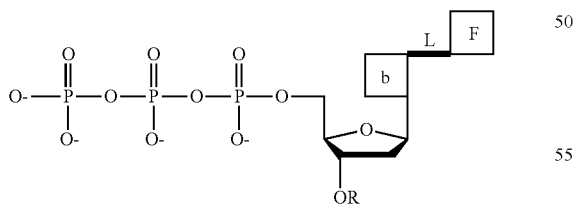

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, (ii) a nucleic acid polymerase and (iii) a nucleic acid primer which hybridizes with the nucleic acid,
under conditions permitting one of the four dNTP analogues that is complementary to the consecutive nucleotide residue to be identified to form a phosphodiester bond with the 3' end of the nucleic acid primer and thereby extend the primer;
b) identifying the fluorophore of the dNTP analogue which has formed the phosphodiester bond, thereby identifying the consecutive nucleotide;
c) cleaving the linker attaching the fluorophore of the dNTP analogue which has formed the phosphodiester bond and cleaving the cleavable chemical group from the dNTP;
d) iteratively repeating steps a) through c) for each of the consecutive nucleotide residues to be identified until the final consecutive nucleotide residue is to be identified;
e) repeating steps a) and b) to identify the final consecutive nucleotide residue,
f) denaturing the extended primer so as to de-hybridize it from the nucleic acid;
g) contacting the nucleic acid with (i) at least four different deoxynucleotide triphosphate (dNTP) analogues, each comprising an adenine, guanine, cytosine, uracil, inosine or 5-nitorindole base and each differing from a deoxynucleotide triphosphate by having a cleavable chemical group attached to the 3' O-atom of the dNTP, (ii) a nucleic acid polymerase and (iii) a second nucleic acid primer which hybridizes with the nucleic acid, under conditions permitting one of the four dNTP analogues that is complementary to the consecutive nucleotide residue to be identified to form a phosphodiester bond with the 3' end of the second nucleic acid primer and thereby extend the second primer;
h) cleaving the chemical group from the 3' O-atom of the dNTP analogue which has formed the phosphodiester bond so as to thereby permit incorporation of a further dNTP analogue into the extended second nucleic acid primer;
i) iteratively repeating steps g) and h) until the second primer is extended up to and including a residue corresponding to the final consecutive nucleotide residue identified in step e);
j) contacting the extended second primer with (i) at least four different deoxynucleotide triphosphate (dNTP) analogues, each having the structure:

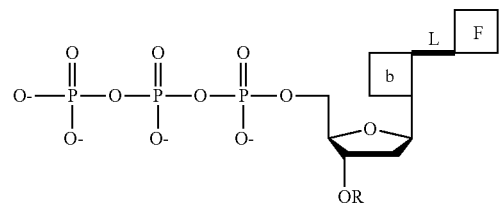

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, under conditions permitting one of the four dNTP analogues that is complementary to the next consecutive nucleotide residue to be identified to form a phosphodiester bond with the 3' end of the extended second nucleic acid primer and thereby further extend the second primer;

k) identifying the fluorophore of the dNTP analogue which has formed the phosphodiester bond, thereby identifying the consecutive nucleotide;

l) cleaving the fluorophore and the cleavable chemical group from the dNTP analogue which formed the phosphodiester bond so as to thereby permit incorporation of a further dNTP analogue into the extended second nucleic acid primer;

m) iteratively repeating steps j) through l) for each of the consecutive nucleotide residues to be identified until the final consecutive nucleotide residue is to be identified;

n) repeating steps j) and k) to identify the final consecutive nucleotide residue, so as to thereby determine the identity of each of the series of consecutive nucleotide residues in the nucleic acid.

In an embodiment the linker in each of step a) and j) independently each comprise the structure:

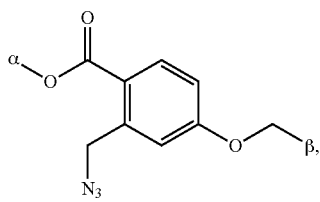

or the structure:

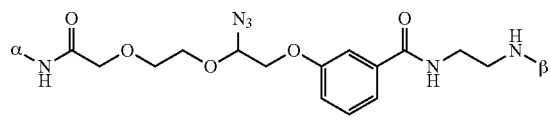

wherein α represents a point of attachment to the base and β represents a point of attachment to the fluorophore, and wherein R is a cleavable chemical group.

In an embodiment a linker is cleaved by contacting the linker with tris(2-carboxyethyl)phosphine.

In an embodiment one or more linkers are photocleavable or chemically cleavable.

In an embodiment one or more chemical groups are photocleavable or chemically cleavable.

In an embodiment R in the structures set forth in steps a) and or j) is independently chosen from a —$N_3$ group or an allyl group.

In an embodiment the cleavable chemical group in step g) is independently chosen from a —$N_3$ group or an allyl group.

A method for determining the identity of each of a series of consecutive nucleotide residues in a nucleic acid comprising:

a) contacting the nucleic acid with (i) at least four different deoxynucleotide triphosphate (dNTP) analogues, each having the structure:

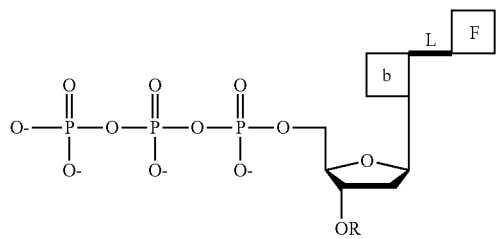

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) cleaving the linker attaching the fluorophore of the dNTP analogue which has formed the phosphodiester bond and cleaving the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, f) denaturing the extended primer so as to de-hybridize it from the nucleic acid;

g) contacting the nucleic acid with (i) three different types of deoxynucleotide triphosphate, (ii) a nucleic acid polymerase and (iii) a second nucleic acid primer which hybridizes with the nucleic acid, under conditions permitting one of the three dNTP analogues that is complementary to the consecutive nucleotide residue to be identified to form a phosphodiester bond with the 3' end of the second nucleic acid primer and thereby extend the second nucleic acid primer;

h) contacting the nucleic acid with (i) three different types of deoxynucleotide triphosphate, wherein at least one of the types of deoxynucleotide triphosphate is not used in step g), under conditions permitting one of the three dNTP analogues that is complementary to the consecutive nucleotide residue to be identified to form a phosphodiester bond with the 3' end of the extended second nucleic acid primer and thereby further extend the second nucleic acid primer;

i) repeating steps g) and h) until the second nucleic acid primer is extended up to and including a residue corresponding to the final consecutive nucleotide residue identified in step e)

j) contacting the extended second nucleic acid primer with (i) at least four different deoxynucleotide triphosphate (dNTP) analogues, each having the structure:

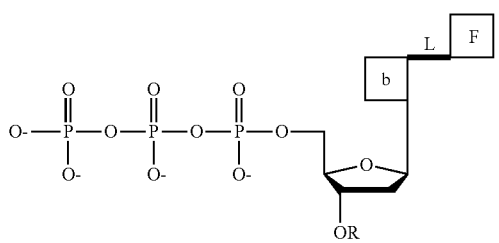

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, under conditions permitting one of the four dNTP analogues that is complementary to the next consecutive nucleotide residue to be identified to form a phosphodiester bond with the 3' end of the extended second nucleic acid primer and thereby further extend the second primer;

k) identifying the fluorophore of the dNTP analogue which has formed the phosphodiester bond, thereby identifying the consecutive nucleotide;

l) cleaving the fluorophore and the cleavable chemical group from the dNTP analogue which formed the phosphodiester bond so as to thereby permit incorporation of a further dNTP analogue into the extended second nucleic acid primer;

m) iteratively repeating steps j) through l) for each of the consecutive nucleotide residues to be identified until the final consecutive nucleotide residue is to be identified;

n) repeating steps j) and k) to identify the final consecutive nucleotide residue, so as to thereby determining the identity of each of the series of consecutive nucleotide residues in the nucleic acid.

In an embodiment in steps g) and h) the three types of dNTPs are chosen from the group dATP, dCTP, dGTP, dTTP or dITP.

In an embodiment the linker in each of step a) and j) independently each comprise the structure:

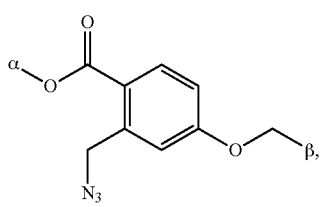

or the structure:

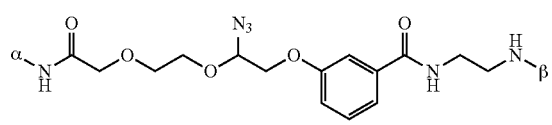

wherein α represents a point of attachment to the base and β represents a point of attachment to the fluorophore, and wherein R is a cleavable chemical group.

In an embodiment a linker is cleaved by contacting the linker with tris(2-carboxyethyl)phosphine.

In an embodiment one or more linkers are photocleavable or chemically cleavable.

In an embodiment one or more chemical groups are photocleavable or chemically cleavable.

In an embodiment R in the structures set forth in steps a) and or j) is independently chosen from a $-N_3$ group or an allyl group.

In an embodiment the cleavable chemical group in step g) is independently chosen from a $-N_3$ group or an allyl group.

A method for determining the identity of each of a series of consecutive nucleotide residues in a nucleic acid comprising:

a) contacting the nucleic acid with (i) at least four different deoxynucleotide triphosphate (dNTP) analogues, each having the structure:

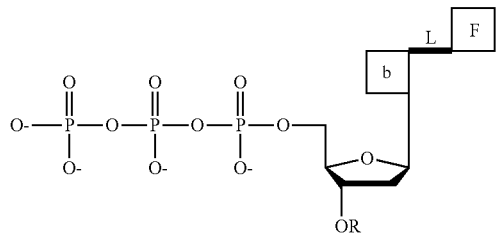

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) cleaving the linker attaching the fluorophore of the dNTP analogue which has formed the phosphodiester bond and cleaving the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, f) denaturing the extended primer so as to de-hybridize it from the nucleic acid;

g) contacting the nucleic acid with (i) three different types of deoxynucleotide triphosphates, (ii) a deoxynucleotide triphosphate analogue, differing from a deoxynucleotide triphosphate by having a cleavable chemical group attached to the 3' O-atom of the dNTP analogue and differing from the three different types of deoxynucleotide triphosphates by having a different base therefrom, (iii) a nucleic acid polymerase and (iv) a second nucleic acid primer which hybridizes with the nucleic acid, under conditions permitting one of the three dNTPs or the dNTP analogue that is complementary to the consecutive nucleotide residue to be identified to form a phosphodiester bond with the 3' end of the second nucleic acid primer and thereby extend the second nucleic acid primer;

h) cleaving the cleavable chemical group from the 3'-O—R group;

repeating steps g) and h) until the second nucleic acid primer is extended up to and including a residue corresponding to the final consecutive nucleotide residue identified in step e)

i) contacting the extended second nucleic acid primer with
(i) at least four different deoxynucleotide triphosphate (dNTP) analogues, each having the structure:

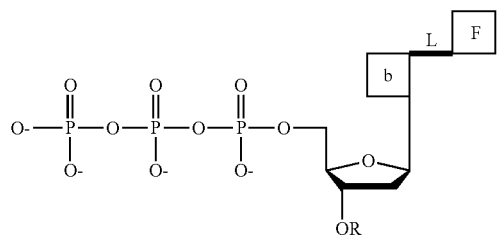

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, under conditions permitting one of the four dNTP analogues that is complementary to the next consecutive nucleotide residue to be identified to form a phosphodiester bond with the 3' end of the extended second nucleic acid primer and thereby further extend the second primer;

j) identifying the fluorophore of the dNTP analogue which has formed the phosphodiester bond, thereby identifying the consecutive nucleotide;

k) cleaving the fluorophore and the cleavable chemical group from the dNTP analogue which formed the phosphodiester bond so as to thereby permit incorporation of a further dNTP analogue into the extended second nucleic acid primer;

l) iteratively repeating steps j) through l) for each of the consecutive nucleotide residues to be identified until the final consecutive nucleotide residue is to be identified;

m) repeating steps j) and k) to identify the final consecutive nucleotide residue, so as to thereby determine the identity of each of the series of consecutive nucleotide residues in the nucleic acid.

In an embodiment in step g) the three types of dNTPs are chosen from the group dATP, dCTP, dGTP and dTTP.

In an embodiment the linker in each of step a) and j) independently each comprise the structure:

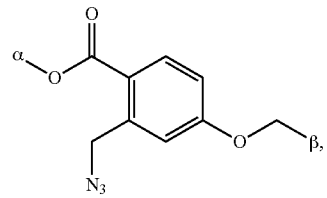

or the structure:

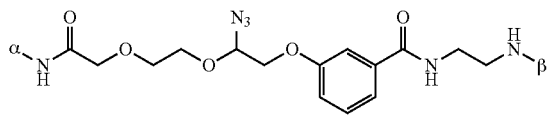

wherein α represents a point of attachment to the base and β represents a point of attachment to the fluorophore, and wherein R is a cleavable chemical group.

In an embodiment a linker is cleaved by contacting the linker with tris(2-carboxyethyl)phosphine.

In an embodiment one or more linkers are photocleavable or chemically cleavable.

In an embodiment one or more chemical groups are photocleavable or chemically cleavable.

In an embodiment R in the structures set forth in steps a) and or j) is independently chosen from a —$N_3$ group or an allyl group.

In an embodiment the cleavable chemical group in step g) is independently chosen from the a —$N_3$ group or an allyl group.

The methods described herein can be applied mutatis mutandis to sequencing RNA using the appropriate ddNTPS or analogues thereof and dNTPS and analogues thereof.

In the methods, base-pairing complementarity allows the sequence of the extended primer or of the target nucleic to be readily determined.

Dehybridize is understood by those skilled in the art to mean to disassociate the hybridized primer (or extended strand thereof) from the target nucleic acid without destroying the target nucleic acid and thus permitting further hybridization of a second primer to the target nucleic acid. Hybridization as used herein in one embodiment means stringent hybridization, for examples as described in Sambrook, J., Russell, D. W., (2000) Molecular Cloning: A Laboratory Manual: Third Edition. Cold Spring Harbor Laboratory Press "Type" of dNTP or ddNTP is used to distinguish dNTP or ddNTPs comprising different bases.

All combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Azido Modified Nucleotide Analogs

While both 3'-O-Allyl-dNTPs and 3'-O-photocleaveble linker(PC)-dNTPs have offered concrete evidence for their implementation in sequencing by synthesis (SBS), a new set of nucleotide analogs, modified with the small azido group ($N_3$), is investigated to seek potential improvement over the current system. There are several advantages for using azido moiety as 3' capping group and also as a dye linker (3'-O-Azido-dNTPs-Azido-Dye), first and foremost being the application of extremely mild cleavage conditions. As disclosed herein, an example of the Staudinger reaction, an azido group can be effectively converted into an amine with phosphine in DNA-friendly aqueous solution (35). This efficient reduction is further enhanced through the utilization of Tris (2-Carboxyethyl)phosphine (TCEP), an odorless and stable agent often used to digest peptide disulfide bonds (FIG. 1).

Figure 2:
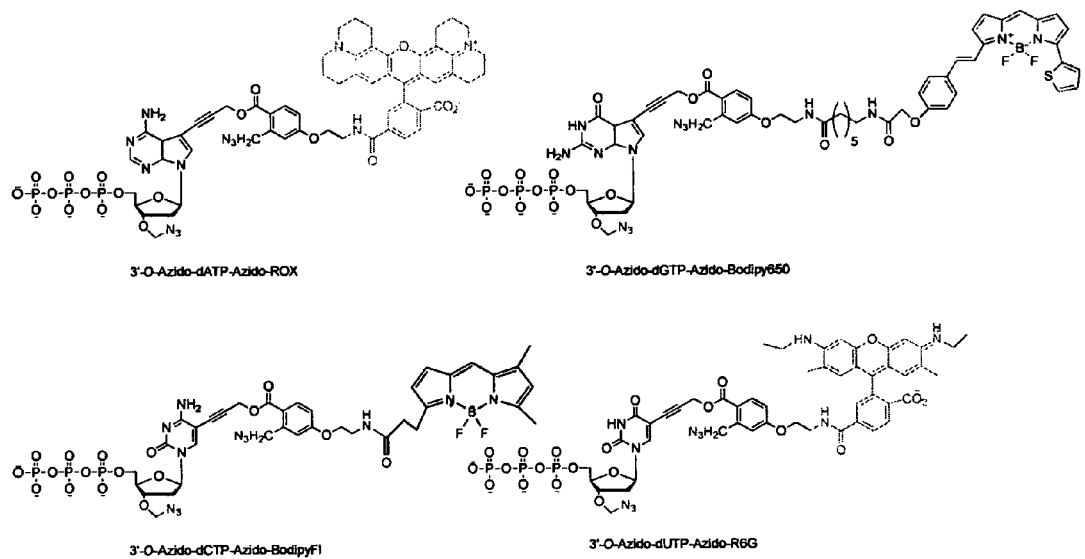
FIG. 2. 3'-O-Azido-dNTPs-Azido-Dye.

Similar to allyl and nitrobenzyl alterations previously reported, two positions of the nucleotide need to be modified with the azido moiety to afford a set of 3'-O-Azido-dNTPs-Azido-Dye. The small azido methyl group (—$CH_2$—$N_3$) is used to cap the 3' position of the sugar base while a novel azido linker connects unique fluorophores to the 5' position of C/U and the 7' position of A/G (see novel structures in FIG. 2).

Figure 3:
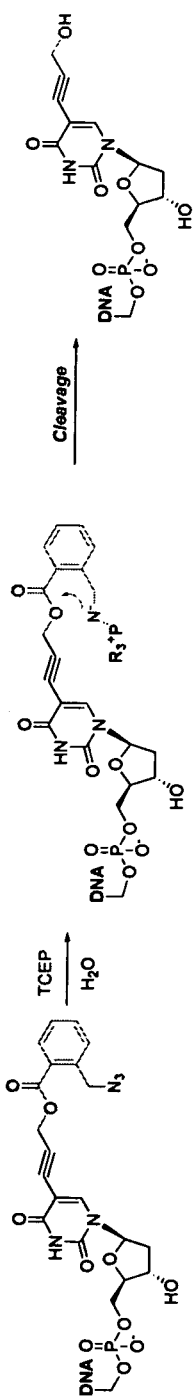
FIG. 3. Staudinger Reduction of the Azido Linker.

With such a formulation the same reagent (TCEP) can be used to cleave the azido groups at both positions simultaneous, although the mechanisms of cleavage differ slightly. According to Staudinger, TCEP reduces the azido-methyl capping group to methylamine at the 3' sugar base. Since the carbon of the methylamine is highly unstable due to its position between two electron-withdrawing elements (oxygen and nitrogen), the methylamine is hydrolyzed in the presence of water that recovers the hydroxyl group at the 3' position. For the azido linker, the same Straudinger reduction takes place. However immediately after the attachment of TCEP to azido, the intermediate attacks the ester bond to afford total cleavage of the fluorophore (FIG. 3).

Figure 4:
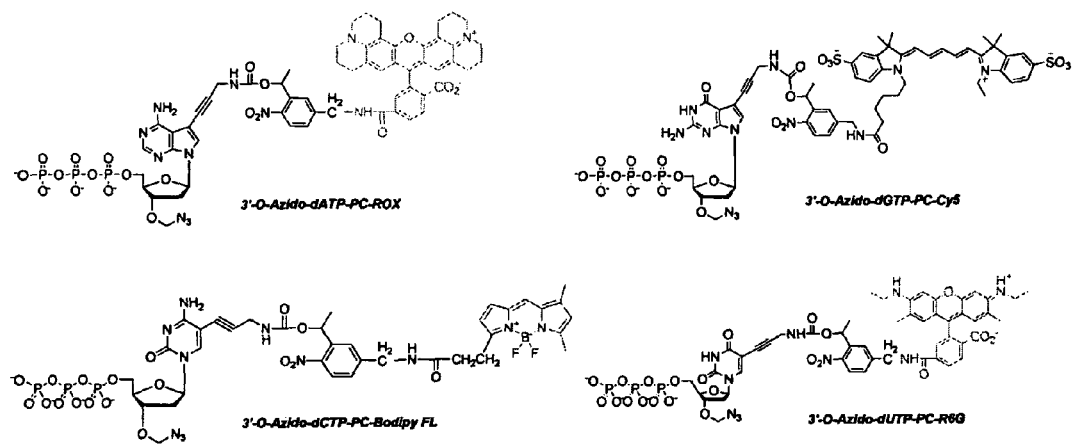
FIG. 4. 3'-O-Azido-dNTP-PC-Dye.

In addition to the dual azido/azido modification, an alternative approach is to attach the fluorophore via a PC (nitrobenzyl) linker while conserving the 3' capping with the azido methyl group (3'-O-Azido-dNTPs-PC-Dye, FIG. 4) and cleaving the azido again using TCEP.

The extension and detection steps for this set of nucleotides are analogous to those for 3'-O-Azido-dNTPs-Azido-Dye. An additional photolysis procedure is involved during the deprotection step. This dual cleavage process might offer different advantages for removing the fluorophore than the Staudinger reduction.

An Alternative Sequencing Method that is a Hybrid Between the Sanger Dideoxy Chain Terminating Reaction, and SBS.

Figure 5:
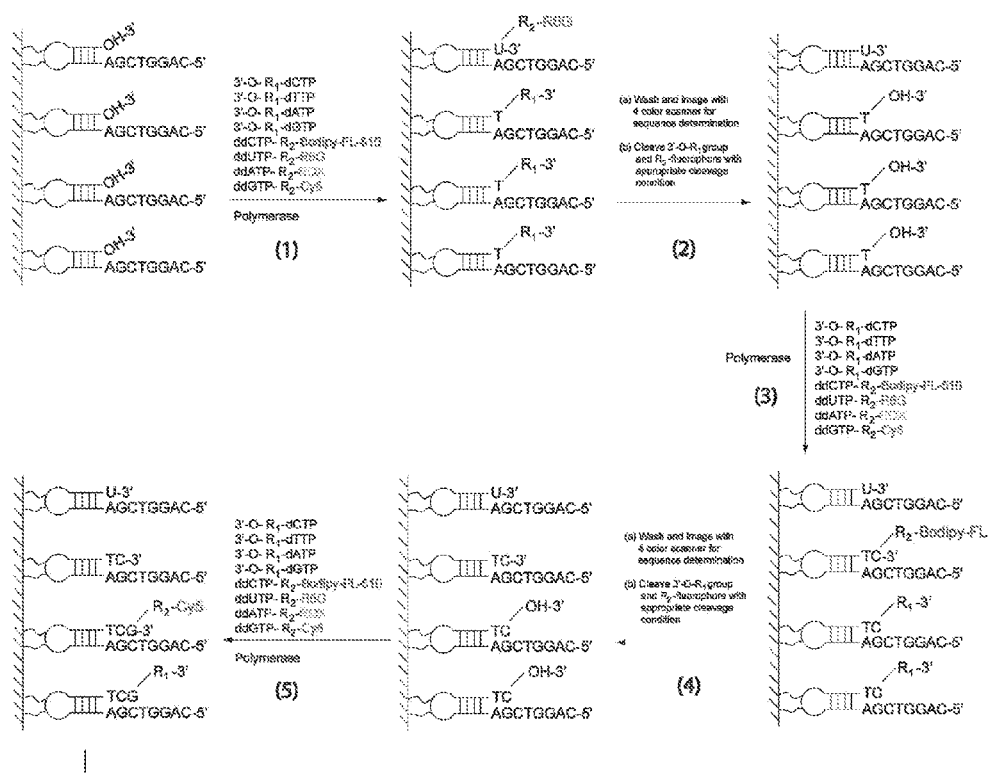
FIG. 5. The hybrid DNA sequencing approach between the Sanger dideoxy chain-terminating reaction and sequencing by synthesis. In this approach, four nucleotides (3'-O—$R_1$-dNTPs) modified as reversible terminators by capping the 3'-OH with a small reversible moiety R1 so that they are still recognized by DNA polymerase as substrates, are used in combination with a small percentage of four cleavable fluorescent dideoxynucleotides (ddNTP-$R_2$-fluorophores) to perform SBS. DNA sequences are determined by the unique fluorescence emission of each fluorophore on the DNA products terminated by ddNTPs. On removing the 3'-OH capping group $R_1$ from the DNA products generated by incorporating the 3'-O—$R_1$-dNTPs, and the cleavage of the $R_2$ linker to remove the fluorophore from the DNA products terminated with the ddNTPs, the polymerase reaction reinitiates to continue the sequence determination.

In this approach, four nucleotides, modified as reversible terminators by capping the 3'-OH with a small reversible moiety so that they are still recognized as substrates by DNA polymerase, are used in combination with a small percentage of four cleavable fluorescent dideoxynucleotides to perform SBS. DNA sequences are determined by the unique fluorescence emission of each fluorophore on the DNA products terminated by ddNTPs. Upon removing the 3'-OH capping group from the DNA products generated by incorporating the 3'-O-modified dNTPs and the fluorophore from the DNA products terminated with the ddNTPs, the polymerase reaction reinitiates to continue the sequence determination (FIG. 5).

Using an azidomethyl group as a chemically reversible capping moiety in the 3'-O-modified dNTPs, and an azido-based cleavable linker to attach the fluorophores to ddNTPs, four 3'-O—$N_3$-dNTPs and four ddNTP-$N_3$-fluorophores were synthesized for the hybrid SBS. The azidomethyl capping moiety on the 3'-OH group and the cleavable fluorophore on the DNA extension products are efficiently removed after fluorescence detection for sequence determination using a chemical method that is compatible to DNA. Various DNA templates, including those with homopolymer regions, were accurately sequenced with read length of over 30 bases using this hybrid SBS method.

Sequence by Synthesis with Template "Walking"

The fundamental rationale behind primer resetting is to regenerate the original primer site or to insert two or more primer sites of known sequences into the target DNA so SBS can be carried out at each site sequentially. In general, three steps are involved with this approach: 1) annealing of the first primer, 2) performing SBS, 3) denaturing the sequenced section of the template to recover a single-stranded DNA for the second primer annealing. These steps are carried out repeatedly until the target DNA is sequenced in its entirety. The advantage of primer resetting lies in its ability to restore all the templates after the denaturation step, including those that are terminated with ddNTPs, so the next cycle of SBS can restart with potentially the same amount of sequenceable DNA as the previous round.

Three approaches for achieving longer read lengths that rely on this template "walking" concept are described. In the first strategy, the DNA sequence is reset by reattaching the original primer, extending the chain with natural or minimally modified nucleotides to the end of the first round sequence, and then sequencing from that point. The second strategy relies on annealing of a second round primer that is longer than the first, containing at its 5' end the same sequence as the original primer, followed by a run of 20 universal nucleotides such as inosine, from which the second round of sequencing can be primed. If the duplex stability of this highly degenerate primer with DNA templates is found to be low, a number of locked nucleotides can be added at either end of the primer to increase the stability of the primer-template complex. In the third strategy, extra priming sites are inserted within a template strand via Type IIS or Type III restriction-recircularization. Each of these approaches has distinct advantages and some difficulties that need to be overcome. None of the three aforementioned strategies are sensitive to the type of library (genomic, cDNA or other), to the method of amplification prior to sequencing (spotting of clones, ePCR, polony PCR), or the mode of sequencing (Hybrid SBS and SBS with C—F-NRTs). Hence they are all sequence unbiased, thus greatly increasing their range of applications in sequencing technologies.

Results

Solution Extension with 3'-O-Azido-dNTPs

Figure 6:
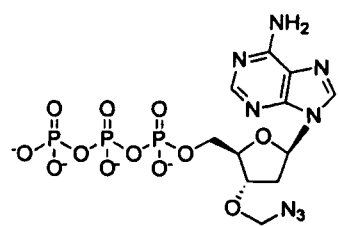
FIG. 6. 3'-O-Azido-dNTPs.
Figure 6:
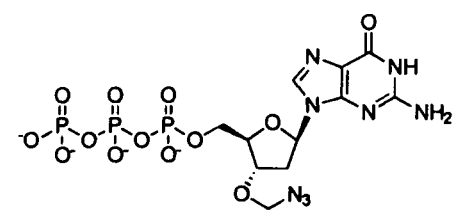
Figure 6:
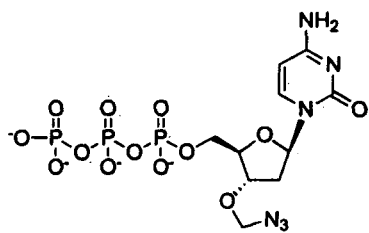
Figure 6:
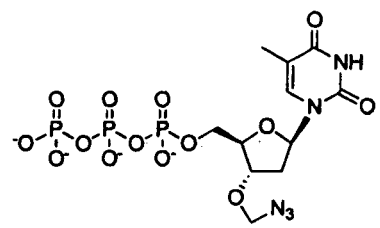

To verify the feasibility of using azido-modified nucleotides in SBS, a set of 3'-O-Azido-dNTPs (FIG. 6) were first designed and synthesized.

Figure 7:
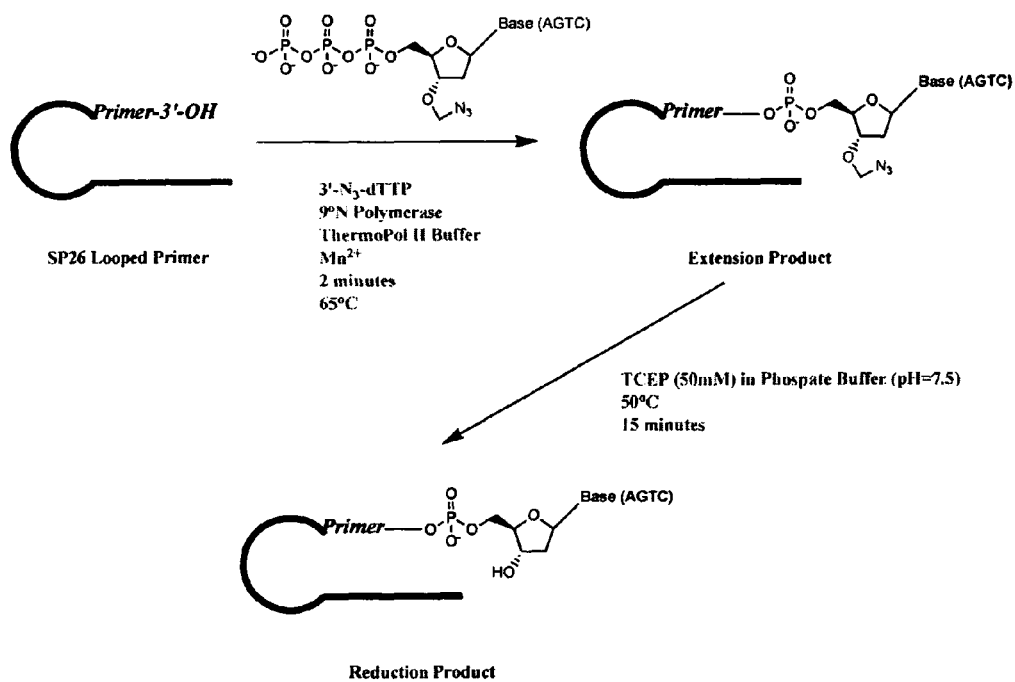
FIG. 7. Solution Incorporation and reduction of 3'-O-Azido-dNTPs: polymerase extension and TCEP reduction scheme.
Figure 8:
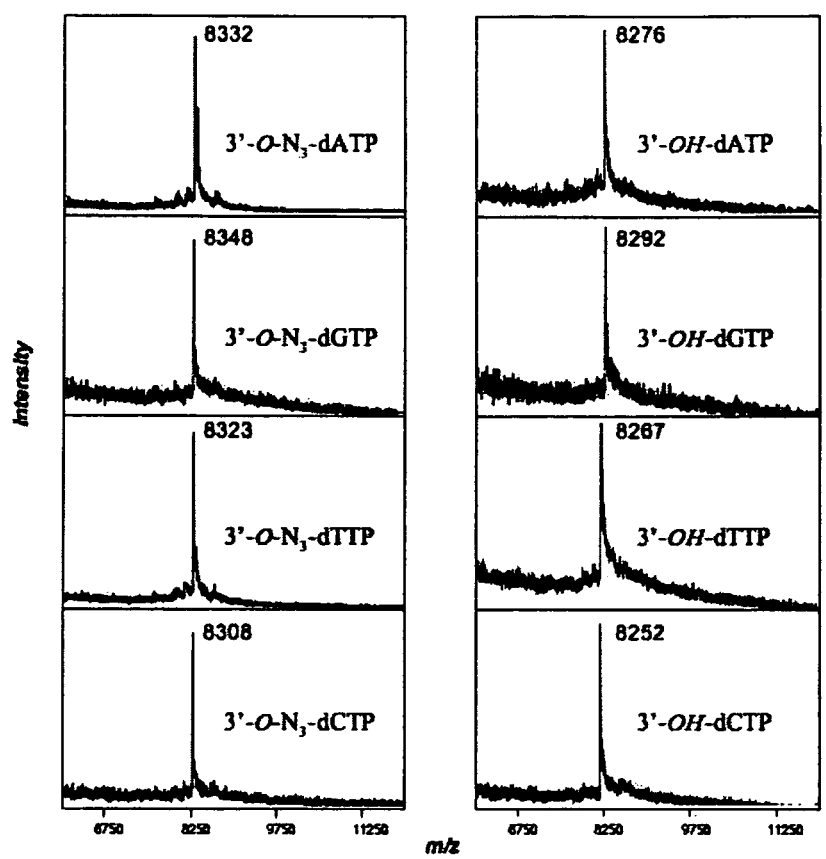
FIG. 8. MALDI-TOF MS spectra of incorporation products (left column), and MALDI-TOF MS spectra of reduction products (right column).

Each nucleotide analog (3'-O-Azido-dATP, mw=541; 3'-O-Azido-dGTP, mw=558; 3'-O-Azido-dCTP, mw=518; 3'-O-Azido-dTTP, mw=533) was incorporated into its corresponding looped primer in solution with manganese (Mn2+, 20 mM) and the mutant 9° N Thermopolymerase. The extensions were carried out at 65° C. for various time spans ranging from 20 minutes to 5 minutes. Even with the shortest reaction time of 5 minutes, 100% incorporation was confirmed with MALDI-TOF mass spectroscopy (MS) by observing the total disappearance of primer peak (m/z=7966) and the emergence of extended product peak (~m/z=8320, FIG. 7). After obtaining the extended product for each nucleotide, deprotection was carried out with varying conditions such as time (1~20 minutes), temperature (20~60° C.), and concentration of TCEP (1~50 mM). It was determined that at 50° C. with 5 mM of TCEP, the 3' azido methyl capping group could be removed completely under 5 minutes. MALDI-TOF mass spectroscopy was again used to ascertain the results (FIG. 8).

3'-O-Azido-dNTPs-Azido Linker-Dye

Solution Extension with 3'-O-Azido-dNTPs-Azido-Dye Immediately after establishing the protocol to work with azido-modified nucleotides in SBS, synthetic work for the set of 3'-O-Azido-dNTPs-Azido Linker-Dye was set forth.

Figure 9:
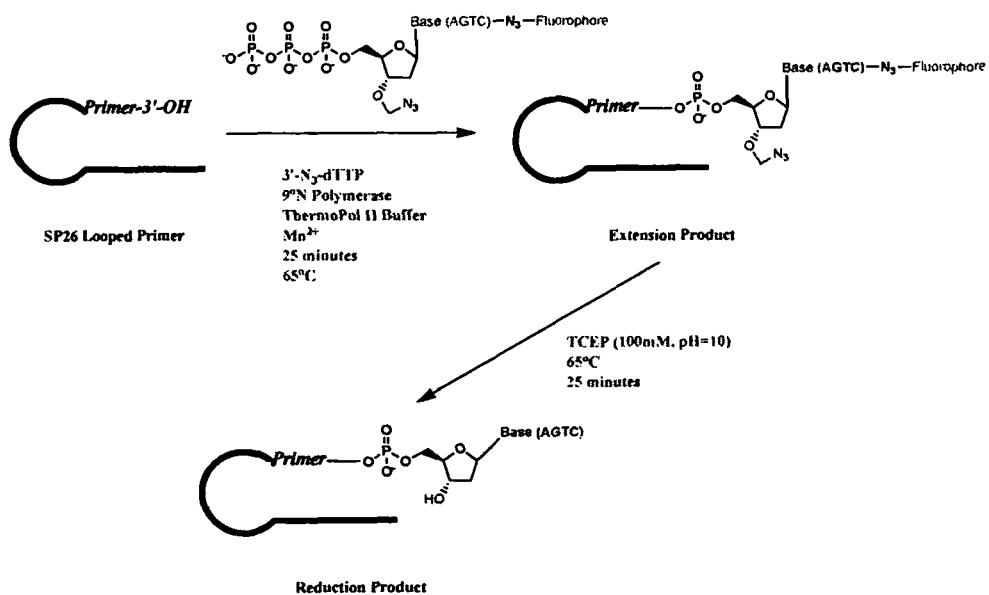
FIG. 9. Solution incorporation and reduction scheme of 3'-O-Azido-dNTPs-Azido-Dye.
Figure 10:
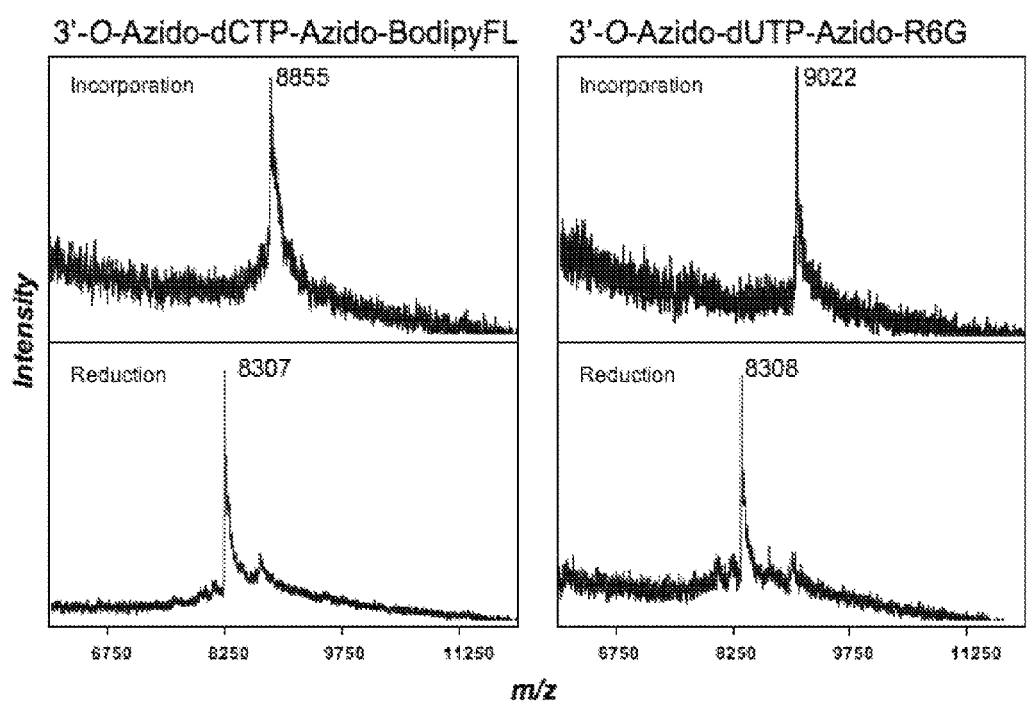
FIG. 10. MALDI-TOF MS spectra results for incorporation shown in FIG. 8.

Two nucleotides, 3'-O-Azido-dCTP-PC-BodipyFL and 3'-O-Azido-dUTP-PC—R6G were successfully synthesized and characterized. To test the incorporation of each nucleotide, extension reactions in solution, similar to those with 3'-O-Azido-dNTPs, were carried out with looped primer (m/z=7966), 9°N Thermopolymerase enzyme, and Mn2+ at 65° C. for 25 minutes. The products were verified through MALDI-TOF MS (FIG. 9). After obtaining the extension products, reduction reactions were performed under various conditions to optimize the process. It was observed that both azido linker and 3' protection group were removed with 100 mM TCEP with pH=10 at 65° C. for 25 minutes (MALDI-TOF MS spectra in FIG. 10).

Surface Extension with 3'-O-Azido-dNTPs-Azido Linker-Dye

Figure 11:
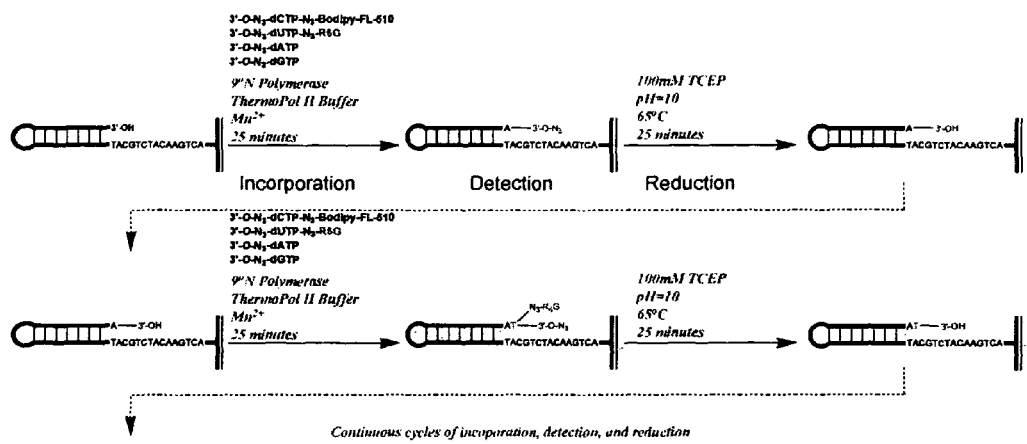
FIG. 11. SBS scheme for 3'-O-Azido-dNTPs-Azido-Dye.
Figure 12:
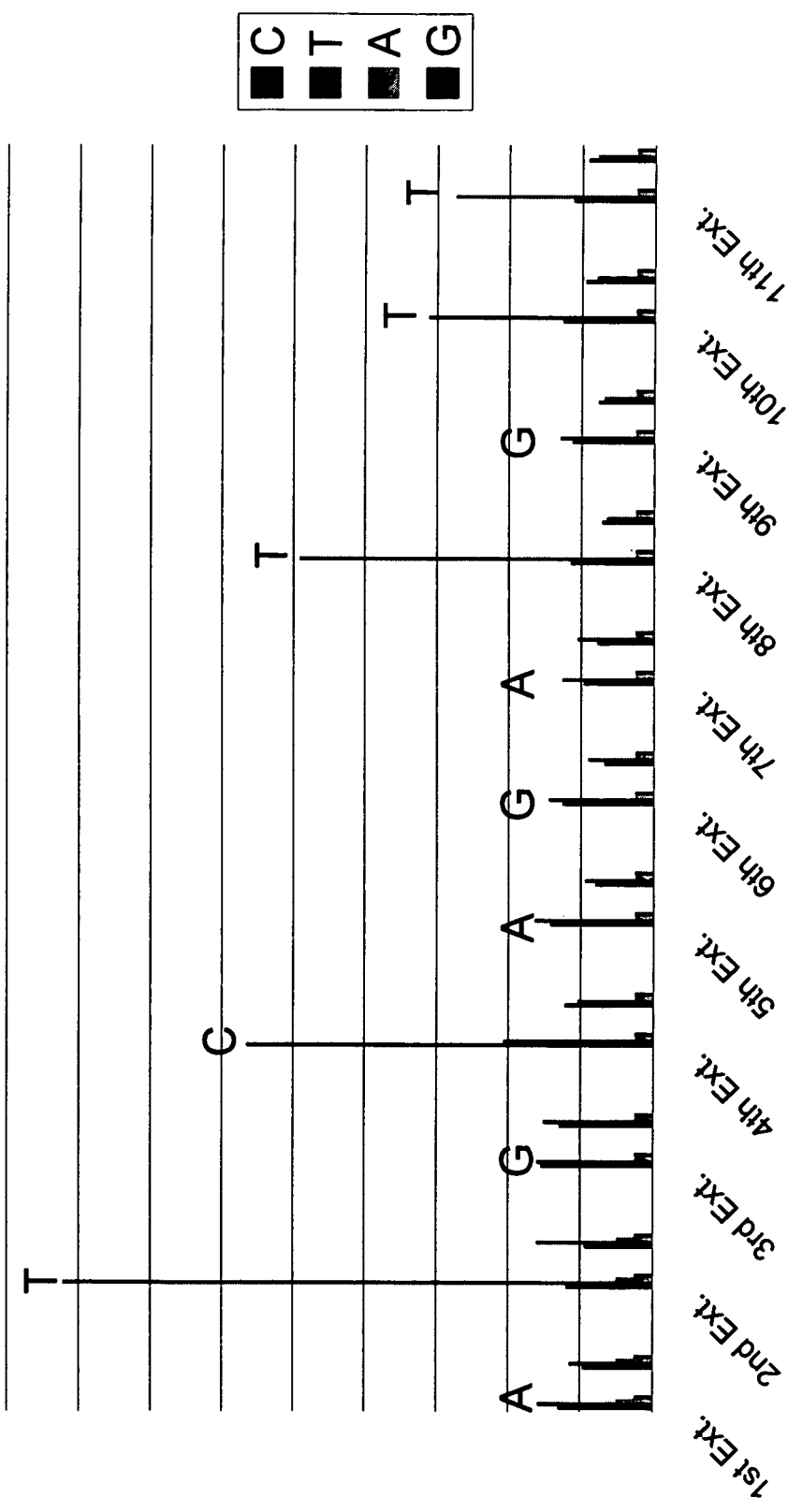
FIG. 12. Results for incorporation shown in FIG. 10.

As a part of the preliminary study, the two chemically cleavable fluorescent nucleotide analogs were used in an SBS reaction to identify the sequence of a self-primed DNA template (130 base pairs) immobilized on a solid surface. A reaction mixture of 3'-O-Azido-dCTP-Azido-BodipyFL, 3'-O-Azido-dUTP-Azido-R6G, 3'-O-Azido-dATP, and 3'-O-Azido-dGTP were prepared for the incorporation. A synchronization step was performed with the full set of 3'-O-Azido-dNTPs after incorporation to extend any remaining priming strand. After detection of the fluorescent signal, the chip surface was immersed in reduction solution (100 mM TCEP, pH=10) and incubated for 25 minutes at 65° C. to cleave both the fluorophore and 3'-O-Azido group. Upon confirmation of the removal of fluorophore, the cycles of extension, detection, and reduction were repeated to sequence the following bases (FIGS. 11 and 12).

SBS on Surface with 3'-O-Azido-dNTPs-PC/Azido-Dye

Upon completing the synthesis of both 3'-O-Azido-dNTPs-PC-Dye and 3'-O-Azido-dNTPs-Azido-Dye sets, sequencing by synthesis of DNA templates attached on solid surface will be carried out. By carefully optimizing incorporation and cleavage conditions, the goal will be the achievement of maximum base read length of each template with high consistency.

PCR Product Attachment on Beads

To expand the efficiency and increase the throughput of SBS, it is ideal to attach large quantities of different DNA templates to solid surface so that each one of these templates can be sequenced during a single cycle of SBS simultaneously. One approach will be to affix PCR product on a single bead, and then immobilize copious amount of such beads on one glass chip. Various types of beads, such as magnetic, melamine, and sepharose, will be tested in order to select one with efficient attachment to surface, durable stability during reaction cycles, and minimal unspecific absorption of fluorophores. By coupling the micro-beads chip with the azido modified reversible terminator nucleotides, SBS technology will reach the next plateau of high-throughput DNA sequencing.

Design and Synthesis of 3'-0-Modified NRTs and Cleavable Fluorescent Dideoxynucleotide Terminators for the Hybrid SBS.

Figure 13:
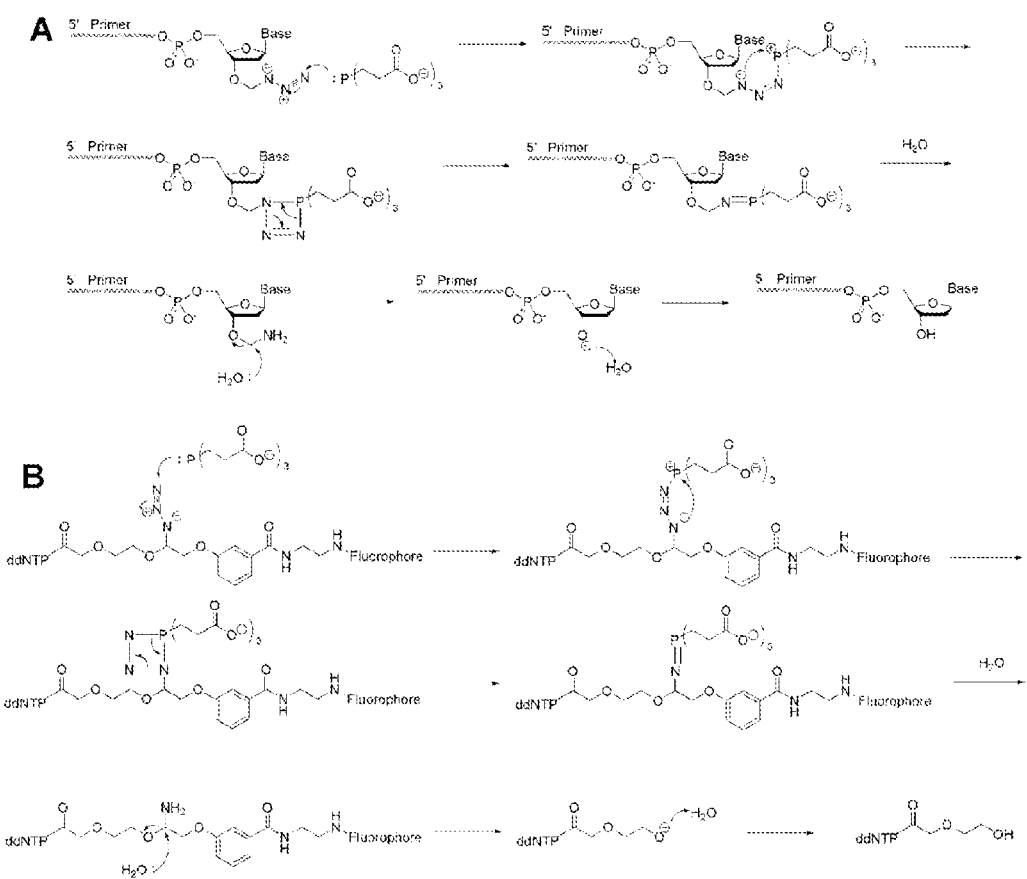
FIG. 13. Mechanisms to cleave the 3'-O-azidomethyl group and the azidolinker-fluorophore from the DNA extension products. A) Staudinger reaction with TCEP to regenerate the 3'-OH group of the DNA extension product. B) Staudinger reaction with TCEP to cleave the fluorophore from the dideoxynucleotide.

Four 3'-O-azidomethyl-modified NRTs (3'-0-$N_3$-dNTPs) (FIG. 6) were synthesized and evaluated for the hybrid SBS. The 3'-O-azidomethyl group on the DNA extension product generated by incorporating each of the NRTs was efficiently removed by the Staudinger reaction by using aqueous Tris(2-carboxyethyl)phosphine (TCEP) solution (36,37) followed by hydrolysis to yield a free 3'-OH group for elongating the DNA chain in subsequent cycles of the hybrid SBS (FIG. 13A).

To demonstrate the feasibility of carrying out the hybrid SBS on a DNA chip, four cleavable fluorescent dideoxynucleotides ddNTP-$N_3$-fluorophores (ddCTP-$N_3$-BodipyFL-510, ddUTP-$N_3$—R6G, ddATP-$N_3$—ROX, and ddGTP-$N_3$-Cy5) were synthesized (FIGS. 14-22). The ddNTP-$N_3$-fluorophores would be combined with the 4 NRTs (FIG. 6) to perform the hybrid SBS. Modified DNA polymerases have been shown to be highly tolerant to nucleotide modifications with bulky groups at the 5 position of pyrimidines (C and U) and the 7 position of purines (A and G) (27). Thus, a unique fluorophore was attached to the 5 position of C/U and the 7 position of A/G through a cleavable linker, which is also based on an azido-modified moiety (37) as a trigger for cleavage, a mechanism that is similar to the removal of the 5'-O-azidomethyl group (FIG. 13B). The ddNTP-$N_3$-fluorophores are found to efficiently incorporate into the growing DNA strand to terminate DNA synthesis for sequence determination. The fluorophore on a DNA extension product, which is generated by incorporation of the cleavable fluorescent ddNTPs, is removed rapidly and quantitatively by TCEP from the DNA extension product in aqueous solution.

Figure 19:
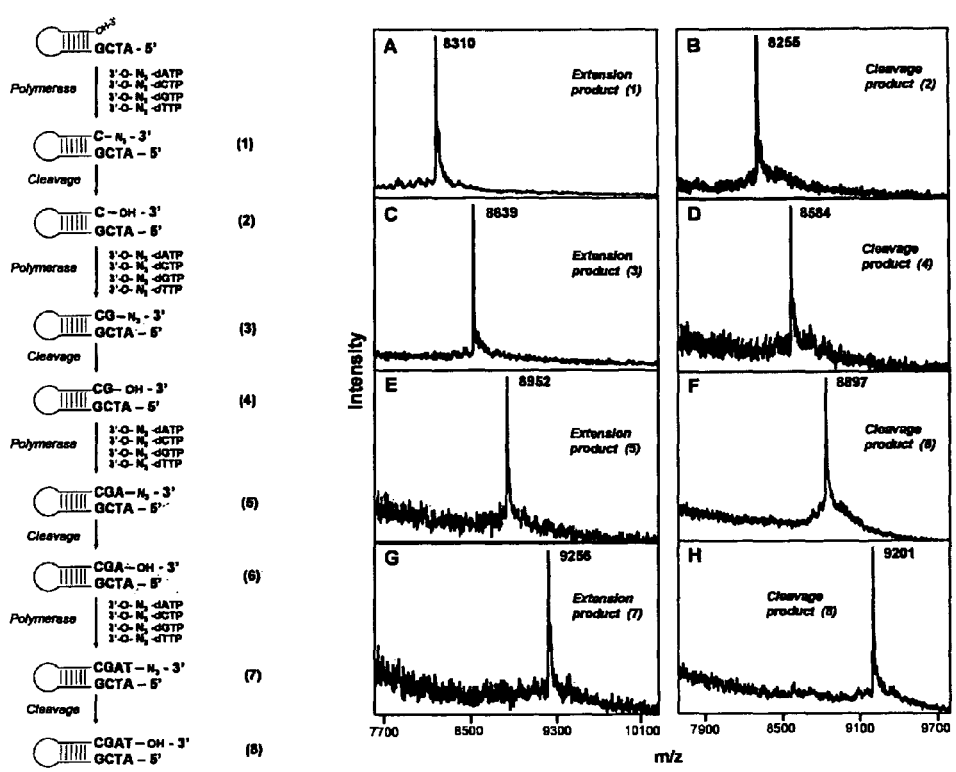

Continuous Polymerase Extension by Using 3'-O-Modified NRTs and Characterization by MALDI-TOF Mass Spectrometry To verify that the 3'-O—$N_3$-dNTPs incorporate accurately in a base specific manner, four continuous DNA extension reaction and cleavage were carried out in solution by using 3'-O—$N_3$-dNTPs as substrates. This allowed the isolation of the DNA product at each step for detailed molecular structure characterization as shown in FIG. 19. The first extension product 5'-primer-C—$N_3$-3' was desalted and analyzed using MALDI-TOF MS (FIG. 19(A)) This product was then incubated in aqueous solution to remove the azidomethyl moiety to yield the cleavage product with a free 3'OH group, which was also analyzed using MALDI-TOF MS (FIG. 19(B)). As can be seen from FIG. 19(A), the MALDI-TOF MS spectrum consist of a distinct peak corresponding to the DNA extension product 5'-primer-C—$N_3$3' (m/z 8,310), which confirms that the NRT can be incorporated base-specifically by DNA polymerase into a growing DNA strand. FIG. 19(B) shows the cleavage result on the DNA extension product. The extended DNA mass peak at m/z 8,310 completely disappeared, whereas the peak corresponding to the cleavage product 5'-primer-C-3' appears as the sole dominant peak at m/z 8,255, which establishes that TCEP incubation completely cleaves the 3'-O-azidomethyl group with high efficiency. The next extension reaction was carried out by using this cleaved product, which now has a free 3'-OH group, as a primer to yield a second extension product, 5'-primer-CG$N_3$-3' (m/z 8,639; FIG. 19C). As described above, the extension product was cleaved to generate product for further MS analysis yielding a single peak at m/z 8,584 (FIG. 19(D)). The third extension reaction to yield 5'-primer-CGA-$N_3$-3' (m/z 8,952; FIG. 19(E)), the fourth extension to yield 5'-primer-CGAT-$N_3$-3' (m/z 9,256; FIG. 19(G)) and their cleavage to yield products (m/z 8,897; FIG. 19(F)) and (m/z 9,201; FIG. 19(H)) were similarly carried out and analyzed by MALDI-TOF MS. These results demonstrate that all four 3'-O—$N_3$-dNTPs are successfully synthesized and efficiently incorporated base-specifically into the growing DNA strand in a continuous polymerase reaction as reversible terminators and the 3'-OH capping group on the DNA extension products is quantitatively cleaved by TCEP.

Figure 20:
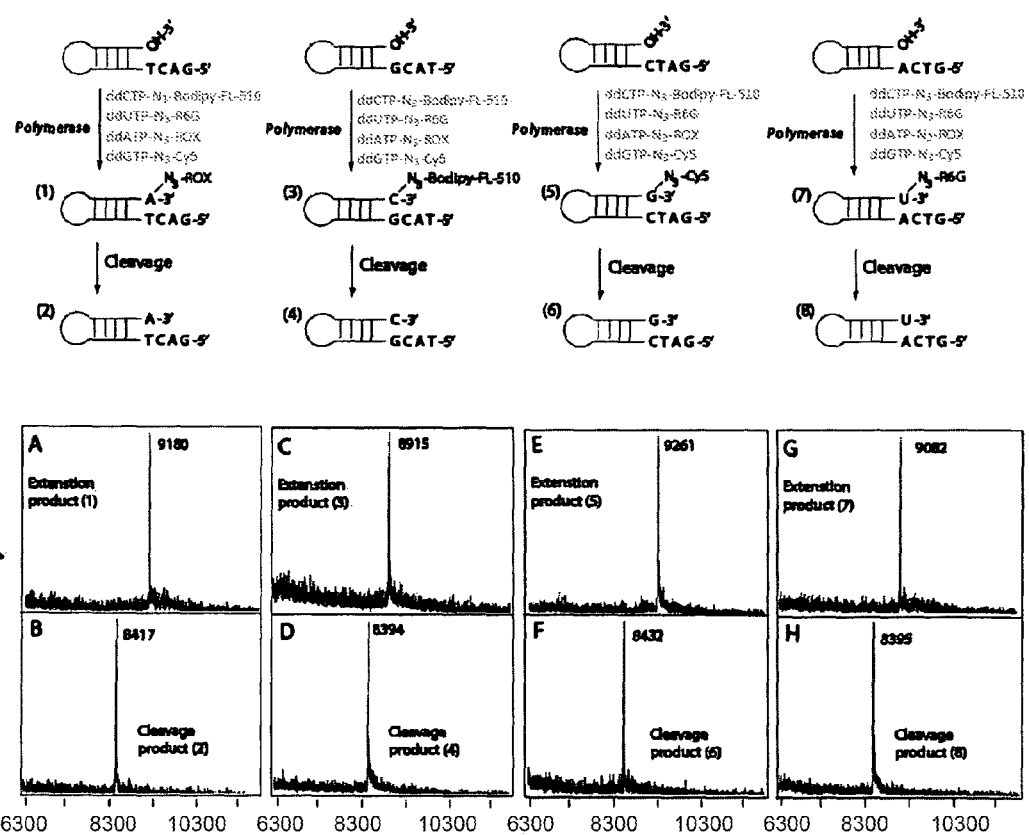
FIG. 20. A detailed scheme (top half of fig.) of polymerase reaction using all four ddATP-$N_3$-fluorophores to extend with an "ddA", "ddC", "ddG" and "ddU" and the subsequent cleavage reaction to cleave off the fluorophore from the DNA extension product. MALDI-TOF MS spectra (bottom half of fig.) verifying base specific incorporation of: (A) ddATP- $N_3$—ROX (peak at 9,180 m/z) among pool of all four cleavable fluorescent dideoxynucleotides, (B) the corresponding cleavage product (8,417 m/z); (C) ddCTP-$N_3$-Bodipy-FL-510 (peak at 8,915 m/z), (D) the corresponding cleavage product (8,394 m/z); (E) ddGTP-$N_3$-Cy5 (peak at 9,317 m/z), (F) the corresponding cleavage product (8,433 m/z); (G) ddUTP-$N_3$—R6G (peak at 9,082 m/z) and (H) the corresponding cleavage product (8,395 m/z).

Polymerase Extension by Cleavable Fluorescent Dideoxynucleotide Terminators and Characterization by MALDI-TOF Mass Spectrometry To verify that the four cleavable fluorescent ddNTPs (ddCTP-$N_3$-Bodipy-FL-510, ddUTP-$N_3$—R6G, ddATP-$N_3$—ROX, and ddGTP-N3-Cy5) (FIG. 14) are incorporated accurately in a base-specific manner in a polymerase reaction, single-base extension reactions with four different self-priming DNA templates whose next complementary base was either A, C, G, or T were carried out in solution. After the reaction, the four different primer extension products were analyzed by MALDI-TOF MS as shown in FIG. 20. Single clear mass peaks at 9,180, 8,915, 9,317, and 9,082 (m/z) corresponding to each primer extension product with no leftover starting materials were produced by using ddNTP-$N_3$-fluorophores (FIGS. 20 A, C, E, and G). Brief incubation of the DNA extension products in an aqueous TCEP solution led to the cleavage of the linker tethering the fluorophore to the dideoxynucleotide. FIGS. 20 B, D, F, and H shows the cleavage results for the DNA products extended with ddNTP-$N_3$-fluorophores. The mass peaks at 9,180, 8,915, 9,317, and 9,082 (m/z) have completely disappeared, whereas single peaks corresponding to the cleavage products appear at 8,417, 8,394, 8,433, and 8,395 (m/z), respectively. These results demonstrate that cleavable fluorescent ddNTPs are successfully synthesized and efficiently terminated the DNA synthesis in a polymerase reaction and that the fluorophores are quantitatively cleaved by TCEP. Thus, these ddNTP analogues meet the key requirements necessary for performing the hybrid SBS in combination with the NRTs.

4-Color DNA Sequencing by Synthesis on a Chip Using Photocleavable Fluorescent Dideoxynucleotide/3'-Modified Photocleavable Nucleotide Combination Remnant of Sanger Sequencing.

Figure 21:
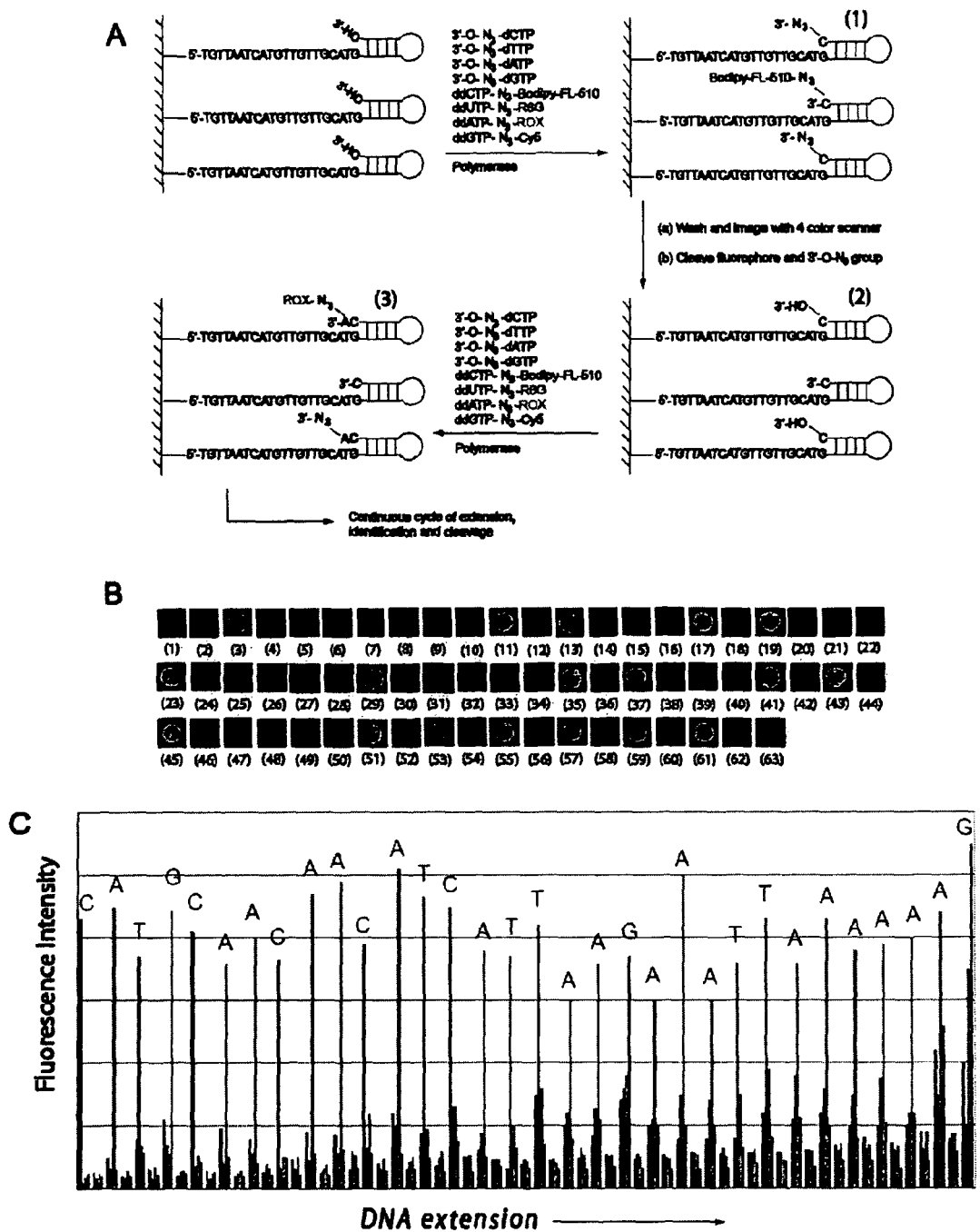
FIG. 21. (A) Reaction scheme of Sanger/sequencing by synthesis hybrid sequencing on a chip using combination of cleavable fluorescent dideoxynucleotides and 3'-O—$N_3$-modified nucleotides. (B) The scanned 4-color fluorescence images (shown here in grayscale) for each step of Sanger/SBS hybrid sequencing on a chip: (1) incorporation of 3'-O—$N_3$-dCTP and ddATP-$N_3$-Bodipy-FL-510; (2) cleavage of $N_3$-Bodipy-FL-510 and 3'-$CH_2N_3$ group; (3) incorporation of 3'-O—$N_3$-dATP and ddATP-$N_3$—ROX; (4) cleavage of $N_3$—ROX and 3'-$CH_2N_3$ group; (5) incorporation of 3'-O—$N_3$-dTTP and ddUTP-$N_3$—R6G; (6) cleavage of $N_3$—R6G and 3'-$CH_2N_3$ group; (7) incorporation of 3'-O—$N_3$-dGTP and ddGTP-$N_3$-Cy5 and; (8) cleavage of $N_3$-dGTP and 3'-$CH_2N_3$ group; images (9) to (63) are similarly produced. (C) A plot (4-color sequencing data) of raw fluorescence emission intensity obtained by using 3'-O—$N_3$-dNTPs and $N_3$-fluorophores. The small groups of peaks between the identified bases are fluorescent background from the DNA chip.

In the four-color hybrid SBS approach, the identity of the incorporated nucleotide is determined by the unique fluorescent emission from the four fluorescent dideoxynucleotide terminators, while the role of the 3'-O-modified NRTs is to further extend the DNA strand to continue the determination of the DNA sequence. Therefore, the ratio between the amount of ddNTP-$N_3$-fluorophores and 3'-O—$N_3$-dNTPs during the polymerase reaction determines how much of the ddNTP-$N_3$-fluorophores incorporate and thus the corresponding fluorescent emission strength. With a finite amount of immobilized DNA template on a solid surface, initially the majority of the priming strands should be extended with 3'-O—$N_3$-dNTPs, while a relative smaller amount should be extended with ddNTP-$N_3$-fluorophores to produce fluorescent signals that are above the fluorescent detection system's sensitivity threshold for sequence determination. As the sequencing cycle continues, the amount of the ddNTP-$N_3$-fluorophores need to be gradually increased to maintain the fluorescence emission strength for detection. Following these guidelines, we performed the hybrid SBS on a chip-immobilized DNA template using the 3'-O—$N_3$-dNTP/ddNTP-$N_3$-fluorophore combination and the results are shown in FIG. 21. The general four-color sequencing reaction scheme on a chip is shown in FIG. 21A.

De novo sequencing reaction on the chip was initiated by extending the self-priming DNA by using a solution consisting of four 3'-O—$N_3$-dNTPs and four ddNTP-$N_3$-fluorophores, and 9°N DNA polymerase. The hybrid SBS allows for the addition of all eight, nucleotide substrates simultaneously to unambiguously determine DNA sequences. This reduces the number of steps needed to complete the sequencing cycle, while increasing the sequencing accuracy because of competition among the substrates in the polymerase reaction. The DNA products extended by ddNTP-$N_3$-fluorophores, after fluorescence detection for sequence determination and cleavage, are no longer involved in the subsequent polymerase reaction cycles because they are permanently terminated. Therefore, further polymerase reaction only occurs on a DNA strand that incorporates the 3'-O—$N_3$-dNTPs, which subsequently turn back into natural nucleotide on cleavage of the 3'-OH capping group, and should have no deleterious effect on the polymerase binding to incorporate subsequent nucleotides for growing the DNA chains. However, successive addition of the previously designed cleavable fluorescent NRTs (22, 37, 38) into a growing DNA strand during SBS leads to a newly synthesized DNA chain with a leftover propargyl amino group at each nucleobase. This may interfere with the ability of the enzyme to efficiently incorporate the next incoming nucleotide, which will lead to loss of synchrony and thereby reduction in the read length. This challenge might potentially be overcome by reengineering DNA polymerases that efficiently recognize and accept the modified DNA strand, or by alternative design of the fluorescent NRTs (39).

To negate any lagging fluorescence signal that is caused by a previously unextended priming strand, a synchronization step was added to reduce the amount of unextended priming strands after the initial extension reaction shown in the scheme of FIG. 21A. A synchronization reaction mixture consisting of just the four 3'-0-$N_3$-dNTPs in relatively high concentration was used along with the 9°N DNA polymerase to extend, any remaining priming strands that retain a free 3'-OH group to synchronize the incorporation.

Figure 22:
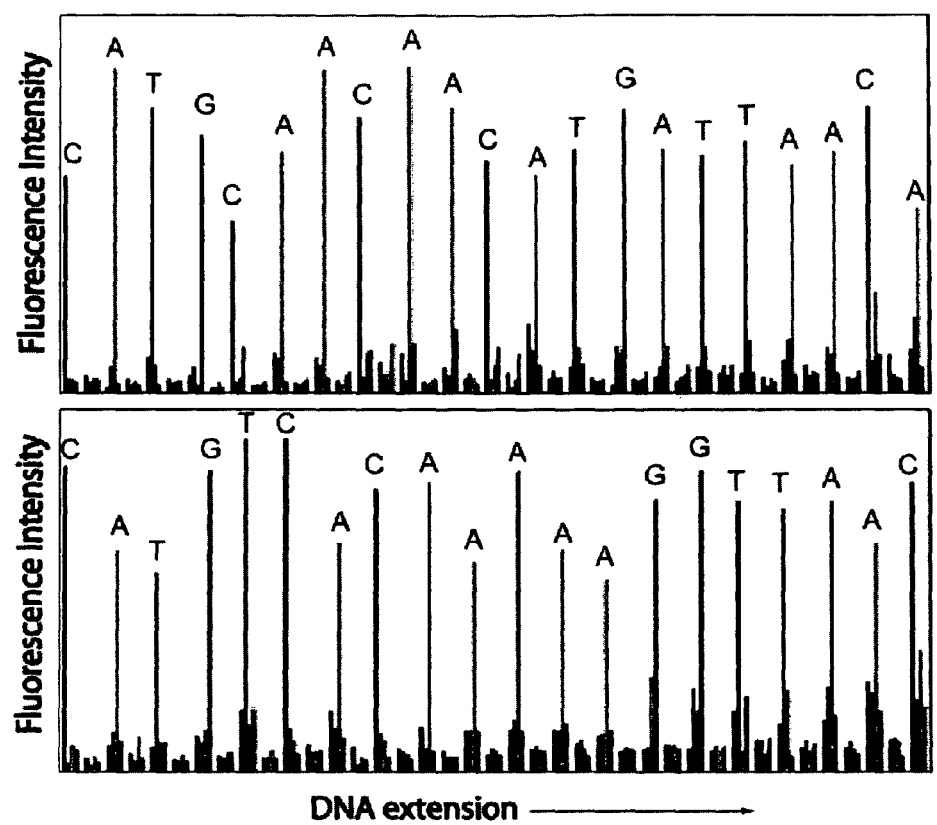
FIG. 22. A plot (four-color sequencing data) of raw fluorescence emission intensity obtained by using 3'-O—N3-dNTPs and ddNTP-N3-fluorophores at the four designated emission wavelengths of the four cleavable fluorescent dideoxynucleotides.

The four-color images from a fluorescence scanner for each step of the hybrid SBS on a chip is shown in FIG. 21B, The first extension of the primer by the complementary fluorescent ddNTP, ddCTP-$N_3$-Bodipy-FL-510, was confirmed by observing a blue signal (the emission from. Bodipy~FL~510) [FIG. 21B (1)]. After fluorescent signal detection, the surface was immersed in a TCEP solution to cleave both the fluorophore from the DNA product extended with ddNTP-$N_3$-fluorophores and the 3'-0-azidomethyl group from the DNA product extended with 3'-0-$N_3$-dNTPs. The surface of the chip was then washed, and a negligible residual fluorescent signal was detected, confirming cleavage of the fluorophore [FIG. 21B (2)]. This was followed by another extension reaction with the 3'-O—$N_3$-dNTP/ddNTP-$N_3$-fluorophore solution to incorporate the next nucleotide complementary to the subsequent base on the template. The entire process of incorporation, synchronization, detection, and cleavage was performed multiple times to identify 32 successive bases in the DNA template. The plot of the fluorescence intensity vs. the progress of sequencing extension (raw four-color sequencing data) is shown in FIG. 21C. The DNA sequences are unambiguously identified with no errors from the four-color raw fluorescence data without any processing. Similar four color sequencing data were obtained for a variety of DNA template (FIG. 22)

Strategy 1: Template "Walking" by Unlabeled Nucleotides

The fundamental rationale behind this template "walking" strategy is the removal of the sequenced strand and reattaching of the original primer to allow the extension, or walking, of the template with a combination of natural and modified nucleotides to the end of the first round sequence so that SBS can be carried out from that point. Since the original sequenced strand is stripped away, including those terminated with ddNTPs, all the templates become available for "walking". Given that "walking" is carried out with either natural or 3'-modified nucleotides, the subsequent round of SBS is performed on nascent DNA strands for maximum read length.

Figure 23:
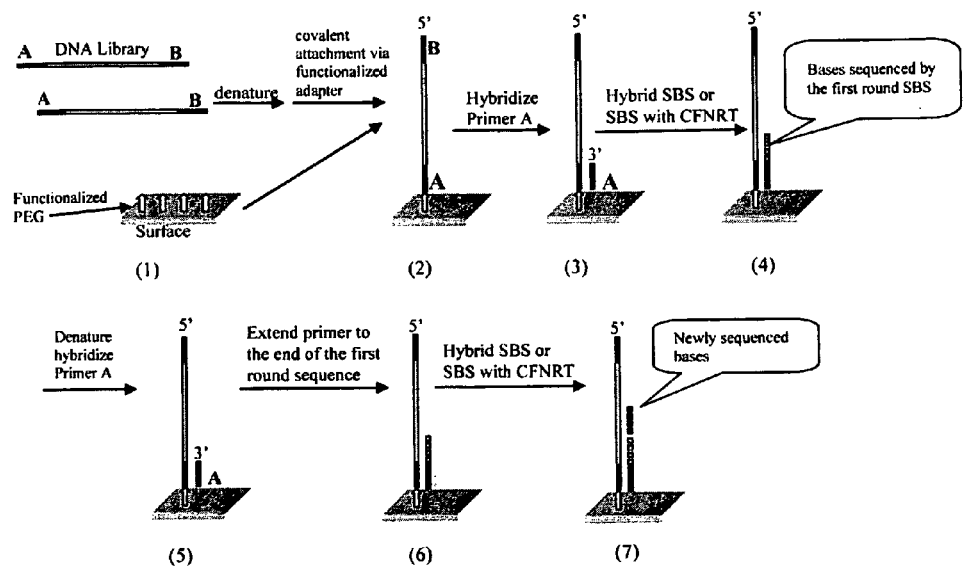
FIG. 23. "Walking" Strategy 1

The advantage of template "walking" is its ability to restore all the templates after the denature step, includes those that are terminated with ddNTPs, so the next cycle of SBS can restart with potentially the same amount of nascent DNA as the previous round. The "walking" methodology is applicable to both hybrid SBS and SBS with C—F-NRTs, and has the potential to dramatically increase the read lengths of these SBS technologies (FIG. 23).

Template "Walking" for Hybrid SBS

1. Hybrid SBS (1$^{st}$ Round)

Figure 24:
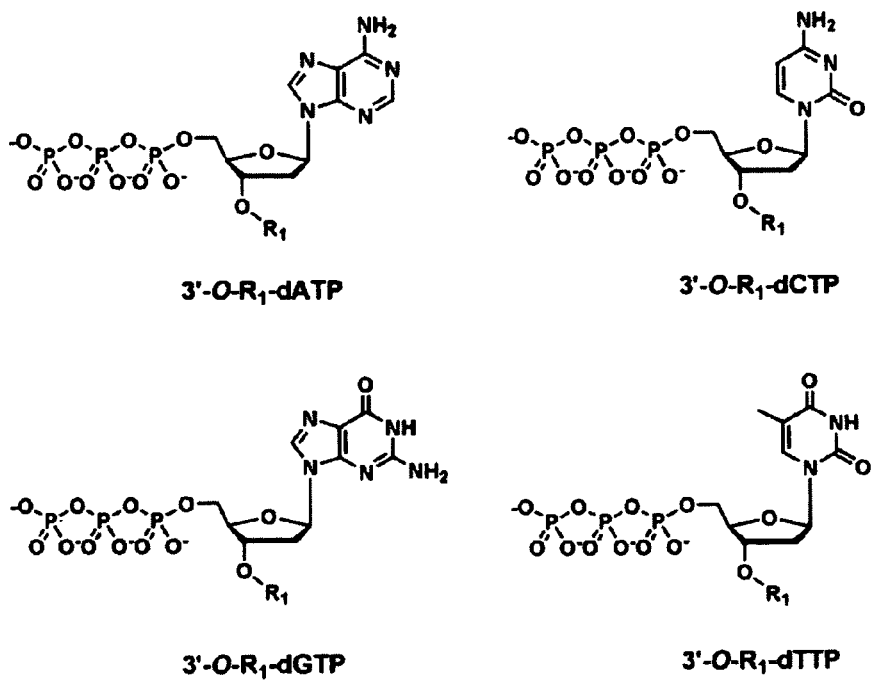
FIG. 24. Structures of the nucleotide reversible terminators
Figure 25:
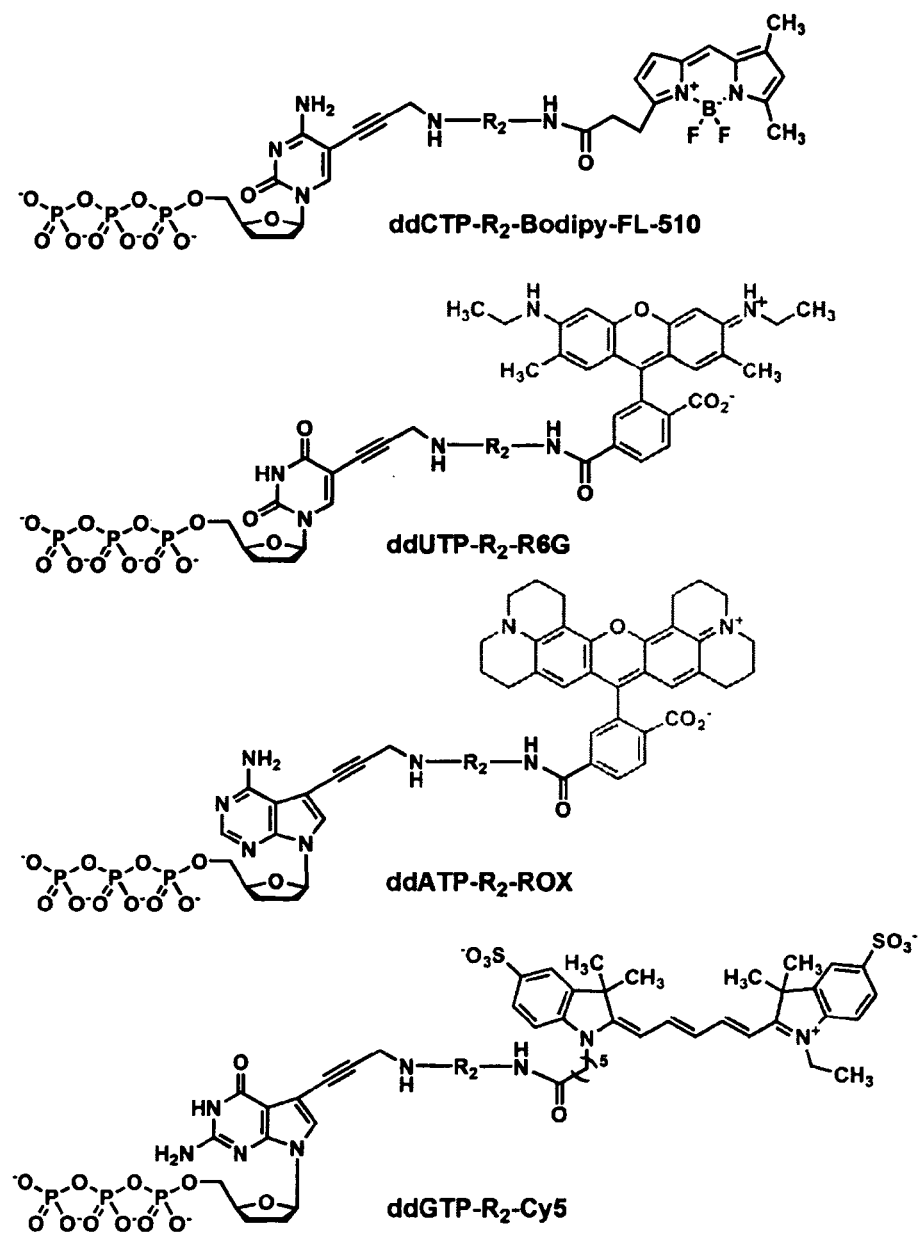
FIG. 25. Structures of cleavable fluorescent dideoxynucleotide terminators
Figure 26:
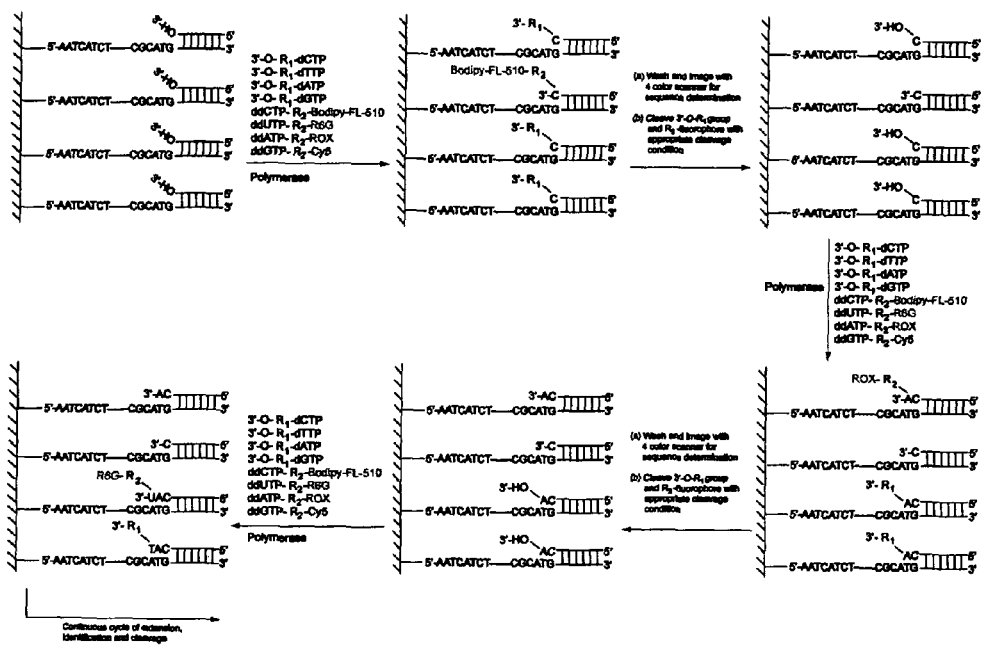
FIG. 26. Hybrid SBS scheme

DNA sequencing by synthesis (SBS) on a solid surface during polymerase reaction offers a paradigm to efficiently decipher multiple DNA sequences in parallel. Hybrid SBS is a hybrid DNA sequencing method between the Sanger dideoxy chain terminating reaction and SBS. In this approach, four nucleotides (FIG. 24) modified as reversible terminators by capping the 3'-OH with a small reversible moiety so that they are still recognized by DNA polymerase as substrates to extend the DNA chain, are used in combination with a small percentage of four cleavable fluorescent dideoxynucleotides (FIG. 25) to perform SBS. Sequences are determined by the unique fluorescence emission of each fluorophore on the DNA products terminated by ddNTPs, while the role of the 3'-O-modified dNTPs is to further extend the DNA strand to continue the determination of the DNA sequence. Upon removing the 3'-OH capping group from the DNA products generated by incorporating the 3'-O-modified dNTPs and the fluorophore from the DNA products terminated with the ddNTPs, the polymerase reaction reinitiates to continue the sequence determination (FIG. 26). Such incorporation, fluorescence measurement and dye removal is repeatedly conducted until the detectable fluorescence intensity is not distinguishable, indicating a situation in which all the elongated primers are terminated with ddNTP. To overcome this "halted sequencing" due to ddNTP termination, a "walking" step is carried out to reset the templates.

2. Template "Walking"

Immediately after the first round of SBS, all of the elongated primers ended terminated with ddNTPs are removed from the template by denaturing. The templates are freed again and available for further sequencing reactions. To achieve template "walking", the same starting primer is annealed to the template again and enzymatic incorporation is conducted to fill the gap between first and second stages of SBS. Five strategies are available for the walking process. Each approach has its advantages and shortcomings, which are summarized in the following.

Figure 27:
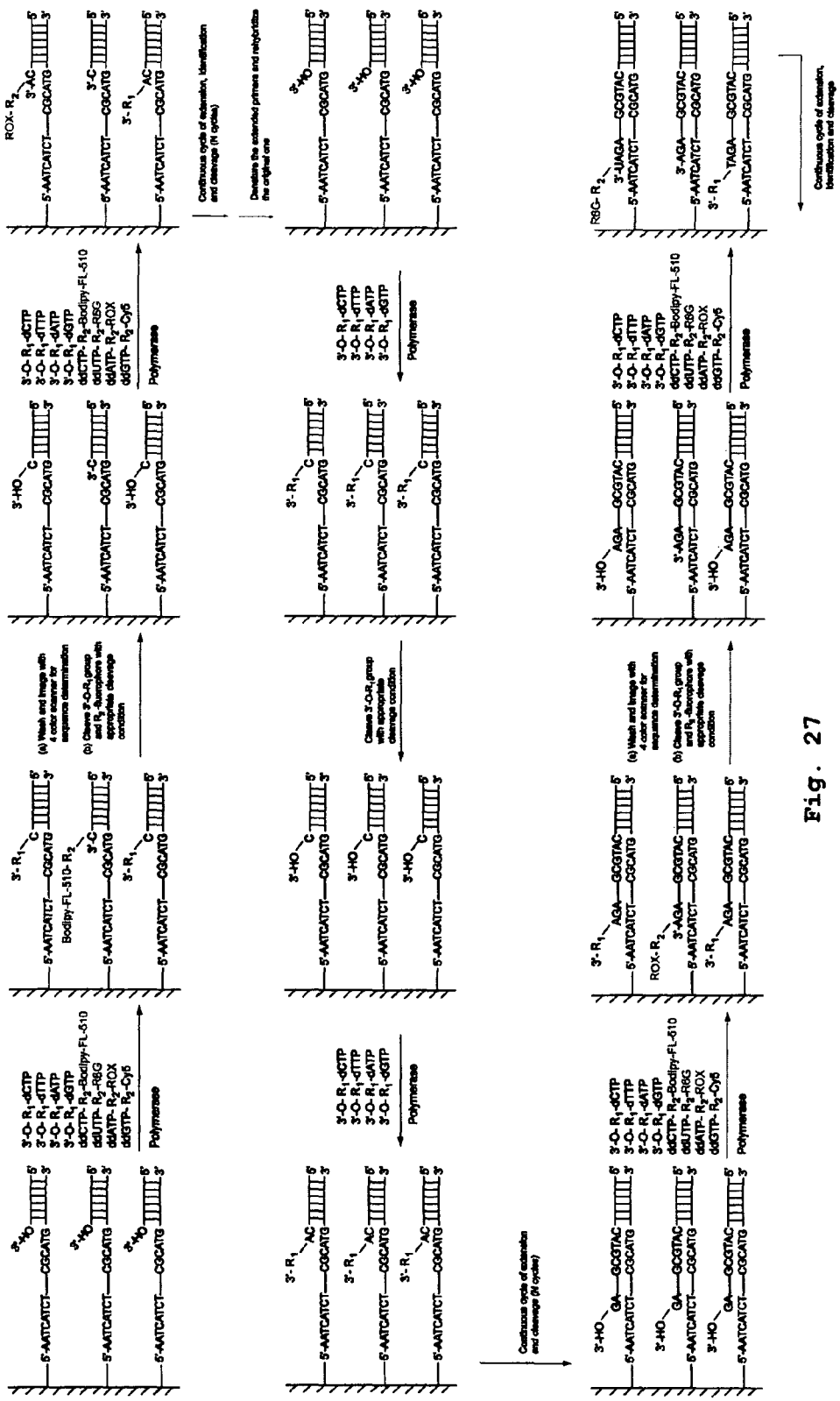
FIG. 27. Template "Walking" Method 1

Method 1. Nucleotide reversible terminators (3'-O—$R_1$-dNTPs) are used as substrates to perform enzymatic incorporation (FIG. 27). After incorporation, specific chemical reaction is applied to regenerate 3'-OH to ensure the subsequent incorporation. The number of repeated cycles of such incorporation and cleavage will exactly match the actual read length in the first stage of SBS, so that this "filling gap" incorporation stops at the same point where the longest ddNTP primer reaches.

Figure 28:
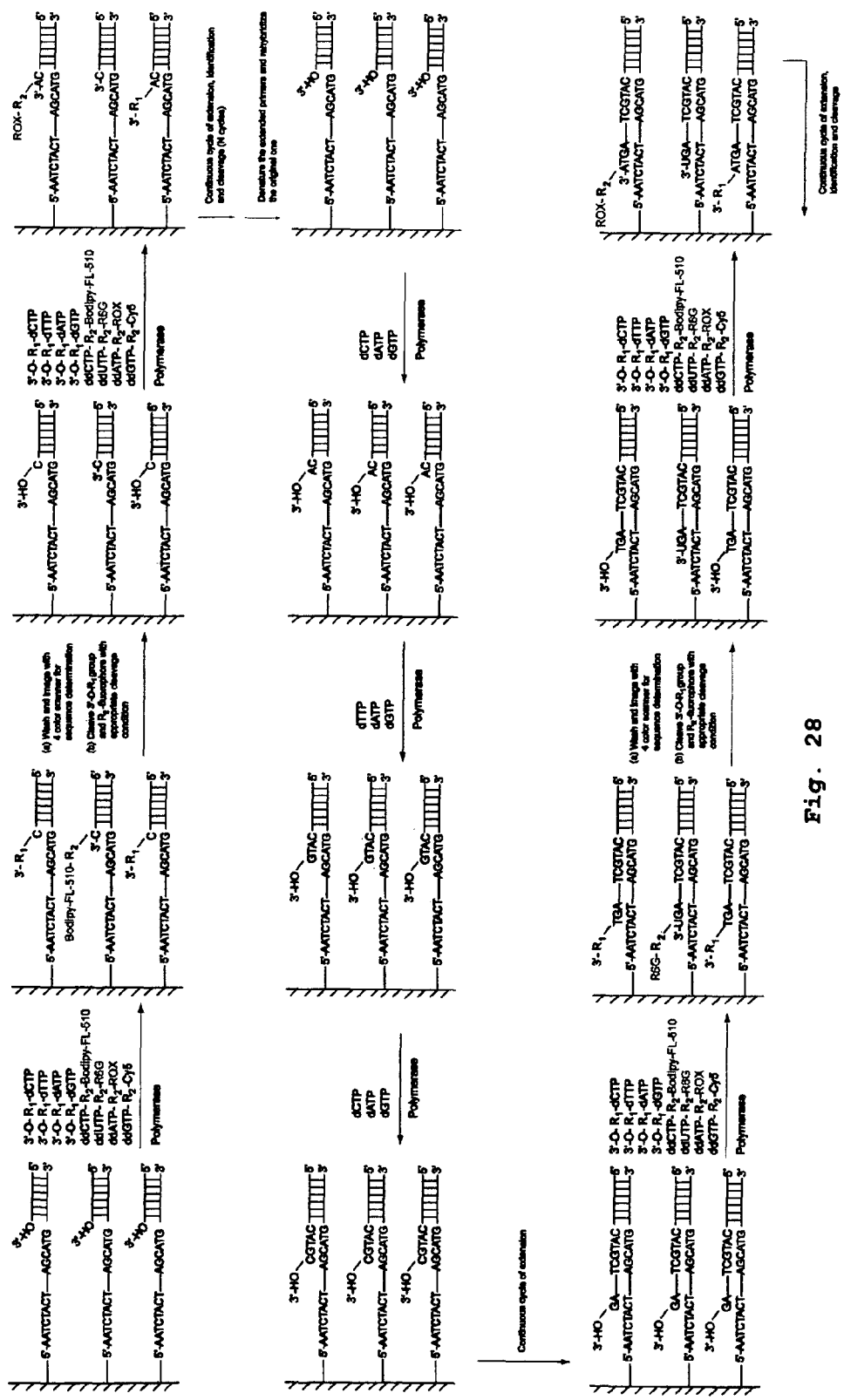
FIG. 28. Template "Walking" Method 2

Methods 2, 3, and 4. Enzymatic incorporation is conducted using two sets of nucleotides as substrates (FIG. 28). For example, the first set of nucleotides composed of dCTP, dATP, and dGTP (sans dTTP) was used to perform incorporation, so that the polymerase reaction stops once it reaches a base "A" in template.

Then enzymatic incorporation is resumed with the second set of nucleotides composed of dTTP, dATP, and dGTP (sans dCTP), resulting in a polymerase reaction that stops at the base "G" in template. The repeated cycles of such incorporations fill the gap between first and second stages of SBS.

Figure 29:
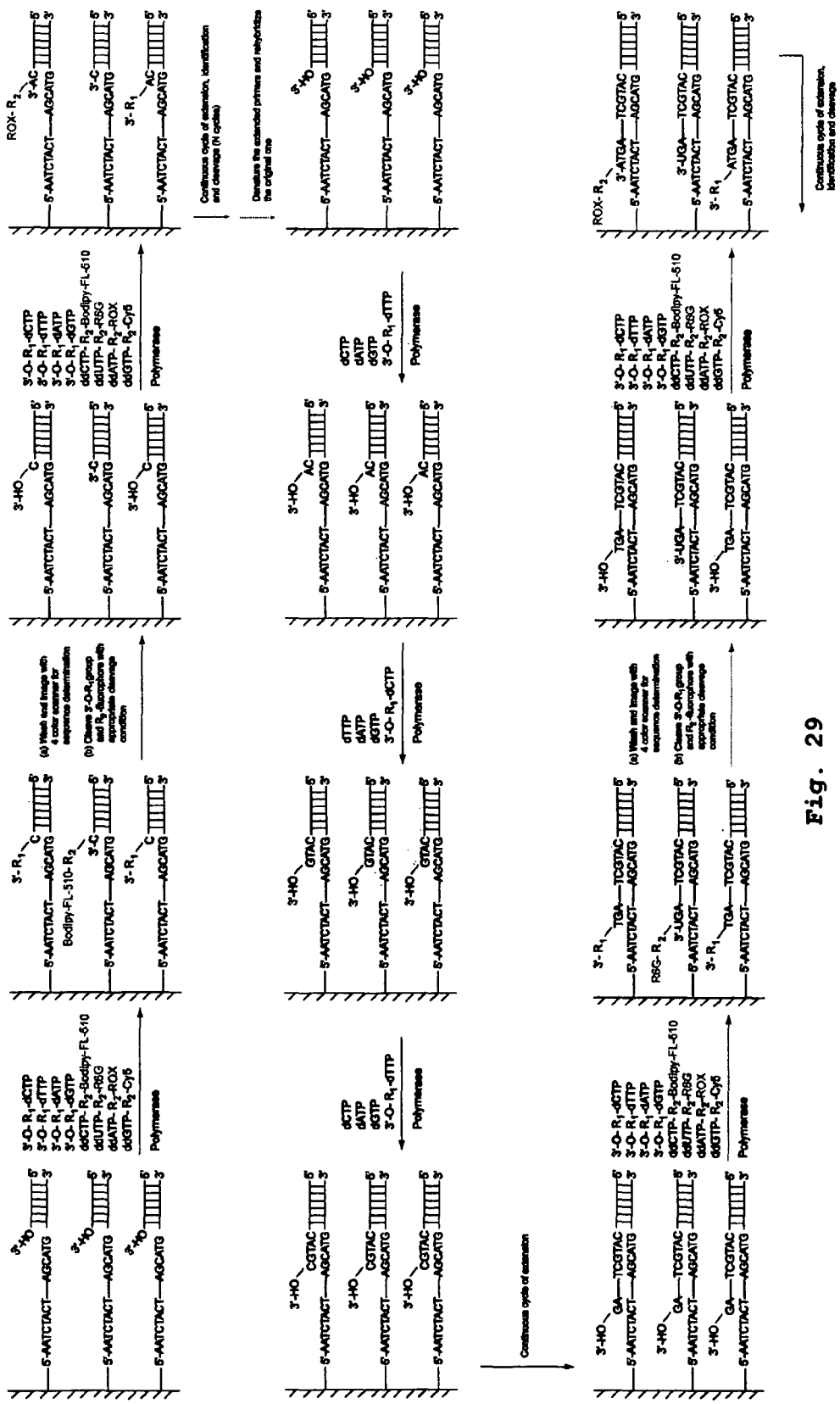
FIG. 29. Template "Walking" Method 3

To minimize the mis-incorporation rate, another enzyme substrate which can be recognized but not incorporated by the polymerase is assigned to each set of nucleotides. For instance, if the DNA polymerase used can only incorporate dNTP but not 3' blocked nucleotides, 3'-O—$R_1$-dTTP will be combined with dCTP, dATP and dGTP as the first set, while 3'-O—$R_1$-dCTP will be combined with dTTP, dATP and dGTP as the second set to elongate the primer (FIG. 29).

Figure 30:
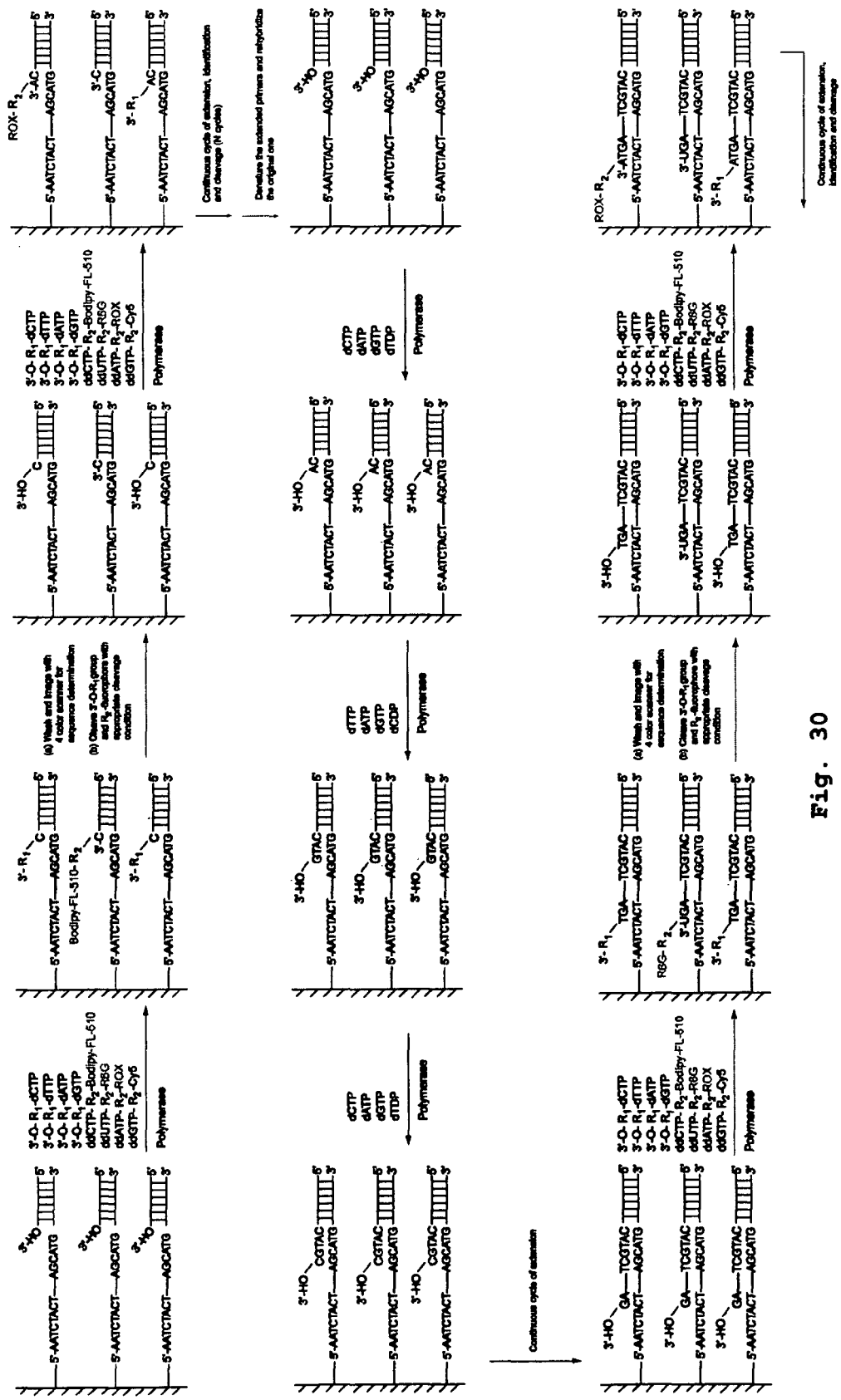
FIG. 30. Template "Walking" Method 4

Alternatively, deoxyribonucleotides diphosphate can also play such role, replacing the 3'-O—$R_1$-dNTPs, during enzymatic incorporation (FIG. 30).

Figure 31:
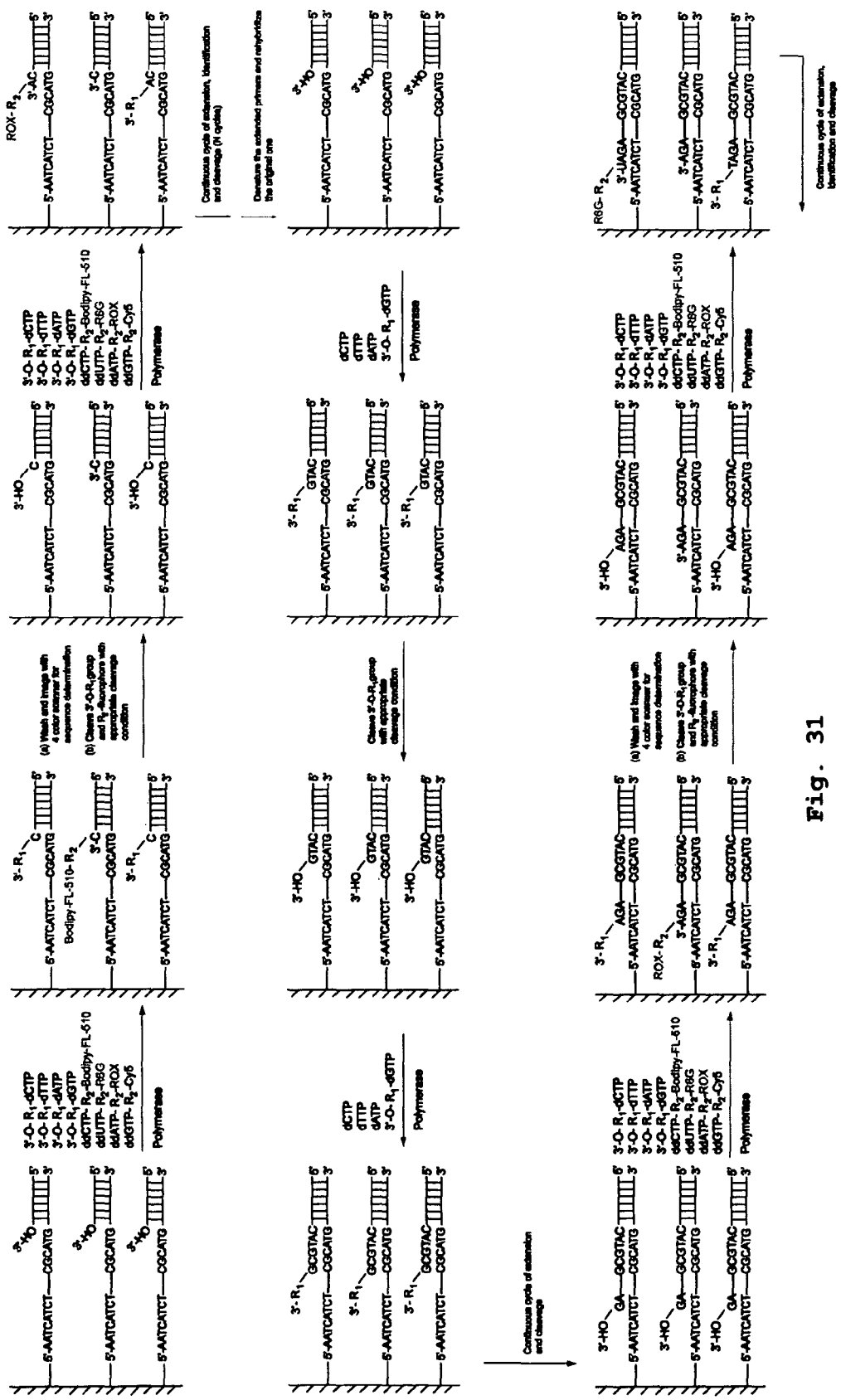
FIG. 31. Template "Walking" Method 5

Method 5. Enzymatic incorporation is conducted using three dNTPs and another nucleotide reversible terminator as substrates (FIG. 31). Primer elongation will only be stopped once it incorporates nucleotide reversible terminator. After incorporation, specific chemical reaction is applied to regenerate 3'-OH which ensure consecutive incorporation of the next round. Repeated cycles of such incorporation and cleavage will fill the gap between first and second stages of SBS.

3. Re-Initiation of Hybrid SBS

Once the "walking" process is completed, the second stage of SBS is conducted using mixture of nucleotide reversible terminators and fluorescently labeled dideoxynucleotides as incorporation substrates same as described above. Another cluster of bases on the template can be continuously revealed, leading to the doubling of the original read length. The SBS-walking-SBS process is repeated to generate maximum read length.

EXAMPLES

Figure 32:
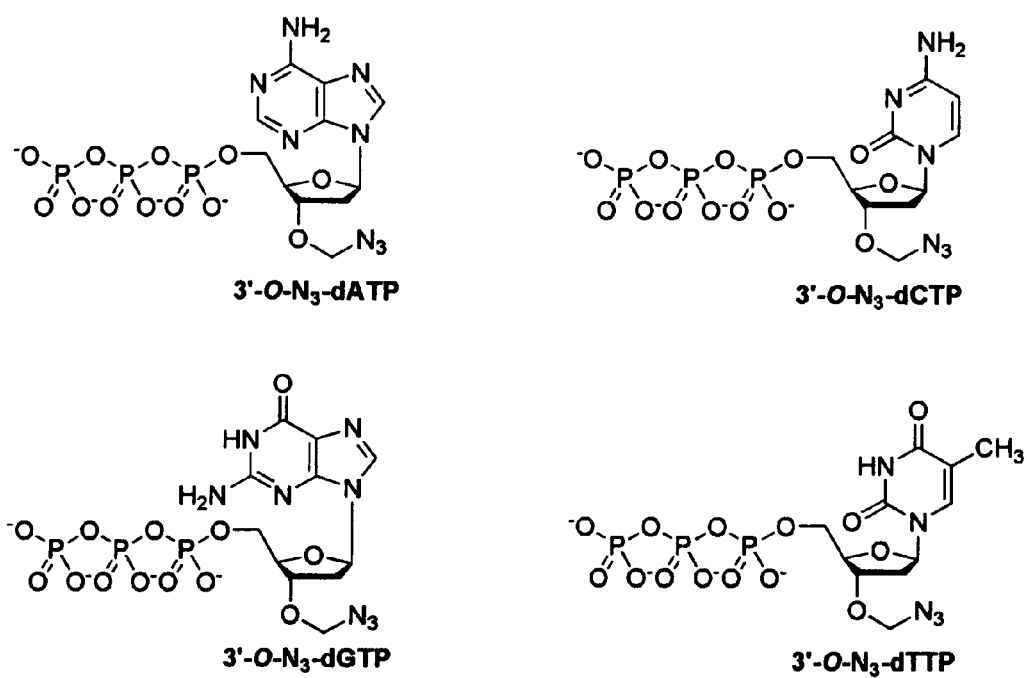
FIG. 32. Structures of the nucleotide reversible terminators, 3'-O—$N_3$-dATP, 3'-O—$N_3$-dCTP, 3'-O—$N_3$-dGTP, 3'-O—$N_3$-dTTP FIG. 33. Structures of cleavable fluorescent dideoxynucleotide terminators ddNTP-$N_3$-fluorophores, with the 4 fluorophores having distinct fluorescent emissions: ddCTP-$N_3$-Bodipy-FL-510 ($\lambda_{abs\ (max)}$=502 nm; $\lambda_{em\ (max)}$=510 nm), ddUTP-$N_3$—R6G ($\lambda_{abs\ (max)}$=525 nm; $\lambda_{em\ (max)}$=550 nm) ddATP-$N_3$—ROX ($\lambda_{abs\ (max)}$=585 nm; $\lambda_{em\ (max)}$=602 nm), and ddGTP-$N_3$-Cy5 ($\lambda_{abs\ (max)}$=649 nm; $\lambda_{em\ (max)}$=670 nm).
Figure 34:
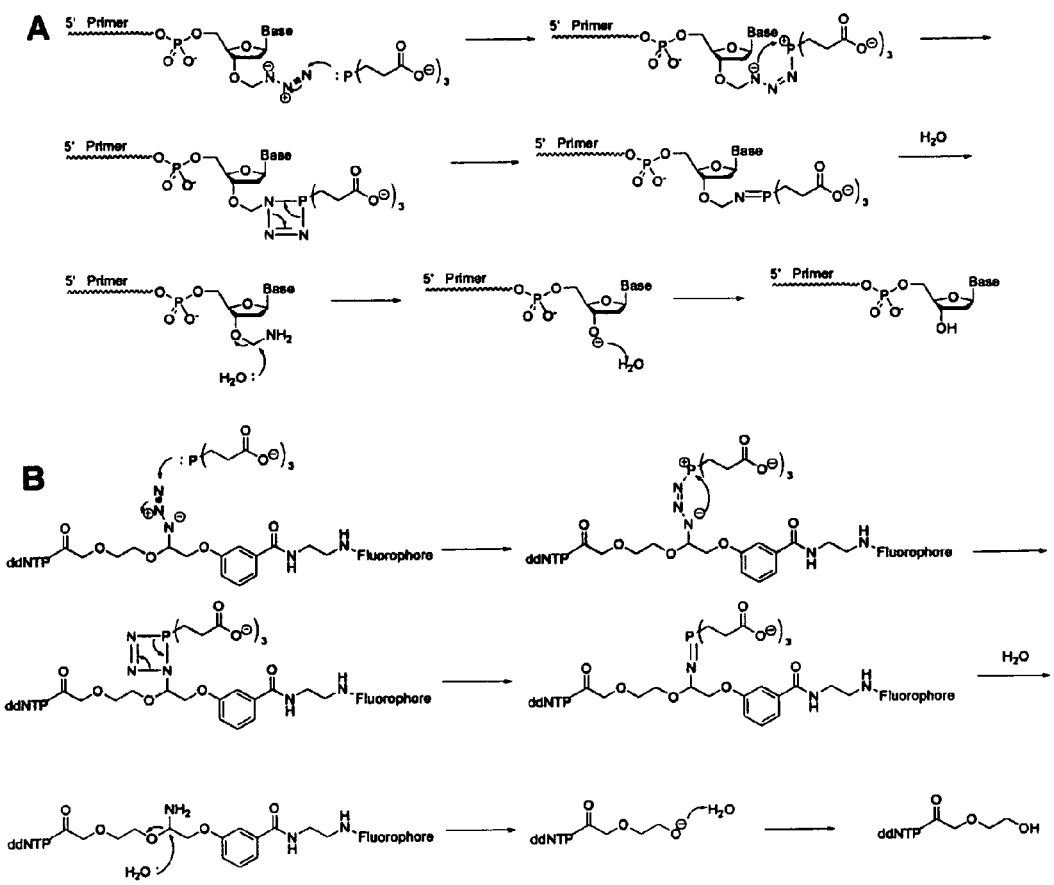
FIG. 34. (A) Staudinger reaction with TCEP to regenerate the 3'-OH group of the DNA extension product. (B) Staudinger reaction with TCEP to cleave the $N_3$-fluorophore from the dideoxynucleotide.

1. Design and Synthesis of 3'-O-Modified NRTs and Cleavable Fluorescent Dideoxynucleotide Terminators for the Hybrid SBS Four 3'-O-azidomethyl-modified NRTs (3'-O—$N_3$-dNTPs) were synthesized and evaluated (FIG. 32) for use in the hybrid SBS approach. The 3'-O-modified NRTs containing an azidomethyl group to cap the 3'-OH on the sugar ring were synthesized based on similar method to that reported by Zavgorodny et al. The 3'-O-azidomethyl group on the DNA extension product generated by incorporating each of the NRTs is efficiently removed by the Staudinger reaction using aqueous Tris(2-carboxy-ethyl)phosphine (TCEP) solution followed by hydrolysis to yield a free 3'-OH group for elongating the DNA chain in subsequent cycles of the hybrid SBS (FIG. 34A).

Figure 33:
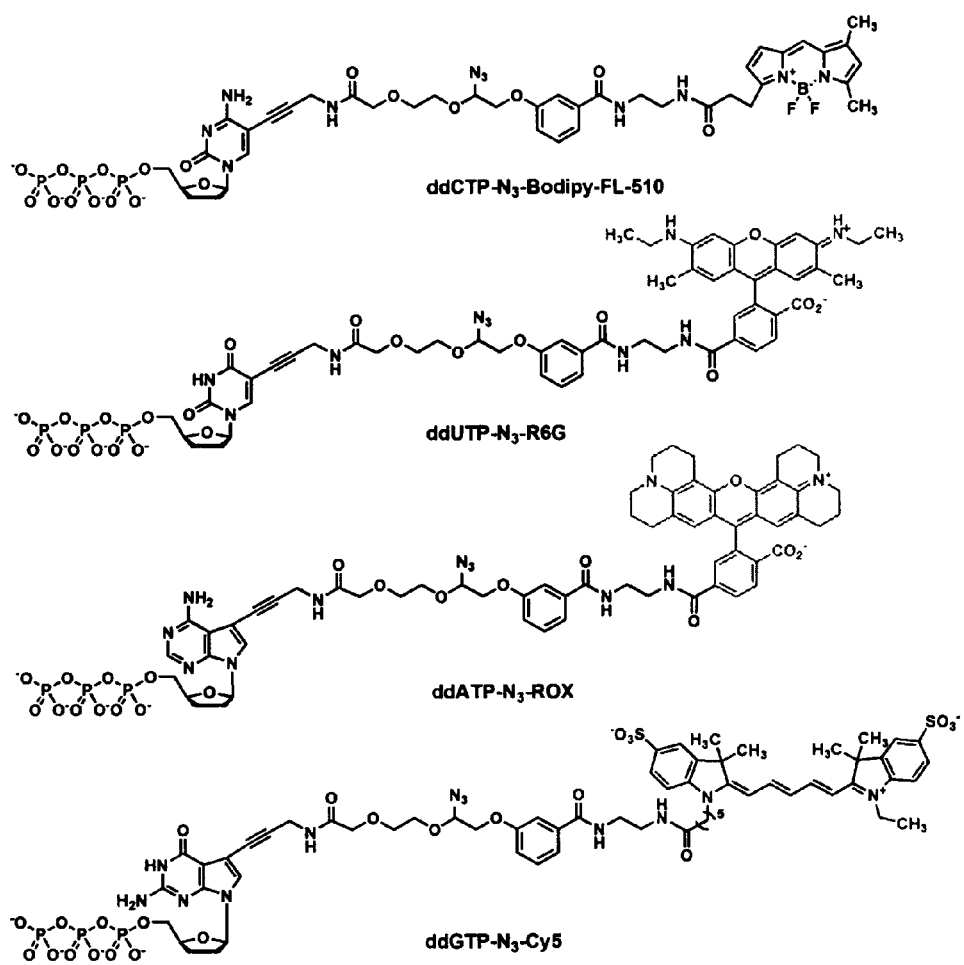

To demonstrate the feasibility of carrying out the hybrid SBS on a DNA chip, four cleavable fluorescent dideoxynucleotide terminators were designed and synthesized, ddNTP-$N_3$-Fluorophores (ddCTP-$N_3$-Bodipy-FL-510, ddUTP-$N_3$—R6G, ddATP-$N_3$—ROX and ddGTP-$N_3$-Cy5) (FIG. 33). The ddNTP-$N_3$-Fluorophore were used in combination with the four NRTs (FIG. 32) to perform the hybrid SBS. Modified DNA polymerases have been shown to be highly tolerant to nucleotide modifications with bulky groups at the 5-position of pyrimidines (C and U) and the 7-position of purines (A and G). Thus, a each unique fluorophore was attached to the 5 position of C/U and the 7 position of A/G through a cleavable linker. The cleavable linker is also based on an azido modified moiety as a trigger for cleavage, a mechanism that is similar to the removal of the 3'-O-azidomethyl group (FIG. 34B).

2. Four-Color DNA Sequencing on a Chip by the Hybrid SBS Approach

Figure 35:
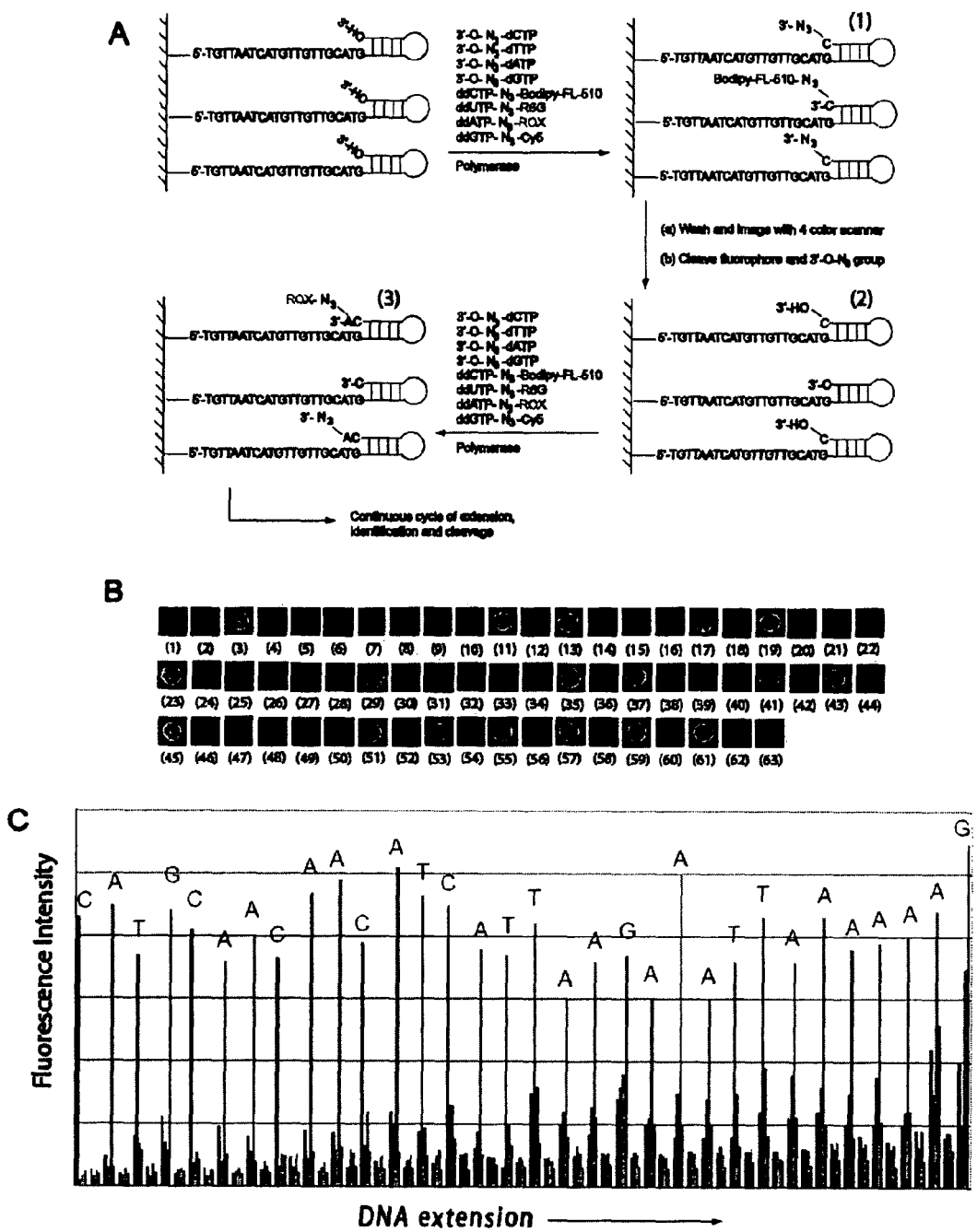
FIG. 35. Four-color DNA sequencing by the hybrid SBS approach
Figure 36:
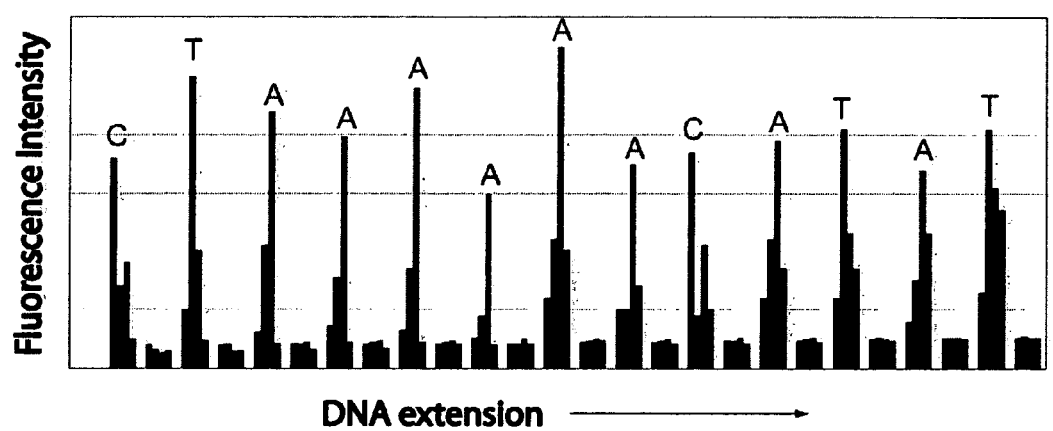
FIG. 36. Four-color DNA sequencing by the hybrid SBS after template "walking"

Hybrid SBS was performed on a chip-immobilized DNA template using the 3'-O—$N_3$-dNTP/ddNTP-$N_3$-fluorophore combination and the results are shown in FIG. 35. The general four-color sequencing reaction scheme on a chip is shown in FIG. 35A. The de novo sequencing reaction on the chip was initiated by extending the self-priming DNA using a solution containing the combination of the four 3'-O—$N_3$-dNTPs and the four ddNTP-$N_3$-fluorophores, and 9°N DNA polymerase.

The four-color images from a fluorescence scanner for each step of the hybrid SBS on a chip is shown in FIG. 35B. The entire process of incorporation, synchronization, detection and cleavage was performed multiple times to identify 32 successive bases in the DNA template. The plot of the fluorescence intensity vs. the progress of sequencing extension (raw 4-color sequencing data) is shown in FIG. 35C. The DNA sequences were unambiguously identified with no errors from the 4-color raw fluorescence data without any processing.

3. Primer Reset and 2nd Round SBS

To demonstrate the concept of walking, the same self-priming DNA was immobilized on surface as template. After identifying the first 32 bases unambiguously with no errors by the first round hybrid SBS, the primer was reset for the second round SBS by elongating the original primer over the sequenced region via enzymatic incorporations. A solution containing dATP, dTTP, dCTP and 3'-O—$N_3$-dGTP was used to perform the polymerase reaction. 9°N DNA polymerase incorporates 3' unblocked nucleotides more efficiently, leading to certain percentage of primers not fully extended by 3'-O—$N_3$-dGTP. To minimize this effect, a synchronization step was added to reduce the amount of out-of-phase primers after the initial extension reaction. A synchronization reaction mixture consisting of just 3'-O—$N_3$-dGTP in relative high concentration was used along with the 9°N DNA polymerase. The 3'-O-azidomethyl group on the DNA extension product generated by incorporating 3'-O—$N_3$-dGTP was efficiently removed by using aqueous Tris(2-carboxy-ethyl)phosphine (TCEP) solution to yield a free 3'-OH group for elongating the DNA chain in subsequent cycles of enzymatic incorporation. The entire process of incorporation, synchronization and cleavage were conducted repeatedly until the sequenced bases during the first round SBS were "walked" over. After the primer was reset by the enzymatic incorporation, the second stage of SBS was conducted using mixture of nucleotide reversible terminators and fluorescently labeled dideoxynucleotides as incorporation substrates same as described above.

Figure 14:
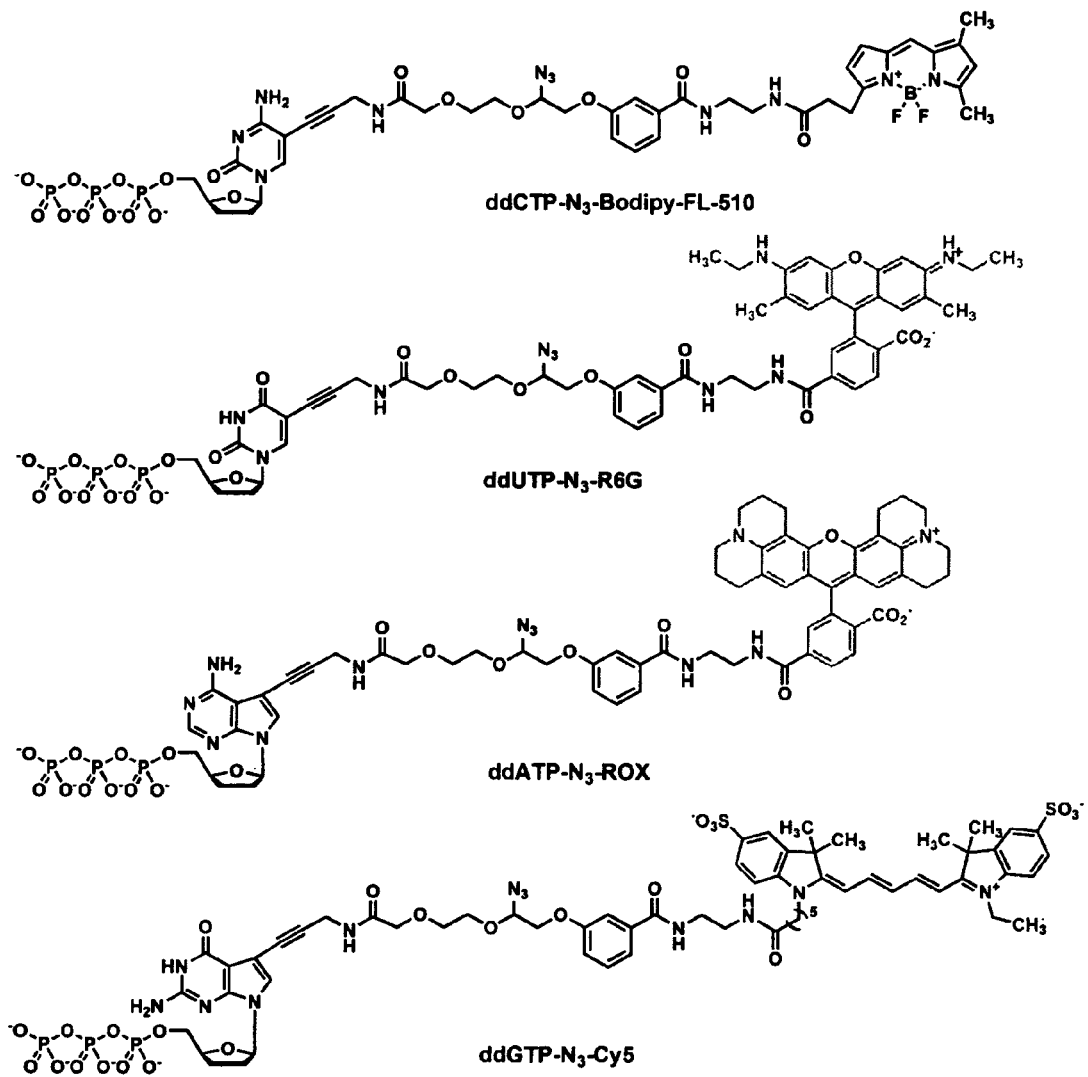
FIG. 14. Structures of cleavable fluorescent dideoxynucleotide terminators ddNTP-$N_3$-fluorophores, with the 4 fluorophores having distinct fluorescent emissions: ddCTP-$N_3$-Bodipy-FL-510 ($\lambda_{abs\ (max)}$=502 nm; $\lambda_{em\ (max)}$=510 nm), ddUTP-$N_3$—R6G ($\lambda_{abs\ (max)}$=525 nm; $\lambda_{em\ (max)}$=550 nm), ddATP-$N_3$—ROX ($\lambda_{abs\ (max)}$=585 nm; $\lambda_{em\ (max)}$=602 nm), and ddGTP-$N_3$-Cy5 ($\lambda_{abs\ (max)}$=670 nm). $\lambda_{em\ (max)}$=670 nm).

Another 13 bases were successfully identified after template "walking" (FIG. 14).

Template "Walking" for SBS with CFNRTs

1. SBS with C—F-NRTs

Figure 37:
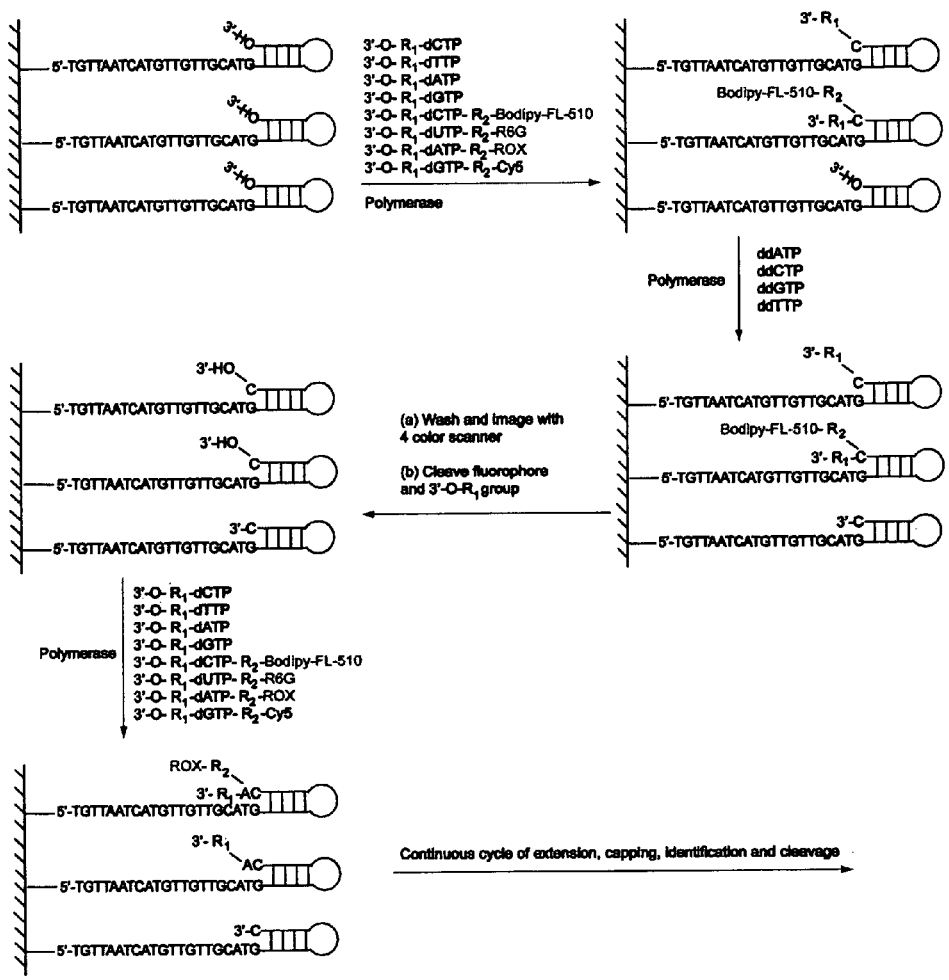
FIG. 37. General Scheme for SBS with C—F-NRTs

DNA sequencing by synthesis (SBS) on a solid surface during polymerase reaction offers a paradigm to efficiently decipher multiple DNA sequences in parallel. Disclosed is the development of a DNA sequencing method that involves the extension of target DNA strand with modified cleavable fluorescent nucleotide reversible terminators (C—F-NRTs, 3'-O—$R_1$-dNTPs-$R_2$-fluorophore) in combination with cleavable nucleotide reversible terminators (C-NRTs, 3'-O—$R_1$-dNTPs). A set of four C—F-NRTs is produced via dual modifications by capping the 3'-OH group with a small chemical moiety and tethering a fluorophore through a cleavable linker to either the 7-position of the purines (A, G) or the 5-position of the pyrimidines (C, T) so that they are still recognized as substrates by DNA polymerase. Another set of four C-NRTs is modified similarly as the C—F-NRTs except no fluorophore is attached, which results in a reduction of the size of C-NRTs and the increment of DNA polymerase incorporation efficiency. In this approach, an extension mixture composed of the C-NRTs with a small percentage of the C—F-NRTs is used to perform SBS. Sequences are determined by the unique fluorescence emission of each fluorophore on the DNA products terminated by the C—F-NRTs. Immediately following the detection step, a synchronization reaction is performed using only the C-NRTs to extend the un-extended DNA strands. A dideoxynucleotides (ddNTPs) capping step is carried out afterwards to completely rid of the remaining un-extended DNA. Upon removing the 3'-OH capping group from the DNA products generated by incorporating both C—F-NRTs and C-NRTs and the fluorophore from the C—F-NRTs, the polymerase reaction reinitiates to continue the sequence determination. The following scheme (FIG. 37) illustrates the general process for SBS with C—F-NRTs.

Figure 38:
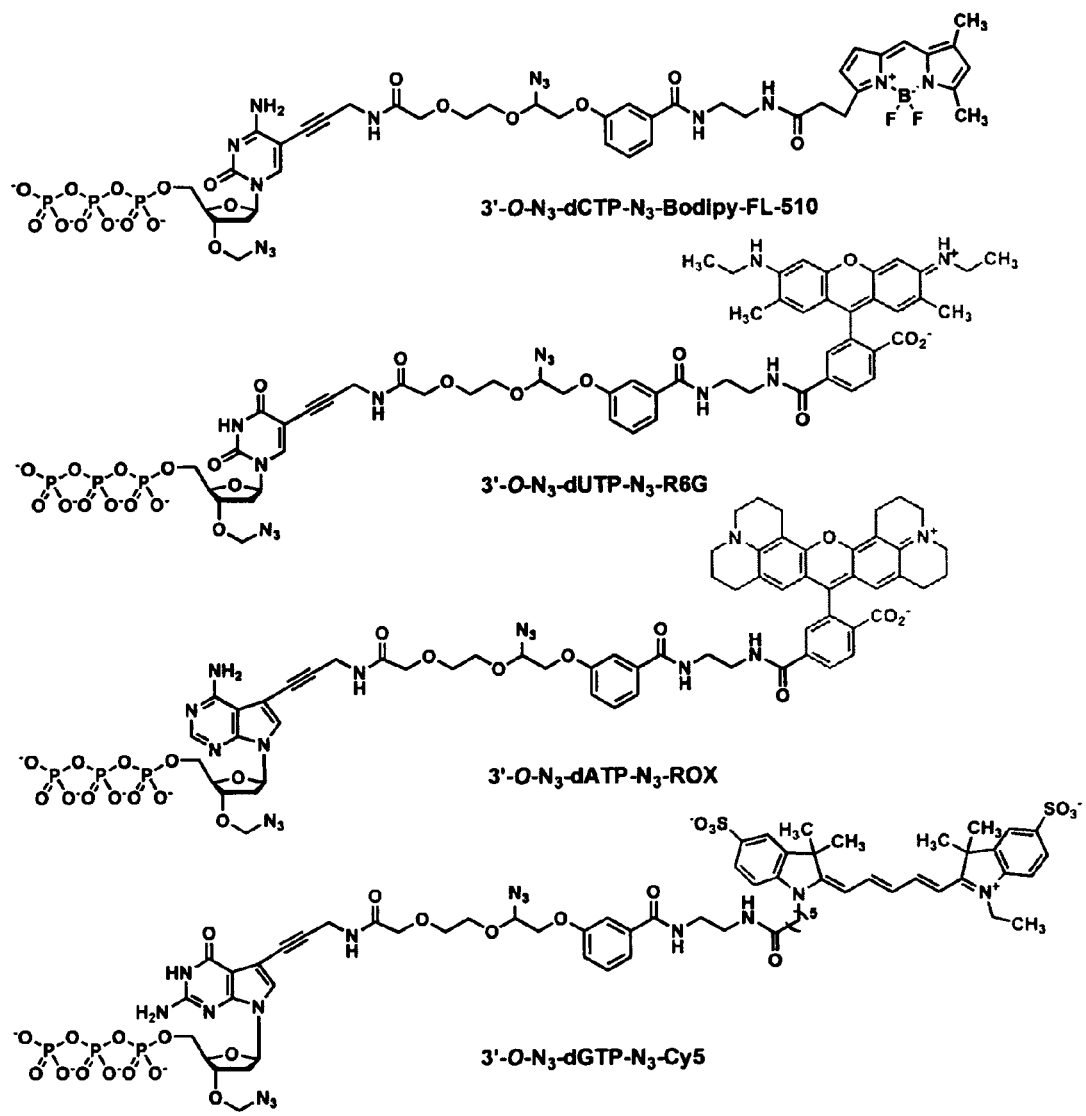
FIG. 38. Structure of 3'-O—$N_3$-dNTPs-$N_3$-fluorophore

Four 3'-O—$N_3$-dNTPs-$N_3$-fluorophore (FIG. 38) and four 3'-O—$N_3$-dNTPs (FIG. 32) were synthesized, using an azidomethyl group as a chemically reversible capping moiety in the 3'-O-modified C—F-NRTs and C-NRTs, and an azido-based cleavable linker to attach the fluorophores to the C—F—NRTs.

Figure 39:
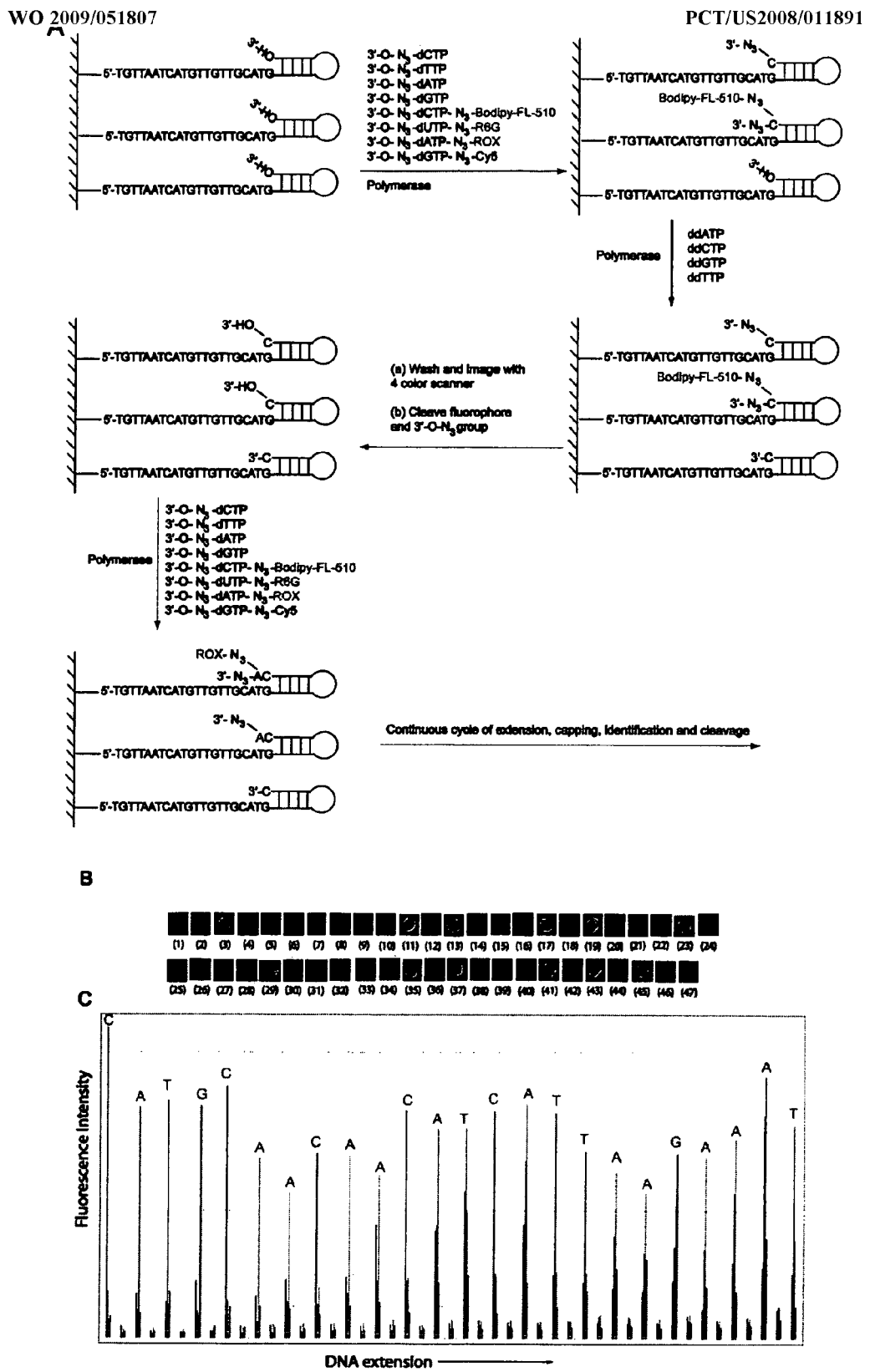
FIG. 39. Four-color DNA SBS with 3'-O—$N_3$-dNTPs-$N_3$-fluorophore. (A) A SBS with C—F-NRTs scheme for four-color sequencing on a chip by using four 3'-O—$N_3$-dNTPs-$N_3$-fluorophore and 3'-O—$N_3$-dNTPs with ddNTPs capping. (B) Four-color fluorescence images for each step of the SBS: (1) incorporation of 3'-O—$N_3$-dCTP-$N_3$-Bodipy-Fl-510 and 3'-O—$N_3$-dCTP; (2) cleavage of $N_3$-Bodipy-Fl-510 and 3'-$CH_2N_3$ group; (3) incorporation of 3'-O—$N_3$-dATP-$N_3$-Rox and 3'-O—$N_3$-dATP; (4) cleavage of $N_3$-Rox and 3'-$CH_2N_3$ group; images 5-47 were produced similarly. (C) A plot (four-color sequencing data) of raw fluorescence emission intensity obtained by using 3'-O—$N_3$-dNTPs-$N_3$-fluorophore and 3'-O—$N_3$-dNTPs. The small groups of peaks between the identified bases are fluorescent background from the DNA chip.
Figure 40:
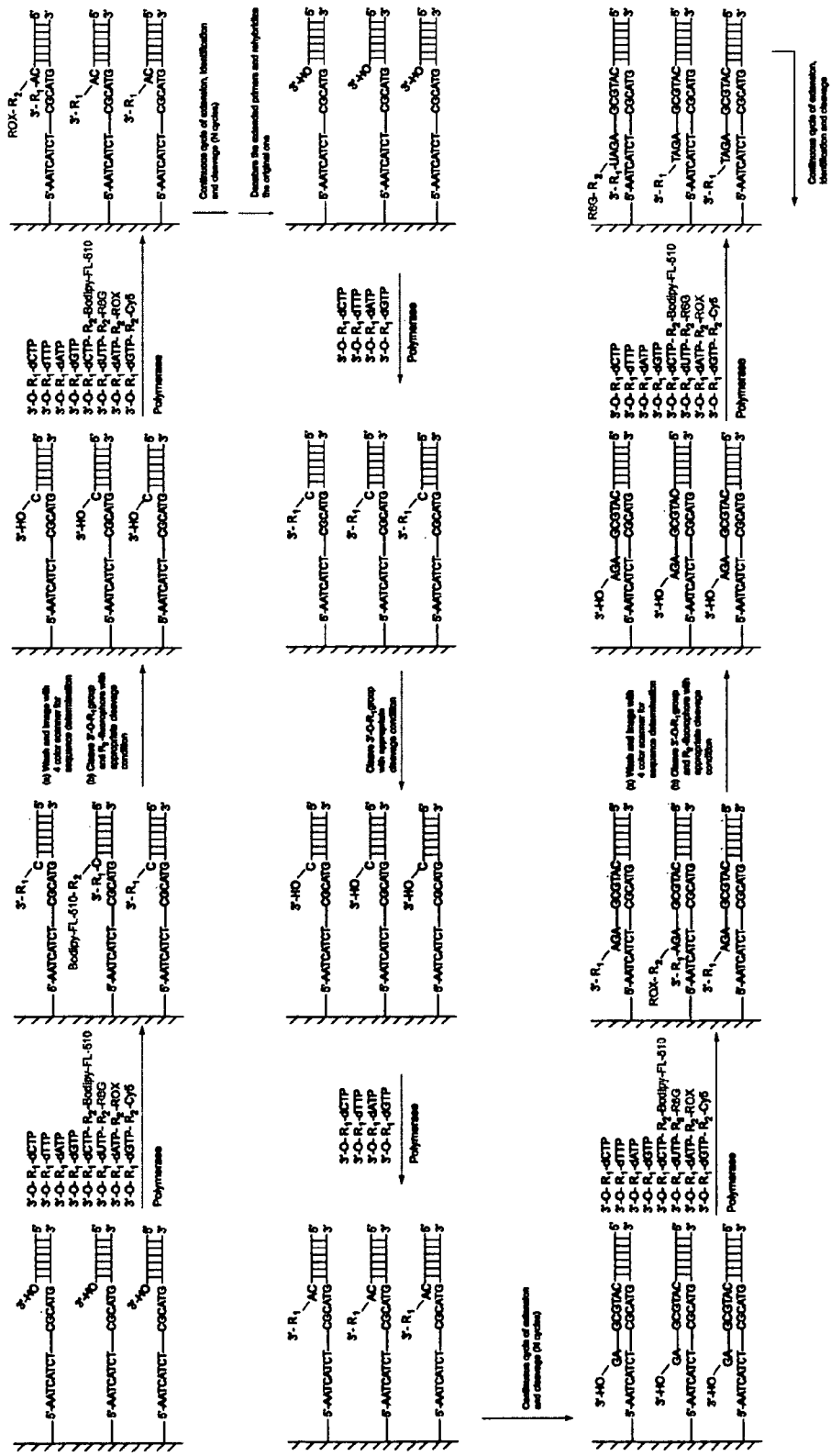
FIG. 40. Template "Walking" Method 1 for SBS with C—F—NRTs
Figure 41:
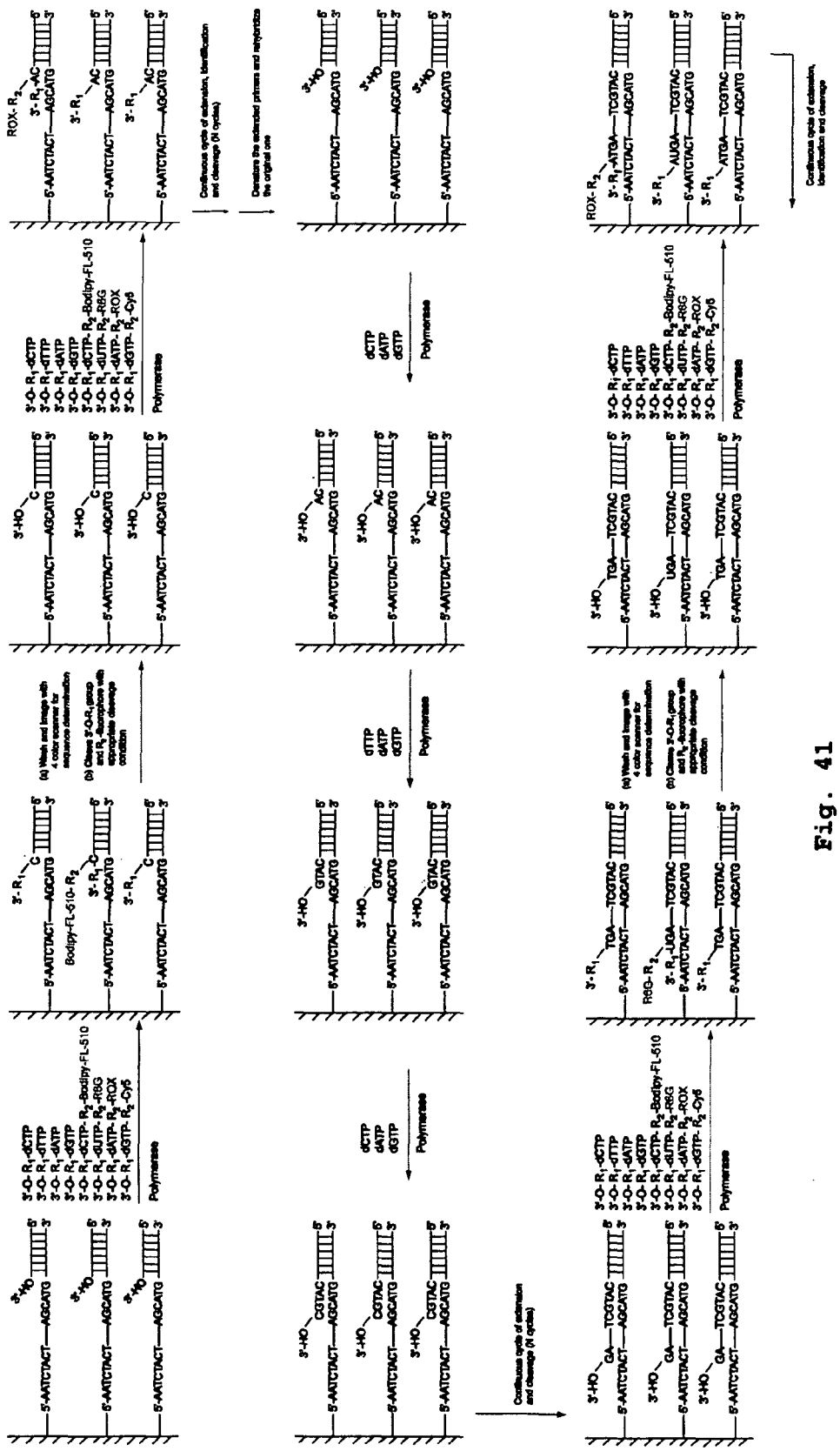
FIG. 41. Template "Walking" Method 2 for SBS with C—F—NRTs
Figure 42:
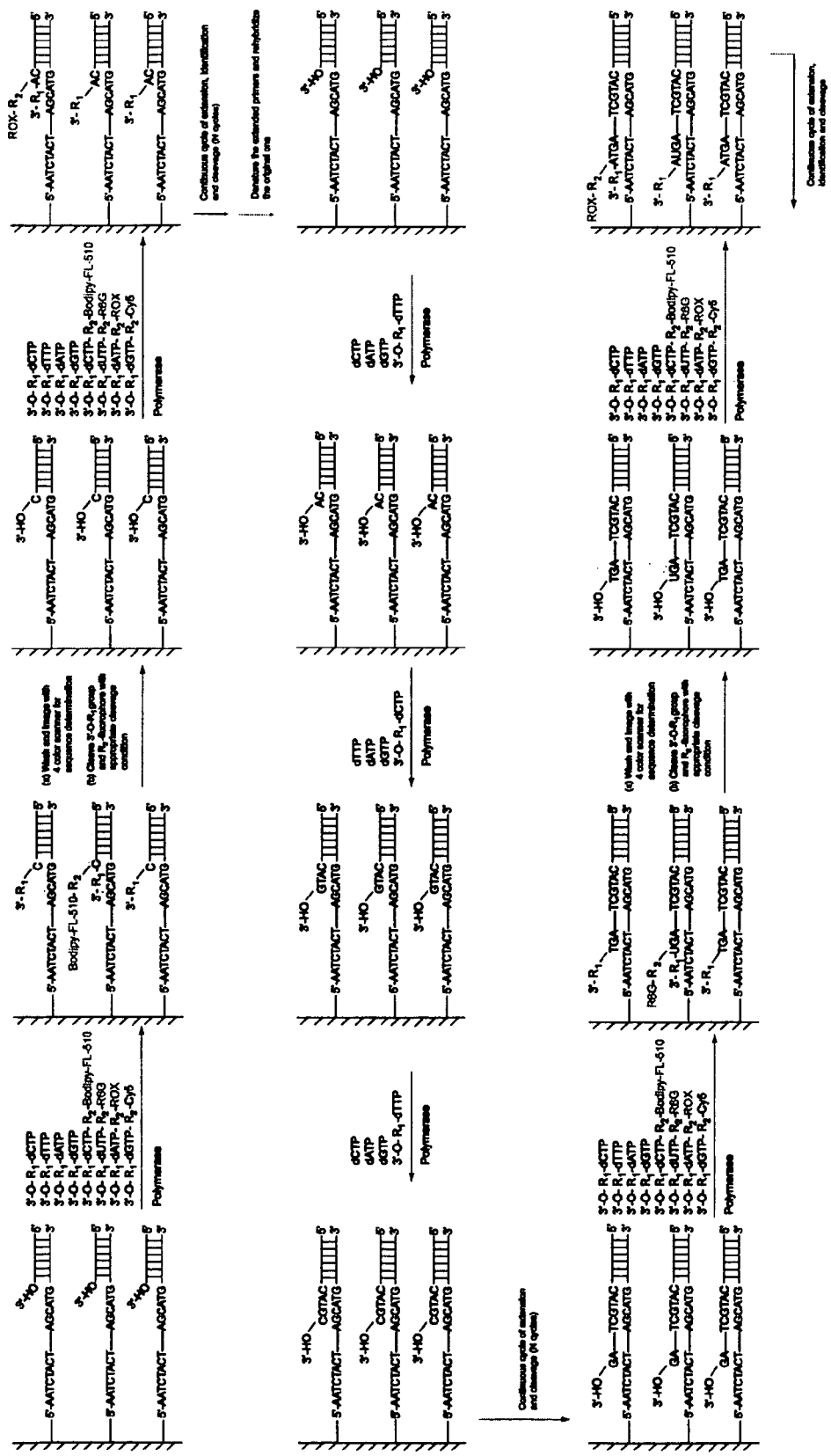
FIG. 42. Template "Walking" Method 3 for SBS with C—F—NRTs
Figure 43:
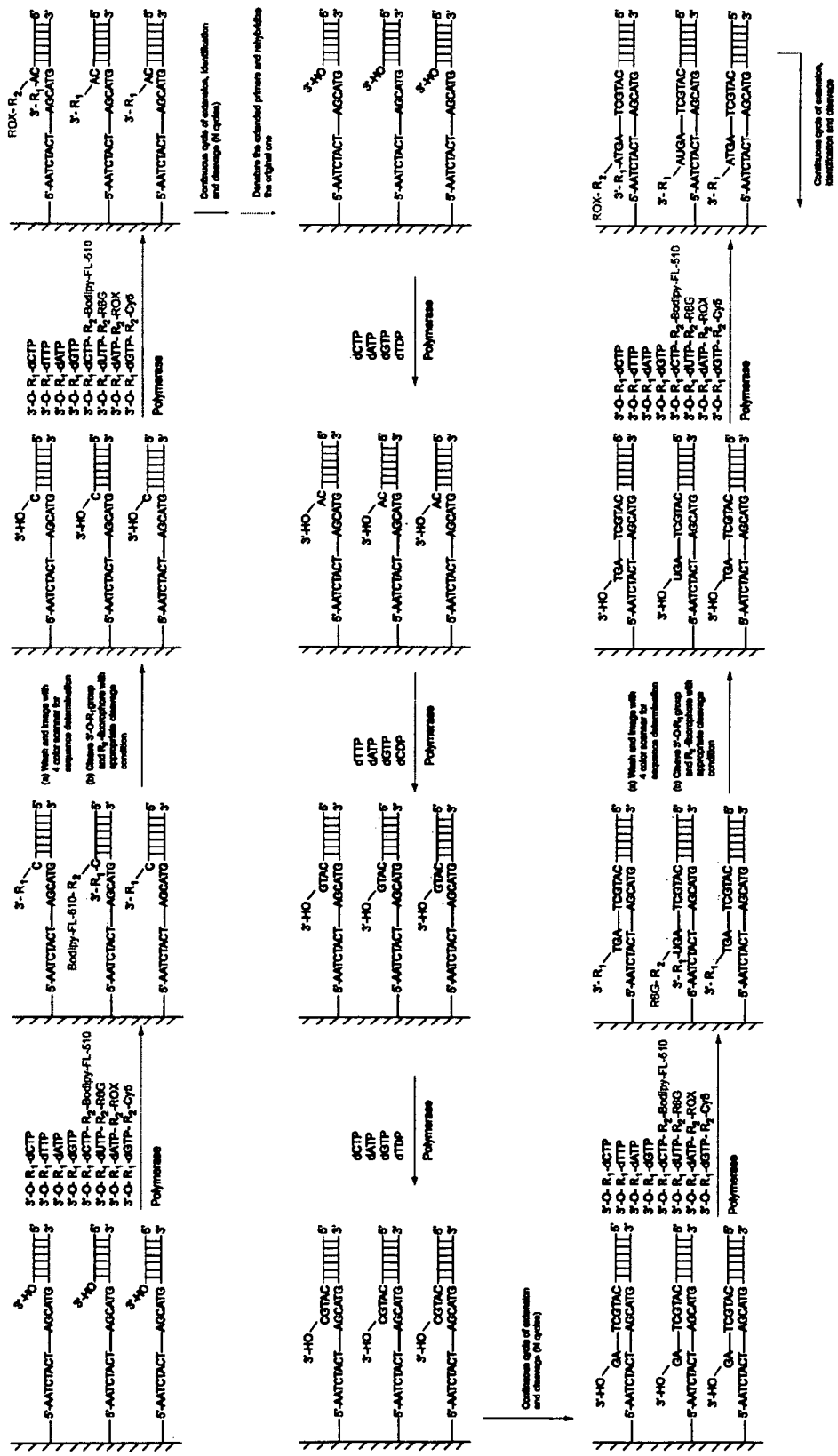
FIG. 43. Template "Walking" Method 4 for SBS with C—F—NRTs
Figure 44:
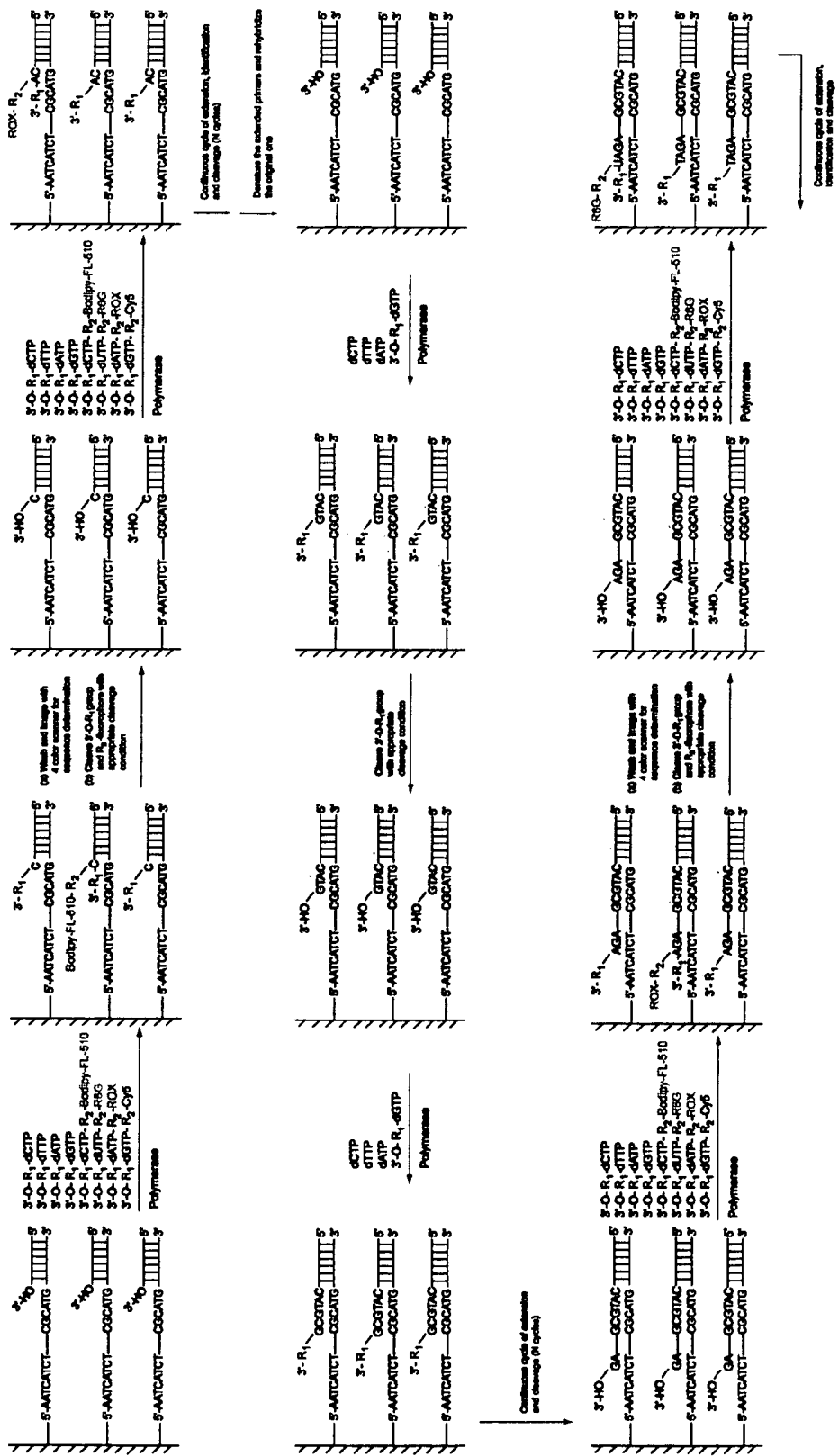
FIG. 44. Template "Walking" Method 5 for SBS with C—F—NRTs

After fluorescence detection for sequence determination, the azidomethyl capping moiety on the 3'-OH and the fluorophore attached to the DNA extension product via the azido-based cleavable linker are efficiently removed using tris(2-carboxyethyl)phosphine (TCEP) in aqueous solution compatible with DNA. Various DNA templates, including those with homopolymer regions were accurately sequenced with read length of over 20 bases using this SBS method on a chip and a four-color fluorescent scanner (FIG. 39).

Four C—F-NRTs (3'-O—$N_3$-dNTPs-$N_3$-fluorophore) were synthesize along with four C-NRTs (3'-O—$N_3$-dNTPs) for the implementation of our four-color de novo DNA sequencing by synthesis approach. During the incorporation stage of SBS, a mixture of the two sets of NRTs is used to extend the DNA strand. Only a small percentage of the 3'-O—$N_3$-dNTPs-$N_3$-fluorophore is used in the mixture so that the majority of the product is extended with the less bulky 3'-O—$N_3$-dNTPs. This approach leads to a more efficient DNA polymerase reaction since the smaller 3'-O—$N_3$-dNTPs are much easier to incorporate. Another advantage of having most of the DNA extended with 3'-O—$N_3$-dNTPs is the fact that after cleavage of the 3'-OH capping group on the product, nascent strand of DNA that have no traces of modification is restored. Such DNA does not have any adverse effect on the DNA polymerase during the subsequent incorporation of the complementary nucleotide. For DNA extended with the 3'-O—$N_3$-dNTPs-$N_3$-fluorophore, which serve as the signal producer, the 3'-OH is also restored after the cleavage step so that the next stage of SBS can be carried out. Therefore, it is possible to recover all the DNA templates after each round of sequencing, dramatically increasing the potential read-length of our SBS methodology. After the incorporation reaction, two separate capping steps, first with 3'-O—$N_3$-dNTPs and then with ddNTPs, are performed. The rationale behind the first capping reaction is to maximize the amount of extension products and to ensure the minimal loss of templates. In case there is any un-extended product after the first capping step, the second capping with ddNTPs is mostly likely to permanently terminate these DNA strands so that all templates are synchronized. Without these precautionary synchronization procedures, mixed fluorescent signals will prevent the identification of the correct nucleotide incorporated. Since both 3'-O—N₃-dNTPs-N₃-fluorophore and 3'-O—N₃-dNTPs are reversible terminators, which allow the sequencing of each base in a serial manner, they can accurately determine the homopolymeric regions of DNA. In addition, due to the fact that all of the steps of our SBS approach are performed on a DNA chip, there is no longer a need for electrophoretic DNA fragment separation as in the classical Sanger sequencing method.

Even though theoretically SBS with C—F-NRTs can be executed without losing templates, the utilization of ddNTPs capping does reduce the number of available templates during the actual sequencing reaction. In addition, the incorporation and cleavage of C—F-NRTs leave a tail on the modified nucleotides that can potentially reduce the incorporation efficiency the subsequent base. Hence template "walking" can be applied to increase read length for this SBS methodology.

2. Template "Walking"

Immediately after the first round of SBS, DNA templates are denatured by heat or mild alkali conditions to rid of the extended primer. The same original primer is re-hybridized to the template chain, and one of the five "walking" methods described in the previous section can be applied to reset the start point for the next round of SBS at the end of the first sequencing run (FIGS. 40, 41, 42, 43, and 44).

3. Re-Initiation of SBS with C—F-NRTs

Once the "walking" process is completed, the primer is extended to the end of the previous round of SBS. At this point, hybrid SBS is carried out to identify the subsequent bases. If the process can be repeated more times, it should be theoretically possible to achieve long and significant read length.

Strategy 2: Template "Walking" with Universal Bases

Figure 45:
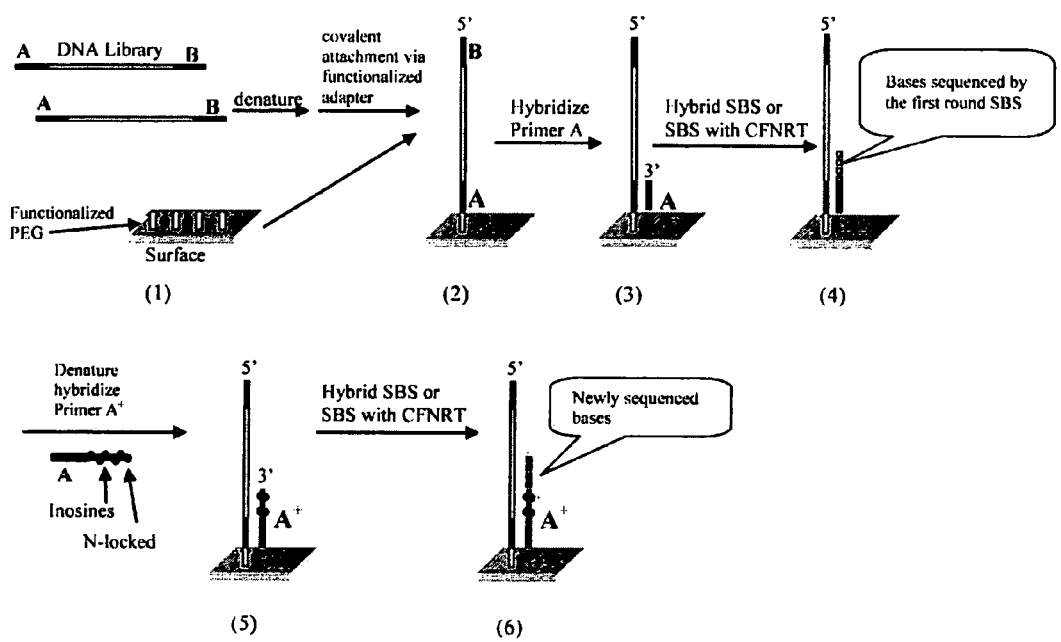
FIG. 45. "Walking" Strategy 2

In this variation on the Strategy 1, the reset is achieved not with nucleotide walking, but with the use of a longer primer partially consisting of universal nucleotides for the second round. Attachment of the template DNA to the surface and the first few steps of the procedure are identical to the first method. However, after stripping the first extended primer for the initial 20 base readout, a long primer with the following features will be hybridized to the template: (a) the first half is identical to the initial primer; (b) the second half is composed almost entirely of universal bases. One possible candidate for the universal base is inosine, which, in its deoxynucleoside form, can base pair with all four nucleotides, though its affinity for C and A is significantly higher than for G and T; a second possibility is 5-nitroindole; (c) the last one or two anchoring bases of the long primers are degenerate with each of the four possible bases being represented. Because the universal bases can form hydrogen bonds with any of the other four bases with some efficiency, they have the capacity to bind to the first 20 or so bases of the sequence. However, the melting temperature of the ensuing hybridization is reduced substantially by the run of inosines, a few of the bases in the first half and the two 3'-anchoring bases can be substituted with locked nucleotides. Locked nucleic acids have a chemical bond between the 2' and 4' carbons of the ribose. While slower to associate with their complementary base, once hybridized, they tend not to dissociate. Thus, they provide a nice solution to ensure that the long primer remains attached appropriately to the template. In addition, the percentage of locked nucleosides in the primer can be manipulated to achieve higher hybridization strength. After hybridization of the above long primer, a second round of either Hybrid SBS or SBS with C—F-NRTs can be performed (FIG. 45).

An alternative approach to Strategy 2 is the use of a detachable loop primer, possibly with a labile sugar and glycosylase treatment. After the first round of sequencing, the loop is removed by enzymatic cleavage and denaturation, and then a new identical loop is attached. In a modification that is a composite of "walking" Strategy 1 and 2, the new loop primer can be composed of an initial portion identical to the first loop primer, a "loop out" region that bypasses the first set of sequenced nucleotides, and a degenerate anchoring nucleotide to initiate the second round of sequencing.

Strategy 3: Multiple Primers "Walking"

In this third strategy, one or two additional primer annealing sites are introduced into the DNA to be sequenced at a distance just about equal to the number of bases that can be sequenced from the first primer.

Figure 46:
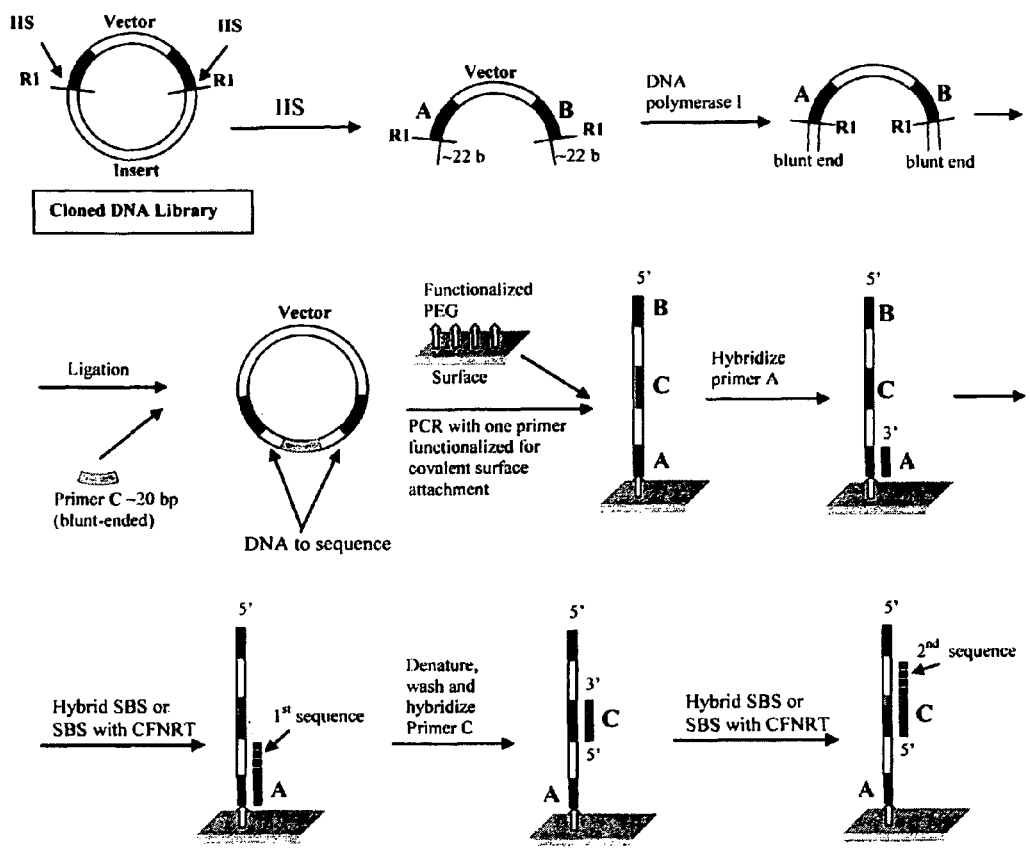
FIG. 46. "Walking" Strategy 3

As illustrated in FIG. 46, template preparation for SBS will utilize the cloning of genomic DNA into a specially designed vector containing type IIS or III restriction sites (MmeI and EcoP15 I) flanking the genomic DNA cloning site. In this procedure size fractionated DNA (minimal length 100 bp) will be ligated into the cloning vector using blunt-end ligation. Upon cloning, the resulting recombinant plasmids will be re-cut at one of the type IIS/III sites and the sticky ends will be filled in with Klenow enzyme. Next, specific sequencing primers will be introduced via ligation inside the genomic DNA inserts, 22 bases distant from the first primer in the case of MmeI or 27 bases away in the case of EcoP15 I. After insertion of the internal priming sites, the constructs will be re-cloned in *E. coli*, the recombinant plasmids isolated and the inserts re-amplified by PCR at vector-insert junctions and attached to the beads for sequencing. Alternatively, emulsion or polony PCR strategies can be used to accomplish attachment of single molecules to individual beads or slide locations and their subsequent amplification at a much lower cost than cloning. In any case, once the DNA is immobilized, the first round of Hybrid SBS or SBS with C—F-NRTs will be primed from the flanking primer, then after stripping these extended primers, the second set of sequencing reactions will be initiated at the internal primer. It should be noted that with this scheme, the two sequenced portions come from opposite ends of the initial DNA, and are in essence paired end reads.

Several novel modifications of this approach can address the desire of many investigators to sequence an entire 100-base stretch of DNA, the length of a typical exon including surrounding intronic bases adjacent to the splice site. For instance, one can prepare a construct with two internal primers. In this case, the initial vector will be designed with MmeI at one flank and EcoP15I on the other; using two consecutive restriction, cloning and circularization steps, the final construct will consist of four alternative priming sites (two on the insert flanks and two internal), which in the case of 100 by segments of genomic DNA will guarantee their complete sequencing with 25-30 cycles of SBS and three primer resets. The extra cycles would enable some of the sequence reads to run into the next primer, which would help to confirm the direction (e.g., the last sequence might end with the MmeI or EcoP15I site. Other tricks would include modifying the ends of the primers to allow looping and reverse direction sequencing, incorporation of one or two decoding bases in the internal primers to confirm directions, and deconvoluting the results after all the data is generated. One would want to have a single set of primers for sequencing, regardless of which strand is attached. In order to achieve this, and to overcome the non-directional nature of their insertion, the internal primer or primers will be designed as palindromes so that sequencing can be initiated in either direction.

Materials and Methods

Figure 15:
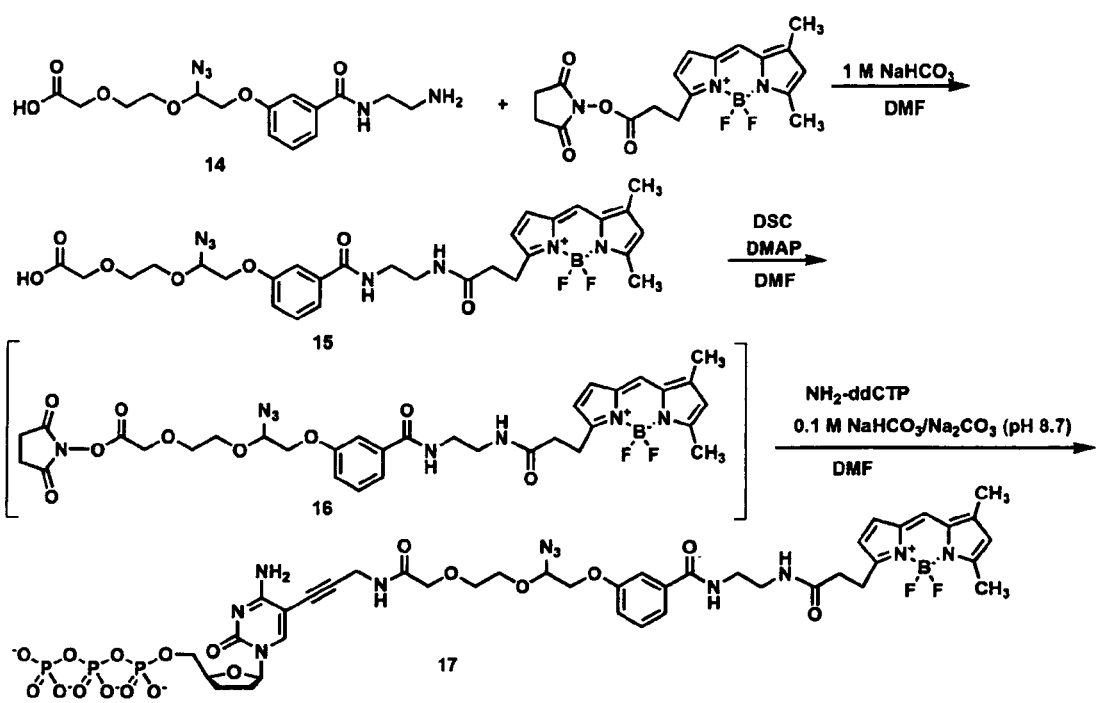
FIG. 15. Synthesis of ddCTP-$N_3$-Bodipy-FL-510
FIG. 16. Synthesis of ddUTP-$N_3$—R6G
FIG. 17. Synthesis of ddATP-$N_3$—ROX
FIG. 18. Synthesis of ddGTP-$N_3$-Cy5
FIG. 19. A detailed scheme (left half of fig.) of polymerase reaction using all four 3'-O—$N_3$-dNTPs to extend with an "3'-O—$N_3$-dATP", "3'-O—$N_3$-dCTP", "3'-O—$N_3$-dGTP" and "3'-O—$N_3$-dTTP" and the subsequent cleavage reaction to cleave off the azidomethyl moiety capping the 3'-OH of the DNA extension product. MALDI-TOF MS spectra (right half of fig.) verifying base specific incorporation of: (A) 3'-O—$N_3$-dCTP (peak at 8,310 m/z), (B) the corresponding cleavage product (8,255 m/z); (C) 3'-O—$N_3$-dGTP (peak at 8,639 m/z), (D) the corresponding cleavage product (8,584 m/z); (E) 3'-O—$N_3$-dATP (peak at 8,952 m/z), (F) the corresponding cleavage product (8,897 m/z); (G) 3'-O—$N_3$-dTTP (peak at 9,256 m/z) and (H) the corresponding cleavage product (9,201 m/z). The azidomethyl moiety capping the 3'-OH group of the DNA extension products is completely removed by TCEP aqueous solution to continue the polymerase reaction.

Synthesis of ddCTP-$N_3$-Bodipy-FL-510 a. Azido-Bodipy-FL-510 (FIG. 15, Compound 15). (2-{2-[3-(2-Amino-ethylcarbamoyl)-phenoxy]-1-azido-ethoxy}-ethoxy)-acetic acid 14 (7.0 mg, 0.019 mmol) prepared according to the literature) was dissolved in DMF (300 μl) and 1 M $NaHCO_3$ aqueous solution (100 μl). A solution of Bodipy-FL-510 NHS (N-hydroxysuccinimide) ester (Invitrogen) (5.0 mg, 0.013 mmol) in DMF (400 μl) was added slowly to the above reaction mixture and then stirred at room temperature for 5 hours with exclusion of light. The crude product was purified on a preparative silica gel TLC plate ($CHCl_3/CH_3OH$, 1:4) to afford 15 (7.6 mg; 91%). $^1H$ NMR (400 MHz, $CD_3OD$) δ7.34-7.42 (m, 4H), 710-7.14 (m, 1H), 6.90 (d, J=4.0 Hz, 1H), 6.29 (d, J=4.0 Hz, 1H), 6.20 (s, 1H), 5.00 (t, J=5.2 Hz, 1H), 4.22-4.25 (m, 1H), 4.10-4.14 (m, 1H), 3.96-4.01 (m, 2H), 3.91 (s, 2H), 3.83-3.88 (m, 1H), 3.70-3.71 (m, 2H), 3.43-3.48 (m, 3H), 3.20-3.24 (m, 2H), 2.61-2.65 (m, 2H), 2.57 (s, 3H), 2.49 (s, 3H); MS (Fab+) calcd for $C_{29}H_{34}BF_2N_7O_7$ $[(M+H)^+]$: 642.4. found: 642.5.

b. ddCTP-$N_3$-Bodipy-FL-510 (FIG. 15, Compound 17). To a stirred solution of 15 in dry DMF (2 ml), DSC (N,N'-disuccinimidyl carbonate) (3.4 mg, 13.2 μmol) and DMAP (4-dimethylaminopyridine) (1.6 mg, 13.2 μmol) were added. The reaction mixture was stirred at room temperature for 2 hours. TLC indicated that 15 was completely converted to compound 16, which was directly used to couple with amino-ddCTP (13 μmol) in $NaHCO_3/Na_2CO_3$ buffer (pH=8.7, 0.1 M) (300 μl). The reaction mixture was stirred at room temperature for 3 hours with exclusion of light. The reaction mixture was purified by a preparative silica gel TLC plate ($CH_3OH/CH_2Cl_2$, 1:1). The crude product was further purified on reverse-phase HPLC to afford 17 (retention time=34.0 min). Compound 17 was further evaluated by performing a single base extension reaction to yield a DNA extension product which was characterized by MALDI-TOF MS (m/z 8915) (FIG. 20C).

Figure 16:
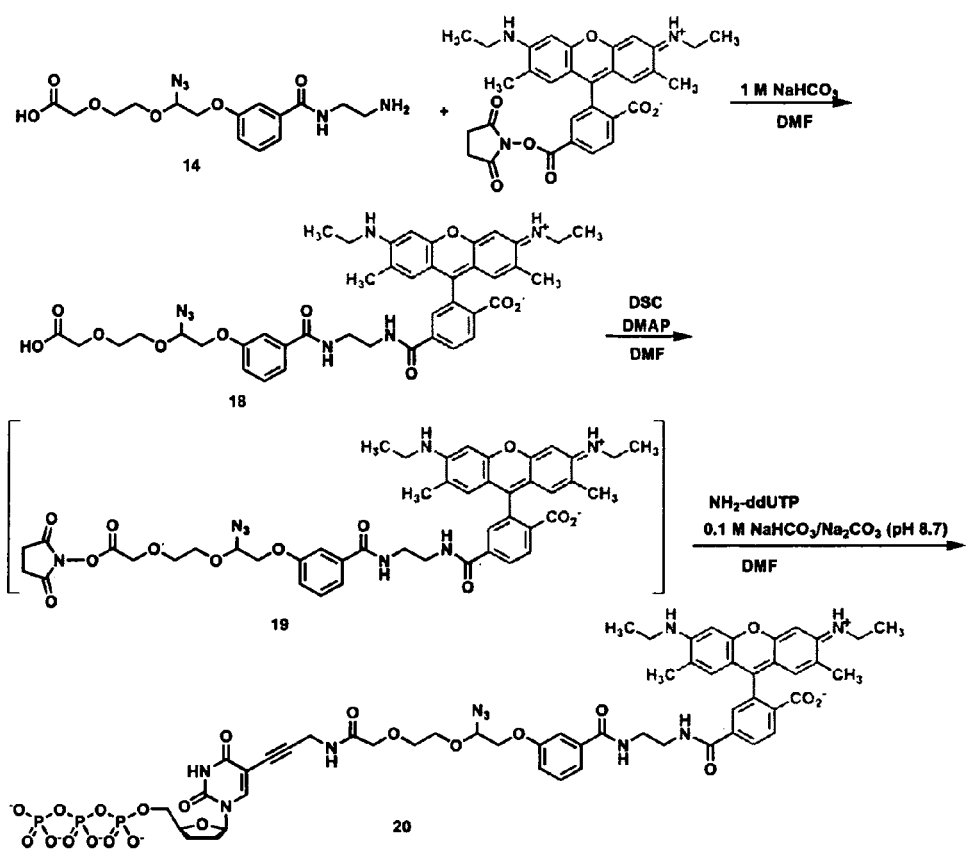

Synthesis of ddUTP-$N_3$—R6G a. Azido-R6G (FIG. 16, Compound 18). The preparation procedure was similar to the synthesis of 15. The crude product was purified by a preparative silica gel TLC plate ($CH_3OH/CH_2Cl_2$, 2:5) to afford 18 (8.2 mg; 89%). $^1H$ NMR (400 MHz, $CD_3OD$) δ 8.12-8.08 (m, 2H), 7.68 (d, J=1.6 Hz, 1H), 7.49-7.45 (m, 1H), 7.38-7.36 (m, 2H), 7.32-7.30 (m, 1H), 7.26-7.22 (m, 1H), 7.14-7.12 (m, 1H), 7.06-7.05 (m, 1H), 6.96 (s, 2H), 6.87 (s, 3H), 5.05 (t, J=5.0 Hz, 1H), 4.15-4.14 (m, 1H), 4.04-4.03 (m, 1H), 3.94-3.92 (m, 2H), 3.86-3.80 (m, 3H), 3.67-3.62 (m, 6H), 3.51 (q, J=7.2 Hz, 4H), 2.08 (s, 6H), 1.36 (t, J=7.2 Hz, 6H); HRMS (Fab+) calcd for $C_{42}H_{46}N_7O_{10}$ $[(M+H)^+]$: 808.3306. found 808.3267.

b. ddUTP-$N_3$—R6G (FIG. 16, Compound 20). The preparation procedure was similar to the synthesis of 17. The crude product was purified on reverse-phase HPLC to afford 20 (retention time=32.9 min). Compound 20 was further evaluated by performing a single base extension reaction to yield a DNA extension product which was characterized by MALDI-TOF MS (m/z 9082) (FIG. 20G).

Figure 17:
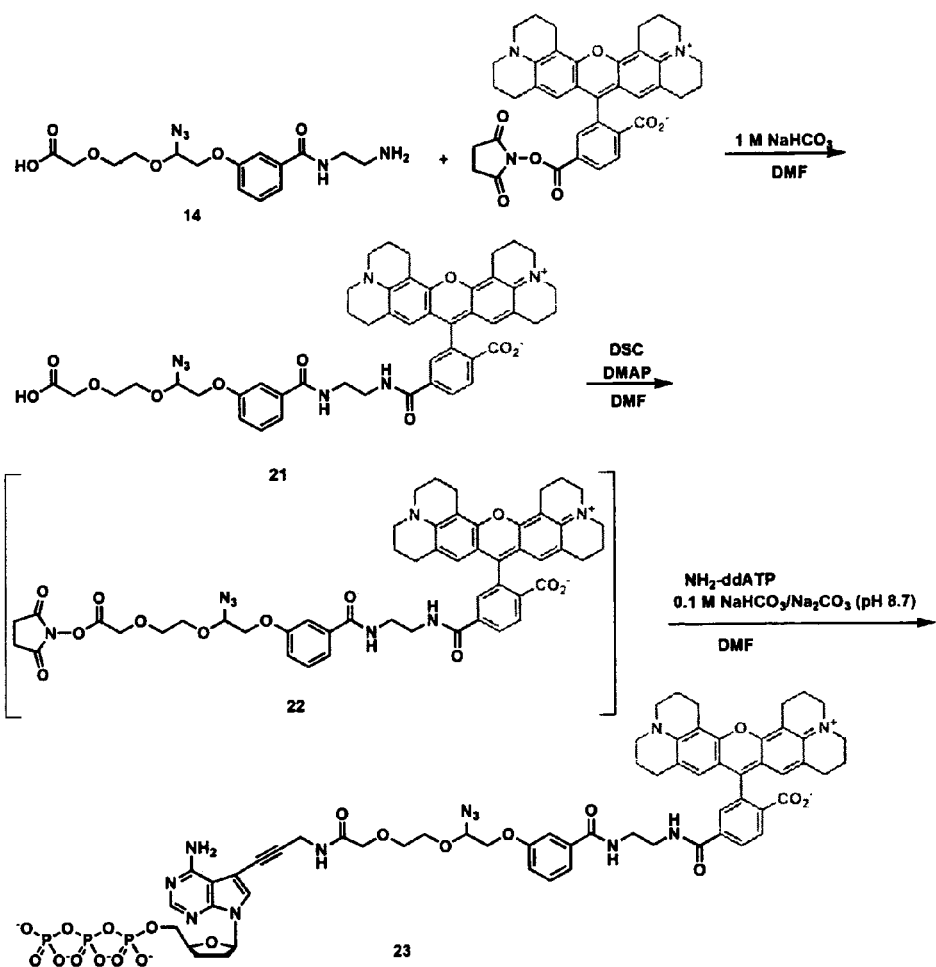

Synthesis of ddATP-$N_3$—ROX a. Azido-ROX (FIG. 17, Compound 21). The preparation procedure was similar to the synthesis of 15. The crude product was purified by a preparative silica gel TLC plate ($CH_3OH/CH_2Cl_2$, 2:5) to afford 21 (6.3 mg; 90%). $^1H$ NMR (400 MHz, $CD_3OD$) δ 8.24 (d, J=3.2 Hz, 2H), 7.65 (s, 1H), 7.49-7.46 (m, 1H), 7.38-7.35 (m, 1H), 7.32-7.30 (m, 1H), 7.26-7.23 (m, 1H), 7.14-7.12 (m, 1H), 7.05-7.04 (m, 1H), 6.70 (s, 2H), 6.87 (s, 3H), 5.02 (t, J=4.0 Hz, 1H), 4.26-4.23 (m, 1H), 4.16-4.12 (m, 2H), 4.00-3.97 (m, 2H), 3.90-3.71 (m, 3H), 3.67-3.45 (m, 8H), 3.04-3.01 (m, 4H), 2.66-2.56 (m, 4H), 2.09-2.08 (m, 4H), 1.90-1.89 (m, 4H); HRMS (Fab+) calcd for $C_{48}H_{50}N_7O_{10}$ $[(M+H)^+]$: 884.3619. found 884.3622.

b. ddATP-azido-ROX (FIG. 17, Compound 23). The preparation procedure was similar to the synthesis of 17. The crude product was purified on reverse-phase HPLC to afford 23 (retention time=36.1 min). Compound 23 was further evaluated by performing a single base extension reaction to yield a DNA extension product which was characterized by MALDI-TOF MS (m/z 9180) (FIG. 20A).

Figure 18:
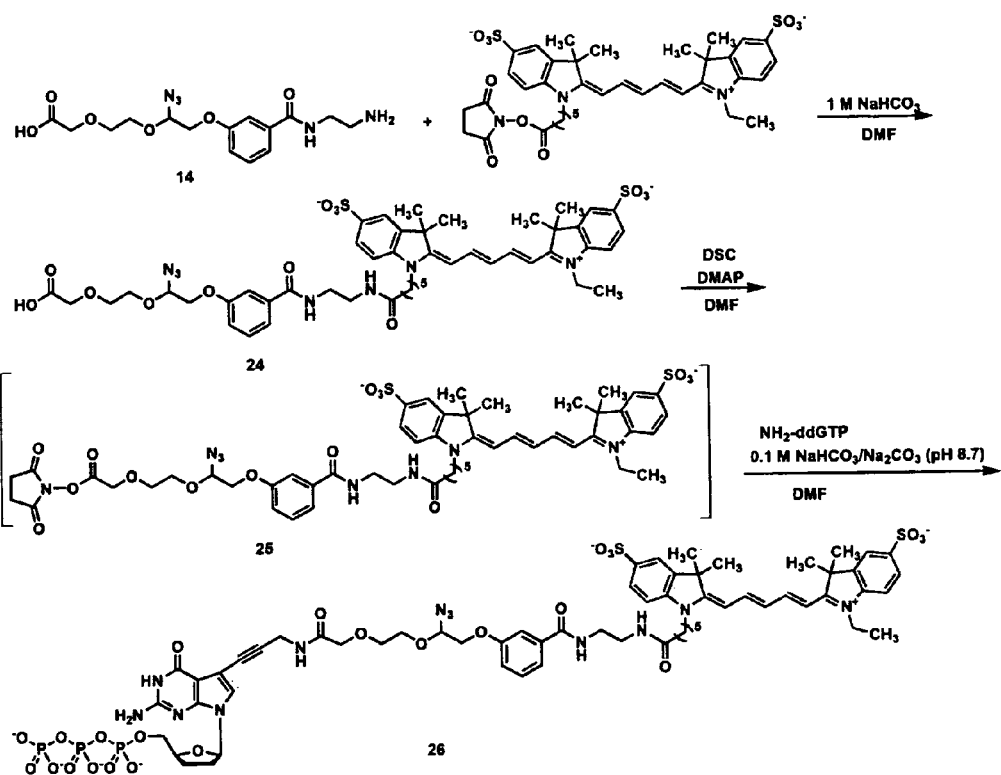

Synthesis of ddGTP-$N_3$-Cy5 a. Azido-Cy5 (FIG. 18, Compound 24). The preparation procedure was similar to the synthesis of 15. The crude product was purified by a preparative silica gel TLC plate ($CH_3OH/CH_2Cl_2$, 2:5) to afford 18 (5.6 mg; 84%). $^1H$ NMR (400 MHz, $CD_3OD$) δ 8.35-8.28 (m, 2H), 7.90-7.86 (m, 3H), 7.46-7.44 (m, 2H), 7.37-7.35 (m, 2H), 7.30-7.28 (d, J=8.0 Hz, 1H), 7.12-7.10 (m, 1H), 6.72 (t, J=12.4 Hz, 1H), 6.37-6.29 (m, 1H), 5.03 (t, J=4.8 Hz, 1H), 4.25-4.24 (m, 1H), 4.22-4.10 (m, 3H), 4.04-3.98 (m, 3H), 3.92 (s, 2H), 3.89-3.86 (m, 1H), 3.72-3.71 (m, 2H), 3.50-3.47 (m, 2H), 3.41-3.38 (m, 2H), 2.57 (m, 1H), 2.24-2.20 (m, 2H), 1.76 (s, 12H), 1.69-1.65 (m, 2H), 1.43-1.36 (m, 6H); MS (Fab+) calcd for $C_{48}H_{58}N_7O_{13}S_2$ $[(M+H)^+]$: 1006.4. found 1006.6.

b. ddGTP-$N_3$-Cy5 (FIG. 18, Compound 26). The preparation procedure was similar to the synthesis of 17. The crude product was purified on reverse-phase HPLC to afford 26 (retention time=31.6 min). Compound 26 was further evaluated by performing a single base extension reaction to yield a DNA extension product which was characterized by MALDI-TOF MS (m/z 9261) (FIG. 20E).

Continuous DNA Polymerase Reaction Using Four 3'-O-Modified Cleavable Nucleotides as Reversible Terminators in Solution.

The four NRTs (3'-O—$N_3$-dATP, 3'-O—$N_3$-dCTP, 3'-O—$N_3$-dGTP and 3'-O—$N_3$-dTTP) have been characterized, by performing four continuous DNA-extension reactions sequentially using a self-priming DNA template (5'-ATCG-GCGCCGCGCCTTGGCGCGGCGC-3' (SEQ ID No:1). The four nucleotides in the template immediately adjacent to the annealing site of the primer are 3'-GCTA-5', which allows the evaluation of the incorporation and cleavage efficiency of the 4 NRTs. First, a polymerase extension reaction using a pool of all four NRTs along with the self-priming DNA template was performed producing a single base extension product. The reaction mixture for this, and all subsequent extension reactions, consisted of 80 pmol of self-priming DNA template, 160 μmol of 3'-O—$N_3$-dNTPs, 1× Thermopol II reaction buffer (New England Biolabs), 40 nmol of $MnCl_2$ and unit of 9°N DNA polymerase (exo-) A485L/Y409V (New England Biolabs) in a total reaction volume of 20 μl. The reaction consisted of incubation at 94° C. for 5 min, 4° C. for 5 min, and 65° C. for 20 min. Subsequently, the extension product was desalted by using a ZipTip and analyzed by Voyager DE MALDI-TOF mass spectrometry (Applied Biosystems). For cleavage, the desalted DNA extension product bearing the 3'-O-azidomethyl group was first resuspended with 5 μl of 50 mM EDTA solution to quench the polymerase activity. This DNA solution was then mixed with 10 μl of 225 mM TCEP solution (pH 9.0) and incubated at 65° C. for 15 min to yield a cleaved DNA product which was characterized by MALDI-TOF MS. The DNA product with the 3'-O-azidomethyl group removed to generate a free 3'-OH group was purified by using an Oligonucleotide Purification Cartridge (Applied Biosystems) and used as a primer for a second extension reaction using 3'-O—$N_3$-dNTPs. The second extended DNA product was then purified by ZipTip and cleaved as described above. The third and the fourth extensions were carried out in a similar manner by using the previously extended and cleaved product as the primer.

Polymerase Extension Reaction Using Cleavable Fluorescent Dideoxynucleotide Terminators in Solution and Characterization by MALDI-TOF MS.

The four cleavable fluorescent dideoxynucleotide terminators, ddNTP-N3-fluorophores (ddCTP-N3-Bodipy-FL-510, ddUTP-N3-R6G, ddATP-N3-ROX, and ddGTP-N3-Cy5) have been characterized, by performing four separate DNA-extension reactions, each with a different self-priming DNA template allowing the four ddNTP analogues to be incorporated. The resulting DNA extension products were analyzed by MALDI-TOF MS. The following four self-priming DNA templates (26-mer hairpin DNA with a 4-base 5'-overhang) were used for the extension: 5'-GACTGCGCCGCGCCTTG-GCGCGGCGC-3' (SEQ ID No:2) for ddATP-$N_3$—ROX; 5'-ATCGGCGCCGCGCCTTGGCGCGGCGC-3' (SEQ ID No:3) for ddCTP-$N_3$-Bodipy-FL-510; 5'-GATCGCGC-CGCGCCTTGGCGCGGCGC-3' (SEQ ID No:4) for ddGTP-$N_3$-Cy5; and 5'-GTCAGCGCCGCGCCTTG-GCGCGGCGC-3' (SEQ ID No:5) for ddUTP-$N_3$—R6G. Each of the extension reactions consisted of all four ddNTP-$N_3$-fluorophores (e.g., 120 μmol each of ddCTP-$N_3$-Bodipy-FL-510, ddUTP-$N_3$—R6G, ddATP-$N_3$—ROX, and ddGTP-$N_3$-Cy5) along with 60 μmol of the self-priming DNA template, 1× Thermopol II reaction buffer, 40 nmol of $MnCl_2$ and 1 unit of 9°N DNA polymerase (exo-) A485L/Y4Q9V in a total reaction volume of 20 μl. The reaction consisted of incubations at 94° C. for 5 min, 4° C. for 5 min, and 65° C. for 20 min. Subsequently, the extension product was purified by reverse-phase HPLC using established procedures (40). The fraction containing the desired product was collected and freeze-dried for analysis by MALDI-TOF MS and cleavage.

For cleavage of the DNA extension product bearing the ddNTP-$N_3$-fluorophores, the purified DNA product was resuspended in 50 ml of 100 mM TCEP solution (pH 9.0) at 65° C. for 15 min and then analyzed by MALDI-TOF MS.

4-Color DNA Sequencing by Synthesis on a Chip Using Photocleavable Fluorescent Dideoxynucleotide/3'-Modified Photocleavable Nucleotide Combination Remnant of Sanger Sequencing.

Ten microliters of a solution consisting of ddCTP-$N_3$-Bodipy-FL-510 (10 fmol), ddUTP-$N_3$—R6G (20 fmol), ddATP-$N_3$—ROX (40 fmol), ddGTP-$N_3$-Cy5 (20 fmol), 3'-O—$N_3$-dCTP (22 pmol), 3'-O—$N_3$-dTTP (22 μmol), 3'-O—$N_3$-dATP (22 pmol), 3'-O—$N_3$-dGTP (4 pmol), 1 unit of 9°N mutant DNA polymerase(exo-) A485L/Y409V, 20 nmol of $MnCl_2$ and 1× Thermopol II reaction buffer was spotted on the DNA chip. The nucleotide complementary to the DNA template was allowed to incorporate into the primer at 62° C. for 15 min. To synchronize any unextended templates, an extension solution consisting of 38 μmol each of 3'-O—$N_3$-dTTP, 3'-O—$N_3$-dATP, 3'-O—$N_3$-dGTP and 75 pmol of 3'-O—$N_3$-dCTP, 1 unit of 9°N mutant DNA polymerase (exo-) A485L/Y409V, 20 nmol of $MnCl_2$ and 1× Thermopol II reaction buffer was added to the same spot and incubated at 62° C. for 15 min. After washing with SPSC buffer containing 0.1% Tween 20 for 1 min, the chip was rinsed with $dH_2O$, and then scanned with a 4-color fluorescence ScanArray Express scanner (Perkin-Elmer Life Sciences) to detect the fluorescence signal. To perform the cleavage, the DNA chip was placed inside a chamber filled with 100 mM TCEP (pH 9.0) and incubated at 65° C. for 10 min. After washing the surface with $dH_2O$, the chip was scanned again to measure the background fluorescence signal. This process was followed by the next polymerase extension reaction using the 3'-O—$N_2$-dNTP/ddNTP-$N_2$-fluorophore solution with the subsequent synchronization, washing, fluorescence detection, and cleavage processes performed as described above. The 3'-O—$N_2$-dNTP/ddNTP-$N_2$-fluorophore ratio was adjusted to obtain relatively even fluorescence signals. The above reaction cycles were repeated multiple times to obtain de novo DNA sequencing data on a DNA template immobilized on a chip.

Construction of a Chip with Immobilized Self-Priming DNA Template

The 5'-amino-labeled self-priming DNA template 5'—$NH_2$—CAC-TCA-CAT-ATG-TTT-TTT-AGC-TTT-TTT-AAT-TTC-TTA-ATG-ATG-TTG-TTG-CAT-GCG-ACT-TAA-GGC-GCT-TGC-GCC-TTA-AGT-CG-3' (SEQ ID No:6) was purchased from IDT (Coralville, Iowa). The DNA template was dissolved at 40 μM in 50 mM sodium phosphate buffer, pH 8.5 and spotted using SpotArray 72 arraying robot (Perkin Elmer) onto high density CodeLink microarray slides (GE Healthcare). After spotting, the slides were incubated at ambient temperature (~24° C.) for 20 hours in a humid chamber containing saturated sodium chloride solution (~75% humidity) to allow for 5'-tethering of the spotted amino-modified DNA templates to the slide surface functionalized with succinimide ester groups. Upon the incubation the slides were removed from the humid chamber and stored in vacuum desiccator at room temperature until further use. The principal advantage of the hairpin structure introduced into the 3'-portion of the self-priming DNA template is its higher stability and the increased priming efficiency for DNA polymerases as compared to a separate primer/template complex, which is prone to spontaneous dissociation.

3'-O—$N_3$-dNTP/ddNTP-$N_3$-Fluorophore Ratio Used for Four-Color DNA Sequencing on a Chip To obtain de novo DNA sequencing data on a DNA template immobilized on a chip, the SBS cycle was repeated multiple times using the combination mixture of solution A consisting of 3'-O—$N_3$-dCTP (3 μM), 3'-O—$N_3$-dTTP (3 μM), 3'-O—$N_3$-dATP (3 μM) and 3'-O—$N_3$-dGTP (0.5 μM) and solution B consisting of ddCTP-$N_3$-Bodipy-FL-510 (50 nM), ddUTP-$N_3$—R6G (100 nM), ddATP-$N_3$—ROX (200 nM) and ddGTP-$N_3$-Cy5 (100 nM) in each polymerase extension reaction. The following volumes of solution A and B in each SBS cycle were used to achieve relatively even fluorescence signals.

| SBS Cycle | Solution A (μl) | Solution B (μl) |
| --- | --- | --- |
| 1st | 7.3 | 0.2 |
| 2nd | 7.3 | 0.2 |
| 3rd | 7.3 | 0.2 |
| 4th | 7.3 | 0.2 |
| 5th | 7.2 | 0.3 |
| 6th | 7.2 | 0.3 |
| 7th | 7.2 | 0.3 |
| 8th | 7.2 | 0.3 |
| 9th | 7.0 | 0.5 |
| 10th | 7.0 | 0.5 |
| 11th | 7.0 | 0.5 |
| 12th | 7.0 | 0.5 |
| 13th | 6.5 | 1.0 |

-continued

| SBS Cycle | Solution A (μl) | Solution B (μl) |
| --- | --- | --- |
| 14th | 6.5 | 1.0 |
| 15th | 6.5 | 1.0 |
| 16th | 6.5 | 1.0 |
| 17th | 6.0 | 1.5 |
| 18th | 6.0 | 1.5 |
| 19th | 6.0 | 1.5 |
| 20th | 5.5 | 2.0 |
| 21st | 5.5 | 2.0 |
| 22nd | 5.5 | 2.0 |
| 23rd | 5.0 | 2.5 |
| 24th | 5.0 | 2.5 |
| 25th | 5.0 | 2.5 |
| 26th | 4.5 | 3.0 |
| 27th | 4.0 | 3.5 |
| 28th | 3.5 | 4.0 |
| 29th | 3.0 | 4.5 |
| 30th | 2.5 | 5.0 |
| 31st | 2.0 | 5.5 |
| 32nd | 0 | 7.5 |

Discussion

Four 3'-O-modified cleavable reversible terminator nucleotides (3'-O—$N_3$-dNTPs) along with four fluorescent ddNTPs have been synthesized and characterized, and used them to produce 4-color de novo DNA sequencing data on a chip by Sanger/SBS hybrid sequencing approach that has the following advantages. With the 3'-O—$N_3$-dNTPs, after cleavage of the 3'OH capping group of the DNA extension product, there are no traces of modification left on the growing DNA strand. Therefore, there are no adverse effects on the DNA polymerase for incorporation of the next complementary nucleotide. Second, the cleavable fluorescent ddNTPs and 3'-O—$N_3$-dNTPs permanent and reversible terminators, respectively, which allow the interrogation of each base in a serial manner, a key procedure enabling accurate determination of homopolymeric regions of DNA. In addition, because all of the steps of the nucleotide incorporation, fluorescence detection for sequence determination, cleavage of the fluorophore, and the 3'-O-azidomethyl group are performed on a DNA chip, there is no longer a need for electrophoretic DNA fragment separation as in the classical Sanger sequencing method.

In the four-color hybrid SBS approach, the identity of the incorporated nucleotide is determined by the unique fluorescence emission from the four fluorescent dideoxynucleotides, whereas the role of the 3'-O-modified NRTs is to further extend the DNA strand. Therefore, the ratio of the ddNTP-$N_3$-fluorophores and 3'-O—$N_3$-dNTPs during the polymerase reaction determines how much of the ddNTP-$N_3$-fluorophores incorporate and, thus, the corresponding fluorescence emission strength. With a finite amount of immobilized DNA template on a solid surface, initially the majority of the priming strands should be extended with 3'-O—$N_3$-dNTPs, whereas a relatively smaller amount should be extended with ddNTP-$N_3$-fluorophores to produce sufficient fluorescent signals that are above the fluorescence detection system's sensitivity threshold for sequence determination. As the sequencing cycle continues, the amount of the ddNTP-$N_3$-fluorophores needs to be gradually increased to maintain the fluorescence emission strength for detection.

We have experimentally determined the ratio of the 3'-O—$N_3$-dNTPs and ddNTP-$N_3$-fluorophores to yield sequencing read length of 32 bases. The signal strength at base 32 is as strong as that of the first base (FIG. 21C), indicating it should be possible to increase the read length of the hybrid SBS further by optimizing the extension conditions to reduce the background fluorescence in the later sequencing cycles. The ultimate read length of this hybrid SBS system depends on three factors: the number of starting DNA molecules on each spot of a DNA chip, the reaction efficiency, and the detection sensitivity of the system. The read length with the Sanger sequencing method commonly reaches >700 bp. The hybrid SBS approach described here may have the potential to reach this read length, especially with improvements in the sensitivity of the fluorescent detection system, where single molecules can be reliably detected.

With sequencing read length from 14 to 30 bases in the next generation DNA sequencing systems, massive parallel digital gene expression analogous to a high-throughput SAGE (41) approach has been reported reaching single copy transcript sensitivity (42), and CHIP-Seq (43-45) based on sequencing tags of ~25 bases has led to many new discoveries in genome function and regulation. It is well established that millions of different PCR template's can be generated on a solid surface through emulsion PCR or clonal amplification (45, 20). Thus, future implementation of the hybrid SBS approach on a high-density bead array platform will provide a high-throughput and accurate DNA sequencing system with wide applications in genome biology and biomedical research.

References

1. Walter, G.; Allan, M., Nucleotide Sequence of the Lac Operator. Proceedings of the National Academy of Science 1973, 17, 3581-3584.
2. Sanger, F.; Nicklen, S.; Coulson, A. R., DNA Sequencing with Chain-terminating Inhibitors. Proceedings of the National Academy of Science 1977, 74, 5463-5467.
3. Ju, J.; Ruan, C.; Fuller, C. W.; Glazer, A. N.; Mathies, R. A., Fluorescence Energy Transer Dye-Labeled Primers for DNA Sequencing and Analysis. Proceedings of the National Academy of Science 1995, 92, 4347-4351.
4. Kan, C. W.; Doherty, E. A.; Barron, A. E., A Novel Thermogelling Matrix for Microchannel DNA Sequencing Based on Poly-N-alkooxyalkylacrylamide Copoloymers. Electrophoresis 2003, 24, 4161-4169.
5. Prober, J. M.; Trainor, G. L.; Dam, R. J.; Hobbs, F. W.; Robertson, C. W.; Zagursky, R. J.; Cocuzza, A. J.; Jensen, M. A.; Baumeister, K., A System for Rapid DNA Sequencing with Fluorescent Chain-Temrinating Dideoxynucleotides. Science 1987, 238, 336-341.
6. Smith, L. M.; Sanders, J. Z.; Kaiser, R. J.; Hughes, P.; Dodd, C.; Connell, C. R.; Heiner, C.; Kent, S. B.; Hood, L. E., Fluorescnce Detection in Automated DNA Sequence Analysis. Nature 1986, 321, 674-679.
7. Bai, X.; Edwards, J. R.; Ju, J., Molecular Engineering Approaches for DNA Sequencing and Analysis. Expert Review of Molecular diagnostics 2005, 5, 797-808.
8. Collins, F. S.; Green, E. D.; Guttmacher, A. E.; Guyer, M. S., A Vision for the Future of Genomics Research. Nature 2003, 422, 835-847.
9. Drmanac, S.; Kita, D.; Labat, I.; Hauser, B.; Schmidt, C.; Burczak, J. D.; Drmanac, R., Accurate Sequencing by Hybridization for DNA Diagnostics and Individual Genomics. Nature Biotechnology 1998, 16, 54-58.
10. Edwards, J. R.; Itagaki, Y.; Ju, J., DNA Sequencing Using Biotinylated Dideoxynucleotides and Mass Sepctrometry. Nucleic Acids Research 2001, 29, e104-e104.
11. Fu, D. J.; Tang, K.; Braun, A.; Reuter, D.; Darnofer-Demar, B.; Little, D. P.; O'Donnell, M. J.; Cantor, C. R.; Koster, H., Sequencing Exons 5 to 8 of the p53 Gene by MALDI-TOF Mass Spectrometry. Nature Biotechnology 1998, 16, 381-384.
12. Roskey, M. T.; Juhasz, P.; Smirnov, I. P.; Takach, E. J.; Martin, S. A.; Haff, L. A., DNA Sequencing by Delayed Extraction-matrix-assisted Laser Desorption/ionization Time of Flight Mass Spectrometry. Proceedings of the National Academy of Science 1996, 93, 4724-4729.

13. Kasianowicz, J. J.; Brandin, E.; Branton, D.; Deamer, D. W., Characterization of Individual Polynucleotide Molecules Using a Membrane Channel. Proceedings of the National Academy of Science 1996, 93, 13770-13773.
14. Meller, A.; Nivon, L.; Brandin, E.; Golovchenko, J.; Branton, D., Rapid Nanopore Dicrimination Between Single Polynucleotide Molecules. Proceedings of the National Academy of Science 2000, 97, 1079-1084.
15. Vercoutere, W.; Hilt, S. T.; Olsen, H.; Deamer, D.; Haussier, D.; Akeson, M., Rapid Discrimination Among Individual DNA Hairpin Molecules at Single-nucleotide Resolution Using an Ion Channel. Nature Biotechnology 2001, 17, 248-252.
16. Howorka, S.; Cheley, S.; Bayley, H., Sequence-specific Detection of Individual DNA Strands Using Engineered Nanopores. Nature Biotechnology 2001, 19, 636-639.
17. Gu, L. Q.; Braha, O.; Conlan, S.; Cheley, S.; Bayley, H., Stochastic Sensing of Organic Analytes by a Pore-forming Protein Containing a Molecular Adapter. Nature 1999, 398, 686-670.
18. Shendure, J.; Porreca, G. J.; Reppas, N. B.; Lin, X.; McCutcheon, J. P.; Rosenbaum, A. M.; Wang, M. D.; Zhang, K.; Mitra, R. D.; Church, G. M., Accurate Multiplex Polony Sequencing of an Evolved Bacterial Genome. Science 2005, 309, 1728-1732.
19. Hyman, E. D., A New Method of Sequencing DNA. Analytical Biochemistry 1988, 174, 423-436.
20. Margulies, M.; Egholm, M.; Altman, W. E.; Attiya, S.; Bader, J. S.; Bemben, L. A.; Berka, J.; Braverman, M. S.; Chen, Y. J.; Chen, Z.; et al., Genome Sequencing in Microfabricated High-density Picolitre Reactors. Nature 2005, 437, 376-380.
21. Ronaghi, M., Pyrosequencing Sheds Light on DNA Sequencing. Genome Research 2001, 11, 3-11.
22. Ju, J.; Kim, D. H.; Bi, L.; Meng, Q.; Bai, X.; Li, Z.; Li, X.; Marma, M. S.; Shi, S.; Wu, J.; Edwards, J. R.; Romu, A.; Turro, N. J., Four-color DNA Sequencing by Synthesis Using Cleavable Fluorescent Nucleotide Reversible Terminators. Proceedings of the National Academy of Science 2006, 103, 19635-19640.
23. Metzker, M. L.; Raghavachari, R.; Richards, S.; Jacutin, S. E.; Civitello, A.; Burgess, K.; Gibbs, R. A., Termination of DNA Synthesis by Novel 3'-modified-deoxyribonucleoside 5'-triphosphates. Nucleic Acids Research 1994, 22, 4259-4267.
24. Lu, G.; Burgess, K., A Diversity Orieted Synthesis of 3'-O-modified Nucleoside Triphosphates for DNA 'Sequencing by Synthesis'. Bioorganic & Medicinal Chemistry Letters 2006, 16, 3902-3905.
25. Metzker, M. L., Emerging Technologies in DNA Sequencing. Genome Research 2005, 15, 1767-1776.
26. Pelletier, H.; Sawaya, M. R.; Kumar, A.; Wilson, S. H.; Kraut, J., Structures of Ternary Complexes of Rat DNA Polymerase Beta, a DNA Template-primer, and ddCTP. Science 1994, 264, 1891-1903.
27. Rosenblum, B. B.; Lee, L. G.; Spurgeon, S. L.; Khan, S. H.; Menchen, S. M.; Heiner, C. R.; Chen, S. M., New Dye-labeled Terminators for Improved DNA Sequencing Patterns. Nucleic Acids Research 1997, 25, (4500-4504).
28. Zhu, Z.; Chao, J.; Yu, H.; Waggoner, A. S., Directly Labeled DNA Probes Using Fluorescent Nucleotides with Differnt Length Linkers. Nucleic Acids Research 1994, 22, 3418-3422.
29. Seo, T. S.; Bai, X.; Kim, D. H.; Meng, Q.; Shi, S.; Ruparel, H.; Li, Z.; Turro, N. J.; Ju, J., Four-color DNA Sequecing by Synthesis on a Chip Using Photocleavable Fluorescent Nucleotides. Proceedings of the National Academy of Science 2005, 102, (5926-5931).
30. Kolb, H. C.; Finn, M. G.; Sharpless, K. B., Click Chemistry: Diverse Chemical Funtion from a Few Good Reactions. Angewandte Chemie International Edition 2001, 40, 2004-2021.
31. Seo, T. S.; Li, Z.; Ruparel, H.; Ju, J., Click Chemistry to Construct Fluorescent Oligonucleotides for DNA Sequencing. Journal of Organic Chemistry 2003, 68, 609-612.
32. Bi, L.; Kim, D. H.; Ju, J., Design and Synthesis of a Chemically Cleavable Fluorescent Nucleotide, 3'-O-Allyl-dGTP-allyl-Bodipy-FL-510, as a Reversible Terminator for DNA Sequencing by Synthesis. Journal of American Chemical Society 2006, 128, (2542-2543).
33. Pillai, V. N. R., Photoremovable Protecting Groups in Organic Synthesis. Synthesis 1980, 1, 1-26.
34. Meng, Q.; Kim, D. H.; Bai, X.; Bi, L.; Turro, N. J.; Ju, J., Design and Synthesis of a Photocleavable Fluorescent Nucleotide 3'-O-Allyl-dGTP-PC-Bodipy-FL-510 as a Reversible Terminator for DNA Sequencing by Synthesis. Journal of Organic Chemistry 2006, 71, 3248-3252.
35. Gololobov, Y. G.; Zhmurova, I. N.; Kasukin, L. F., Sixty Years of Staudinger Reaction. Tetrahedron 1981, 37, 437-472.
36. Saxon E, Bertozzi C R (2000) Science 287:2007-2010.
37. Milton J, Ruediger S, Liu X (2006) United States Patent Application US20060160081A1.
38. Barnes, C., Balasubramanian, S., Liu, X., Swerdlow, H., Milton, J. (2006) U.S. Pat. No. 7,057,026.
39. Wu, W., et al. (2007) Nucleic Acid Research 35:6339-6349
40. Zavgorodny S, et al. (2000) Nucleosides, Nucleotides Nucleic Acids 19:1977-1991.
41. Velculescu V E, Zhang L, Vogelstein B, Kinzler K W (1995) *Science* 270:484-487.
42. Kim J B, Porreca G J, Song L, Greenway S C, Gorham J M, Church G M, Seidman C E, Seidman J G (2007) *Science* 316:1481-1484.
43. Mikkelsen T S, Ku M, Jaffe D B, Issac B, Lieberman E, Giannoukos G, Alvarez P, Brockman W, Kim T K, Koche R P, et al. (2007) *Nature* 448:553-560.
44. Johnson D S, Mortazavi A, Myers R M, Wold B (2007) *Science* 316: 1497-1502.
45. Barski A, Cuddapah S, Cui K, Roh T Y, Schones D E, Wang Z, Wei G, Chepelev I, Zhao K (2007) *Cell* 129: 823-837.

What is claimed is:

1. A compound having a first, a second, and a third portion, wherein the second portion has the following structure:

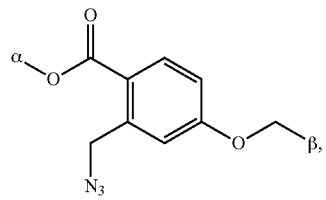

wherein α represents a point of attachment to the first portion and β represents a point of attachment to the third portion;

wherein the first portion comprises a deoxynucleotide or a dideoxynucleotide and the third portion comprises a detectable marker.

2. The compound of claim 1, wherein the detectable marker is a fluorescent dye.

3. The compound of claim 1, wherein the first portion is a deoxynucleotide comprising a methylazido group attached to a 3' O atom thereof.

4. The compound of claim 2, having the structure:

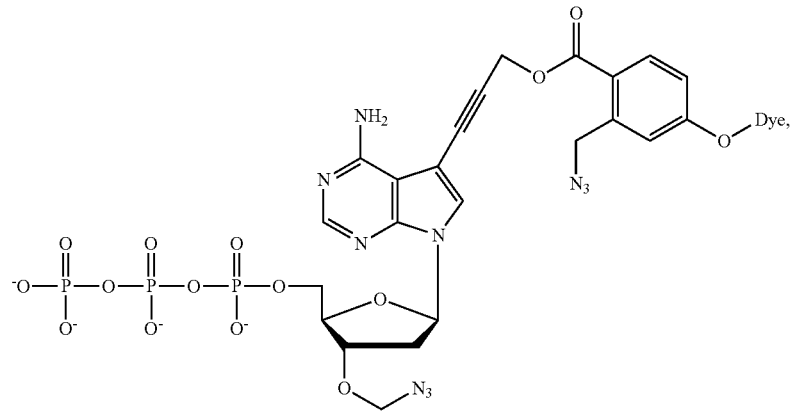

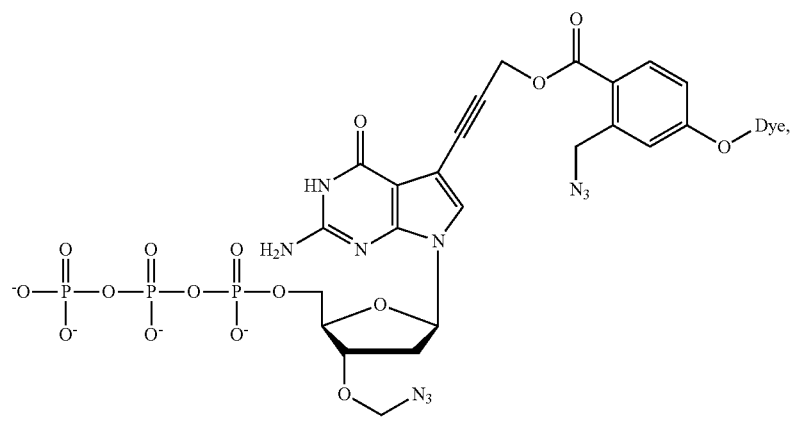

-continued
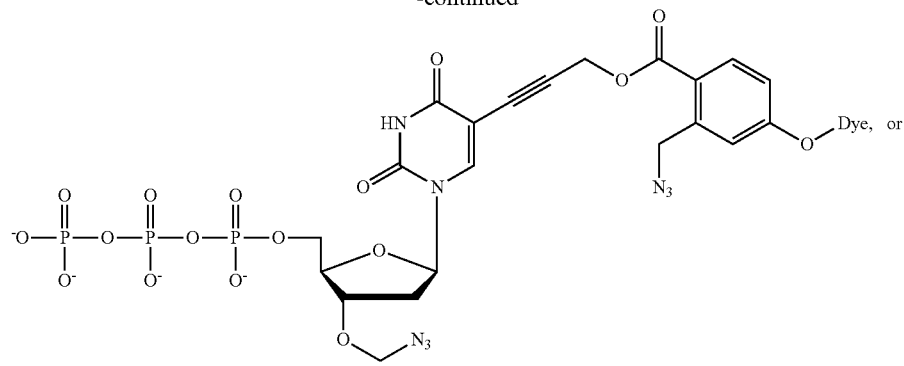
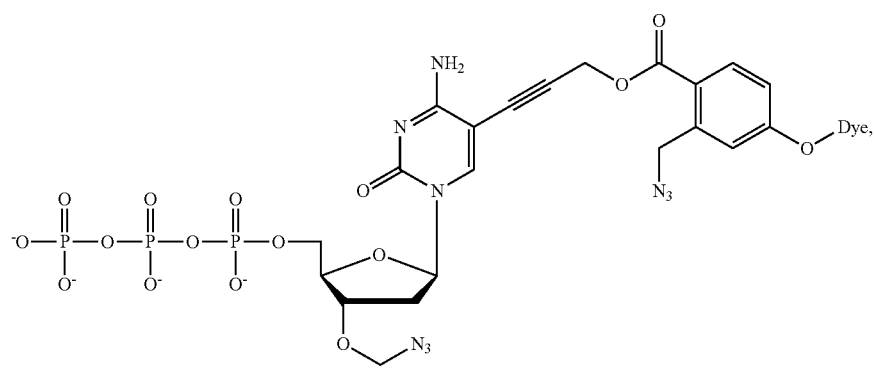
wherein the dye in each structure is a fluorescent dye.
5. The compound of claim 4 having the structure:
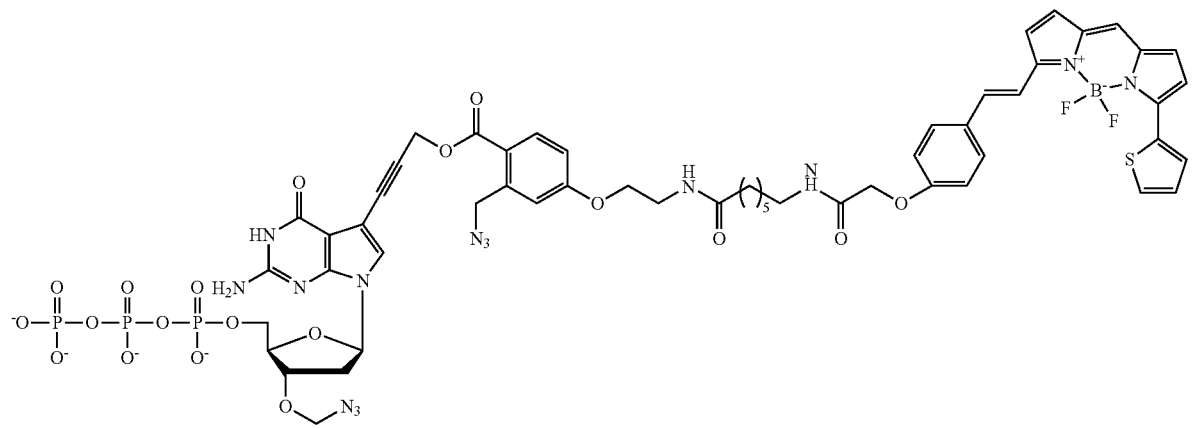

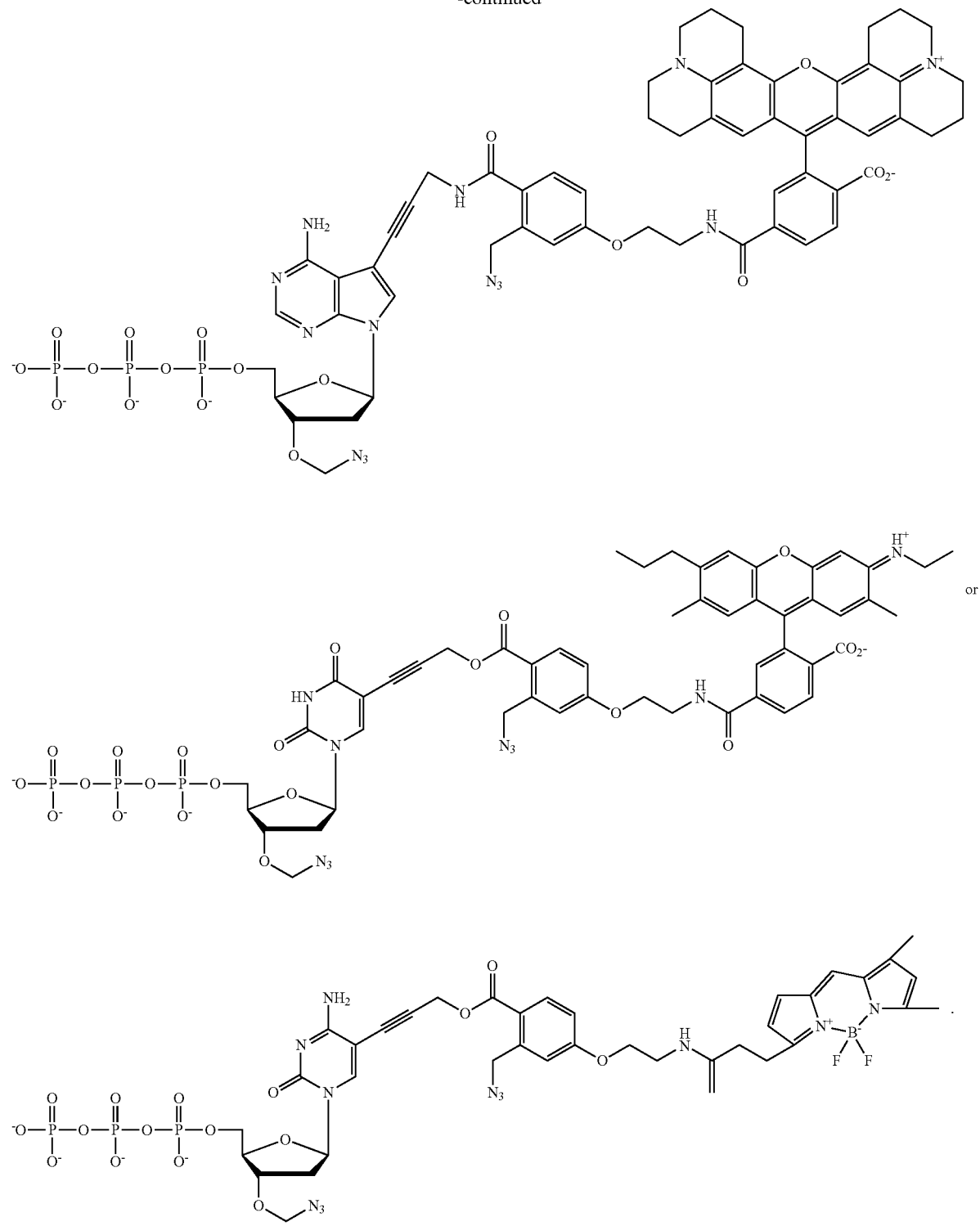

6. An array comprising a nucleic acid attached to a solid surface, wherein the nucleic acid comprises a methylazido group attached to a 3' O atom thereof and a molecule having the structure:

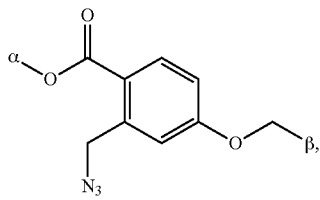

wherein α represents a point of attachment to the base of the nucleic acid and β represents a point of attachment to a detectable marker.

7. A method for determining the identity of each of a series of consecutive nucleotide residues in a nucleic acid comprising:

a) contacting the nucleic acid with (i) at least four different deoxynucleotide triphosphate (dNTP) analogues, each having the structure:

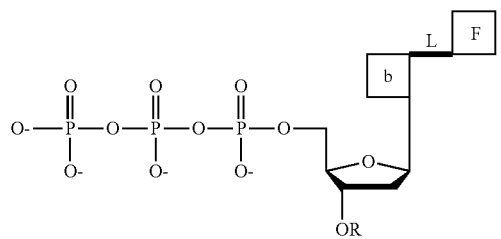

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, (ii) a nucleic acid polymerase and (iii) a nucleic acid primer which hybridizes with the nucleic acid, under conditions permitting one of the four dNTP analogues that is complementary to the consecutive nucleotide residue to be identified to form a phosphodiester bond with the 3' end of the nucleic acid primer and thereby extend the primer;

b) identifying the fluorophore of the dNTP analogue which has formed the phosphodiester bond, thereby identifying the consecutive nucleotide;

c) cleaving the linker attaching the fluorophore of the dNTP analogue which has formed the phosphodiester bond and cleaving the cleavable chemical group from the dNTP;

d) iteratively repeating steps a) through c) for each of the consecutive nucleotide residues to be identified until the final consecutive nucleotide residue is to be identified;

e) repeating steps a) and b) to identify the final consecutive nucleotide residue, f) denaturing the extended primer so as to de-hybridize it from the nucleic acid;

g) contacting the nucleic acid with (i) at least four different deoxynucleotide triphosphate (dNTP) analogues, each comprising an adenine, guanine, cytosine, uracil, inosine or 5-nitorindole base and each differing from a deoxynucleotide triphosphate by having a cleavable chemical group attached to the 3' O-atom of the dNTP, (ii) a nucleic acid polymerase and (iii) a second nucleic acid primer which hybridizes with the nucleic acid, under conditions permitting one of the four dNTP analogues that is complementary to the consecutive nucleotide residue to be identified to form a phosphodiester bond with the 3' end of the second nucleic acid primer and thereby extend the second primer;

h) cleaving the chemical group from the 3' O-atom of the dNTP analogue which has formed the phosphodiester bond so as to thereby permit incorporation of a further dNTP analogue into the extended second nucleic acid primer;

i) iteratively repeating steps g) and h) until the second primer is extended up to and including a residue corresponding to the final consecutive nucleotide residue identified in step e);

j) contacting the extended second primer with (i) at least four different deoxynucleotide triphosphate (dNTP) analogues, each having the structure:

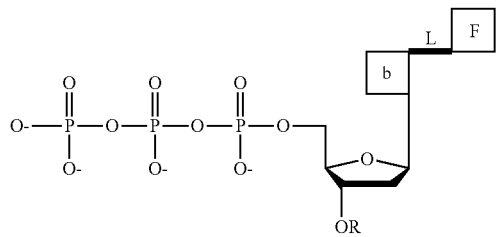

wherein F is a fluorophore, b is a base which is adenine, guanine, cytosine, uracil or thymine, wherein the fluorophore attached through a linker to each type of base differs in its emission or excitation spectra from a fluorophore attached to each of the remaining types of bases, and each of the four dNTP analogues differs from the remaining three dNTP analogues by having a different base, wherein L is a cleavable linker molecule, and R is a cleavable chemical group which is not hydrogen, under conditions permitting one of the four dNTP analogues that is complementary to the next consecutive nucleotide residue to be identified to form a phosphodiester bond with the 3' end of the extended second nucleic acid primer and thereby further extend the second primer;

k) identifying the fluorophore of the dNTP analogue which has formed the phosphodiester bond, thereby identifying the consecutive nucleotide;

l) cleaving the fluorophore and the cleavable chemical group from the dNTP analogue which formed the phosphodiester bond so as to thereby permit incorporation of a further dNTP analogue into the extended second nucleic acid primer;

m) iteratively repeating steps j) through l) for each of the consecutive nucleotide residues to be identified until the final consecutive nucleotide residue is to be identified;

n) repeating steps j) and k) to identify the final consecutive nucleotide residue, so as to thereby determine the identity of each of the series of consecutive nucleotide residues in the nucleic acid;
wherein the linker in each of step a) and j) independently each comprise the structure:

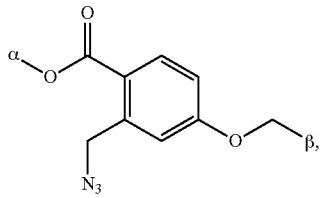

or the structure:

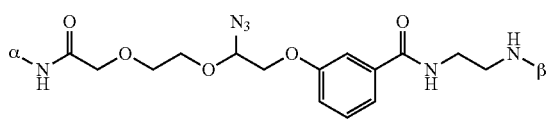

wherein α represents a point of attachment to the base and β represents a point of attachment to the fluorophore, and wherein R is a cleavable chemical group.

8. The method of claim 7, wherein a linker is cleaved by contacting the linker with tris(2-carboxyethyl)phosphine.

9. The method of claim 7, wherein one or more linkers are photocleavable or chemically cleavable.

10. The method of claim 7, wherein one or more chemical groups are photocleavable or chemically cleavable.

11. The method of claim 7, wherein R in the structures set forth in steps a) and/or j) is independently chosen from a —$N_3$ group or an allyl group.

12. The method of claim 7, wherein the cleavable chemical group in step g) is independently chosen from a —$N_3$ group or an allyl group.

* * * * *

UNITED STATES PATENT AND TRADEMARK OFFICE
CERTIFICATE OF CORRECTION

PATENT NO. : 9,175,342 B2  
APPLICATION NO. : 13/951269  
DATED : November 3, 2015  
INVENTOR(S) : Jingyue Ju et al.

Page 1 of 1

It is certified that error appears in the above-identified patent and that said Letters Patent is hereby corrected as shown below:

Column 1, Lines 14-17 should read as follows:

This invention was made with government support under HG003582 awarded by the National Institutes of Health. The government has certain rights in the invention.

Signed and Sealed this  
Fifth Day of April, 2016

Michelle K. Lee  
*Director of the United States Patent and Trademark Office*

SEQUENCE LISTING

<160> NUMBER OF SEQ ID NOS: 17

<210> SEQ ID NO 1
<211> LENGTH: 26
<212> TYPE: DNA
<213> ORGANISM: Artificial Sequence

```
<220> FEATURE:
<223> OTHER INFORMATION: self-priming DNA template for Polymerase
      extension reaction

<400> SEQUENCE: 1
atcggcgccg cgccttggcg cggcgc                                          26

<210> SEQ ID NO 2
<211> LENGTH: 26
<212> TYPE: DNA
<213> ORGANISM: Artificial Sequence
<220> FEATURE:
<223> OTHER INFORMATION: self-priming DNA template for polymerase
      extension reaction

<400> SEQUENCE: 2
gactgcgccg cgccttggcg cggcgc                                          26

<210> SEQ ID NO 3
<211> LENGTH: 26
<212> TYPE: DNA
<213> ORGANISM: Artificial Sequence
<220> FEATURE:
<223> OTHER INFORMATION: self-priming DNA template for polymerase
      extension reaction

<400> SEQUENCE: 3
atcggcgccg cgccttggcg cggcgc                                          26

<210> SEQ ID NO 4
<211> LENGTH: 26
<212> TYPE: DNA
<213> ORGANISM: Artificial Sequence
<220> FEATURE:
<223> OTHER INFORMATION: self-priming DNA template for polymerase
      extension reaction for ddGTP-N3-Cy5

<400> SEQUENCE: 4
gatcgcgccg cgccttggcg cggcgc                                          26

<210> SEQ ID NO 5
<211> LENGTH: 26
<212> TYPE: DNA
<213> ORGANISM: Artificial Sequence
<220> FEATURE:
<223> OTHER INFORMATION: self-priming DNA template for polymerase
      extension reaction for ddNTP-N3-R6G

<400> SEQUENCE: 5
gtcagcgccg cgccttggcg cggcgc                                          26

<210> SEQ ID NO 6
<211> LENGTH: 80
<212> TYPE: DNA
<213> ORGANISM: Artificial Sequence
<220> FEATURE:
<223> OTHER INFORMATION: 5'-amino-labeled self-priming DNA template for
      polymerase extension reaction

<400> SEQUENCE: 6
cactcacata tgttttttag cttttttaat ttcttaatga tgttgttgca tgcgacttaa     60
ggcgcttgcg ccttaagtcg                                                 80

<210> SEQ ID NO 7
<211> LENGTH: 15
<212> TYPE: DNA
```

```
<213> ORGANISM: Artificial Sequence
<220> FEATURE:
<223> OTHER INFORMATION: 15 nucleotides of a 130 bp self-priming DNA
      template for polymerase extension reaction

<400> SEQUENCE: 7
actgaacatc tgcat                                                          15

<210> SEQ ID NO 8
<211> LENGTH: 21
<212> TYPE: DNA
<213> ORGANISM: Artificial Sequence
<220> FEATURE:
<223> OTHER INFORMATION: 21 nucleotides of a self-priming DNA template
      for polymerase extension reaction

<400> SEQUENCE: 8
tgttaatcat gttgttgcat g                                                   21

<210> SEQ ID NO 9
<211> LENGTH: 14
<212> TYPE: DNA
<213> ORGANISM: Artificial Sequence
<220> FEATURE:
<223> OTHER INFORMATION: DNA template for template "walking"

<400> SEQUENCE: 9
aatcatctcg catg                                                           14

<210> SEQ ID NO 10
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 9
<220> FEATURE:
<221> NAME/KEY: modified_base
<222> LOCATION: (10)..(10)
<223> OTHER INFORMATION: R6G-R2

<400> SEQUENCE: 10
catgcgagau                                                                10

<210> SEQ ID NO 11
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 9
<220> FEATURE:
<221> NAME/KEY: modified_base
<222> LOCATION: (10)..(10)
<223> OTHER INFORMATION: 3'-R1

<400> SEQUENCE: 11
catgcgagat                                                                10

<210> SEQ ID NO 12
<211> LENGTH: 14
<212> TYPE: DNA
<213> ORGANISM: Artificial Sequence
<220> FEATURE:
<223> OTHER INFORMATION: DNA template for template "walking"

<400> SEQUENCE: 12
aatctactag catg                                                           14
```

```
<210> SEQ ID NO 13
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 12
<220> FEATURE:
<221> NAME/KEY: modified_base
<222> LOCATION: (10)..(10)
<223> OTHER INFORMATION: ROX-R2

<400> SEQUENCE: 13
catgctagta                                                          10

<210> SEQ ID NO 14
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 12
<220> FEATURE:
<221> NAME/KEY: modified_base
<222> LOCATION: (10)..(10)
<223> OTHER INFORMATION: 3'-R1

<400> SEQUENCE: 14
catgctagta                                                          10

<210> SEQ ID NO 15
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 9
<220> FEATURE:
<221> NAME/KEY: modified_base
<222> LOCATION: (10)..(10)
<223> OTHER INFORMATION: R6G-R2; 3'-R1

<400> SEQUENCE: 15
catgcgagau                                                          10

<210> SEQ ID NO 16
<211> LENGTH: 10
<212> TYPE: DNA
<213> ORGANISM: Artificial Sequence
<220> FEATURE:
<223> OTHER INFORMATION: Polymerase extension reaction product of SEQ ID
      No: 12
<220> FEATURE:
<221> NAME/KEY: modified_base
<222> LOCATION: (10)..(10)
<223> OTHER INFORMATION: ROX-R2; 3'-R1

<400> SEQUENCE: 16
catgctagta                                                          10

<210> SEQ ID NO 17
<211> LENGTH: 10
<212> TYPE: DNA
```

```
<213> ORGANISM: Artificial Sequence
<220> FEATURE:
<223> OTHER INFORMATION: Polymerase extension reaction product of SEQ ID
      No: 12
<220> FEATURE:
<221> NAME/KEY: modified_base
<222> LOCATION: (10)..(10)
<223> OTHER INFORMATION: 3'-R1

<400> SEQUENCE: 17
catgctagua                                                          10
```